United States Patent
Yoshimoto et al.

(10) Patent No.: US 9,867,372 B2
(45) Date of Patent: *Jan. 16, 2018

(54) TETRAZOLINONE COMPOUND AND USE OF SAME

(71) Applicant: SUMITOMO CHEMICAL COMPANY, LIMITED, Tokyo (JP)

(72) Inventors: Yuya Yoshimoto, Takarazuka (JP); Sadayuki Arimori, Takarazuka (JP); Zengye Hou, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/785,034

(22) PCT Filed: Apr. 23, 2014

(86) PCT No.: PCT/JP2014/062036
§ 371 (c)(1),
(2) Date: Oct. 16, 2015

(87) PCT Pub. No.: WO2014/175465
PCT Pub. Date: Oct. 30, 2014

(65) Prior Publication Data
US 2016/0081339 A1    Mar. 24, 2016

(30) Foreign Application Priority Data

Apr. 26, 2013 (JP) .................. 2013-093420
Oct. 29, 2013 (JP) .................. 2013-224056
Dec. 20, 2013 (JP) .................. 2013-263418

(51) Int. Cl.
| | |
|---|---|
| C07D 401/12 | (2006.01) |
| C07D 401/14 | (2006.01) |
| C07D 403/12 | (2006.01) |
| C07D 405/12 | (2006.01) |
| C07D 405/14 | (2006.01) |
| C07D 413/14 | (2006.01) |
| C07D 257/04 | (2006.01) |
| A01N 43/713 | (2006.01) |
| A01N 43/76 | (2006.01) |

(52) U.S. Cl.
CPC .......... *A01N 43/713* (2013.01); *A01N 43/76* (2013.01); *C07D 257/04* (2013.01); *C07D 401/12* (2013.01); *C07D 401/14* (2013.01); *C07D 403/12* (2013.01); *C07D 405/12* (2013.01); *C07D 405/14* (2013.01); *C07D 413/14* (2013.01)

(58) Field of Classification Search
None
See application file for complete search history.

(56) References Cited

U.S. PATENT DOCUMENTS

| | | |
|---|---|---|
| 6,583,090 B1 | 6/2003 | Gewehr et al. |
| 2014/0323305 A1 | 10/2014 | Rheinheimer et al. |
| 2015/0031733 A1 | 1/2015 | Yoshimoto et al. |

(Continued)

FOREIGN PATENT DOCUMENTS

| | | |
|---|---|---|
| JP | 9-208565 A | 8/1997 |
| JP | 2001-506984 A | 5/2001 |

(Continued)

OTHER PUBLICATIONS

Chinese Office Action and Search Report, dated Sep. 23, 2016, for Chinese Application No. 201480035650.8, with an English translation of the Chinese Office Action.

(Continued)

*Primary Examiner* — Alicia L Otton
(74) *Attorney, Agent, or Firm* — Birch, Stewart, Kolasch & Birch, LLP

(57) ABSTRACT

A tetrazolinone compound of formula (1):

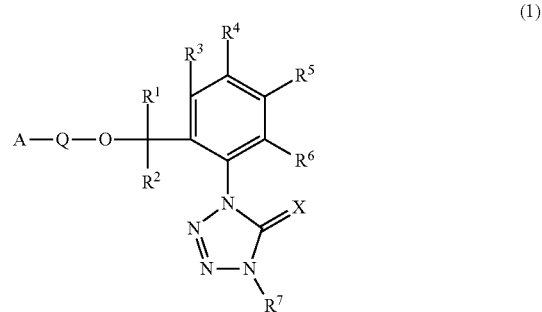

wherein $R^1$ and $R^2$ each independently represents a hydrogen atom, etc.;
$R^3$ represents a C1-C6 alkyl group, etc.; $R^4$, $R^5$, and $R^6$ each independently represents a hydrogen atom, etc.; A represents a C6-C16 aryl group optionally having one or more atoms or groups selected from Group P, etc.; Q represents the following group Q1, etc.; and

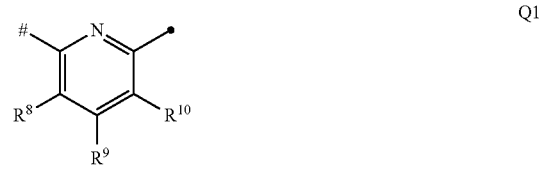

X represents an oxygen atom or a sulfur atom, has excellent control activity against pests.

31 Claims, No Drawings

(56) References Cited

U.S. PATENT DOCUMENTS

| | | |
|---|---|---|
| 2015/0051171 A1 | 2/2015 | Yoshimoto et al. |
| 2015/0203511 A1 | 7/2015 | Arimori et al. |
| 2015/0223460 A1 | 8/2015 | Arimori et al. |
| 2015/0299146 A1 | 10/2015 | Hasegawa et al. |
| 2015/0336908 A1 | 11/2015 | Shioda et al. |
| 2016/0150787 A1* | 6/2016 | Azuma ............... C07D 403/12 514/252.05 |

FOREIGN PATENT DOCUMENTS

| | | |
|---|---|---|
| JP | 2002-506060 A | 2/2002 |
| WO | WO 96/36229 A1 | 11/1996 |
| WO | WO 98/23156 A1 | 6/1998 |
| WO | WO 2013/092224 A1 | 6/2013 |
| WO | WO 2014/051161 A1 | 4/2014 |
| WO | WO 2014/051165 A1 | 4/2014 |
| WO | WO 2014/104268 A1 | 7/2014 |
| WO | WO 2014/104382 A1 | 7/2014 |
| WO | WO 2014/192953 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 * | 2/2015 ........... C07D 257/04 |
| WO | WO 2015/016373 A1 | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/056806 A1 | 4/2015 |
| WO | WO 2015/056811 A1 | 4/2015 |
| WO | WO 2015/060461 A1 | 4/2015 |
| WO | WO 2015/064727 A1 | 5/2015 |

OTHER PUBLICATIONS

International Search Report, issued in PCT/JP2014/062036, dated Jul. 29, 2014.

Extended European Search Report, dated Aug. 9, 2016, for European Application No. 14788852.3.

International Preliminary Report on Patentability and Written Opinion of the International Searching Authority (Forms PCT/IB/373 and PCT/ISA/237), dated Oct. 27, 2015, for International Application No. PCT/JP2014/062036.

Chinese Office Action, dated May 24, 2017, for Chinese Application No. 201480035650.8, with an English translation.

* cited by examiner

TETRAZOLINONE COMPOUND AND USE OF SAME

TECHNICAL FIELD

The present invention relates to tetrazolinone compounds and applications thereof.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

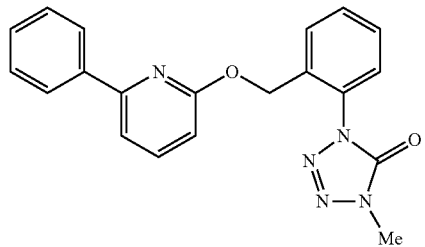

and formula (B):

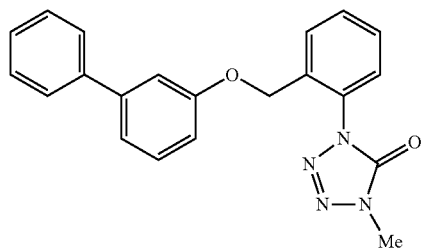

(see WO 96/36229 A).

The present invention provides compounds having excellent control activity against pests.

Disclosure of the Invention

The present inventors have intensively studied so as to find compounds having excellent control activity against pests, and found that a tetrazolinone compound represented by formula (1) has excellent control activity against pests, thus completing the present invention.

The present invention includes the followings [1] to [5].

[1] A tetrazolinone compound represented by formula (1):

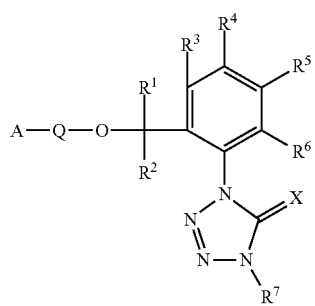

wherein $R^1$ and $R^2$ each independently represents a hydrogen atom, a halogen atom, or a C1-C3 alkyl group;

$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxyl group, a thiol group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;

$R^4$, $R^5$, and $R^6$ each independently represents a hydrogen atom, a halogen atom, a C1-C4 alkyl group, a C1-C4 haloalkyl group, a C3-C5 cycloalkyl group, a C3-C5 halocycloalkyl group, a C1-C4 alkoxy group, or a C1-C4 haloalkoxy group;

$R^7$ represents a C1-C6 alkyl group, a hydrogen atom, a C1-C6 haloalkyl group, a C2-C6 alkenyl group, a C2-C6 haloalkenyl group, a C2-C6 alkoxyalkyl group, a C3-C6 cycloalkyl group, or a C3-C6 halocycloalkyl group;

A represents a C6-C16 aryl group optionally having one or more atoms or groups selected from Group P, a C3-C12 cycloalkyl group optionally having one or more atoms or groups selected from Group P, a C2-C9 heterocyclyl group optionally having one or more atoms or groups selected from Group P (provided that the C2-C9 heterocyclyl group has, as a ring-constituent atom, one or more atoms selected from the group consisting of a nitrogen atom, an oxygen atom, and a sulfur atom and, when the C2-C9 heterocyclyl group has two or more atoms selected from the group consisting of a nitrogen atom, an oxygen atom, and a sulfur atom, each atom may be the same as or different from at least one other group, and also the carbon or nitrogen atom constituting the ring of the C2-C9 heterocyclyl group is bound to Q), or a C3-C12 cycloalkenyl group optionally having one or more atoms or groups selected from Group P (provided that the C6-C16 aryl group, the C3-C12 cycloalkyl group, the C2-C9 heterocyclyl group, and the C3-C12 cycloalkenyl group optionally have one or more atoms or groups selected from Group P and, when these groups have two or more atoms or groups selected from Group P, each atom or group may be the same as or different from at least one other atom or group);

Q represents the following group Q1, Q2, Q3, Q4, Q5, Q6, Q7, Q8, Q9, Q10, Q11, or Q12 {the symbol # represents a binding site for A, and the symbol • represents a binding site for an oxygen atom};

Q:

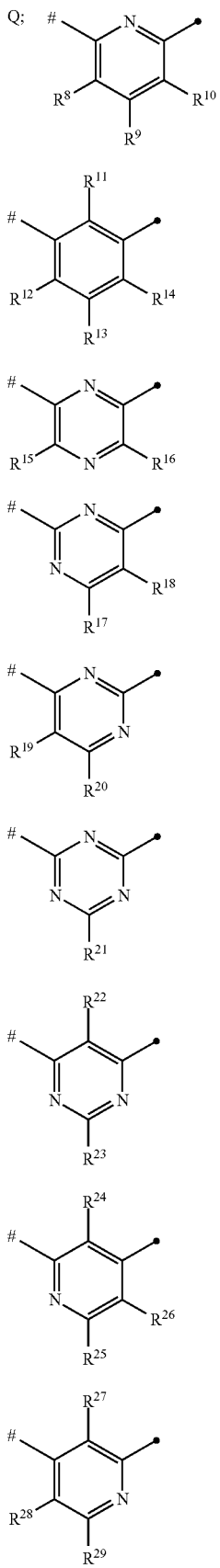

-continued

Q10

Q11

Q12

R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³, R²⁴, R²⁵, R²⁶, R²⁷, R²⁸, R²⁹, R³⁰, R³¹, R³², R³³, R³⁴, R³⁵, and R³⁶ each independently representing a hydrogen atom, a halogen atom, a C1-C6 alkyl group optionally having one or more atoms or groups selected from Group P¹, a C3-C6 cycloalkyl group optionally having one or more atoms or groups selected from Group P¹, a C1-C6 alkoxy group, a C1-C6 haloalkoxy group, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, an amino group optionally having a C1-C6 alkyl group, an amino group optionally having a C1-C6 haloalkyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C9 trialkylsilyl group, a C2-C6 alkylcarbonyl group, a C2-C6 alkoxycarbonyl group, or an aminocarbonyl group optionally having a C1-C6 alkyl group; and X represents an oxygen atom or a sulfur atom:

Group P: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an amino group optionally having a C1-C6 alkyl group, an aminosulfonyl group optionally having a C1-C6 alkyl group and/or a C6-C12 aryl group, and an aminocarbonyl group optionally having a C1-C6 alkyl group; and Group $P^1$: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group.

[2] The tetrazolinone compound according to [1], wherein Q is Q1.

[3] The tetrazolinone compound according to [1], wherein Q is Q2.

[4] The tetrazolinone compound according to [1], wherein Q is Q3.

[5] The tetrazolinone compound according to [1], wherein Q is Q4.

[6] The tetrazolinone compound according to [1], wherein Q is Q5.

[7] The tetrazolinone compound according to [1], wherein Q is Q6.

[8] The tetrazolinone compound according to [1], wherein Q is Q7.

[9] The tetrazolinone compound according to [1], wherein Q is Q8.

[10] The tetrazolinone compound according to [1], wherein Q is Q9.

[11] The tetrazolinone compound according to [1], wherein Q is Q10.

[12] The tetrazolinone compound according to [1], wherein Q is Q11.

[13] The tetrazolinone compound according to [1], wherein Q is Q12.

[14] The tetrazolinone compound according to any one of [1] to [13], wherein $R^4$, $R^2$, $R^4$, $R^5$, and $R^6$ are hydrogen atoms;
$R^7$ is a methyl group; and
X is an oxygen atom.

[15] The tetrazolinone compound according to any one of [1] to [14], wherein A is a C6-C16 aryl group optionally having one or more atoms or groups selected from Group P (provided that when the C6-C16 aryl group has two or more atoms or groups selected from Group P, each atom or group may be the same as or different from at least one other atom or group).

[16] The tetrazolinone compound according to any one of [1] to [15], wherein A is formula (2):

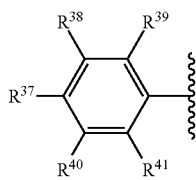

(2)

wherein
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an aminosulfonyl group optionally having a C1-C6 alkyl group and/or a C6-C12 aryl group, or an aminocarbonyl group optionally having a C1-C6 alkyl group.

[17] The tetrazolinone compound according to any one of [1], [2], [14], [15], or [16], wherein Q is Q1;
$R^3$ is a C1-C3 alkyl group, a C3-C4 cycloalkyl group, a halogen atom, a C1-C3 haloalkyl group, a C2-C3 alkenyl group, a C1-C3 alkoxy group, a C1-C2 alkylthio group, a C2-C3 alkynyl group, a C1-C3 haloalkoxy group, or a C1-C2 haloalkylthio group;
$R^8$, $R^9$, and $R^{10}$ each independently represents a hydrogen atom, a halogen atom, a C1-C6 alkyl group optionally having a group selected from Group $P^1$, a C3-C6 cycloalkyl group optionally having a group selected from Group $P^1$, a C1-C6 alkoxy group, or a C1-C6 haloalkoxy group;
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C1-C6 alkoxy group, a C1-C6 haloalkoxy group, a C1-C6 alkylthio group, a C3-C6 cycloalkyloxy group, a C2-C6 alkylcarbonyloxy group, a formyl group, a C2-C6 alkoxycarbonyl group, a C2-C6 alkylcarbonyl group, a nitro group, a cyano group, a hydroxyl group, a C6-C16 aryloxy group, a C1-C6 alkylsulfonyl group, a C1-C6 alkylsulfinyl group, an aminosulfonyl group optionally having a C1-C6 alkyl group and/or a C6-C12 aryl group, or an aminocarbonyl group optionally having a C1-C6 alkyl group.

[18] The tetrazolinone compound according to any one of [1], [2], and [14] to [17], wherein $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; and
$R^{37}$, $R^{38}$, $R^{39}$, $R^{40}$, and $R^{41}$ each independently represents a halogen atom, a hydrogen atom, a C1-C3 alkyl group, a C1-C3 haloalkyl group, a C1-C3 alkoxy group, or a C1-C3 haloalkoxy group.

[19] The tetrazolinone compound according to any one of [1], [2], and [14] to [18], wherein $R^3$ is a methyl group, a cyclopropyl group, a chlorine atom, a bromine atom, an ethyl group, or a methoxy group;

$R^{37}$ is a methoxy group, a trifluoromethoxy group, a fluorine atom, a chlorine atom, or a bromine atom; and
$R^{38}$, $R^{39}$, $R^{40}$, and $R^{41}$ each independently represents a hydrogen atom or a fluorine atom.

[20] The tetrazolinone compound according to any one of [1], [3], [14], [15], and [16], wherein Q is Q2;
$R^3$ is a C1-C3 alkyl group, a C3-C4 cycloalkyl group, a halogen atom, a C1-C3 haloalkyl group, a C2-C3 alkenyl group, a C1-C3 alkoxy group, a C1-C2 alkylthio group, a C2-C3 alkynyl group, a C1-C3 haloalkoxy group, or a C1-C2 haloalkylthio group;
$R^{11}$, $R^{12}$, $R^{13}$ and $R^{14}$ each independently represents a hydrogen atom, a halogen atom, a C1-C6 alkyl group optionally having a group selected from Group $P^1$, a C3-C6 cycloalkyl group optionally having a group selected from Group $P^1$, a C1-C6 alkoxy group, or a C1-C6 haloalkoxy group;
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C1-C6 alkoxy group, a C1-C6 haloalkoxy group, a C1-C6 alkylthio group, a C3-C6 cycloalkyloxy group, a C2-C6 alkylcarbonyloxy group, a formyl group, a C2-C6 alkoxycarbonyl group, a C2-C6 alkylcarbonyl group, a nitro group, a cyano group, a hydroxyl group, a C6-C16 aryloxy group, a C1-C6 alkylsulfonyl group, a C1-C6 alkylsulfinyl group, an aminosulfonyl group optionally having a C1-C6 alkyl group and/or a C6-C12 aryl group, or an aminocarbonyl group optionally having a C1-C6 alkyl group.

[21] The tetrazolinone compound according to any one of claims [1], [3], [14] to [16], and [20], wherein $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; and
$R^{37}$, $R^{38}$, $R^{39}$, $R^{40}$, and $R^{41}$ each independently represents a halogen atom, a hydrogen atom, a C1-C3 alkyl group, a C1-C3 haloalkyl group, a C1-C3 alkoxy group, or a C1-C3 haloalkoxy group.

[22] The tetrazolinone compound according to any one of [1], [3], [14] to [16], [20], and [21], wherein $R^3$ is a methyl group, a cyclopropyl group, a chlorine atom, a bromine atom, an ethyl group, or a methoxy group;
$R^{37}$ is a methoxy group, a trifluoromethoxy group, a fluorine atom, a chlorine atom, or a bromine atom; and
$R^{38}$, $R^{39}$, $R^{40}$, and $R^{41}$ each independently represents a hydrogen atom or a fluorine atom.

[23] The tetrazolinone compound according to any one of [1] to [14], wherein A is a C3-C12 cycloalkyl group optionally having one or more atoms or groups selected from Group P, a C2-C9 heterocyclyl group optionally having one or more atoms or groups selected from Group P provided that the C2-C9 heterocyclyl group has, as a ring-constituent atom, one or more atoms selected from the group consisting of a nitrogen atom, an oxygen atom, and a sulfur atom, and when the C2-C9 heterocyclyl group has two or more atoms selected from the group consisting of a nitrogen atom, an oxygen atom, and a sulfur atom, each atom may be the same as or different from at least one other atom, and the carbon or nitrogen atom constituting the ring of the C2-C9 heterocyclyl group is bound to Q, or a C3-C12 cycloalkenyl group optionally having one or more atoms or groups selected from Group P,
provided that, when the C3-C12 cycloalkyl group, the C2-C9 heterocyclyl group, and the C3-C12 cycloalkenyl group have two or more atoms or groups selected from Group P, each atom or group may be the same as or different from at least one other atom or group.

[24] The tetrazolinone compound according to any one of [1] to [14], wherein A is a C2-C9 heteroaryl group optionally having one or more atoms or groups selected from Group P.

[25] A pest control agent comprising the tetrazolinone compound according to any one of [1] to [24].

[26] A method for controlling pests, which comprises treating plants or soil with an effective amount of the tetrazolinone compound according to any one of [1] to [24].

[27] Use of the tetrazolinone compound according to any one of [1] to [24] for controlling pests.

[28] A tetrazolinone compound represented by formula (3):

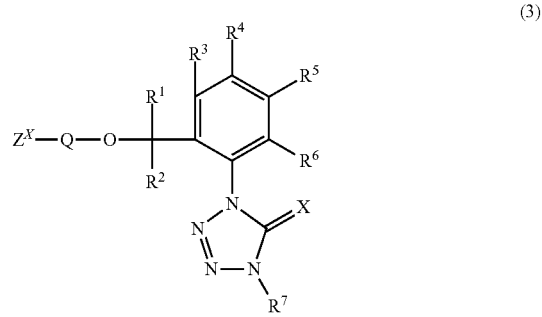

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxyl group, a thiol group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;
$R^4$, $R^5$, and $R^6$ each independently represents a hydrogen atom, a halogen atom, a C1-C4 alkyl group, a C1-C4 haloalkyl group, a C3-C5 cycloalkyl group, a C3-C5 halocycloalkyl group, a C1-C4 alkoxy group, or a C1-C4 haloalkoxy group;
$R^7$ represents a C1-C6 alkyl group, a hydrogen atom, a C1-C6 haloalkyl group, a C2-C6 alkenyl group, a C2-C6 haloalkenyl group, a C2-C6 alkoxyalkyl group, a C3-C6 cycloalkyl group, or a C3-C6 halocycloalkyl group;
$Z^X$ represents a halogen atom;

Q represents the following group Q1, Q2, Q3, Q4, Q5, Q6, Q7, Q8, Q9, Q10, Q11, or Q12; and X represents an oxygen or sulfur atom

[29] The tetrazolinone compound according to [28], wherein
Q is Q1, Q2, or Q4;
$R^3$ is a methyl group, a cyclopropyl group, a chlorine atom, a bromine atom, an ethyl group, or a methoxy group;
$R^1$, $R^2$, $R^4$, $R^5$, and $R^6$ are hydrogen atoms;
$R^7$ is a methyl group; and
X is an oxygen atom.

[30] The tetrazolinone compound according to any one of [1], [2], and [14] to [18], wherein $R^3$ is a methyl group, a cyclopropyl group, a chlorine atom, a bromine atom, an ethyl group, or a methoxy group;
$R^{37}$ is a methoxy group, a trifluoromethoxy group, a fluorine atom, a chlorine atom, or a bromine atom;
$R^{38}$, $R^{39}$, and $R^{40}$ each independently represents a hydrogen atom or a fluorine atom; and
$R^{41}$ is a hydrogen atom, a methoxy group, or an ethoxy group.

[31] The tetrazolinone compound according to any one of [1], [2], [14], and [24], wherein Q is Q1; and
A is formula (4):

$$\begin{array}{c} R^{43} \quad R^{44} \\ R^{42} \diagup\!\!\!\!\diagdown \\ \diagdown\!\!\!\!\diagup \\ N \\ R^{45} \end{array} \quad (4)$$

wherein
$R^{42}$, $R^{43}$, $R^{44}$, and $R^{45}$ each independently represents a halogen atom, a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an aminosulfonyl group optionally having a C1-C6 alkyl group and/or a C6-C12 aryl group, or an aminocarbonyl group optionally having a C1-C6 alkyl group.

[32] The tetrazolinone compound according to any one of [1], [2], [14], [24], and [31], wherein $R^3$ is a methyl group, a cyclopropyl group, a chlorine atom, a bromine atom, an ethyl group, or a methoxy group;
$R^{42}$ is a hydrogen atom, a methoxy group, an ethoxy group, a fluorine atom, a chlorine atom, a bromine atom, a methyl group, an ethyl group, or a trifluoromethyl group;
$R^{43}$ and $R^{44}$ each independently represents a hydrogen atom or a fluorine atom; and
$R^{45}$ is a hydrogen atom, a methoxy group, or an ethoxy group.

[33] The tetrazolinone compound according to any one of [1], [3], [14], and [24], wherein Q is Q2; and
A is formula (4).

[34] The tetrazolinone compound according to any one of [1], [3], [14], [24], and [33], wherein $R^3$ is a methyl group, a cyclopropyl group, a chlorine atom, a bromine atom, an ethyl group, or a methoxy group;
$R^{42}$ is a hydrogen atom, a methoxy group, an ethoxy group, a fluorine atom, a chlorine atom, a bromine atom, a methyl group, an ethyl group, or a trifluoromethyl group;
$R^{43}$ and $R^{44}$ each independently represents a hydrogen atom or a fluorine atom; and
$R^{45}$ is a hydrogen atom, a methoxy group, or an ethoxy group.

According to the present invention, pests can be controlled.

MODE FOR CARRYING OUT THE INVENTION

The compound of the present invention is a tetrazolinone compound represented by formula (1).
A pest control agent containing the present compound is referred to as the present control agent.
The present invention also provides a tetrazolinone compound represented by formula (3) to be used in the production of the present compound (hereinafter referred to as the present tetrazolinone compound X), and the present tetrazolinone compound X has control activity against pests.
Substituents as used herein will be mentioned in detail below.
Examples of the halogen atom include a fluorine atom, a chlorine atom, a bromine atom, and an iodine atom.
The C1-C6 alkyl group represents a straight or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a pentyl group, and a hexyl group.
The C1-C6 haloalkyl group represents a group in which at least one hydrogen atom of a C1-C6 alkyl group is substituted with a halogen atom, and examples thereof include a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group.
The C2-C6 alkenyl group represents a straight or branched alkenyl group having 2 to 6 carbon atoms, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 1-hexenyl group, and a 5-hexenyl group.

The C2-C6 haloalkenyl group represents a group in which at least one hydrogen atom of a straight or branched alkenyl group having 2 to 6 carbon atoms is substituted with a halogen atom, and examples thereof include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, and a 3,3-difluoro-2-propenyl group.

The C2-C6 alkynyl group represents a straight or branched alkynyl group having 2 to 6 carbon atoms, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, and a 5-hexynyl group.

The C2-C6 haloalkynyl group represents a group in which at least one hydrogen atom of a straight or branched alkynyl group having 2 to 6 carbon atoms is substituted with a halogen atom, and examples thereof include a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

Examples of the C3-C6 cycloalkyl group include a cyclopropyl group, a cyclobutyl group, a cyclopentyl group, and a cyclohexyl group.

The C3-C6 halocycloalkyl group represents a group in which at least one hydrogen atom of a C3-C6 cycloalkyl group is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclohexyl group, a 4,4-difluorocyclohexyl group, and a 4-chlorocyclohexyl group.

The C1-C6 alkoxy group represents a straight or branched alkoxy group having 1 to 6 carbon atoms, and examples thereof include a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, and a 4-methylpentyloxy group.

The C1-C6 haloalkoxy group represents a group in which at least one hydrogen atom of a C1-C6 alkoxy group is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, and a periodohexyloxy group.

The C1-C6 alkylthio group represents a straight or branched alkylthio group having 1 to 6 carbon atoms, and examples thereof include a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, an isohexylthio group, and a sec-hexylthio group.

The C1-C6 haloalkylthio group represents a group in which at least one hydrogen atom of a C1-C6 alkylthio group is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2-difluoroethylthio group, a heptafluoropropylthio group, a 3,3,3-trifluoropropylthio group, a 3,3,3-trichloropropylthio group, a 2,2-difluoropropylthio group, a 2,3,3-trifluoropropylthio group, and a perfluorohexylthio group.

Examples of the C3-C6 cycloalkyloxy group include a cyclopropyloxy group, a cyclobutyloxy group, a cyclopentyloxy group, and a cyclohexyloxy group.

The C3-C6 halocycloalkyloxy group represents a group in which at least one hydrogen atom of a C3-C6 cycloalkyloxy group is substituted with a halogen atom, and examples thereof include a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

The C3-C6 alkenyloxy group represents a straight or branched alkenyloxy group having 3 to 6 carbon atoms, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The C3-C6 alkynyloxy group represents a straight or branched alkynyloxy group having 3 to 6 carbon atoms, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, and a 5-hexynyloxy group.

The C3-C6 haloalkenyloxy group represents a group in which at least one hydrogen atom of a C3-C6 alkenyloxy group is substituted with a halogen atom, and examples thereof include a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 4,5,5,5-tetrafluoro-4-trifluoromethyl-2-pentenyloxy group, and a 5-bromo-4,5,5-trifluoro-4-trifluoromethyl-2-pentenyloxy group.

The C3-C6 haloalkynyloxy group represents a group in which at least one hydrogen atom of a C3-C6 alkynyloxy group is substituted with a halogen atom, and examples thereof include a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

The C3-C6 alkenylthio group represents a straight or branched alkenylthio group having 3 to 6 carbon atoms, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

The C3-C6 alkynylthio group represents a straight or branched C3-C6 alkynylthio group, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, and a 5-hexynylthio group.

The C3-C6 haloalkenylthio group represents a group in which at least one hydrogen atom of a C3-C6 alkenylthio group is substituted with a halogen atom, and examples thereof include a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 3,3-difluoro-2-methyl-2-propenylthio group, a 4,4-difluoro-3-methyl-3-butenylthio group, a 4,4,4-trifluoro-3-methyl-2-butenylthio group, a 3,5,5-trifluoro-2,4-pentadienylthio group, and a 4,5,5,5-tetrafluoro-4-trifluoromethyl-2-pentenylthio group.

The C3-C6 haloalkynylthio group represents a group in which at least one hydrogen atom of a C3-C6 alkynylthio group is substituted with a halogen atom, and examples thereof include a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkylcarbonyl group represents a straight or branched alkylcarbonyl group in which the number of carbon atoms including carbon atoms of carbonyl is 2 to 6, and examples thereof include an acetyl group, propionyl group, a butanoyl group, a pentanoyl group, and a hexanoyl group.

The C2-C6 haloalkylcarbonyl group represents a group in which at least one hydrogen atom of a C2-C6 alkylcarbonyl group is substituted with a halogen atom, and examples thereof include a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 4,4,4-trifluorobutanoyl group, a 4,4,4-trichlorobutanoyl group, a nonafluoropentanoyl group, and a perfluorohexanoyl group.

The C2-C6 alkylcarbonyloxy group represents a straight or branched alkylcarbonyloxy group in which the number of carbon atoms including carbon atoms of carbonyl is 2 to 6, and examples thereof include an acetoxy group, a propionyloxy group, a butanoyloxy group, a pentanoyloxy group, and a hexanoyloxy group.

The C2-C6 alkylcarbonylthio group represents a straight or branched alkylcarbonylthio group in which the number of carbon atoms including carbon atoms of carbonyl is 2 to 6, and examples thereof include an acetylthio group, a propionylthio group, a butanoylthio group, a pentanoylthio group, and a hexanoylthio group.

The C2-C6 alkoxycarbonyl group represents a straight or branched alkoxycarbonyl group in which the number of carbon atoms including carbon atoms of carbonyl is 2 to 6, and examples thereof include a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

The aminocarbonyl group optionally having a C1-C6 alkyl group represents an aminocarbonyl group in which one or two hydrogen atoms on nitrogen, each independently may be substituted with a C1-C6 alkyl group, and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group.

Examples of the C6-C16 aryl group include a phenyl group, a naphthyl group, an acenaphthyl group, a phenanthryl group, an anthryl group, and a pyrenyl group.

The C6-C16 aryl group optionally having one or more atoms or groups selected from Group P represents a C6-C16 aryl group in which hydrogen atoms of a C6-C16 aryl group are optionally substituted with one or more atoms or groups selected from Group P and, when the number of atoms or groups selected from Group P is 2 or more, each atom or group may be the same as or different from at least one other atom or group. Examples of the C6-C16 aryl group optionally having one or more atoms or groups selected from Group P include a phenyl group, a 4-chlorophenyl group, a 4-bromophenyl group, a 4-fluorophenyl group, a 4-methylphenyl group, a 4-trifluoromethylphenyl group, a 4-methoxyphenyl group, a 4-trifluoromethoxyphenyl group, a 4-cyanophenyl group, a 4-nitrophenyl group, a 4-dimethylaminophenyl group, a 4-methylthiophenyl group, a 3-fluorophenyl group, a 3-methoxyphenyl group, a 3,4,5-trifluorophenyl group, a 3-fluoro-4-methoxyphenyl group, and a 2-fluoro-4-methoxyphenyl group.

The C6-C16 haloaryl group represents a group in which at least one hydrogen atom of a C6-C16 aryl group is substituted with a halogen atom, and examples thereof include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, and a 6-fluoro-1-pyrenyl group.

Examples of the C6-C16 aryloxy group include a phenyloxy group, a naphthyloxy group, an acenaphthyloxy group, a phenanthryloxy group, an anthryloxy group, and a pyrenyloxy group.

The C6-C16 haloaryloxy group represents a group in which at least one hydrogen atom of a C6-C16 aryloxy group is substituted with a halogen atom, and examples thereof include a 2-fluorophenyloxy group, a 3-fluorophenyloxy group, a 4-fluorophenyloxy group, a 2-chlorophenyloxy group, a 3-chlorophenyloxy group, a 4-chlorophenyloxy group, a 2-bromophenyloxy group, a 3-bromophenyloxy group, a 4-bromophenyloxy group, a 2-iodophenyloxy group, a 3-iodophenyloxy group, a 4-iodophenyloxy group, a 2,4-difluorophenyloxy group, a 2,5-dichlorophenyloxy group, a 2,4,6-trifluorophenyloxy group, a 2,3,4-trichlorophenyloxy group, a pentafluorophenyloxy group, a pentachlorophenyloxy group, a 2-bromo-4-fluorophenyloxy group, a 2-chloro-3-fluorophenyloxy group, a 2-fluoro-1-naphthyloxy group, and a 6-fluoro-1-pyrenyloxy group.

Examples of the C6-C16 arylthio group include a phenylthio group, a naphthylthio group, an acenaphthylthio group, a phenanthrylthio group, an anthrylthio group, and a pyrenylthio group.

The C6-C16 haloarylthio group represents a group in which at least one hydrogen atom of a C6-C16 arylthio group is substituted with a halogen atom, and examples thereof include a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, a 2,5-dichlorophenylthio group, a 2,3,4-trifluorophenylthio group, a pentachlorophenylthio group, a 2-bromo-3-fluorophenylthio group, a 2-chloro-4-fluorophenylthio group, a 3-chloro-4-fluorophenylthio group, a 3-fluoro-1-naphthylthio group, and a 6-fluoro-1-pyrenylthio group.

Examples of the C7-C18 aralkyl group include a benzyl group, a phenethyl group, a 3-phenylpropyl group, a 4-phenylbutyl group, a 5-phenylpentyl group, a 6-phenylhexyl group, a 7-phenylheptyl group, a 8-phenyloctyl group, a 9-phenylnonyl group, a 10-phenyldecyl group, a 11-phenylundecyl group, a 12-phenyldodecyl group, a 1-naphthylmethyl group, a 2-(1-naphthyl)ethyl group, a 3-(1-naphthyl)propyl group, a 4-(1-naphthyl)butyl group, a 2-naphthylmethyl group, a 2-(2-naphthyl)ethyl group, a 3-(2-naphthyl)propyl group, a 4-(2-naphthyl)butyl group, a 1-anthrylmethyl group, a 2-(1-anthryl)ethyl group, a 3-(1-anthryl)propyl group, and a 4-(9-anthryl)butyl group.

The C7-C18 haloaralkyl group represents a group in which at least one hydrogen atom of the aryl moiety and/or the alkyl moiety of a C7-C18 aralkyl group is substituted with a halogen atom, and examples thereof include a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 2-(4-bromophenyl)ethyl group, a 3-(4-iodophenyl)propyl group, a 4-(4-fluorophenyl)butyl group, 6-fluoro-1-pyrenylmethyl group, and a 1,1-difluoro-1-phenylmethyl group.

Examples of the C7-C18 arylalkoxy group include a benzyloxy group, a phenethyloxy group, a 3-phenylpropyloxy group, a 4-phenylbutyloxy group, a 5-phenylpentyloxy group, a 6-phenylhexyloxy group, a naphthylmethyloxy group, a naphthylethyloxy group, a naphthylpropyloxy group, a naphthylbutyloxy group, an anthrylmethyloxy group, an anthrylethyloxy group, an anthrylpropyloxy group, and an anthrylbutyloxy group.

The C7-C18 haloarylalkoxy group represents a group in which at least one hydrogen atom of the aryl moiety and/or the alkoxy moiety of a C7-C18 arylalkoxy group is substituted with a halogen atom, and examples thereof include a 4-fluorobenzyloxy group, a 2-chlorobenzyloxy group, a 3-bromobenzyloxy group, a 4-iodobenzyloxy group, a 2,4-difluorobenzyloxy group, a 2,5-dichlorobenzyloxy group, a 3,4,5-trifluorobenzyloxy group, a 2,3,4-trichlorobenzyloxy group, a pentafluorobenzyloxy group, a 4-bromo-2-fluorobenzyloxy group, a 2-chloro-3-fluorobenzyloxy group, a 6-chloro-2-fluorobenzyloxy group, a 2-(4-fluorophenyl)ethyloxy group, a 2-(3-chlorophenyl)ethyloxy group, a 2-(2-bromophenyl)ethyloxy group, a 3-(4-iodophenyl)propyloxy group, a 3-(3-fluorophenyl)propyloxy group, a 3-(2-chlorophenyl)propyloxy group, a 4-fluoro-1-naphthylmethyloxy group, a 1-chloro-2-naphthylmethyloxy group, a 2-(5-fluoro-1-naphthyl)ethyloxy group, a 3-(6-chloro-2-naphthyl)propyloxy group, a 4-(5-bromo-1-naphthyl)butyloxy group, a 3-fluoro-1-acenaphthylmethyloxy group, a 9-fluoro-1-phenanthrylmethyloxy group, a 10-fluoro-9-anthrylmethyloxy group, a 6-fluoro-1-pyrenylmethyloxy group, and a 1,1-difluoro-1-phenylmethyloxy group.

The C3-C12 trialkylsilyl group represents a group in which three hydrogen atoms on a silyl group, each independently may be substituted with an alkyl group, and examples thereof include a trimethylsilyl group, a tert-butyldimethylsilyl group, a triethylsilyl group, an isopropyldimethylsilyl group, a triisopropylsilyl group, a tri(tert-butyl)silyl group, and a tributylsilyl group.

The C5-C14 trialkylsilylethynyl group represents an ethynyl group to be bound to a C3-C12 trialkylsilyl group, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tributylsilylethynyl group.

The aminosulfonyl group optionally having a C1-C6 alkyl group and/or a C6-C12 aryl group represents an aminosulfonyl group in which one or two hydrogen atoms on nitrogen, each independently may be substituted with a C1-C6 alkyl group and/or a C6-C12 aryl group, and examples thereof include an aminosulfonyl group, an N-methylaminosulfonyl group, an N-ethylaminosulfonyl group, an N-propylaminosulfonyl group, an N-isopropylaminosulfonyl group, an N-butylaminosulfonyl group, an N,N-dimethylaminosulfonyl group, an N,N-diethylaminosulfonyl group, an N,N-dipropylaminosulfonyl group, an N,N-diisopropylaminosulfonyl group, an N-ethyl-N-methylaminosulfonyl group, an N-propyl-N-methylaminosulfonyl group, an N-phenylaminosulfonyl group, an N,N-diphenylaminosulfonyl group, an N-methyl-N-phenylaminosulfonyl group, an N-ethyl-N-phenylaminosulfonyl group, an N-propyl-N-phenylaminosulfonyl group, an N-(1-naphthyl)aminosulfonyl group, an N-(1-naphthyl)N-methylaminosulfonyl group, an N-(2-naphthyl)aminosulfonyl group, and an N-(2-naphthyl)N-methylaminosulfonyl group.

The C1-C6 alkylsulfonyl group may be either straight or branched, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group, and a 4-methylpentylsulfonyl group.

The C1-C6 haloalkylsulfonyl group represents a group in which at least one hydrogen atom of a straight or branched alkylsulfonyl group having 1 to 6 carbon atoms is substituted with a halogen atom, and examples thereof include a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a heptafluoropropylsulfonyl group, a heptachloropropylsulfonyl group, a 3,3,3-trifluoropropylsulfonyl group, and a 3,3,3-trichloropropylsulfonyl group.

Examples of the C6-C16 arylsulfonyl group include a phenylsulfonyl group, a naphthylsulfonyl group, an acenaphthylsulfonyl group, a phenanthrylsulfonyl group, an anthrylsulfonyl group, and a 1-pyrenylsulfonyl group.

The C6-C16 haloarylsulfonyl group represents a group in which at least one hydrogen atom of a C6-C16 arylsulfonyl group is substituted with a halogen atom, and examples thereof include a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, a 4-iodophenylsulfonyl group, a 2,4-difluorophenylsulfonyl group, a 2,4-dichlorophenylsulfonyl group, a 2,6-dichlorophenylsulfonyl group, a 2,4,6-trifluorophenylsulfonyl group, a 3,4,5-trifluorophenylsulfonyl group, a 2,4,6-trichlorophenylsulfonyl group, a 3,4,5-trichlorophenylsulfonyl group, a pentafluorophenylsulfonyl group, a 3-bromo-4-fluorophenylsulfonyl group, a 4-bromo-3-fluorophenylsulfonyl group, a 4-bromo-2-fluorophenylsulfonyl group, a 2-bromo-6-fluorophenylsulfonyl group, a 2-chloro-4-fluorophenylsulfonyl group, a 2-chloro-6-fluorophenylsulfonyl group, a 2-fluoro-1-naphthylsulfonyl group, and a 6-fluoro-1-pyrenylsulfonyl group.

The C1-C6 alkylsulfinyl group may be either straight or branched, and examples thereof include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group, and a 4-methylpentylsulfinyl group.

The C1-C6 haloalkylsulfinyl group represents a group in which at least one hydrogen atom of a C1-C6 alkylsulfinyl group is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, and a perfluorohexylsulfinyl group.

Examples of the C6-C16 arylsulfinyl group include a phenylsulfinyl group, a naphthylsulfinyl group, an acenaphthylsulfinyl group, a phenanthrylsulfinyl group, an anthrylsulfinyl group, and a 1-pyrenylsulfinyl group.

The C6-C16 haloarylsulfinyl group represents a group in which at least one hydrogen atom of a C6-C16 arylsulfinyl group is substituted with a halogen atom, and examples thereof include a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, a 2-iodophenylsulfinyl group, a 3-iodophenylsulfinyl group, a 4-iodophenylsulfinyl group, a 2,4-difluorophenylsulfinyl group, a 2,5-difluorophenylsulfinyl group, a 2,6-difluorophenylsulfinyl group, a 3,5-difluorophenylsulfinyl group, a 2,4-dichlorophenylsulfinyl group, a 3,4,5-trifluorophenylsulfinyl group, a 2-bromo-5-fluorophenylsulfinyl group, a 2-chloro-4-fluorophenylsulfinyl group, a 4-chloro-2-fluorophenylsulfinyl group, a 2-fluoro-1-naphthylsulfinyl group, and a 6-fluoro-1-pyrenylsulfinyl group.

Examples of the C3-C12 cycloalkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The C3-C12 cycloalkyl group optionally having one or more atoms or groups selected from Group P represents a group in which hydrogen atoms of a C3-C12 cycloalkyl group are optionally substituted with one or more atoms or groups selected from Group P and, when the number of atoms or groups selected from Group P is 2 or more, each atom or group may be the same as or different from at least one other atom or group. Examples of the C3-C12 cycloalkyl group optionally having one or more atoms or groups selected from Group P include a cyclopropyl group, a 1-methylcyclopropyl group, a 4-bromocyclohexyl group, a 4-chlorocyclohexyl group, a 4-fluorocyclohexyl group, a 4,4-difluorocyclohexyl group, a 4-methoxycyclohexyl group, a 4-methylcyclohexyl group, and a 2,6-dichlorocyclohexyl group.

Examples of the C3-C12 cycloalkenyl group include a 1-cyclopropenyl group, a 1-cyclobutenyl group, a 1-cyclopentenyl group, a 1-cyclohexenyl group, a 2-cyclohexenyl group, a 3-cyclohexenyl group, a 1-cycloheptenyl group, a 1-cyclooctenyl group, a 1-cyclononenyl group, a 1-cyclodecenyl group, a 1-cycloundecenyl group, a 1-cyclododecenyl group, a 1-cyclopentadienyl group, a 1,3-cyclohexadienyl group, a 1,4-cyclohexadienyl group, and a 1,5-cyclooctadienyl group.

The C3-C12 cycloalkenyl group optionally having one or more atoms or groups selected from Group P represents a C3-C12 cycloalkenyl group in which hydrogen atoms of a C3-C12 cycloalkenyl group are optionally substituted with one or more atoms or groups selected from Group P and, when the number of atoms or groups selected from Group P is 2 or more, each atom or group may be the same as or different from at least one other atom or group. Examples of the C3-C12 cycloalkenyl group optionally having one or more atoms or groups selected from Group P include a 1-cyclohexenyl group, a 2-cyclohexenyl group, a 3-cyclohexenyl group, a 4-chloro-1-cyclohexenyl group, a 4-fluoro-1-cyclohexenyl group, a 4,4-difluoro-1-cyclohexenyl group, a 4-methoxy-1-cyclohexenyl group, a 4-chloro-2-cyclohexenyl group, a 4-fluoro-2-cyclohexenyl group, a 4-methoxy-2-cyclohexenyl group, and a 4-chloro-3-cyclohexenyl group.

Examples of the C1-C3 alkyl group include a methyl group, an ethyl group, a propyl group, and an isopropyl group.

Examples of the C1-C3 haloalkyl group include a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group, and a 1-(fluoromethyl)-2-fluoroethyl group.

Examples of the C1-C4 alkyl group include a methyl group, an ethyl group, a propyl group, an isopropyl group, a butyl group, an isobutyl group, a sec-butyl group, and a tert-butyl group.

The C1-C4 haloalkyl group represents a group in which at least one hydrogen atom of a C1-C4 alkyl group is substituted with a halogen atom, and examples thereof include a monofluoromethyl group, a monochloromethyl group, a dichloromethyl group, a difluoromethyl group, a trifluoromethyl group, a trichloromethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, and a 4-fluorobutyl group.

Examples of the C3-C5 cycloalkyl group include a cyclopropyl group, a cyclobutyl group, and a cyclopentyl group.

The C3-C5 halocycloalkyl group represents a group in which at least one hydrogen atom of a C3-C5 cycloalkyl group is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclopentyl group, and a 3-chlorocyclopentyl group.

Examples of the C1-C4 alkoxy group include a methoxy group, an ethoxy group, a propyloxy group, an isopropyloxy group, a butyloxy group, an isobutyloxy group, a sec-butyloxy group, and a tert-butyloxy group.

The C1-C4 haloalkoxy group represents a group in which at least one hydrogen atom of a C1-C4 alkoxy group is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a 3,3,3-trifluoropropoxy group, a 3,3,3-trichloropropoxy group, a 3,3,3-tribromopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, and a nonafluorobutoxy group.

The C2-C6 alkoxyalkyl group may be either straight or branched, and represents a group in which the total number of carbon atoms of the alkoxy moiety and the alkyl moiety is 2 to 6, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a pentyloxymethyl group, a 1-methoxyethyl group, a 2-methoxyethyl group, a 2-ethoxyethyl group, a 2-propyloxyethyl group, a 2-isopropyloxyethyl group, a 2-butyloxyethyl group, a 3-methoxypropyl group, a 3-ethoxypropyl group, a 3-propyloxypropyl group, a 3-methoxybutyl group, a 3-ethoxybutyl group, a 4-methoxybutyl group, a 4-ethoxybutyl group, and a 5-methoxypentyl group.

The amino group optionally having a C1-C6 alkyl group represents an amino group in which one or two hydrogen atoms on nitrogen, each independently may be substituted with a C1-C6 alkyl group, and examples thereof include an amino group, an N-methylamino group, an N-ethylamino group, an N-propylamino group, an N-isopropylamino group, an N-butylamino group, an N,N-dimethylamino group, an N,N-diethylamino group, an N,N-dipropylamino group, an N-ethyl-N-methylamino group, and an N-propyl-N-methylamino group.

Examples of the C3-C9 trialkylsilyl group include a trimethylsilyl group, a tert-butyldimethylsilyl group, a triethylsilyl group, an isopropyldimethylsilyl group, and a triisopropylsilyl group.

The C1-C4 alkylsulfonyl group may be either straight or branched, and examples thereof include a methylsulfonyl group, an ethylsulfonyl group, a propylsulfonyl group, an isopropylsulfonyl group, a butylsulfonyl group, an isobutylsulfonyl group, and a sec-butylsulfonyl group.

The C1-C4 haloalkylsulfonyl group represents a group in which at least one hydrogen atom of a C1-C4 alkylsulfonyl group is substituted with a halogen atom, and examples thereof include a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a heptafluoropropylsulfonyl group, a heptachloropropylsulfonyl group, a 3,3,3-trifluoropropylsulfonyl group, a 3,3,3-trichloropropylsulfonyl group, and a nonafluorobutylsulfonyl group.

The C1-C4 alkylsulfinyl group may be either straight or branched, and examples thereof include a methylsulfinyl group, an ethylsulfinyl group, a propylsulfinyl group, an isopropylsulfinyl group, a butylsulfinyl group, an isobutylsulfinyl group, and a sec-butylsulfinyl group.

The C1-C4 haloalkylsulfinyl group represents a group in which at least one hydrogen atom of a C1-C4 alkylsulfinyl group is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a heptafluoropropylsulfinyl group, a heptachloropropylsulfinyl group, a 3,3,3-trifluoropropylsulfinyl group, a 3,3,3-trichloropropylsulfinyl group, a nonafluorobutylsulfinyl group, and a nonachlorobutylsulfinyl group.

The C2-C5 alkoxyalkyl group may be either straight or branched, and represents a group in which the total number of carbon atoms of the alkoxy moiety and the alkyl moiety is 2 to 5, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, a 2-propyloxyethyl group, a 2-isopropyloxyethyl group, a 3-methoxypropyl group, a 3-ethoxypropyl group, a 3-methoxybutyl group, and a 4-methoxybutyl group.

The C2-C5 alkylthioalkyl group may be either straight or branched, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

Examples of the C2-C3 alkenyl group include a vinyl group, a 1-propenyl group, and a 2-propenyl group.

Examples of the C2-C3 alkynyl group include an ethynyl group, a 1-propynyl group, and a 2-propynyl group.

Examples of the C3-C4 cycloalkyl group include a cyclopropyl group and a cyclobutyl group.

Examples of the C1-C3 alkoxy group include a methoxy group, an ethoxy group, a propyloxy group, and an isopropyloxy group.

The C1-C3 haloalkoxy group represents a group in which at least one hydrogen atom of a C1-C3 alkoxy group is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a 3,3,3-trifluoropropoxy group, a 3,3,3-trichloropropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

Examples of the C1-C2 alkylthio group include a methylthio group and an ethylthio group.

The C1-C2 haloalkylthio group represents a group in which at least one hydrogen atom of a C1-C2 alkylthio group is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, and a 2,2-difluoroethylthio group.

The amino group optionally having a C1-C6 haloalkyl group represents an amino group in which one or two hydrogen atoms on nitrogen, each independently may be substituted with a C1-C6 haloalkyl group, and examples thereof include an amino group, a 2,2,2-trifluoroethylamino group, an N,N-(2,2-ditrifluoroethyl)-amino group, an N,N-(2,2-ditrichloroethyl)-amino group, and a pentafluoropropylamino group.

Examples of the C1-C4 alkylthio group include a methylthio group, an ethylthio group, a propylthio group, an isopropylthio group, a butylthio group, an isobutylthio group, and a tert-butylthio group.

The C1-C4 haloalkylthio group represents a group in which at least one hydrogen atom of a C1-C4 alkylthio group is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a 2,2,2-trichloroethylthio group, a 2,2,2-trifluoroethylthio group, a 2,2,2-trifluoroethylthio group, and a 2,2-difluoroethylthio group.

The C2-C9 heterocyclyl group represents a 5-, 6-, or 7-membered saturated heterocyclic group, or a 5-, 6-, or 7-membered heteroaryl group, and the saturated heterocyclic group or the heteroaryl group has, as a ring-constituent atom, one or more atoms selected from a nitrogen atom, an oxygen atom, or a sulfur atom and, when the saturated heterocyclic group or the heteroaryl group has two or more atoms selected from a nitrogen atom, an oxygen atom, or a sulfur atom, each atom may be the same as or different from at least one other atom.

Examples of the 5-, 6-, or 7-membered non-aromatic saturated cyclic group include a pyrrolidin-1-yl group, a piperidin-1-yl group, a piperazin-1-yl group, a 4-methylpiperazin-1-yl group, a morpholin-4-yl group, a thiomorpholin-4-yl group, or a 1-azepanyl group.

Examples of the 5-, 6-, or 7-membered C2-C9 heteroaryl group include a 1-pyrrolyl group, a 1-pyrazolyl group, a 1-imidazolyl group, a 1,2,4-triazol-1-yl group, a 2-furyl group, a 3-furyl group, a 2-thienyl group, a 3-thienyl group, a 2-pyrrolyl group, a 3-pyrrolyl group, a 3-isooxazolyl group, a 4-isooxazolyl group, a 5-isooxazolyl group, a 3-isothiazolyl group, a 4-isothiazolyl group, a 5-isothiazolyl group, a 3-pyrazolyl group, a 4-pyrazolyl group, a 5-pyrazolyl group, a 2-oxazolyl group, a 4-oxazolyl group, a 5-oxazolyl group, a 2-thiazolyl group, a 4-thiazolyl group, a 5-thiazolyl group, a 2-imidazolyl group, a 4-imidazolyl group, a 2-pyridinyl group, a 3-pyridinyl group, a 4-pyridinyl group, a 3-pyridazinyl group, a 4-pyridazinyl group, a 2-pyrimidinyl group, a 4-pyrimidinyl group, a 5-pyrimidinyl group, a 2-pyrazinyl group, a 1,3,5-triazin-2-yl group, a 1,2,4-triazin-3-yl group, a 6-quinolinyl group, a 7-quinolinyl group, a 3-quinolinyl group, a 6-isoquinolinyl group, a 6-quinazolinyl group, a 6-quinoxalinyl group, a 2-purinyl group, a 5-benzofuranyl group, a benzo[1,3]dioxol-5-yl group, and a benzoxazol-5-yl group.

The C2-C9 heterocyclyl group optionally having one or more atoms or groups selected from Group P (provided that the C2-C9 heterocyclyl group has, as a ring-constituent atom, one or more atoms selected from the group consisting of a nitrogen atom, an oxygen atom, and a sulfur atom and, when the C2-C9 heterocyclyl group has two or more atoms selected from the group consisting of a nitrogen atom, an oxygen atom, and a sulfur atom, each atom may be the same as or different from at least one other group. Furthermore, the carbon or nitrogen atom constituting the ring of the C2-C9 heterocyclyl group is bound to Q) represents a group in which hydrogen atoms of a C2-C9 heterocyclyl group are optionally substituted with one or more atoms or groups selected from Group P, and represents a C2-C9 heteroaryl group optionally having one or more atoms or groups selected from Group P, and a non-aromatic saturated cyclic group optionally having one or more atoms or groups selected from Group P. When the number of atoms or groups selected from Group P is 2 or more, each atom or group may be the same as or different from at least one other atom or group. Examples of the C2-C9 heterocyclyl group optionally having one or more atoms or groups selected from Group P (provided that the C2-C9 heterocyclyl group has, as a ring-constituent atom, one or more atoms selected from the group consisting of a nitrogen atom, an oxygen atom, and a sulfur atom and, when two or more atoms selected from the group consisting of a nitrogen atom, an oxygen atom, and a sulfur atom, each atom may be the same as or different from at least one other group. Furthermore, the carbon or nitrogen atom constituting the ring of the C2-C9 heterocyclyl group is bound to Q) include a 4-methylpiperazin-1-yl group, a morpholin-4-yl group, a piperidin-1-yl group, a 4-methylpiperidin-1-yl group, a 1-pyrazolyl group, a 3,4-dimethylpyrazol-1-yl group, a 4-methoxy-3,5-dimethylpyrazol-1-yl group, a 2-pyridinyl group, a 5-methoxy-2-pyridinyl group, a 5-chloro-2-pyridinyl group, a 3-pyridinyl group, a 6-methoxy-3-pyridinyl group, a 6-chloro-3-pyridinyl group, a 4-pyridinyl group, a 2-pyrazinyl group, a 5-methoxy-2-pyrazinyl group, a 5-chloro-2-pyrazinyl group, a 3-pyridazinyl group, a 6-methoxy-3-pyridazinyl group, a 6-chloro-3-pyridazinyl group, a 2-pyrimidinyl group, a 5-methoxy-2-pyrimidinyl group, a 5-pyrimidinyl group, a 2-chloro-5-pyrimidinyl group, a 5-benzofuranyl group, a 2-methylbenzofuran-5-yl group, a benzo[1,3]dioxol-5-yl group, a 2,2-dimethylbenzo[1,3]dioxol-5-yl group, a 2,2-difluorobenzo[1,3]dioxol-5-yl group, a benzoxazol-5-yl group, and a 2-methylbenzoxazol-5-yl group.

Examples of the aspect of the present compound include compounds in which the substituent in formula (1) is shown below:
a compound in which A is an aryl group;
a compound in which A is a pyridyl group;
a compound in which A is a haloaryl group;
a compound in which A is an aryl group having a C1-C3 alkyl group;
a compound in which A is an aryl group having a C1-C3 haloalkyl group;
a compound in which A is an aryl group having a C1-C3 alkoxy group;
a compound in which A is an aryl group having a C1-C3 haloalkoxy group;
a compound in which A is a pyridyl group having a C1-C3 alkoxy group;
a compound in which A is a 4-chlorophenyl group;
a compound in which A is a 4-fluorophenyl group;
a compound in which A is a 4-bromophenyl group;
a compound in which A is a 4-methoxyphenyl group;
a compound in which A is a 4-ethoxyphenyl group;
a compound in which A is a 4-isopropyloxyphenyl group;
a compound in which A is a 4-trifluoromethoxyphenyl group;
a compound in which $R^1$ is a hydrogen atom;
a compound in which $R^2$ is a hydrogen atom;
a compound in which $R^4$ is a hydrogen atom;
a compound in which $R^5$ is a hydrogen atom;
a compound in which $R^6$ is a hydrogen atom;
a compound in which $R^3$ is a C1-C3 alkyl group;
a compound in which $R^3$ is a C3-C4 cycloalkyl group;
a compound in which $R^3$ is a halogen atom;
a compound in which $R^3$ is a C1-C3 haloalkyl group;
a compound in which $R^3$ is a C2-C3 alkenyl group;
a compound in which $R^3$ is a C1-C3 alkoxy group;
a compound in which $R^3$ is a C2-C3 alkynyl group;
a compound in which $R^3$ is a C1-C3 haloalkoxy group;
a compound in which $R^3$ is a C1-C3 alkyl group, a halogen atom, a C1-C3 haloalkyl group, a C2-C3 alkenyl group, a C1-C3 alkoxy group, a C2-C3 alkynyl group, or a C1-C3 haloalkoxy group;
a compound in which $R^3$ is a methyl group;
a compound in which $R^3$ is an ethyl group;
a compound in which $R^3$ is a propyl group;
a compound in which $R^3$ is a cyclopropyl group;
a compound in which $R^3$ is a trifluoromethyl group;
a compound in which $R^3$ is a difluoromethyl group;
a compound in which $R^3$ is a vinyl group;
a compound in which $R^3$ is a 2-propenyl group;
a compound in which $R^3$ is a chlorine atom;
a compound in which $R^3$ is a bromine atom;
a compound in which $R^3$ is an iodine atom;
a compound in which $R^3$ is a fluorine atom;
a compound in which $R^3$ is a methoxy group;
a compound in which $R^3$ is an ethoxy group;
a compound in which $R^7$ is a methyl group;
a compound in which X is an oxygen atom; and
a compound in which X is a sulfur atom.

A tetrazolinone compound in which A is a formula (2).
[Aspect 1]
A tetrazolinone compound in which A is a formula (2), $R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C1-C6 alkoxy group, a C1-C6 haloalkoxy group, a C1-C6 alkylthio group, a C3-C6 cycloalkyloxy group, a C2-C6 alkylcarbonyloxy group, a formyl group, a C2-C6 alkoxycarbonyl group, a C2-C6 alkylcarbonyl group, a nitro group, a cyano group, a hydroxyl group, a C6-C16 aryloxy group, a C1-C6 alkylsulfonyl group, a C1-C6 alkylsulfinyl group, an aminosulfonyl group optionally having a C1-C6 alkyl group and/or a C6-C12 aryl group, or an amino group optionally having a C1-C6 alkyl group; $R^1$, $R^2$, $R^4$, $R^5$, and $R^6$ are hydrogen atoms; $R^7$ is a methyl group; and X is an oxygen atom.

A tetrazolinone compound in which $R^3$ is a C1-C3 alkyl group in [Aspect 1].

A tetrazolinone compound in which $R^3$ is a C3-C4 cycloalkyl group in [Aspect 1].

A tetrazolinone compound in which $R^3$ is a halogen atom in [Aspect 1].

A tetrazolinone compound in which $R^3$ is a C1-C3 haloalkyl group in [Aspect 1].

A tetrazolinone compound in which $R^3$ is a C2-C3 alkenyl group in [Aspect 1].

A tetrazolinone compound in which $R^3$ is a C1-C3 alkoxy group in [Aspect 1].

A tetrazolinone compound in which $R^3$ is a C2-C3 alkynyl group in [Aspect 1].

A tetrazolinone compound in which $R^3$ is a C1-C3 haloalkoxy group in [Aspect 1].

A tetrazolinone compound in which $R^3$ is a fluorine atom, a chlorine atom, a bromine atom, an iodine atom, or a methyl group in [Aspect 1].

A tetrazolinone compound in which $R^3$ is a C1-C3 alkyl group, a C1-C3 haloalkyl group, a C3-C4 cycloalkyl group, a C2-C3 alkenyl group, or a C2-C3 alkynyl group in [Aspect 1].

A tetrazolinone compound in which $R^3$ is a C1-C3 alkoxy group or a C1-C3 haloalkoxy group in [Aspect 1].

A tetrazolinone compound in which $R^3$ is a methyl group in [Aspect 1].

A tetrazolinone compound in which $R^3$ is an ethyl group in [Aspect 1].

A tetrazolinone compound in which $R^3$ is a cyclopropyl group in [Aspect 1].

A tetrazolinone compound in which $R^3$ is a chlorine atom in [Aspect 1].

A tetrazolinone compound in which $R^3$ is a bromine atom in [Aspect 1].

A tetrazolinone compound in which $R^3$ is a methoxy group in [Aspect 1].

A tetrazolinone compound in which $R^3$ is a C1-C3 alkyl group and Q is Q1 in [Aspect 1].

A tetrazolinone compound in which $R^3$ is a C3-C4 cycloalkyl group and Q is Q1 in [Aspect 1].

A tetrazolinone compound in which $R^3$ is a halogen atom and Q is Q1 in [Aspect 1].

A tetrazolinone compound in which $R^3$ is a C1-C3 haloalkyl group and Q is Q1 in [Aspect 1].

A tetrazolinone compound in which $R^3$ is a C2-C3 alkenyl group and Q is Q1 in [Aspect 1].

A tetrazolinone compound in which $R^3$ is a C1-C3 alkoxy group and Q is Q1 in [Aspect 1].

A tetrazolinone compound in which $R^3$ is a C2-C3 alkynyl group and Q is Q1 in [Aspect 1].

A tetrazolinone compound in which $R^3$ is a C1-C3 haloalkoxy group and Q is Q1 in [Aspect 1].

A tetrazolinone compound in which $R^3$ is a methyl group and Q is Q1 in [Aspect 1].

A tetrazolinone compound in which $R^3$ is an ethyl group and Q is Q1 in [Aspect 1].

A tetrazolinone compound in which $R^3$ is a cyclopropyl group, and Q is Q1 in [Aspect 1].

A tetrazolinone compound in which $R^3$ is a chlorine atom and Q is Q1 in [Aspect 1].

A tetrazolinone compound in which $R^3$ is a bromine atom and Q is Q1 in [Aspect 1].

A tetrazolinone compound in which $R^3$ is a methoxy group and Q is Q1 in [Aspect 1].

A tetrazolinone compound in which $R^3$ is a C1-C3 alkyl group and Q is Q2 in [Aspect 1].

A tetrazolinone compound in which $R^3$ is a C3-C4 cycloalkyl group and Q is Q2 in [Aspect 1].

A tetrazolinone compound in which $R^3$ is a halogen atom and Q is Q2 in [Aspect 1].

A tetrazolinone compound in which $R^3$ is a C1-C3 haloalkyl group and Q is Q2 in [Aspect 1].

A tetrazolinone compound in which $R^3$ is a C2-C3 alkenyl group and Q is Q2 in [Aspect 1].

A tetrazolinone compound in which $R^3$ is a C1-C3 alkoxy group and Q is Q2 in [Aspect 1].

A tetrazolinone compound in which $R^3$ is a C2-C3 alkynyl group and Q is Q2 in [Aspect 1].

A tetrazolinone compound in which $R^3$ is a C1-C3 haloalkoxy group and Q is Q2 in [Aspect 1].

A tetrazolinone compound in which $R^3$ is a methyl group and Q is Q2 in [Aspect 1].

A tetrazolinone compound in which $R^3$ is an ethyl group and Q is Q2 in [Aspect 1].

A tetrazolinone compound in which $R^3$ is a cyclopropyl group and Q is Q2 in [Aspect 1].

A tetrazolinone compound in which $R^3$ is a chlorine atom and Q is Q2 in [Aspect 1].

A tetrazolinone compound in which $R^3$ is a bromine atom and Q is Q2 in [Aspect 1].

A tetrazolinone compound in which $R^3$ is a methoxy group and Q is Q2 in [Aspect 1].

A tetrazolinone compound in which $R^3$ is a C1-C3 alkyl group and Q is Q3 in [Aspect 1].

A tetrazolinone compound in which $R^3$ is a C3-C4 cycloalkyl group and Q is Q3 in [Aspect 1].

A tetrazolinone compound in which $R^3$ is a halogen atom and Q is Q3 in [Aspect 1].

A tetrazolinone compound in which $R^3$ is a C1-C3 haloalkyl group and Q is Q3 in [Aspect 1].

A tetrazolinone compound in which $R^3$ is a C2-C3 alkenyl group and Q is Q3 in [Aspect 1].

A tetrazolinone compound in which $R^3$ is a C1-C3 alkoxy group and Q is Q3 in [Aspect 1].

A tetrazolinone compound in which $R^3$ is a C2-C3 alkynyl group and Q is Q3 in [Aspect 1].

A tetrazolinone compound in which $R^3$ is a C1-C3 haloalkoxy group and Q is Q3 in [Aspect 1].

A tetrazolinone compound in which $R^3$ is a methyl group and Q is Q3 in [Aspect 1].

A tetrazolinone compound in which $R^3$ is an ethyl group and Q is Q3 in [Aspect 1].

A tetrazolinone compound in which $R^3$ is a cyclopropyl group and Q is Q3 in [Aspect 1].

A tetrazolinone compound in which $R^3$ is a chlorine atom and Q is Q3 in [Aspect 1].

A tetrazolinone compound in which $R^3$ is a bromine atom and Q is Q3 in [Aspect 1].

A tetrazolinone compound in which $R^3$ is a methoxy group and Q is Q3 in [Aspect 1].

A tetrazolinone compound in which $R^3$ is a C1-C3 alkyl group and Q is Q4 in [Aspect 1]

A tetrazolinone compound in which $R^3$ is a C3-C4 cycloalkyl group and Q is Q4 in [Aspect 1].

A tetrazolinone compound in which $R^3$ is a halogen atom and Q is Q4 in [Aspect 1].

A tetrazolinone compound in which $R^3$ is a C1-C3 haloalkyl group and Q is Q4 in [Aspect 1].

A tetrazolinone compound in which $R^3$ is a C2-C3 alkenyl group and Q is Q4 in [Aspect 1].

A tetrazolinone compound in which $R^3$ is a C1-C3 alkoxy group and Q is Q4 in [Aspect 1].

A tetrazolinone compound in which $R^3$ is a C2-C3 alkynyl group and Q is Q4 in [Aspect 1].

A tetrazolinone compound in which $R^3$ is a C1-C3 haloalkoxy group and Q is Q4 in [Aspect 1].

A tetrazolinone compound in which $R^3$ is a methyl group and Q is Q4 in [Aspect 1].

A tetrazolinone compound in which $R^3$ is an ethyl group and Q is Q4 in [Aspect 1].

A tetrazolinone compound in which $R^3$ is a cyclopropyl group and Q is Q4 in [Aspect 1].

A tetrazolinone compound in which $R^3$ is a chlorine atom and Q is Q4 in [Aspect 1].

A tetrazolinone compound in which $R^3$ is a bromine atom and Q is Q4 in [Aspect 1].

A tetrazolinone compound in which $R^3$ is a methoxy group and Q is Q4 in [Aspect 1].

A tetrazolinone compound in which $R^3$ is a C1-C3 alkyl group and Q is Q5 in [Aspect 1].

A tetrazolinone compound in which $R^3$ is a C3-C4 cycloalkyl group and Q is Q5 in [Aspect 1].

A tetrazolinone compound in which $R^3$ is a halogen atom, and Q is Q5 in [Aspect 1].

A tetrazolinone compound in which $R^3$ is a C1-C3 haloalkyl group and Q is Q5 in [Aspect 1].

A tetrazolinone compound in which $R^3$ is a C2-C3 alkenyl group and Q is Q5 in [Aspect 1].

A tetrazolinone compound in which $R^3$ is a C1-C3 alkoxy group and Q is Q5 in [Aspect 1].

A tetrazolinone compound in which $R^3$ is a C2-C3 alkynyl group and Q is Q5 in [Aspect 1].

A tetrazolinone compound in which $R^3$ is a C1-C3 haloalkoxy group and Q is Q5 in [Aspect 1].

A tetrazolinone compound in which $R^3$ is a methyl group and Q is Q5 in [Aspect 1].

A tetrazolinone compound in which $R^3$ is an ethyl group and Q is Q5 in [Aspect 1].

A tetrazolinone compound in which $R^3$ is a cyclopropyl group and Q is Q5 in [Aspect 1].

A tetrazolinone compound in which $R^3$ is a chlorine atom and Q is Q5 in [Aspect 1].

A tetrazolinone compound in which $R^3$ is a bromine atom and Q is Q5 in [Aspect 1].

A tetrazolinone compound in which $R^3$ is a methoxy group and Q is Q5 in [Aspect 1].

A tetrazolinone compound in which $R^3$ is a C1-C3 alkyl group and Q is Q6 in [Aspect 1].

A tetrazolinone compound in which $R^3$ is a C3-C4 cycloalkyl group and Q is Q6 in [Aspect 1].

A tetrazolinone compound in which $R^3$ is a halogen atom and Q is Q6 in [Aspect 1].

A tetrazolinone compound in which $R^3$ is a C1-C3 haloalkyl group and Q is Q6 in [Aspect 1].

A tetrazolinone compound in which $R^3$ is a C2-C3 alkenyl group and Q is Q6 in [Aspect 1].

A tetrazolinone compound in which $R^3$ is a C1-C3 alkoxy group and Q is Q6 in [Aspect 1].

A tetrazolinone compound in which $R^3$ is a C2-C3 alkynyl group and Q is Q6 in [Aspect 1].

A tetrazolinone compound in which $R^3$ is a C1-C3 haloalkoxy group and Q is Q6 in [Aspect 1].

A tetrazolinone compound in which $R^3$ is a methyl group and Q is Q6 in [Aspect 1].

A tetrazolinone compound in which $R^3$ is an ethyl group and Q is Q6 in [Aspect 1].

A tetrazolinone compound in which $R^3$ is a cyclopropyl group and Q is Q6 in [Aspect 1].

A tetrazolinone compound in which $R^3$ is a chlorine atom and Q is Q6 in [Aspect 1].

A tetrazolinone compound in which $R^3$ is a bromine atom and Q is Q6 in [Aspect 1].

A tetrazolinone compound in which $R^3$ is a methoxy group and Q is Q6 in [Aspect 1].

A tetrazolinone compound in which $R^3$ is a C1-C3 alkyl group and Q is Q7 in [Aspect 1].

A tetrazolinone compound in which $R^3$ is a C3-C4 cycloalkyl group and Q is Q7 in [Aspect 1].

A tetrazolinone compound in which $R^3$ is a halogen atom and Q is Q7 in [Aspect 1].

A tetrazolinone compound in which $R^3$ is a C1-C3 haloalkyl group and Q is Q7 in [Aspect 1].

A tetrazolinone compound in which $R^3$ is a C2-C3 alkenyl group and Q is Q7 in [Aspect 1].

A tetrazolinone compound in which $R^3$ is a C1-C3 alkoxy group and Q is Q7 in [Aspect 1].

A tetrazolinone compound in which $R^3$ is a C2-C3 alkynyl group and Q is Q7 in [Aspect 1].

A tetrazolinone compound in which $R^3$ is a C1-C3 haloalkoxy group and Q is Q7 in [Aspect 1].

A tetrazolinone compound in which $R^3$ is a methyl group and Q is Q7 in [Aspect 1].

A tetrazolinone compound in which $R^3$ is an ethyl group and Q is Q7 in [Aspect 1].

A tetrazolinone compound in which $R^3$ is a cyclopropyl group and Q is Q7 in [Aspect 1].

A tetrazolinone compound in which $R^3$ is a chlorine atom and Q is Q7 in [Aspect 1].

A tetrazolinone compound in which $R^3$ is a bromine atom and Q is Q7 in [Aspect 1].

A tetrazolinone compound in which $R^3$ is a methoxy group and Q is Q7 in [Aspect 1].

A tetrazolinone compound in which $R^3$ is a C1-C3 alkyl group and Q is Q8 in [Aspect 1].

A tetrazolinone compound in which $R^3$ is a C3-C4 cycloalkyl group and Q is Q8 in [Aspect 1].

A tetrazolinone compound in which $R^3$ is a halogen atom and Q is Q8 in [Aspect 1].

A tetrazolinone compound in which $R^3$ is a C1-C3 haloalkyl group and Q is Q8 in [Aspect 1].

A tetrazolinone compound in which $R^3$ is a C2-C3 alkenyl group and Q is Q8 in [Aspect 1].

A tetrazolinone compound in which $R^3$ is a C1-C3 alkoxy group and Q is Q8 in [Aspect 1].

A tetrazolinone compound in which $R^3$ is a C2-C3 alkynyl group and Q is Q8 in [Aspect 1].

A tetrazolinone compound in which $R^3$ is a C1-C3 haloalkoxy group and Q is Q8 in [Aspect 1].

A tetrazolinone compound in which $R^3$ is a methyl group and Q is Q8 in [Aspect 1].

A tetrazolinone compound in which $R^3$ is an ethyl group and Q is Q8 in [Aspect 1].

A tetrazolinone compound in which $R^3$ is a cyclopropyl group and Q is Q8 in [Aspect 1].

A tetrazolinone compound in which $R^3$ is a chlorine atom and Q is Q8 in [Aspect 1].

A tetrazolinone compound in which $R^3$ is a bromine atom and Q is Q8 in [Aspect 1].

A tetrazolinone compound in which $R^3$ is a methoxy group and Q is Q8 in [Aspect 1].

A tetrazolinone compound in which $R^3$ is a C1-C3 alkyl group and Q is Q9 in [Aspect 1].

A tetrazolinone compound in which $R^3$ is a C3-C4 cycloalkyl group and Q is Q9 in [Aspect 1].

A tetrazolinone compound in which $R^3$ is a halogen atom and Q is Q9 in [Aspect 1].

A tetrazolinone compound in which $R^3$ is a C1-C3 haloalkyl group and Q is Q9 in [Aspect 1].

A tetrazolinone compound in which $R^3$ is a C2-C3 alkenyl group and Q is Q9 in [Aspect 1].

A tetrazolinone compound in which $R^3$ is a C1-C3 alkoxy group and Q is Q9 in [Aspect 1].

A tetrazolinone compound in which $R^3$ is a C2-C3 alkynyl group and Q is Q9 in [Aspect 1].

A tetrazolinone compound in which $R^3$ is a C1-C3 haloalkoxy group and Q is Q9 in [Aspect 1].

A tetrazolinone compound in which $R^3$ is a methyl group and Q is Q9 in [Aspect 1].

A tetrazolinone compound in which $R^3$ is an ethyl group and Q is Q9 in [Aspect 1].

A tetrazolinone compound in which $R^3$ is a cyclopropyl group and Q is Q9 in [Aspect 1].

A tetrazolinone compound in which $R^3$ is a chlorine atom and Q is Q9 in [Aspect 1].

A tetrazolinone compound in which $R^3$ is a bromine atom and Q is Q9 in [Aspect 1].

A tetrazolinone compound in which $R^3$ is a methoxy group and Q is Q9 in [Aspect 1].

A tetrazolinone compound in which $R^3$ is a C1-C3 alkyl group and Q is Q10 in [Aspect 1].

A tetrazolinone compound in which $R^3$ is a C3-C4 cycloalkyl group and Q is Q10 in [Aspect 1].

A tetrazolinone compound in which $R^3$ is a halogen atom and Q is Q10 in [Aspect 1].

A tetrazolinone compound in which $R^3$ is a C1-C3 haloalkyl group and Q is Q10 in [Aspect 1].

A tetrazolinone compound in which $R^3$ is a C2-C3 alkenyl group and Q is Q10 in [Aspect 1].

A tetrazolinone compound in which $R^3$ is a C1-C3 alkoxy group and Q is Q10 in [Aspect 1].

A tetrazolinone compound in which $R^3$ is a C2-C3 alkynyl group and Q is Q10 in [Aspect 1].

A tetrazolinone compound in which $R^3$ is a C1-C3 haloalkoxy group and Q is Q10 in [Aspect 1].

A tetrazolinone compound in which $R^3$ is a methyl group and Q is Q10 in [Aspect 1].

A tetrazolinone compound in which $R^3$ is an ethyl group and Q is Q10 in [Aspect 1].

A tetrazolinone compound in which $R^3$ is a cyclopropyl group and Q is Q10 in [Aspect 1].

A tetrazolinone compound in which $R^3$ is a chlorine atom and Q is Q10 in [Aspect 1].

A tetrazolinone compound in which $R^3$ is a bromine atom and Q is Q10 in [Aspect 1].

A tetrazolinone compound in which $R^3$ is a methoxy group and Q is Q10 in [Aspect 1].

A tetrazolinone compound in which $R^3$ is a C1-C3 alkyl group and Q is Q11 in [Aspect 1].

A tetrazolinone compound in which $R^3$ is a C3-C4 cycloalkyl group and Q is Q11 in [Aspect 1].

A tetrazolinone compound in which $R^3$ is a halogen atom and Q is Q11 in [Aspect 1].

A tetrazolinone compound in which $R^3$ is a C1-C3 haloalkyl group and Q is Q11 in [Aspect 1].

A tetrazolinone compound in which $R^3$ is a C2-C3 alkenyl group and Q is Q11 in [Aspect 1].

A tetrazolinone compound in which $R^3$ is a C1-C3 alkoxy group and Q is Q11 in [Aspect 1].

A tetrazolinone compound in which $R^3$ is a C2-C3 alkynyl group and Q is Q11 in [Aspect 1].

A tetrazolinone compound in which $R^3$ is a C1-C3 haloalkoxy group and Q is Q11 in [Aspect 1].

A tetrazolinone compound in which $R^3$ is a methyl group and Q is Q11 in [Aspect 1].

A tetrazolinone compound in which $R^3$ is an ethyl group and Q is Q11 in [Aspect 1].

A tetrazolinone compound in which $R^3$ is a cyclopropyl group and Q is Q11 in [Aspect 1].

A tetrazolinone compound in which $R^3$ is a chlorine atom and Q is Q11 in [Aspect 1].

A tetrazolinone compound in which $R^3$ is a bromine atom and Q is Q11 in [Aspect 1].

A tetrazolinone compound in which $R^3$ is a methoxy group and Q is Q11 in [Aspect 1].

A tetrazolinone compound in which $R^3$ is a C1-C3 alkyl group and Q is Q12 in [Aspect 1].

A tetrazolinone compound in which $R^3$ is a C3-C4 cycloalkyl group and Q is Q12 in [Aspect 1].

A tetrazolinone compound in which $R^3$ is a halogen atom and Q is Q12 in [Aspect 1].

A tetrazolinone compound in which $R^3$ is a C1-C3 haloalkyl group and Q is Q12 in [Aspect 1].

A tetrazolinone compound in which $R^3$ is a C2-C3 alkenyl group and Q is Q12 in [Aspect 1].

A tetrazolinone compound in which $R^3$ is a C1-C3 alkoxy group and Q is Q12 in [Aspect 1].

A tetrazolinone compound in which $R^3$ is a C2-C3 alkynyl group and Q is Q12 in [Aspect 1].

A tetrazolinone compound in which $R^3$ is a C1-C3 haloalkoxy group and Q is Q12 in [Aspect 1].

A tetrazolinone compound in which $R^3$ is a methyl group and Q is Q12 in [Aspect 1].

A tetrazolinone compound in which $R^3$ is an ethyl group and Q is Q12 in [Aspect 1].

A tetrazolinone compound in which $R^3$ is a cyclopropyl group and Q is Q12 in [Aspect 1].

A tetrazolinone compound in which $R^3$ is a chlorine atom and Q is Q12 in [Aspect 1].

A tetrazolinone compound in which $R^3$ is a bromine atom and Q is Q12 in [Aspect 1].

A tetrazolinone compound in which $R^3$ is a methoxy group and Q is Q12 in [Aspect 1].

[Aspect 2]

A tetrazolinone compound in which A is formula (2), $R^{37}$ represents a halogen atom, a hydrogen atom, a C1-C3 alkyl group, a C1-C3 haloalkyl group, a C1-C3 alkoxy group, or a C1-C3 haloalkoxy group; $R^{38}$, $R^{39}$, $R^{40}$, and $R^{41}$ each independently represents a hydrogen atom or a halogen atom; $R^1$, $R^2$, $R^4$, $R^5$, and $R^6$ are hydrogen atoms; $R^7$ is a methyl group; and X is an oxygen atom.

A tetrazolinone compound in which $R^3$ is a C1-C3 alkyl group in [Aspect 2].

A tetrazolinone compound in which $R^3$ is a C3-C4 cycloalkyl group in [Aspect 2].

A tetrazolinone compound in which $R^3$ is a halogen atom in [Aspect 2].

A tetrazolinone compound in which $R^3$ is a C1-C3 haloalkyl group in [Aspect 2].

A tetrazolinone compound in which $R^3$ is a C2-C3 alkenyl group in [Aspect 2].

A tetrazolinone compound in which $R^3$ is a C1-C3 alkoxy group in [Aspect 2].

A tetrazolinone compound in which $R^3$ is a C2-C3 alkynyl group in [Aspect 2].

A tetrazolinone compound in which $R^3$ is a C1-C3 haloalkoxy group in [Aspect 2].

A tetrazolinone compound in which $R^3$ is a methyl group in [Aspect 2].

A tetrazolinone compound in which $R^3$ is an ethyl group in [Aspect 2].

A tetrazolinone compound in which $R^3$ is a cyclopropyl group in [Aspect 2].

A tetrazolinone compound in which $R^3$ is a chlorine atom in [Aspect 2].

A tetrazolinone compound in which $R^3$ is a bromine atom in [Aspect 2].

A tetrazolinone compound in which $R^3$ is a methoxy group in [Aspect 2].

A tetrazolinone compound in which $R^3$ is a C1-C3 alkyl group and Q is Q1 in [Aspect 2].

A tetrazolinone compound in which $R^3$ is a C3-C4 cycloalkyl group and Q is Q1 in [Aspect 2].

A tetrazolinone compound in which $R^3$ is a halogen atom and Q is Q1 in [Aspect 2].

A tetrazolinone compound in which $R^3$ is a C1-C3 haloalkyl group and Q is Q1 in [Aspect 2].

A tetrazolinone compound in which $R^3$ is a C2-C3 alkenyl group and Q is Q1 in [Aspect 2].

A tetrazolinone compound in which $R^3$ is a C1-C3 alkoxy group and Q is Q1 in [Aspect 2].

A tetrazolinone compound in which $R^3$ is a C2-C3 alkynyl group and Q is Q1 in [Aspect 2].

A tetrazolinone compound in which $R^3$ is a C1-C3 haloalkoxy group and Q is Q1 in [Aspect 2].

A tetrazolinone compound in which $R^3$ is a methyl group and Q is Q1 in [Aspect 2].

A tetrazolinone compound in which $R^3$ is an ethyl group and Q is Q1 in [Aspect 2].

A tetrazolinone compound in which $R^3$ is a cyclopropyl group and Q is Q1 in [Aspect 2].

A tetrazolinone compound in which $R^3$ is a chlorine atom and Q is Q1 in [Aspect 2].

A tetrazolinone compound in which $R^3$ is a bromine atom and Q is Q1 in [Aspect 2].

A tetrazolinone compound in which $R^3$ is a methoxy group and Q is Q1 in [Aspect 2].

A tetrazolinone compound in which $R^3$ is a C1-C3 alkyl group and Q is Q2 in [Aspect 2].

A tetrazolinone compound in which $R^3$ is a C3-C4 cycloalkyl group and Q is Q2 in [Aspect 2].

A tetrazolinone compound in which $R^3$ is a halogen atom and Q is Q2 in [Aspect 2].

A tetrazolinone compound in which $R^3$ is a C1-C3 haloalkyl group and Q is Q2 in [Aspect 2].

A tetrazolinone compound in which $R^3$ is a C2-C3 alkenyl group and Q is Q2 in [Aspect 2].

A tetrazolinone compound in which $R^3$ is a C1-C3 alkoxy group and Q is Q2 in [Aspect 2].

A tetrazolinone compound in which $R^3$ is a C2-C3 alkynyl group and Q is Q2 in [Aspect 2].

A tetrazolinone compound in which $R^3$ is a C1-C3 haloalkoxy group and Q is Q2 in [Aspect 2].

A tetrazolinone compound in which $R^3$ is a methyl group and Q is Q2 in [Aspect 2].

A tetrazolinone compound in which $R^3$ is an ethyl group and Q is Q2 in [Aspect 2].

A tetrazolinone compound in which $R^3$ is a cyclopropyl group and Q is Q2 in [Aspect 2].

A tetrazolinone compound in which $R^3$ is a chlorine atom and Q is Q2 in [Aspect 2].

A tetrazolinone compound in which $R^3$ is a bromine atom and Q is Q2 in [Aspect 2].

A tetrazolinone compound in which $R^3$ is a methoxy group and Q is Q2 in [Aspect 2].

A tetrazolinone compound in which $R^3$ is a C1-C3 alkyl group and Q is Q3 in [Aspect 2].

A tetrazolinone compound in which $R^3$ is a C3-C4 cycloalkyl group and Q is Q3 in [Aspect 2].

A tetrazolinone compound in which $R^3$ is a halogen atom and Q is Q3 in [Aspect 2].

A tetrazolinone compound in which $R^3$ is a C1-C3 haloalkyl group and Q is Q3 in [Aspect 2].

A tetrazolinone compound in which $R^3$ is a C2-C3 alkenyl group and Q is Q3 in [Aspect 2].

A tetrazolinone compound in which $R^3$ is a C1-C3 alkoxy group and Q is Q3 in [Aspect 2].

A tetrazolinone compound in which $R^3$ is a C2-C3 alkynyl group and Q is Q3 in [Aspect 2].

A tetrazolinone compound in which $R^3$ is a C1-C3 haloalkoxy group and Q is Q3 in [Aspect 2].

A tetrazolinone compound in which $R^3$ is a methyl group and Q is Q3 in [Aspect 2].

A tetrazolinone compound in which $R^3$ is an ethyl group and Q is Q3 in [Aspect 2].

A tetrazolinone compound in which $R^3$ is a cyclopropyl group and Q is Q3 in [Aspect 2].

A tetrazolinone compound in which $R^3$ is a chlorine atom and Q is Q3 in [Aspect 2].

A tetrazolinone compound in which $R^3$ is a bromine atom and Q is Q3 in [Aspect 2].

A tetrazolinone compound in which $R^3$ is a methoxy group and Q is Q3 in [Aspect 2].

A tetrazolinone compound in which $R^3$ is a C1-C3 alkyl group and Q is Q4 in [Aspect 2].

A tetrazolinone compound in which $R^3$ is a C3-C4 cycloalkyl group and Q is Q4 in [Aspect 2].

A tetrazolinone compound in which $R^3$ is a halogen atom and Q is Q4 in [Aspect 2].

A tetrazolinone compound in which $R^3$ is a C1-C3 haloalkyl group and Q is Q4 in [Aspect 2].

A tetrazolinone compound in which $R^3$ is a C2-C3 alkenyl group and Q is Q4 in [Aspect 2].

A tetrazolinone compound in which $R^3$ is a C1-C3 alkoxy group and Q is Q4 in [Aspect 2].

A tetrazolinone compound in which $R^3$ is a C2-C3 alkynyl group and Q is Q4 in [Aspect 2].

A tetrazolinone compound in which $R^3$ is a C1-C3 haloalkoxy group and Q is Q4 in [Aspect 2].

A tetrazolinone compound in which $R^3$ is a methyl group and Q is Q4 in [Aspect 2].

A tetrazolinone compound in which $R^3$ is an ethyl group and Q is Q4 in [Aspect 2].

A tetrazolinone compound in which $R^3$ is a cyclopropyl group and Q is Q4 in [Aspect 2].

A tetrazolinone compound in which $R^3$ is a chlorine atom and Q is Q4 in [Aspect 2].

A tetrazolinone compound in which $R^3$ is a bromine atom and Q is Q4 in [Aspect 2].

A tetrazolinone compound in which $R^3$ is a methoxy group and Q is Q4 in [Aspect 2].

A tetrazolinone compound in which $R^3$ is a C1-C3 alkyl group and Q is Q5 in [Aspect 2].

A tetrazolinone compound in which $R^3$ is a C3-C4 cycloalkyl group and Q is Q5 in [Aspect 2].

A tetrazolinone compound in which $R^3$ is a halogen atom and Q is Q5 in [Aspect 2].

A tetrazolinone compound in which R³ is a C1-C3 haloalkyl group and Q is Q5 in [Aspect 2].

A tetrazolinone compound in which R³ is a C2-C3 alkenyl group and Q is Q5 in [Aspect 2].

A tetrazolinone compound in which R³ is a C1-C3 alkoxy group and Q is Q5 in [Aspect 2].

A tetrazolinone compound in which R³ is a C2-C3 alkynyl group and Q is Q5 in [Aspect 2].

A tetrazolinone compound in which R³ is a C1-C3 haloalkoxy group and Q is Q5 in [Aspect 2].

A tetrazolinone compound in which R³ is a methyl group and Q is Q5 in [Aspect 2].

A tetrazolinone compound in which R³ is an ethyl group and Q is Q5 in [Aspect 2].

A tetrazolinone compound in which R³ is a cyclopropyl group and Q is Q5 in [Aspect 2].

A tetrazolinone compound in which R³ is a chlorine atom and Q is Q5 in [Aspect 2].

A tetrazolinone compound in which R³ is a bromine atom and Q is Q5 in [Aspect 2].

A tetrazolinone compound in which R³ is a methoxy group and Q is Q5 in [Aspect 2].

A tetrazolinone compound in which R³ is a C1-C3 alkyl group and Q is Q6 in [Aspect 2].

A tetrazolinone compound in which R³ is a C3-C4 cycloalkyl group and Q is Q6 in [Aspect 2].

A tetrazolinone compound in which R³ is a halogen atom and Q is Q6 in [Aspect 2].

A tetrazolinone compound in which R³ is a C1-C3 haloalkyl group and Q is Q6 in [Aspect 2].

A tetrazolinone compound in which R³ is a C2-C3 alkenyl group and Q is Q6 in [Aspect 2].

A tetrazolinone compound in which R³ is a C1-C3 alkoxy group and Q is Q6 in [Aspect 2].

A tetrazolinone compound in which R³ is a C2-C3 alkynyl group and Q is Q6 in [Aspect 2].

A tetrazolinone compound in which R³ is a C1-C3 haloalkoxy group and Q is Q6 in [Aspect 2].

A tetrazolinone compound in which R³ is a methyl group and Q is Q6 in [Aspect 2].

A tetrazolinone compound in which R³ is an ethyl group and Q is Q6 in [Aspect 2].

A tetrazolinone compound in which R³ is a cyclopropyl group and Q is Q6 in [Aspect 2].

A tetrazolinone compound in which R³ is a chlorine atom and Q is Q6 in [Aspect 2].

A tetrazolinone compound in which R³ is a bromine atom and Q is Q6 in [Aspect 2].

A tetrazolinone compound in which R³ is a methoxy group and Q is Q6 in [Aspect 2].

A tetrazolinone compound in which R³ is a C1-C3 alkyl group and Q is Q7 in [Aspect 2].

A tetrazolinone compound in which R³ is a C3-C4 cycloalkyl group and Q is Q7 in [Aspect 2].

A tetrazolinone compound in which R³ is a halogen atom, and Q is Q7 in [Aspect 2].

A tetrazolinone compound in which R³ is a C1-C3 haloalkyl group and Q is Q7 in [Aspect 2].

A tetrazolinone compound in which R³ is a C2-C3 alkenyl group and Q is Q7 in [Aspect 2].

A tetrazolinone compound in which R³ is a C1-C3 alkoxy group and Q is Q7 in [Aspect 2].

A tetrazolinone compound in which R³ is a C2-C3 alkynyl group and Q is Q7 in [Aspect 2].

A tetrazolinone compound in which R³ is a C1-C3 haloalkoxy group and Q is Q7 in [Aspect 2].

A tetrazolinone compound in which R³ is a methyl group and Q is Q7 in [Aspect 2].

A tetrazolinone compound in which R³ is an ethyl group and Q is Q7 in [Aspect 2].

A tetrazolinone compound in which R³ is a cyclopropyl group and Q is Q7 in [Aspect 2].

A tetrazolinone compound in which R³ is a chlorine atom and Q is Q7 in [Aspect 2].

A tetrazolinone compound in which R³ is a bromine atom and Q is Q7 in [Aspect 2].

A tetrazolinone compound in which R³ is a methoxy group and Q is Q7 in [Aspect 2].

A tetrazolinone compound in which R³ is a C1-C3 alkyl group and Q is Q8 in [Aspect 2].

A tetrazolinone compound in which R³ is a C3-C4 cycloalkyl group and Q is Q8 in [Aspect 2].

A tetrazolinone compound in which R³ is a halogen atom and Q is Q8 in [Aspect 2].

A tetrazolinone compound in which R³ is a C1-C3 haloalkyl group and Q is Q8 in [Aspect 2].

A tetrazolinone compound in which R³ is a C2-C3 alkenyl group and Q is Q8 in [Aspect 2].

A tetrazolinone compound in which R³ is a C1-C3 alkoxy group and Q is Q8 in [Aspect 2].

A tetrazolinone compound in which R³ is a C2-C3 alkynyl group and Q is Q8 in [Aspect 2].

A tetrazolinone compound in which R³ is a C1-C3 haloalkoxy group and Q is Q8 in [Aspect 2].

A tetrazolinone compound in which R³ is a methyl group and Q is Q8 in [Aspect 2].

A tetrazolinone compound in which R³ is an ethyl group and Q is Q8 in [Aspect 2].

A tetrazolinone compound in which R³ is a cyclopropyl group and Q is Q8 in [Aspect 2].

A tetrazolinone compound in which R³ is a chlorine atom and Q is Q8 in [Aspect 2].

A tetrazolinone compound in which R³ is a bromine atom and Q is Q8 in [Aspect 2].

A tetrazolinone compound in which R³ is a methoxy group and Q is Q8 in [Aspect 2].

A tetrazolinone compound in which R³ is a C1-C3 alkyl group and Q is Q9 in [Aspect 2].

A tetrazolinone compound in which R³ is a C3-C4 cycloalkyl group and Q is Q9 in [Aspect 2].

A tetrazolinone compound in which R³ is a halogen atom and Q is Q9 in [Aspect 2].

A tetrazolinone compound in which R³ is a C1-C3 haloalkyl group and Q is Q9 in [Aspect 2].

A tetrazolinone compound in which R³ is a C2-C3 alkenyl group and Q is Q9 in [Aspect 2].

A tetrazolinone compound in which R³ is a C1-C3 alkoxy group and Q is Q9 in [Aspect 2].

A tetrazolinone compound in which R³ is a C2-C3 alkynyl group and Q is Q9 in [Aspect 2].

A tetrazolinone compound in which R³ is a C1-C3 haloalkoxy group and Q is Q9 in [Aspect 2].

A tetrazolinone compound in which R³ is a methyl group and Q is Q9 in [Aspect 2].

A tetrazolinone compound in which R³ is an ethyl group and Q is Q9 in [Aspect 2].

A tetrazolinone compound in which R³ is a cyclopropyl group and Q is Q9 in [Aspect 2].

A tetrazolinone compound in which R³ is a chlorine atom and Q is Q9 in [Aspect 2].

A tetrazolinone compound in which R³ is a bromine atom and Q is Q9 in [Aspect 2].

A tetrazolinone compound in which $R^3$ is a methoxy group and Q is Q9 in [Aspect 2].

A tetrazolinone compound in which $R^3$ is a C1-C3 alkyl group and Q is Q10 in [Aspect 2].

A tetrazolinone compound in which $R^3$ is a C3-C4 cycloalkyl group and Q is Q10 in [Aspect 2].

A tetrazolinone compound in which $R^3$ is a halogen atom and Q is Q10 in [Aspect 2].

A tetrazolinone compound in which $R^3$ is a C1-C3 haloalkyl group and Q is Q10 in [Aspect 2].

A tetrazolinone compound in which $R^3$ is a C2-C3 alkenyl group and Q is Q10 in [Aspect 2].

A tetrazolinone compound in which $R^3$ is a C1-C3 alkoxy group and Q is Q10 in [Aspect 2].

A tetrazolinone compound in which $R^3$ is a C2-C3 alkynyl group and Q is Q10 in [Aspect 2].

A tetrazolinone compound in which $R^3$ is a C1-C3 haloalkoxy group and Q is Q10 in [Aspect 2].

A tetrazolinone compound in which $R^3$ is a methyl group and Q is Q10 in [Aspect 2].

A tetrazolinone compound in which $R^3$ is an ethyl group and Q is Q10 in [Aspect 2].

A tetrazolinone compound in which $R^3$ is a cyclopropyl group and Q is Q10 in [Aspect 2].

A tetrazolinone compound in which $R^3$ is a chlorine atom and Q is Q10 in [Aspect 2].

A tetrazolinone compound in which $R^3$ is a bromine atom and Q is Q10 in [Aspect 2].

A tetrazolinone compound in which $R^3$ is a methoxy group and Q is Q10 in [Aspect 2].

A tetrazolinone compound in which $R^3$ is a C1-C3 alkyl group and Q is Q11 in [Aspect 2].

A tetrazolinone compound in which $R^3$ is a C3-C4 cycloalkyl group and Q is Q11 in [Aspect 2].

A tetrazolinone compound in which $R^3$ is a halogen atom and Q is Q11 in [Aspect 2].

A tetrazolinone compound in which $R^3$ is a C1-C3 haloalkyl group and Q is Q11 in [Aspect 2].

A tetrazolinone compound in which $R^3$ is a C2-C3 alkenyl group and Q is Q11 in [Aspect 2].

A tetrazolinone compound in which $R^3$ is a C1-C3 alkoxy group and Q is Q11 in [Aspect 2].

A tetrazolinone compound in which $R^3$ is a C2-C3 alkynyl group and Q is Q11 in [Aspect 2].

A tetrazolinone compound in which $R^3$ is a C1-C3 haloalkoxy group and Q is Q11 in [Aspect 2].

A tetrazolinone compound in which $R^3$ is a methyl group and Q is Q11 in [Aspect 2].

A tetrazolinone compound in which $R^3$ is an ethyl group and Q is Q11 in [Aspect 2].

A tetrazolinone compound in which $R^3$ is a cyclopropyl group and Q is Q11 in [Aspect 2].

A tetrazolinone compound in which $R^3$ is a chlorine atom and Q is Q11 in [Aspect 2].

A tetrazolinone compound in which $R^3$ is a bromine atom and Q is Q11 in [Aspect 2].

A tetrazolinone compound in which $R^3$ is a methoxy group and Q is Q11 in [Aspect 2].

A tetrazolinone compound in which $R^3$ is a C1-C3 alkyl group and Q is Q12 in [Aspect 2].

A tetrazolinone compound in which $R^3$ is a C3-C4 cycloalkyl group and Q is Q12 in [Aspect 2].

A tetrazolinone compound in which $R^3$ is a halogen atom and Q is Q12 in [Aspect 2].

A tetrazolinone compound in which $R^3$ is a C1-C3 haloalkyl group and Q is Q12 in [Aspect 2].

A tetrazolinone compound in which $R^3$ is a C2-C3 alkenyl group and Q is Q12 in [Aspect 2].

A tetrazolinone compound in which $R^3$ is a C1-C3 alkoxy group and Q is Q12 in [Aspect 2].

A tetrazolinone compound in which $R^3$ is a C2-C3 alkynyl group and Q is Q12 in [Aspect 2].

A tetrazolinone compound in which $R^3$ is a C1-C3 haloalkoxy group and Q is Q12 in [Aspect 2].

A tetrazolinone compound in which $R^3$ is a methyl group and Q is Q12 in [Aspect 2].

A tetrazolinone compound in which $R^3$ is an ethyl group and Q is Q12 in [Aspect 2].

A tetrazolinone compound in which $R^3$ is a cyclopropyl group and Q is Q12 in [Aspect 2].

A tetrazolinone compound in which $R^3$ is a chlorine atom and Q is Q12 in [Aspect 2].

A tetrazolinone compound in which $R^3$ is a bromine atom and Q is Q12 in [Aspect 2].

A tetrazolinone compound in which $R^3$ is a methoxy group and Q is Q12 in [Aspect 2].

[Aspect 3]

A tetrazolinone compound in which A is formula (2), $R^{37}$ is a halogen atom; $R^{38}$, $R^{39}$, $R^{40}$, and $R^{41}$ each independently represents a hydrogen atom or a halogen atom; $R^1$, $R^2$, $R^4$, $R^5$, and $R^6$ are hydrogen atoms; $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; $R^7$ is a methyl group; and X is an oxygen atom.

[Aspect 4]

A tetrazolinone compound in which A is formula (2), $R^{37}$ is a C1-C3 alkoxy group; $R^{38}$, $R^{39}$, $R^{40}$, and $R^{41}$ each independently represents a hydrogen atom or a halogen atom; $R^1$, $R^2$, $R^4$, $R^5$, and $R^6$ are hydrogen atoms; $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; $R^7$ is a methyl group; and X is an oxygen atom.

[Aspect 5]

A tetrazolinone compound in which A is formula (2), $R^{37}$ is a C1-C3 haloalkoxy group; $R^{38}$, $R^{39}$, $R^{40}$, and $R^{41}$ each independently represents a hydrogen atom or a halogen atom; $R^1$, $R^2$, $R^4$, $R^5$, and $R^6$ are hydrogen atoms; $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; $R^7$ is a methyl group; and X is an oxygen atom.

A tetrazolinone compound in which A is formula (2), $R^{37}$ is a C1-C3 alkoxy group or a C1-C3 haloalkoxy group; $R^{38}$, $R^{39}$, $R^{40}$, and $R^{41}$ each independently represents a hydrogen atom or a halogen atom; $R^1$, $R^2$, $R^4$, $R^5$, and $R^6$ are hydrogen atoms; $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; $R^7$ is a methyl group; and X is an oxygen atom.

A tetrazolinone compound in which Q is Q1 in [Aspect 3].
A tetrazolinone compound in which Q is Q1 in [Aspect 4].
A tetrazolinone compound in which Q is Q1 in [Aspect 5].
A tetrazolinone compound in which Q is Q2 in [Aspect 3].
A tetrazolinone compound in which Q is Q2 in [Aspect 4].
A tetrazolinone compound in which Q is Q2 in [Aspect 5].
A tetrazolinone compound in which Q is Q3 in [Aspect 3].
A tetrazolinone compound in which Q is Q3 in [Aspect 4].
A tetrazolinone compound in which Q is Q3 in [Aspect 5].

A tetrazolinone compound in which Q is Q4 in [Aspect 3].
A tetrazolinone compound in which Q is Q4 in [Aspect 4].
A tetrazolinone compound in which Q is Q4 in [Aspect 5].
A tetrazolinone compound in which Q is Q5 in [Aspect 3].
A tetrazolinone compound in which Q is Q5 in [Aspect 4].
A tetrazolinone compound in which Q is Q5 in [Aspect 5].
A tetrazolinone compound in which Q is Q6 in [Aspect 3].
A tetrazolinone compound in which Q is Q6 in [Aspect 4].
A tetrazolinone compound in which Q is Q6 in [Aspect 5].
A tetrazolinone compound in which Q is Q7 in [Aspect 3].
A tetrazolinone compound in which Q is Q7 in [Aspect 4].
A tetrazolinone compound in which Q is Q7 in [Aspect 5].
A tetrazolinone compound in which Q is Q8 in [Aspect 3].
A tetrazolinone compound in which Q is Q8 in [Aspect 4].
A tetrazolinone compound in which Q is Q8 in [Aspect 5].
A tetrazolinone compound in which Q is Q9 in [Aspect 3].
A tetrazolinone compound in which Q is Q9 in [Aspect 4].
A tetrazolinone compound in which Q is Q9 in [Aspect 5].
A tetrazolinone compound in which Q is Q10 in [Aspect 3].
A tetrazolinone compound in which Q is Q10 in [Aspect 4].
A tetrazolinone compound in which Q is Q10 in [Aspect 5].
A tetrazolinone compound in which Q is Q11 in [Aspect 3].
A tetrazolinone compound in which Q is Q11 in [Aspect 4].
A tetrazolinone compound in which Q is Q11 in [Aspect 5].
A tetrazolinone compound in which Q is Q12 in [Aspect 3].
A tetrazolinone compound in which Q is Q12 in [Aspect 4].
A tetrazolinone compound in which Q is Q12 in [Aspect 5].

A tetrazolinone compound of formula (1) in which $R^1$, $R^2$, $R^4$, $R^5$, and $R^6$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group optionally having one or more atoms or groups selected from Group P, a C2-C9 heterocyclyl group optionally having one or more atoms or groups selected from Group P, or a C3-C12 cycloalkenyl group optionally having one or more atoms or groups selected from Group P.

A tetrazolinone compound of formula (1) in which $R^1$, $R^2$, $R^4$, $R^5$, and $R^6$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group, a C2-C9 heterocyclyl group, or a C3-C12 cycloalkenyl group (provided that the C6-C16 aryl group, the C2-C9 heterocyclyl group, and the C3-C12 cycloalkenyl group optionally have one or more atoms or groups selected from the group consisting of a halogen atom, a C1-C6 alkyl group, a C1-C6 haloalkyl group, a C1-C6 alkoxy group, a C1-C6 haloalkoxy group, a C1-C6 alkylthio group, a nitro group, an amino group optionally having a C1-C6 alkyl group, a cyano group, and a C6-C16 aryloxy group).

A tetrazolinone compound of formula (1) in which Q is Q1; $R^1$, $R^2$, $R^4$, $R^5$, $R^6$, $R^8$, $R^9$, and $R^{10}$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; A is a C6-C16 aryl group, a C2-C9 heterocyclyl group, or a C3-C12 cycloalkenyl group (provided that the C6-C16 aryl group, the C2-C9 heterocyclyl group, and the C3-C12 cycloalkenyl group optionally have one or more atoms or groups selected from the group consisting of a halogen atom, a C1-C6 alkyl group, a C1-C6 haloalkyl group, a C1-C6 alkoxy group, a C1-C6 haloalkoxy group, a C1-C6 alkylthio group, a nitro group, an amino group optionally having a C1-C6 alkyl group, a cyano group, and a C6-C16 aryloxy group).

A tetrazolinone compound of formula (1) in which Q is Q1; $R^1$, $R^2$, $R^4$, $R^5$, $R^6$, $R^8$, $R^9$, and $R^{10}$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C2-C9 heterocyclyl group or a C3-C12 cycloalkenyl group (provided that the C2-C9 heterocyclyl group and the C3-C12 cycloalkenyl group optionally have one or more atoms or groups selected from the group consisting of a halogen atom, a C1-C6 alkyl group, and a C1-C6 alkoxy group.

A tetrazolinone compound of formula (1) in which Q is Q1; $R^1$, $R^2$, $R^4$, $R^5$, $R^6$, $R^8$, $R^9$, and $R^{10}$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group (provided that the C6-C16 aryl group optionally have one or more atoms or groups selected from the group consisting of a halogen atom, a C1-C6 alkyl group, a C1-C6 haloalkyl group, a C1-C6 alkoxy group, a C1-C6 haloalkoxy group, a C1-C6 alkylthio group, a nitro group, an amino group optionally having a C1-C6 alkyl group, a cyano group, and a C6-C16 aryloxy group).

A tetrazolinone compound of formula (1) in which Q is Q2; $R^1$, $R^2$, $R^4$, $R^5$, $R^6$, $R^{12}$, and $R^{13}$ are hydrogen atoms; $R^{11}$ is a hydrogen atom or a halogen atom; $R^{14}$ is a hydrogen atom or a C1-C6 alkyl group; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group, a C2-C9 heterocyclyl group, or a C3-C12 cycloalkenyl group (provided that the C6-C16 aryl group, the C2-C9 heterocyclyl group, and the C3-C12 cycloalkenyl group optionally have one or more atoms or groups selected from the group consisting of an amino group optionally having a C1-C6 alkyl group, a halogen atom, a C1-C6 alkyl group, a C1-C6 haloalkyl group, a C1-C6 alkoxy group, a C1-C6 haloalkoxy group, and a C1-C6 alkylthio group).

A tetrazolinone compound of formula (1) in which Q is Q2; $R^1$, $R^2$, $R^4$, $R^5$, $R^6$, $R^{12}$, and $R^{13}$ are hydrogen atoms; $R^{11}$ is a hydrogen atom or a halogen atom; $R^{14}$ is a hydrogen atom or a C1-C6 alkyl group; $R^3$ is a C1-C6 alkyl group, a C3-C6 cycloalkyl group, a halogen atom, or a C1-C6 alkoxy group; $R^7$ is a methyl group; X is an oxygen atom; and A is a C2-C9 heterocyclyl group or a C3-C12 cycloalkenyl group (provided that the C2-C9 heterocyclyl group and the C3-C12 cycloalkenyl group optionally have one or more atoms or groups selected from the group consisting of a halogen atom, a C1-C6 alkyl group, and a C1-C6 alkoxy group.

A tetrazolinone compound of formula (1) in which Q is Q2; $R^1$, $R^2$, $R^4$, $R^5$, $R^6$, $R^{12}$, and $R^{13}$ are hydrogen atoms; $R^{11}$ is a hydrogen atom or a halogen atom; $R^{14}$ is a hydrogen atom or a C1-C6 alkyl group; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group (provided that the C6-C16 aryl group optionally has one or more atoms or groups selected from the group consisting of an amino group optionally having a C1-C6 alkyl group, a halogen atom, a C1-C6 alkyl group, a C1-C6 haloalkyl group, a C1-C6 alkoxy group, a C1-C6 haloalkoxy group, and a C1-C6 alkylthio group).

A tetrazolinone compound of formula (1) in which $R^1$, $R^2$, $R^4$, $R^5$, and $R^6$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group or a C2-C9 heterocyclyl group (provided that the C6-C16 aryl group and the C2-C9 heterocyclyl group optionally have one or more atoms or groups selected from the group consisting of a halogen atom, a C1-C6 alkyl group, and a C1-C6 alkoxy group).

A tetrazolinone compound of formula (1) in which $R^1$, $R^2$, $R^4$, $R^5$, and $R^6$ are hydrogen atoms; $R^3$ is a C1-C6 alkyl group, a C3-C6 cycloalkyl group, a halogen atom, or a C1-C6 alkoxy group; $R^7$ is a methyl group; X is an oxygen atom; and A is a C6-C16 aryl group (provided that the C6-C16 aryl group optionally have one or more atoms or groups selected from the group consisting of a halogen atom, a C1-C6 alkyl group, and a C1-C6 alkoxy group).

A tetrazolinone compound of formula (1) in which $R^1$, $R^2$, $R^4$, $R^5$, and $R^6$ are hydrogen atom; $R^3$ is a C1-C6 alkyl group, a C3-C6 cycloalkyl group, a halogen atom, or a C1-C6 alkoxy group; $R^7$ is a methyl group; X is an oxygen atom; and A is a C2-C9 heterocyclyl group (provided that the C2-C9 heterocyclyl group optionally has one or more atoms or groups selected from the group consisting of a halogen atom, a C1-C6 alkyl group, and a C1-C6 alkoxy group).

[Aspect 6]

A tetrazolinone compound of formula (1) in which Q is Q1; $R^1$, $R^2$, $R^4$, $R^5$, $R^6$, $R^8$, $R^9$, and $R^{10}$ are hydrogen atoms; $R^3$ is a C1-C6 alkyl group, a C3-C6 cycloalkyl group, a halogen atom, or a C1-C6 alkoxy group; $R^7$ is a C1-C6 alkyl group; X is an oxygen atom; and A is a phenyl group, a pyridinyl group, a benzoxazolyl group, a quinolyl group, a piperidinyl group, a morpholinyl group, a piperazinyl group, or a cyclohexenyl group (provided that the phenyl group, the pyridinyl group, the benzoxazolyl group, the quinolinyl group, the piperidinyl group, the morpholinyl group, the piperazinyl group, and the cyclohexenyl group optionally have one or more atoms or groups selected from the group consisting of a halogen atom, a C1-C6 alkyl group, a C1-C6 haloalkyl group, a C1-C6 alkoxy group, a C1-C6 haloalkoxy group, a C1-C6 alkylthio group, a nitro group, an amino group optionally having a C1-C6 alkyl group, a cyano group, a formyl group, a C2-C6 alkylcarbonyl group, a C2-C6 alkoxycarbonyl group, a C1-C6 alkylsulfonyl group, an aminosulfonyl group optionally having a C1-C6 alkyl group, and a phenoxy group).

A tetrazolinone compound in which $R^3$ is a C1-C6 alkyl group and A is a phenyl group in [Aspect 6].

A tetrazolinone compound in which $R^3$ is a C3-C6 cycloalkyl group and A is a phenyl group in [Aspect 6].

A tetrazolinone compound in which $R^3$ is a halogen atom and A is a phenyl group in [Aspect 6].

A tetrazolinone compound in which $R^3$ is a C1-C6 alkoxy group and A is a phenyl group in [Aspect 6].

A tetrazolinone compound in which $R^3$ is a C1-C6 alkyl group and A is a quinolyl group in [Aspect 6].

[Aspect 7]

A tetrazolinone compound of formula (1) in which Q is Q2; $R^{11}$, $R^{12}$, $R^{13}$, and $R^{14}$ each independently represents a hydrogen atom, a halogen atom, or a C1-C6 alkyl group; $R^1$, $R^2$, $R^4$, $R^5$, and $R^6$ are hydrogen atoms; $R^3$ is a 1-C6 alkyl group, a C3-C6 cycloalkyl group, a halogen atom, or a C1-C6 alkoxy group; $R^5$ is a C1-C6 alkyl group; X is an oxygen atom; and A is a phenyl group, a pyridinyl group, a benzo[1,3]dioxol-5-yl group, a benzoxazolyl group, a quinolyl group, a pyrimidinyl group, a pyridazinyl group, or a cyclohexenyl group (provided that the phenyl group, the pyridinyl group, the benzo[1,3]dioxol-5-yl group, the benzoxazolyl group, the quinolyl group, the pyrimidinyl group, the pyridazinyl group, and the cyclohexenyl group optionally have one or more atoms or groups selected from the group consisting of a halogen atom, a C1-C6 alkyl group, a C1-C6 haloalkyl group, a C1-C6 alkoxy group, a C1-C6 haloalkoxy group, a C1-C6 alkylthio group, and an amino group optionally having a C1-C6 alkyl group).

A tetrazolinone compound in which $R^3$ is a C1-C6 alkyl group and A is a phenyl group in [Aspect 7].

A tetrazolinone compound in which $R^3$ is a C3-C6 cycloalkyl group and A is a phenyl group in [Aspect 7].

A tetrazolinone compound in which $R^3$ is a halogen atom and A is a phenyl group in [Aspect 7].

A tetrazolinone compound in which $R^3$ is a C1-C6 alkoxy group and A is a phenyl group in [Aspect 7].

A tetrazolinone compound of formula (1) in which Q is Q3; $R^1$, $R^2$, $R^4$, $R^5$, $R^6$, $R^{15}$, and $R^{16}$ are hydrogen atoms; $R^3$ is a C1-C6 alkyl group; $R^7$ is a C1-C6 alkyl group; X is an oxygen atom; and A is a phenyl group optionally having a C1-C6 alkoxy group.

A tetrazolinone compound of formula (1) in which Q is Q4; $R^1$, $R^2$, $R^4$, $R^5$, $R^6$, $R^{17}$, and $R^{18}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a halogen atom and a C1-C6 alkoxy group).

A tetrazolinone compound of formula (1) in which Q is Q5; $R^1$, $R^2$, $R^4$, $R^5$, $R^6$, $R^{19}$, and $R^{20}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a halogen atom and a C1-C6 alkoxy group).

A tetrazolinone compound of formula (1) in which Q is Q6; $R^1$, $R^2$, $R^4$, $R^5$, $R^6$, and $R^{21}$ are hydrogen atoms; $R^3$ is a C1-C6 alkyl group; $R^7$ is a C1-C6 alkyl group; X is an oxygen atom; and A is a phenyl group optionally having a C1-C6 alkoxy group.

A tetrazolinone compound of formula (1) in which Q is Q7; $R^1$, $R^2$, $R^4$, $R^5$, $R^6$, $R^{22}$, and $R^{23}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a cyano group, a C1-C6 alkoxy group, and an amino group optionally having a C1-C6 alkyl group).

A tetrazolinone compound of formula (1) in which Q is Q8; $R^1$, $R^2$, $R^4$, $R^5$, $R^6$, $R^{24}$, and $R^{25}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a halogen atom and a C1-C6 alkoxy group).

A tetrazolinone compound of formula (1) in which Q is Q9; $R^1$, $R^2$, $R^4$, $R^5$, $R^6$, $R^{27}$, $R^{28}$, and $R^{29}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a halogen atom and a C1-C6 alkoxy group).

A tetrazolinone compound of formula (1) in which Q is Q10; $R^1$, $R^2$, $R^4$, $R^5$, $R^6$, $R^{30}$, $R^{31}$, and $R^{32}$ are hydrogen atoms; $R^3$ is a C1-C6 alkyl group; $R^7$ is a C1-C6 alkyl group; X is an oxygen atom; and A is a phenyl group (provided that the phenyl group optionally has one or more atoms or groups selected from the group consisting of a halogen atom and a C1-C6 alkoxy group).

[Aspect 8]

A tetrazolinone compound of formula (1) in which A is formula (2), Q is Q1,
$R^{37}$ is a halogen atom, a C1-C6 alkyl group, a C1-C6 haloalkyl group, a C1-C6 alkoxy group, or a C1-C6 haloalkoxy group,
$R^{38}$, $R^{39}$, and $R^{40}$ are hydrogen atoms; $R^{41}$ is a C1-C3 alkoxy group or a C1-C3 haloalkoxy group; $R^4$, $R^2$, $R^4$, $R^5$, and $R^6$ are hydrogen atoms; $R^7$ is a methyl group; $R^8$, $R^9$, and $R^{10}$ are hydrogen atoms or halogen atoms; and X is an oxygen atom.

A tetrazolinone compound in which $R^3$ is a C1-C6 alkyl group in [Aspect 8].

A tetrazolinone compound in which $R^3$ is a C3-C6 cycloalkyl group in [Aspect 8].

A tetrazolinone compound in which $R^3$ is a halogen atom in [Aspect 8].

A tetrazolinone compound in which $R^3$ is a C1-C6 alkoxy group in [Aspect 8].

A tetrazolinone compound of formula (1) in which A is formula (4).

[Aspect 9]

A tetrazolinone compound in which A is formula (4), $R^{42}$ is a halogen atom, a C1-C6 alkyl group, a C1-C6 haloalkyl group, a C1-C6 alkoxy group, or a C1-C6 haloalkoxy group; $R^{43}$ and $R^{44}$ are hydrogen atoms; $R^{45}$ is a C1-C3 alkoxy group or a C1-C3 haloalkoxy group; $R^1$, $R^2$, $R^4$, $R^5$, and $R^6$ are hydrogen atoms; $R^7$ is a methyl group; and X is an oxygen atom.

A tetrazolinone compound in which $R^3$ is a C1-C6 alkyl group and Q is Q1 in [Aspect 9].

A tetrazolinone compound in which $R^3$ is a C3-C6 cycloalkyl group and Q is Q1 in [Aspect 9].

A tetrazolinone compound in which $R^3$ is a halogen atom and Q is Q1 in [Aspect 9].

A tetrazolinone compound in which $R^3$ is a C1-C6 alkoxy group and Q is Q1 in [Aspect 9].

A tetrazolinone compound in which $R^3$ is a C1-C6 alkyl group and Q is Q2 in [Aspect 9].

A tetrazolinone compound in which $R^3$ is a C3-C6 cycloalkyl group and Q is Q2 in [Aspect 9].

A tetrazolinone compound in which $R^3$ is a halogen atom and Q is Q2 in [Aspect 9].

A tetrazolinone compound in which $R^3$ is a C1-C6 alkoxy group and Q is Q2 in [Aspect 9].

As used herein, compounds represented by general formulas include individual stereoisomers and stereoisomer mixtures, such as all active geometrical isomers and optical isomers.

Next, a process for producing the present compound will be described.

The present compound can be produced, for example, by the following Production Processes.

(Production Process A)

The present compound represented by formula (1) (hereinafter referred to as the compound (1)) can be produced by reacting a compound represented by formula (A1) (hereinafter referred to as the compound (A1)) with a compound represented by formula (A2) (hereinafter referred to as the compound (A2)) in the presence of a base:

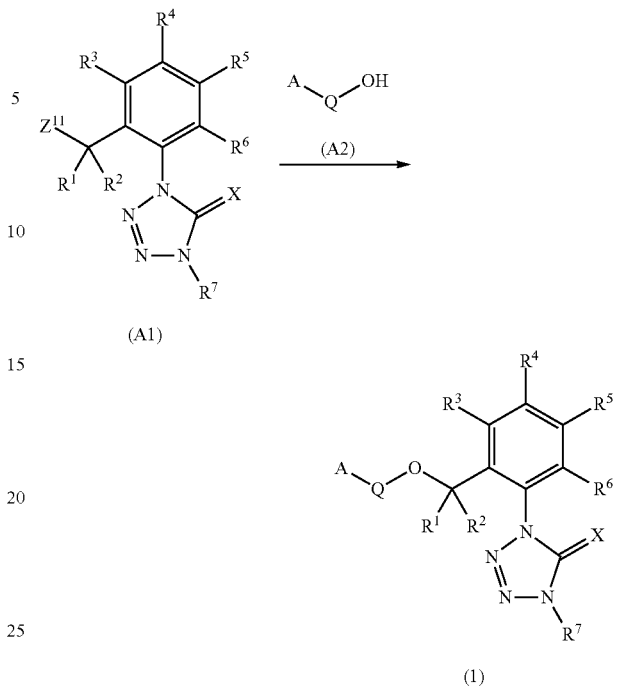

wherein $R^1$, $R^2$, $R^3$, $R^4$, $R^5$, $R^6$, $R^7$, X, A, and Q are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

Among the compounds (1), a compound in which A is $A^1$ (hereinafter referred to as the compound (1-1)) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

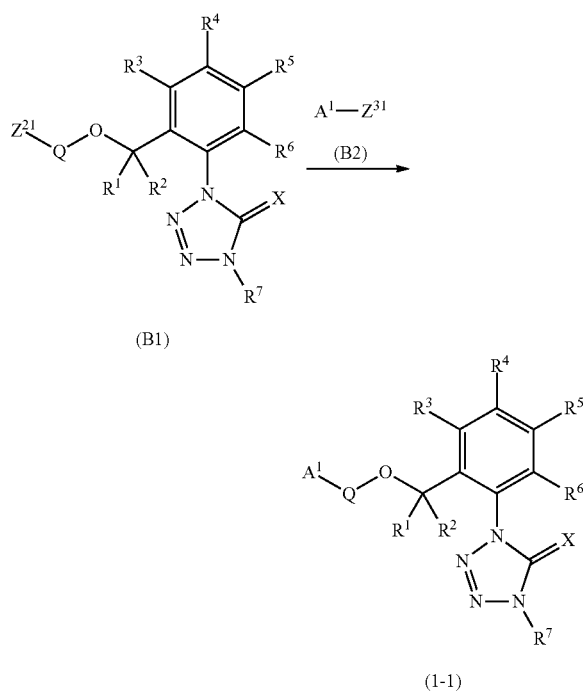

wherein $R^1$, $R^2$, $R^3$, $R^4$, $R^5$, $R^6$, $R^7$, X, and Q are the same as defined above, $A^1$ represents a C6-C16 aryl group optionally having one or more atoms or groups selected from Group P, a C2-C9 heteroaryl group optionally having one or more atoms or groups selected from Group P, a C3-C12 cycloalkyl group optionally having one or more atoms or groups selected from Group P, or a C3-C12 cycloalkenyl group optionally having one or more atoms or groups selected from Group P, $Z^{21}$ represents a chlorine atom, a bromine atom, or an iodine atom, and $Z^{31}$ represents $B(OH)_2$, an alkoxyboryl group, or trifluoroborate $BF_3^-K^+$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce the compound (B2) which is a boric acid ester derivative, for example, by reacting an iodine compound ($A^1$-I) or a bromo compound ($A^1$-Br) with an alkyllithium such as butyllithium, followed by a reaction with a boric acid ester. It is possible to produce the compound (B2), which is a boric acid ester derivative, by optionally hydrolyzing the compound (B2) as the boric acid ester derivative obtained in the above-mentioned reaction. It is also possible to produce the compound (B2), which is trifluoroborate $BF_3^-K^+$, by fluorinating a certain compound (B2) with potassium hydrogen fluoride in accordance with a known method mentioned in Molander et al. Acc. Chem. Res., 2007, 40, 275.

Examples of the catalyst to be used in the reaction between the compound (B1) and the compound (B2) include palladium(II) acetate, dichlorobis(triphenylphosphine)palladium, tetrakistriphenylphosphinepalladium(0), palladium(II) acetate/triscyclohexylphosphine, bis(diphenylphoshineferrocenyl)palladium(II) dichloride, tris(dibenzylideneacetone)dipalladium, and the like.

Examples of the base to be used in the reaction between the compound (B1) and the compound (B2) include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction between the compound (B1) and the compound (B2), the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction between the compound (B1) and the compound (B2) is usually within a range of 0 to 150° C. The reaction time of the reaction is usually within a range of 0.1 to 24 hours.

After completion of the reaction, the present compound represented by formula (1-1) can be isolated by performing post-treatment operations such as extraction of the reaction mixture with an organic solvent, and drying and concentration of the organic layer. The isolated present compound can be further purified by chromatography, recrystallization, and the like.

(Production Process C)

Among the compounds (1), a compound in which A is $A^2$ (hereinafter referred to as the compound (1-2)) can be produced by subjecting a compound represented by formula (B1) and a compound represented by formula (C1) (hereinafter referred to as the compound (C1)) to a coupling reaction in the presence of a base and a catalyst:

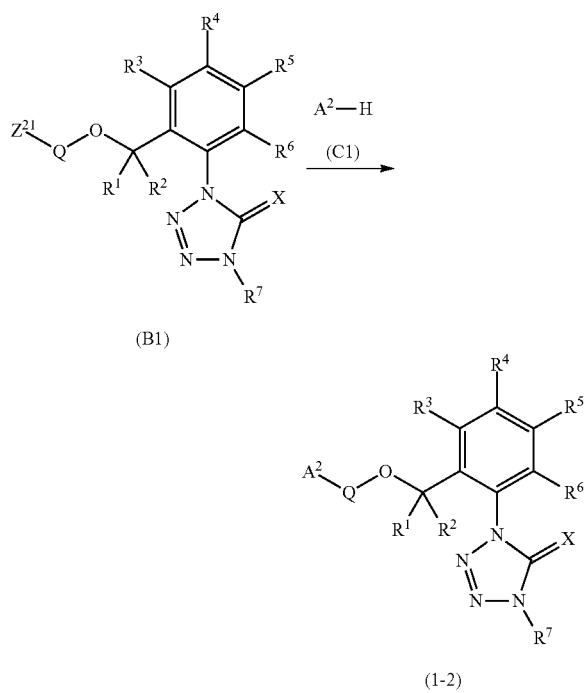

wherein $R^1$, $R^2$, $R^3$, $R^4$, $R^5$, $R^6$, $R^7$, X, Q, and $Z^{21}$ are the same as defined above, and $A^2$ represents a C2-C9 heterocyclyl group optionally having one or more atoms or groups selected from Group P (provided that the heterocyclyl group optionally has, as a ring-constituent atom, one or more nitrogen atoms and also one or more oxygen atoms or sulfur atoms, and nitrogen and hydrogen atoms constituting the heterocyclyl group are bound to each other).

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

It is possible to usually use, as the compound (C1) to be used in the reaction, commercially available compounds. Specific examples thereof include morpholine, piperidine, piperazine, N-methylpiperazine, thiomorpholine, n-propyl bromide, pyrrolidine, ethylenimine, azacyclobutane, hexamethyleneimine, pyrrole, imidazole, pyrazole, and the like. Examples of the catalyst to be used in the reaction include copper(I) iodide, copper(II) acetate, cobalt(II) chloride, palladium(II) acetate, dichlorobis(triphenylphosphine)palladium, tetrakistriphenylphosphinepalladium(0), palladium (II) acetate/triscyclohexylphosphine, bis (diphenylphoshineferrocenyl)palladium(II) dichloride, and tris(dibenzylideneacetone)dipalladium.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (C1) is usually used in the proportion within a range of 1 to 10 mols, the catalyst is usually used in the proportion within a range of 0.001 to 5 mol, and the base is usually used in the proportion within a range of 1 to 10 mols, based on 1 mol of the compound (B1).

If necessary, ligands such as 1,10-phenanthroline and tetramethylethylenediamine may be added in the reaction, and these compounds are usually used in the proportion of 0.001 to 5 mols based on 1 mol of the compound (B1).

The reaction temperature of the reaction is usually within a range of −20 to 150° C. The reaction time of the reaction is usually within a range of 0.1 to 24 hours.

After completion of the reaction, the present compound represented by formula (1-2) can be isolated by performing post-treatment operations such as extraction of the reaction mixture with an organic solvent, and drying and concentration of the organic layer. The isolated present compound can be further purified by chromatography, recrystallization, and the like.

(Production Process D)

Among the compounds (1), a compound in which $R^7$ is a hydrogen atom (hereinafter referred to as the compound (1-3)) can be produced by reacting a compound represented by formula (D1) (hereinafter referred to as the compound (D1)) with an azidation agent:

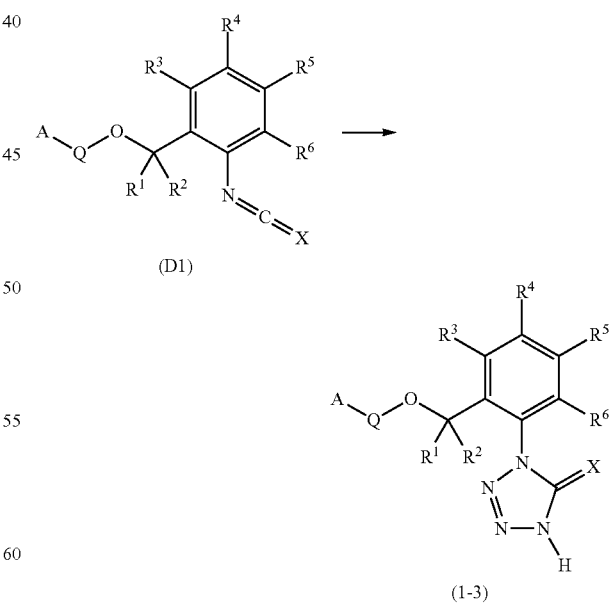

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (D1).

The reaction temperature of the reaction is usually within a range of −20 to 150° C. The reaction time of the reaction is usually within a range of 0.1 to 24 hours.

If necessary, Lewis acid such as aluminum chloride or zinc chloride may be added in the reaction, and these compounds are usually used in the proportion of 0.05 to 5 mols based on 1 mol of the compound (D1).

After completion of the reaction, the present compound represented by formula (1-3) can be isolated by performing post-treatment operations such as extraction of the reaction mixture with an organic solvent, and drying and concentration of the organic layer. The isolated present compound can be further purified by chromatography, recrystallization, and the like.

(Production Process E)

The compound (1) can be produced by reacting the compound (1-3) with a compound represented by formula (E1) (hereinafter referred to as the compound (E1)) in the presence of a base:

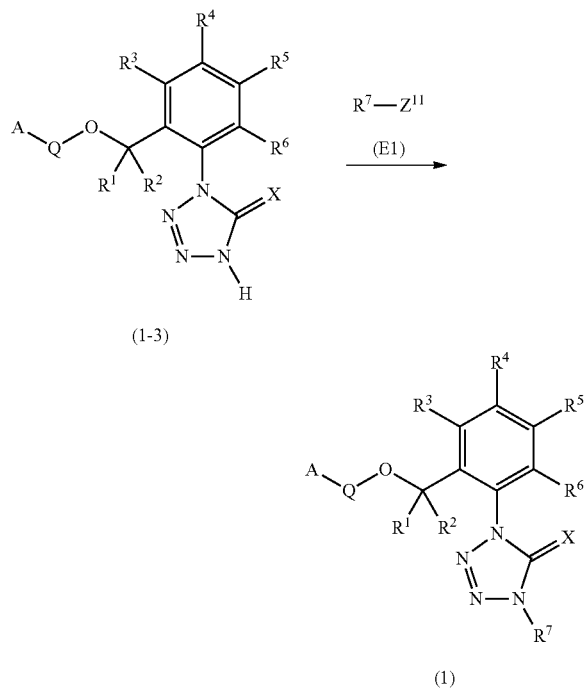

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually used, as the compound (E1) to be used in the reaction, commercially available products. Specific examples thereof include alkyl halides such as chlorodifluoromethane, methyl bromide, ethyl bromide, n-propyl bromide, methyl iodide, ethyl iodide, n-propyl bromide, allyl bromide, cyclopropyl bromide, and 1,1-difluoro-2-iodoethane; dialkyl sulfates such as dimethyl sulfate; and alkyl or arylsulfonic acid esters, such as methyl p-toluenesulfonate, ethyl p-toluenesulfonate, n-propyl p-toluenesulfonate, methyl methanesulfonate, ethyl methanesulfonate, and n-propyl methanesulfonate.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols and the base is usually used in the proportion within a range of 1 to 10 mols, based on 1 mol of the compound (1-3).

The reaction temperature of the reaction is usually within a range of −20 to 150° C. The reaction time of the reaction is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the compounds (1), a compound in which X is a sulfur atom (hereinafter referred to as the compound (1-S)) can be produced by a known sulfidation reaction from a compound in which X is an oxygen atom (hereinafter referred to as the compound (1-O)) of the present compounds represented by formula (1):

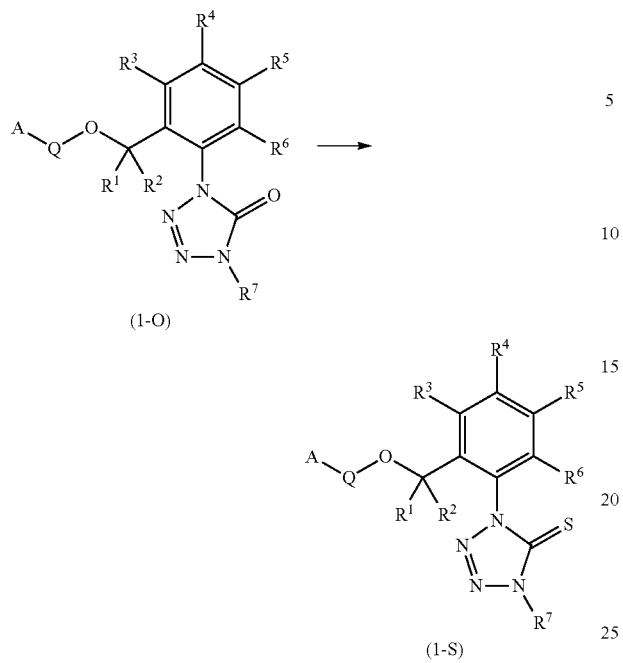

(1-O)

(1-S)

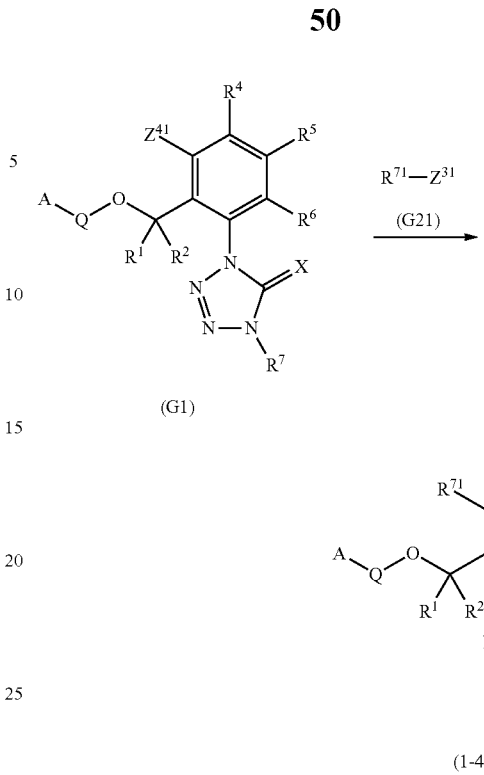

(G1)

(1-4)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

If necessary, organic bases such as pyridine and trimethylamine; and inorganic bases such as alkali metal hydroxide and alkali metal carbonate may be added in the reaction, and the amount of the base to be added is within a range of 0.5 to 1.5 mols based on the compound (1-O).

After completion of the reaction, the present compound represented by formula (1-S) can be isolated by performing post-treatment operations such as extraction of the reaction mixture with an organic solvent, and drying and concentration of the organic layer. The isolated present compound can be further purified by chromatography, recrystallization, and the like.

(Production Process G)

Among the compounds (1), a compound represented by formula (1-4) in which $R^3$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

wherein $R^1$, $R^2$, $R^4$, $R^5$, $R^6$, $R^7$, X, A, Q, and $Z^{31}$ are the same as defined above, $Z^{41}$ represents a chlorine atom, a bromine atom, an iodine atom, or a trifluoromethanesulfonyloxy group, and $R^{71}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, or a C3-C6 halocycloalkyl group.

The reaction can be carried out in accordance with the reaction mentioned in Production Process B.

Among the compounds (1), a compound represented by formula (1-5) in which $R^4$ is $R^{72}$ (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

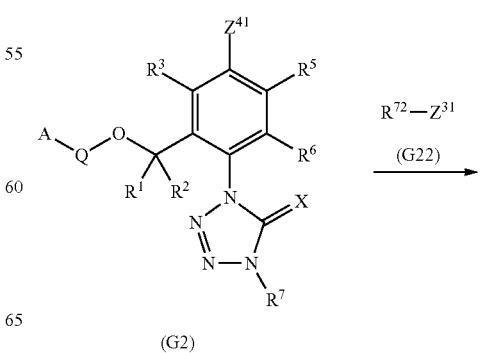

(G2)

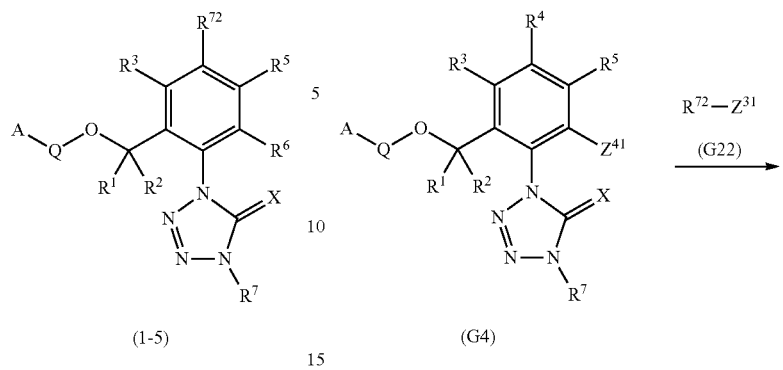

(1-5)　　　(G4)

wherein $R^1$, $R^2$, $R^3$, $R^5$, $R^6$, $R^7$, X, A, Q, $Z^{31}$ and $Z^{41}$ are the same as defined above, and $R^{72}$ represents a C1-C4 alkyl group, a C1-C4 haloalkyl group, a C3-C5 cycloalkyl group, or a C3-C5 halocycloalkyl group.

The reaction can be carried out in accordance with the reaction mentioned in Production Process B.

Among the compounds (1), a compound represented by formula (1-6) in which $R^5$ is $R^{72}$ (hereinafter referred to as the compound (1-6)) can be produced in accordance with the reaction mentioned in Production Process B, using a compound represented by formula (G3) (hereinafter referred to as the compound (G3)) and the compound (G22):

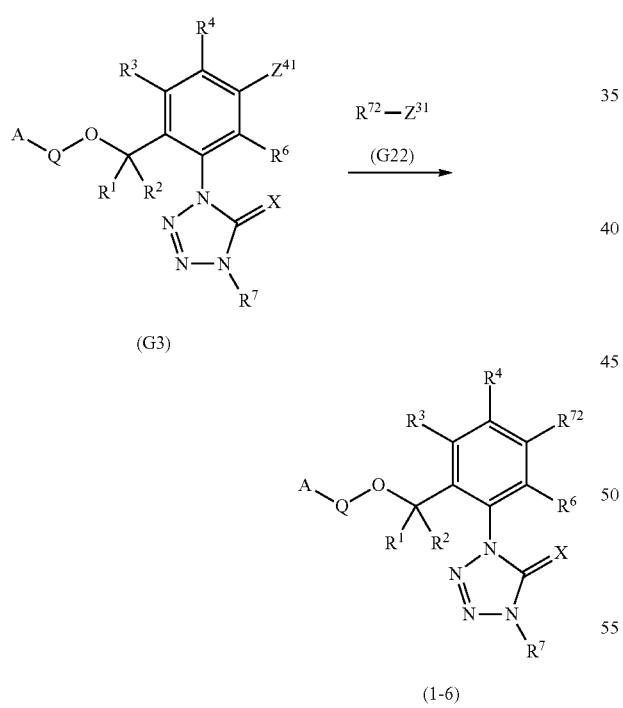

(1-7)

wherein symbols are the same as defined above.

Among the compounds (1), a compound in which two or more substituents selected from $R^3$, $R^4$, $R^5$, and $R^6$ are $R^{71}$ and/or $R^{72}$ can be produced in accordance with Production Process B.

It is also possible to produce the compound (1-4), the compound (1-5), the compound (1-6), and the compound (1-7) using the other known coupling reaction in place of the coupling reaction of Production Process B.

(Production Process H)

Among the compounds (1), a compound represented by formula (1-8) in which Q is Q1 and $R^8$ is $R^{73}$ (hereinafter referred to as the compound (1-8)) can be produced in accordance with the reaction mentioned in Production Process B, using a compound represented by formula (H1) (hereinafter referred to as the compound (H1)) and a compound represented by formula (H21) (hereinafter referred to as the compound (H21)):

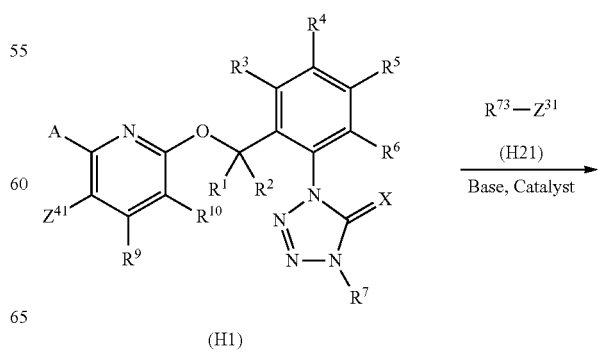

(H1)

wherein symbols are the same as defined above.

Among the compounds (1), a compound represented by formula (1-7) in which $R^6$ is $R^{72}$ (hereinafter referred to as the compound (1-7)) can be produced in accordance with the reaction mentioned in Production Process B, using a compound represented by formula (G4) (hereinafter referred to as the compound (G4)) and the compound (G22):

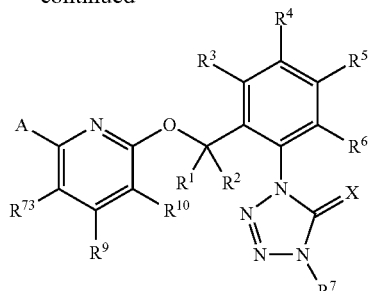

(1-8)

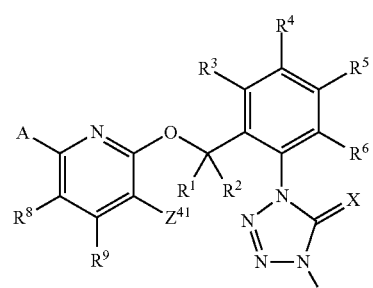

(H3)

wherein $R^1$, $R^2$, $R^3$, $R^4$, $R^5$, $R^6$, $R^7$, $R^9$, $R^{10}$, X, A, $Z^{31}$, and $Z^{41}$ are the same as defined above, and $R^{73}$ represents a C1-C6 alkyl group optionally having a group selected from Group $P^1$, a C3-C6 cycloalkyl group having a group selected from Group $P^1$, a C2-C6 alkenyl group, a C2-C6 haloalkenyl group, a C2-C6 alkynyl group, or a C2-C6 haloalkynyl group.

Among the compounds (1), a compound represented by formula (1-9) in which Q is Q1 and $R^9$ is $R^{73}$ (hereinafter referred to as the compound (1-9)) can be produced in accordance with the reaction mentioned in Production Process B, using a compound represented by formula (H2) (hereinafter referred to as the compound (H2)) and the compound (H21):

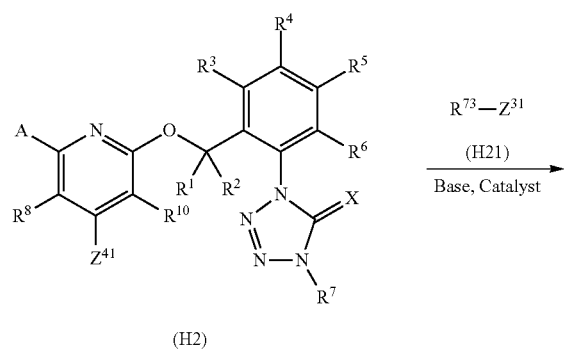

(1-9)

wherein symbols are the same as defined above.

Among the compounds (1), a compound represented by formula (1-10) in which Q is Q1 and $R^{10}$ is $R^{73}$ (hereinafter referred to as the compound (1-10)) can be produced in accordance with the reaction mentioned in Production Process B, using a compound represented by formula (H3) (hereinafter referred to as the compound (H3)) and the compound (H21):

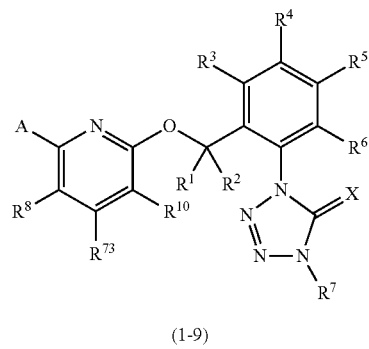

(1-10)

wherein symbols are the same as defined above.

Among the compounds (1), a compound in which two or more substituents selected from $R^8$, $R^9$, and $R^{10}$ are $R^{73}$ can be produced in accordance with Production Process B.

It is also possible to produce the compound (1) using the other known coupling reaction in place of the coupling reaction of Production Process B.

(Production Process I)

Among the compounds (1), a compound represented by formula (1-11) in which Q is Q2 and $R^{11}$ is $R^{73}$ (hereinafter referred to as the compound (1-11)) can be produced in accordance with the reaction mentioned in Production Process B, using a compound represented by formula (I1) (hereinafter referred to as the compound (I1)) and the compound (H21):

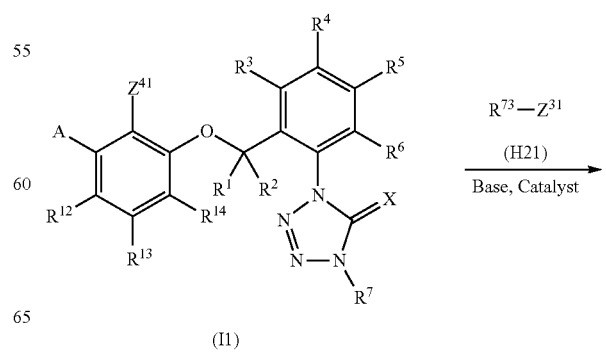

(I1)

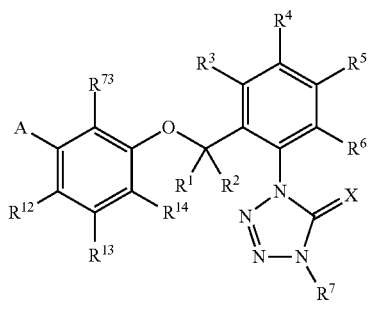

(1-11)

wherein symbols are the same as defined above.

Among the compounds (1), a compound represented by formula (1-12) in which Q is Q2 and $R^{12}$ is $R^{73}$ (hereinafter referred to as the compound (1-12)) can be produced in accordance with the reaction mentioned in Production Process B, using a compound represented by formula (I2) (hereinafter referred to as the compound (I2)) and the compound (H21):

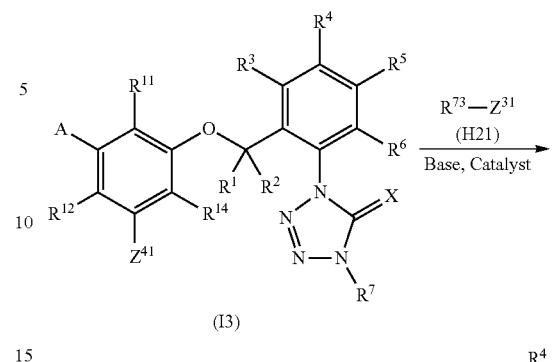

(I3)

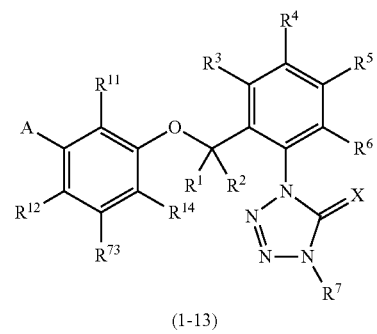

(1-13)

wherein symbols are the same as defined above.

Among the compounds (1), a compound represented by formula (1-14) in which Q is Q2 and $R^{14}$ is $R^{73}$ (hereinafter referred to as the compound (1-14)) can be produced in accordance with the reaction mentioned in Production Process B, using a compound represented by formula (I4) (hereinafter referred to as the compound (I4)) and the compound (H21):

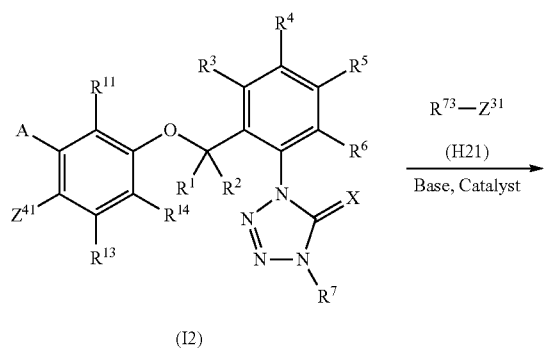

(I2)

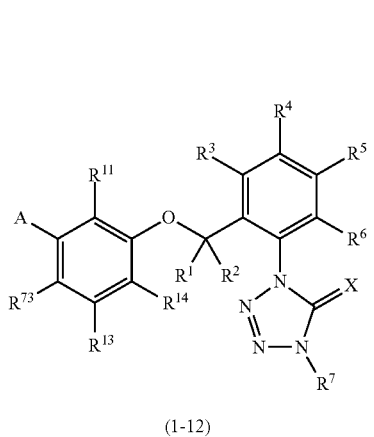

(1-12)

wherein symbols are the same as defined above.

Among the compounds (1), a compound represented by formula (1-13) in which Q is Q2 and $R^{13}$ is $R^{73}$ (hereinafter referred to as the compound (1-13)) can be produced in accordance with the reaction mentioned in Production Process B, using a compound represented by formula (I3) (hereinafter referred to as the compound (I3)) and the compound (H21):

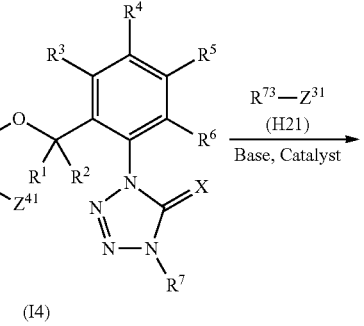

(I4)

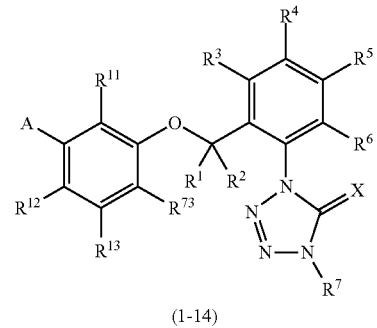

(1-14)

wherein symbols are the same as defined above.

Among the compounds (1), a compound in which two or more substituents selected from $R^{11}$, $R^{12}$, $R^{13}$, and $R^{14}$ are $R^{73}$ can be produced in accordance with Production Process B.

It is also possible to produce the compound (1) using the other known coupling reaction in place of the coupling reaction of Production Process B.

(Production Process J)

Among the compounds (1), a compound represented by formula (1-15) in which Q is Q3 and $R^{15}$ is $R^{73}$ (hereinafter referred to as the compound (1-15)) can be produced in accordance with the reaction mentioned in Production Process B, using a compound represented by formula (J1) (hereinafter referred to as the compound (J1)) and the compound (H21):

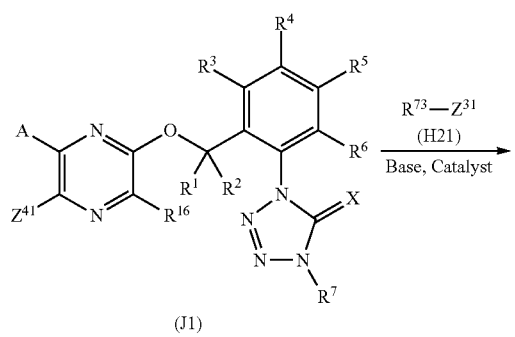

wherein symbols are the same as defined above.

Among the compounds (1), a compound represented by formula (1-16) in which Q is Q3 and $R^{16}$ is $R^{73}$ (hereinafter referred to as the compound (1-16)) can be produced in accordance with the reaction mentioned in Production Process B, using a compound represented by formula (J2) (hereinafter referred to as the compound (J2)) and the compound (H21):

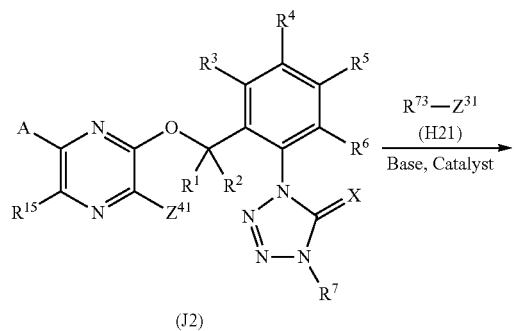

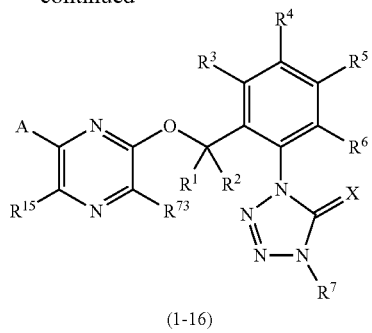

wherein symbols are the same as defined above.

Among the compounds (1), a compound in which $R^{15}$ and $R^{16}$ are $R^{73}$ can be produced in accordance with Production Process B.

It is also possible to produce the compound (1) using the other known coupling reaction in place of the coupling reaction of Production Process B.

(Production Process K)

Among the compounds (1), a compound represented by formula (1-17) in which Q is Q4 and $R^{17}$ is $R^{73}$ (hereinafter referred to as the compound (1-17)) can be produced in accordance with the reaction mentioned in Production Process B, using a compound represented by formula (K1) (hereinafter referred to as the compound (K1)) and the compound (H21):

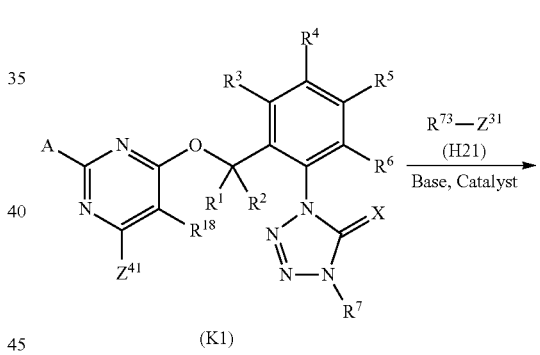

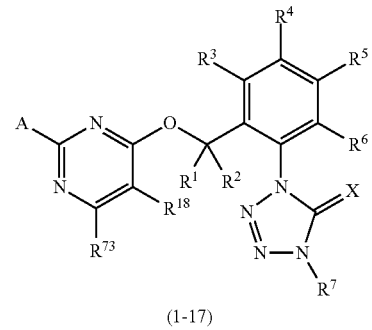

wherein symbols are the same as defined above.

Among the compounds (1), a compound represented by formula (1-18) in which Q is Q4 and $R^{18}$ is $R^{73}$ (hereinafter referred to as the compound (1-18)) can be produced in accordance with the reaction mentioned in Production Process B, using a compound represented by formula (K2) (hereinafter referred to as the compound (K2)) and the compound (H21):

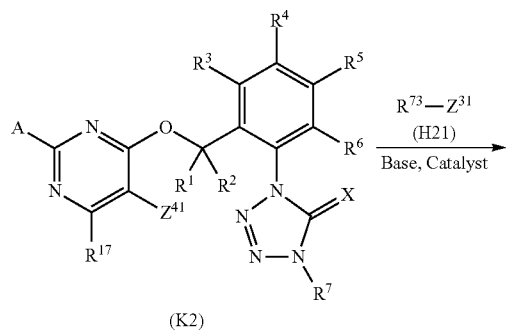

(K2)

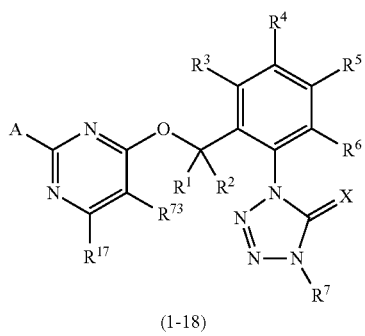

(1-18)

wherein symbols are the same as defined above.

Among the compounds (1), a compound in which $R^{17}$ and $R^{18}$ are $R^{73}$ can be produced in accordance with Production Process B.

It is also possible to produce the compound (1) using the other known coupling reaction in place of the coupling reaction of Production Process B.

(Production Process L)

Among the compounds (1), a compound represented by formula (1-19) in which Q is Q5 and $R^{19}$ is $R^{73}$ (hereinafter referred to as the compound (1-19)) can be produced in accordance with the reaction mentioned in Production Process B, using a compound represented by formula (L1) (hereinafter referred to as the compound (L1)) and the compound (H21):

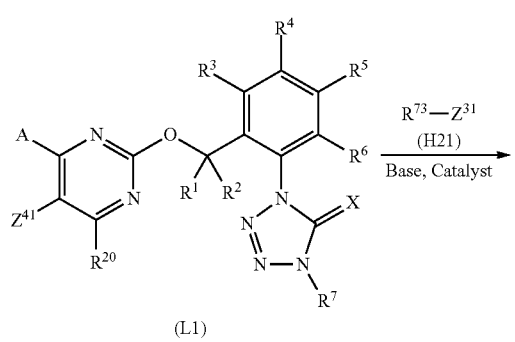

(L1)

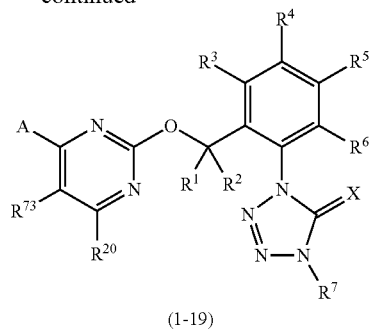

(1-19)

wherein symbols are the same as defined above.

Among the compounds (1), a compound represented by formula (1-20) in which Q is Q5 and $R^{20}$ is $R^{73}$ (hereinafter referred to as the compound (1-20)) can be produced in accordance with the reaction mentioned in Production Process B, using a compound represented by formula (L2) (hereinafter referred to as the compound (L2)) and the compound (H21):

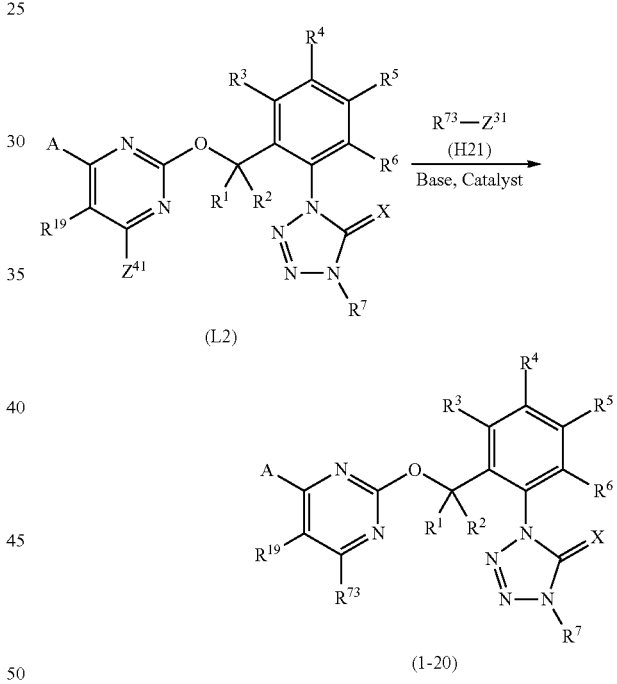

wherein symbols are the same as defined above.

Among the compounds (1), a compound in which $R^{19}$ and $R^{20}$ are $R^{73}$ can be produced in accordance with Production Process B.

It is also possible to produce the compound (1) using the other known coupling reaction in place of the coupling reaction of Production Process B.

(Production Process M)

Among the compounds (1), a compound represented by formula (1-21) in which Q is Q6 and $R^{21}$ is $R^{73}$ (hereinafter referred to as the compound (1-21)) can be produced in accordance with the reaction mentioned in Production Process B, using a compound represented by formula (M1) (hereinafter referred to as the compound (M1)) and the compound (H21):

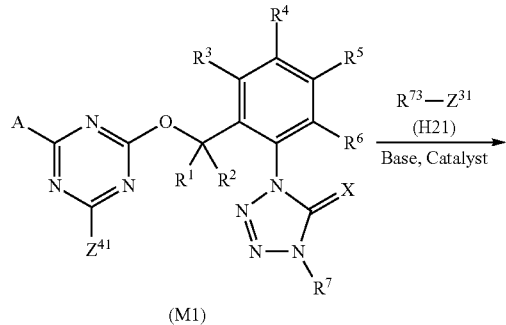

(M1)

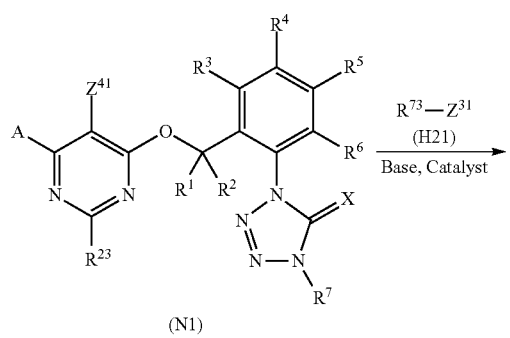

(1-21)

wherein symbols are the same as defined above.

It is also possible to produce the compound (1) using the other known coupling reaction in place of the coupling reaction of Production Process B.

(Production Process N)

Among the compounds (1), a compound represented by formula (1-22) in which Q is Q7 and $R^{22}$ is $R^{73}$ (hereinafter referred to as the compound (1-22)) can be produced in accordance with the reaction mentioned in Production Process B, using a compound represented by formula (N1) (hereinafter referred to as the compound (N1)) and the compound (H21):

(N1)

(1-22)

wherein symbols are the same as defined above.

Among the compounds (1), a compound represented by formula (1-23) in which Q is Q7 and $R^{23}$ is $R^{73}$ (hereinafter referred to as the compound (1-23)) can be produced in accordance with the reaction mentioned in Production Process B, using a compound represented by formula (N2) (hereinafter referred to as the compound (N2)) and the compound (H21):

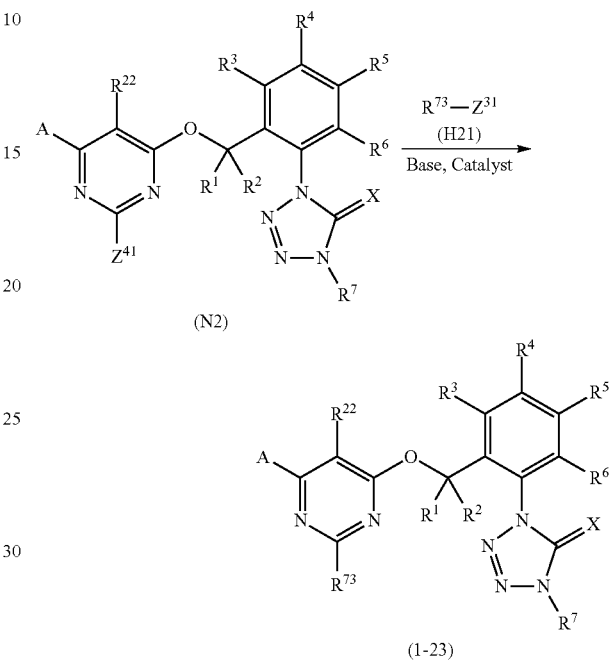

(N2)

(1-23)

wherein symbols are the same as defined above.

Among the compounds (1), a compound in which $R^{22}$ and $R^{23}$ are $R^{73}$ can be produced in accordance with Production Process B.

It is also possible to produce the compound (1) using the other known coupling reaction in place of the coupling reaction of Production Process B.

(Production Process O)

Among the compounds (1), a compound represented by formula (1-24) in which Q is Q8 and $R^{24}$ is $R^{73}$ (hereinafter referred to as the compound (1-24)) can be produced in accordance with the reaction mentioned in Production Process B, using a compound represented by formula (O1) (hereinafter referred to as the compound (O1)) and the compound (H21):

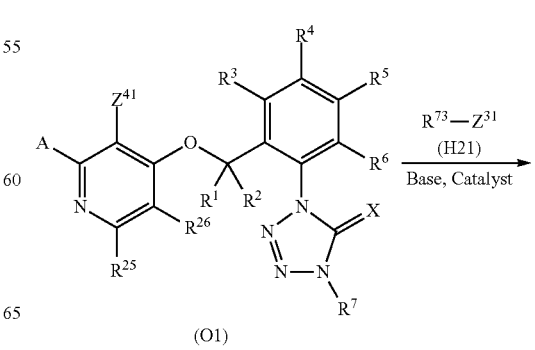

(O1)

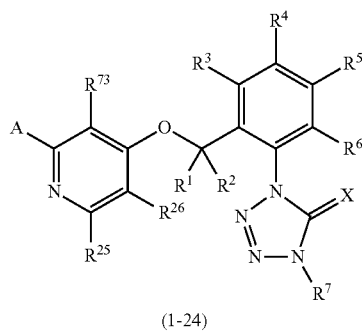

(1-24)

wherein symbols are the same as defined above.

Among the compounds (1), a compound represented by formula (1-25) in which Q is Q8 and $R^{25}$ is $R^{73}$ (hereinafter referred to as the compound (1-25)) can be produced in accordance with the reaction mentioned in Production Process B, using a compound represented by formula (O2) (hereinafter referred to as the compound (O2)) and the compound (H21):

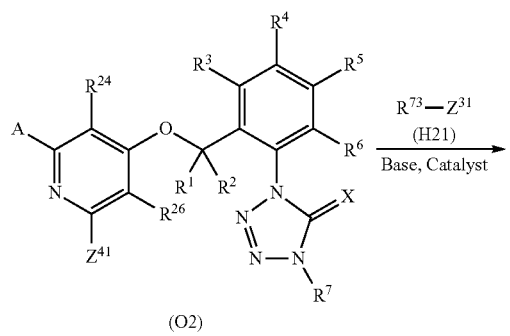

(O2) → (1-25)

wherein symbols are the same as defined above.

Among the compounds (1), a compound represented by formula (1-26) in which Q is Q8 and $R^{26}$ is $R^{73}$ (hereinafter referred to as the compound (1-26)) can be produced in accordance with the reaction mentioned in Production Process B, using a compound represented by formula (O3) (hereinafter referred to as the compound (O3)) and the compound (H21):

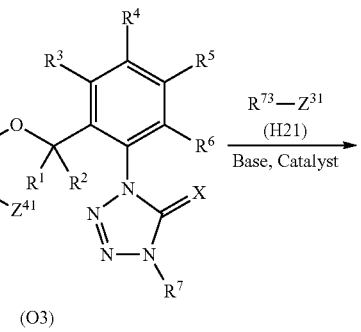

(O3) → (1-26)

wherein symbols are the same as defined above.

Among the compounds (1), a compound in which two or more substituents selected from $R^{24}$, $R^{25}$, and $R^{26}$ are $R^{73}$ can be produced in accordance with Production Process B.

It is also possible to produce the compound (1) using the other known coupling reaction in place of the coupling reaction of Production Process B.

(Production Process P)

Among the compounds (1), a compound represented by formula (1-27) in which Q is Q9 and $R^{27}$ is $R^{73}$ (hereinafter referred to as the compound (1-27)) can be produced in accordance with the reaction mentioned in Production Process B, using a compound represented by formula (P1) (hereinafter referred to as the compound (P1)) and the compound (H21):

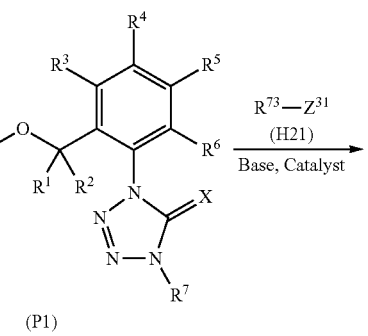

(P1)

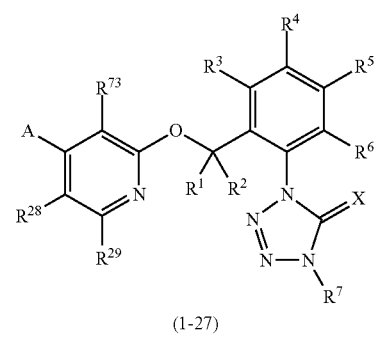

(1-27)

wherein symbols are the same as defined above.

Among the compounds (1), a compound represented by formula (1-28) in which Q is Q9 and $R^{28}$ is $R^{73}$ (hereinafter referred to as the compound (1-28)) can be produced in accordance with the reaction mentioned in Production Process B, using a compound represented by formula (P2) (hereinafter referred to as the compound (P2)) and the compound (H21):

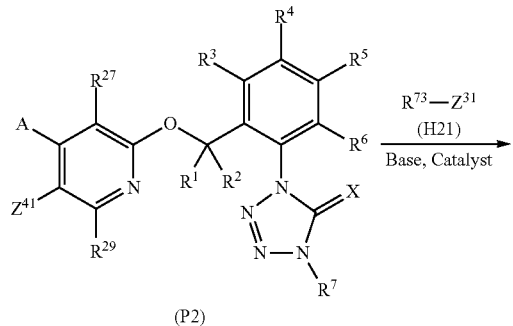

(P2)

(1-28)

wherein symbols are the same as defined above.

Among the compounds (1), a compound represented by formula (1-29) in which Q is Q9 and $R^{29}$ is $R^{73}$ (hereinafter referred to as the compound (1-29)) can be produced in accordance with the reaction mentioned in Production Process B, using a compound represented by formula (P3) (hereinafter referred to as the compound (P3)) and the compound (H21):

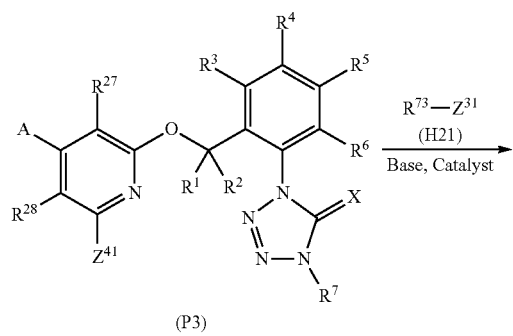

(P3)

(1-29)

wherein symbols are the same as defined above.

Among the compounds (1), a compound in which two or more substituents selected from $R^{27}$, $R^{28}$, and $R^{29}$ are $R^{73}$ can be produced in accordance with Production Process B.

It is also possible to produce the compound (1) using the other known coupling reaction in place of the coupling reaction of Production Process B.

(Production Process Q)

Among the compounds (1), a compound represented by formula (1-30) in which Q is Q10 and $R^{30}$ is $R^{73}$ (hereinafter referred to as the compound (1-30)) can be produced in accordance with the reaction mentioned in Production Process B, using a compound represented by formula (R1) (hereinafter referred to as the compound (R1)) and the compound (H21):

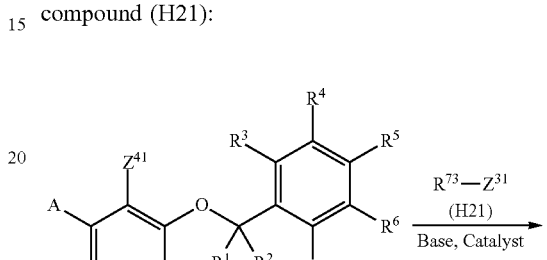

(R1)

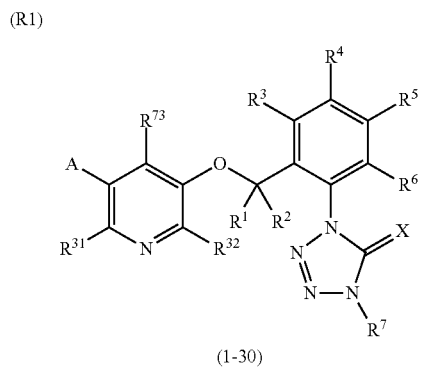

(1-30)

wherein symbols are the same as defined above.

Among the compounds (1), a compound represented by formula (1-31) in which Q is Q10 and $R^{31}$ is $R^{73}$ (hereinafter referred to as the compound (1-31)) can be produced in accordance with the reaction mentioned in Production Process B, using a compound represented by formula (R2) (hereinafter referred to as the compound (R2)) and the compound (H21):

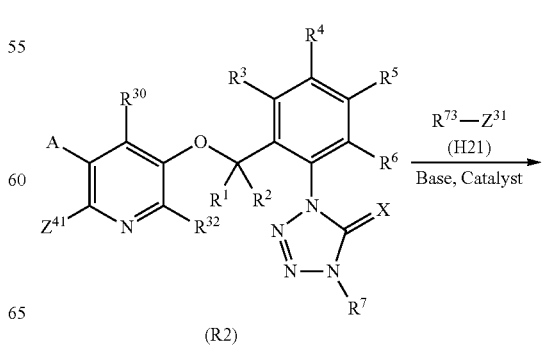

(R2)

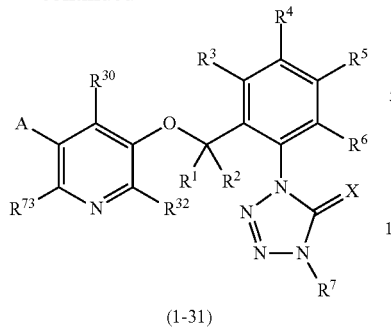

(1-31)

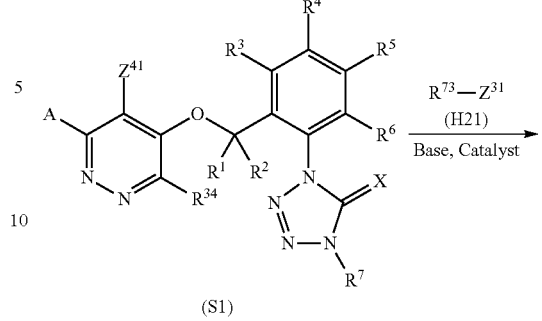

(S1)

wherein symbols are the same as defined above.

Among the compounds (1), a compound represented by formula (1-32) in which Q is Q10 and $R^{32}$ is $R^{73}$ (hereinafter referred to as the compound (1-32)) can be produced in accordance with the reaction mentioned in Production Process B, using a compound represented by formula (R3) (hereinafter referred to as the compound (R3)) and the compound (H21):

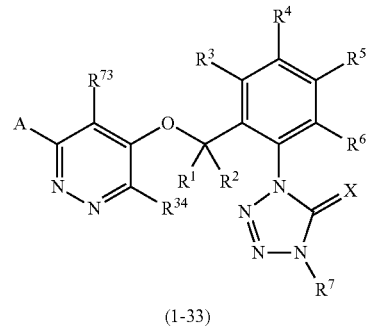

(1-33)

wherein symbols are the same as defined above.

Among the compounds (1), a compound represented by formula (1-34) in which Q is Q11 and $R^{34}$ is $R^{73}$ (hereinafter referred to as the compound (1-34)) can be produced in accordance with the reaction mentioned in Production Process B, using a compound represented by formula (S2) (hereinafter referred to as the compound (S2)) and the compound (H21):

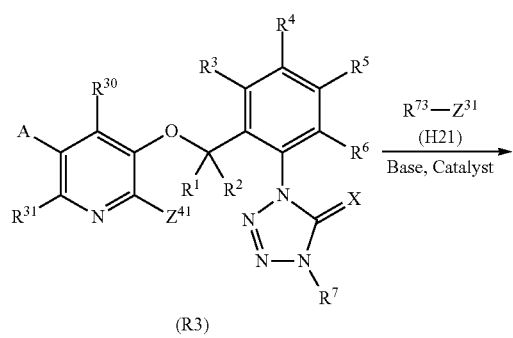

(R3)

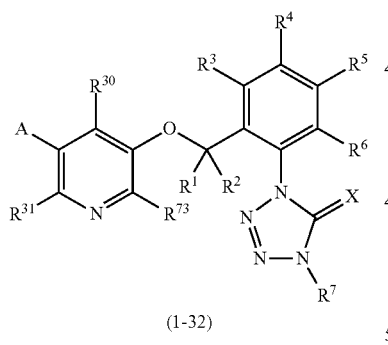

(1-32)

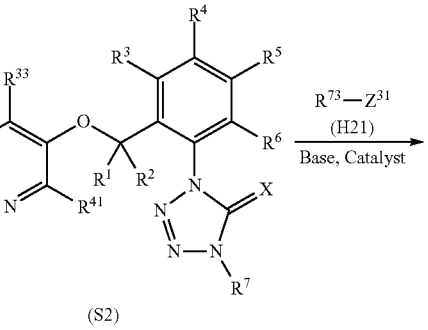

(S2)

wherein symbols are the same as defined above.

Among the compounds (1), a compound in which two or more substituents selected from $R^{30}$, $R^{31}$, and $R^{32}$ are $R^{73}$ can be produced in accordance with Production Process B.

It is also possible to produce the compound (1) using the other known coupling reaction in place of the coupling reaction of Production Process B.

(Production Process R)

Among the compounds (1), a compound represented by formula (1-33) in which Q is Q11 and $R^{33}$ is $R^{73}$ (hereinafter referred to as the compound (1-33)) can be produced in accordance with the reaction mentioned in Production Process B, using a compound represented by formula (S1) (hereinafter referred to as the compound (S1)) and the compound (H21):

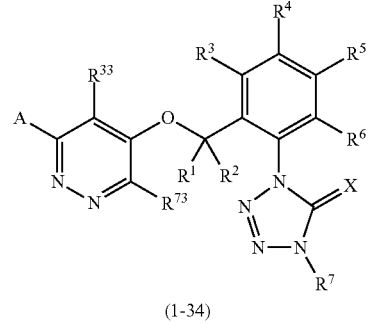

(1-34)

wherein symbols are the same as defined above.

Among the compounds (1), a compound in which $R^{33}$ and $R^{34}$ are $R^{73}$ can be produced in accordance with Production Process B.

It is also possible to produce the compound (1) using the other known coupling reaction in place of the coupling reaction of Production Process B.

(Production Process S)

Among the compounds (1), a compound represented by formula (1-35) in which Q is Q12 and $R^{35}$ is $R^{73}$ (hereinafter referred to as the compound (1-35)) can be produced in accordance with the reaction mentioned in Production Process B, using a compound represented by formula (T1) (hereinafter referred to as the compound (T1)) and the compound (H21):

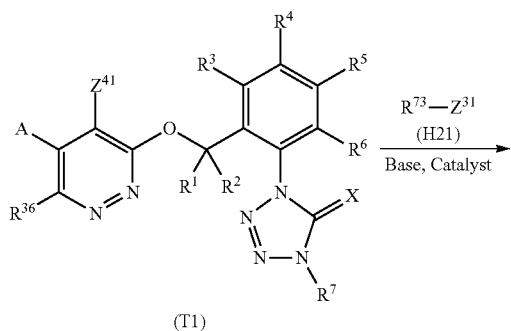

wherein symbols are the same as defined above.

Among the compounds (1), a compound represented by formula (1-36) in which Q is Q12 and $R^{36}$ is $R^{73}$ (hereinafter referred to as the compound (1-36)) can be produced in accordance with the reaction mentioned in Production Process B, using a compound represented by formula (T2) (hereinafter referred to as the compound (T2)) and the compound (H21):

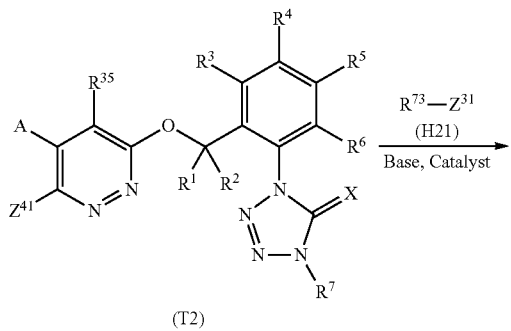

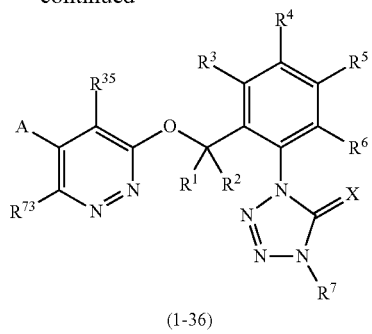

wherein symbols are the same as defined above.

Among the compounds (1), a compound in which $R^{35}$ and $R^{36}$ are $R^{73}$ can be produced in accordance with Production Process B.

It is also possible to produce the compound (1) using the other known coupling reaction in place of the coupling reaction of Production Process B.

Production Processes of the present tetrazolinone compound will be mentioned below.

The present tetrazolinone compound X can be produced, for example, by the following Production Processes.

(Synthesis Process A)

A compound represented by formula (BT1) (hereinafter referred to as the compound (BT1)) can be produced in accordance with the reaction mentioned in Production Process A, using a compound represented by formula (XO1) (hereinafter referred to as the compound (XO1)) and a compound represented by formula (XOT2) (hereinafter referred to as the compound (XOT2)):

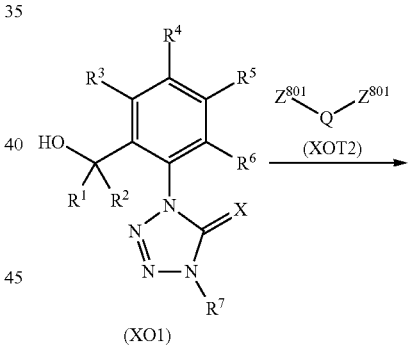

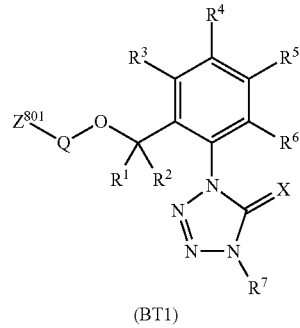

wherein $Z^{801}$ represents a fluorine atom, a chlorine atom, a bromine atom, or an iodine atom, and $R^1$, $R^2$, $R^3$, $R^4$, $R^5$, $R^6$, $R^7$, X, and Q are the same as defined above.

(Synthesis Process B)

The compound (BT1) can be produced in accordance with the reaction mentioned in Production Process A, using the compound (A1) and a compound represented by formula (XUT1) (hereinafter referred to as the compound (XUT1)):

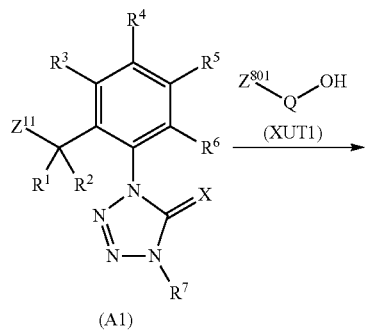

(A1)

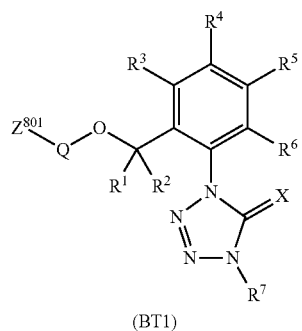

(BT1)

wherein symbols are the same as defined above.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by (XA2) (hereinafter referred to as the compound (XA2)) with an azidation agent:

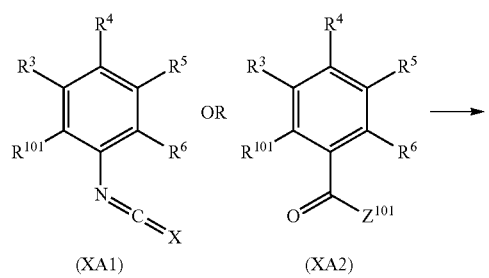

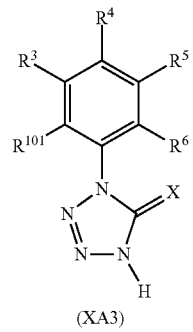

(XA3)

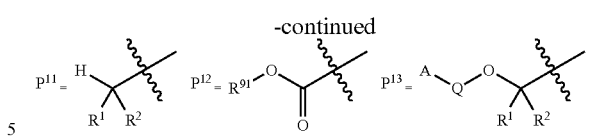

wherein $R^1$, $R^2$, $R^3$, $R^4$, $R^5$, $R^6$, X, A, and Q are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time of the reaction is usually within a range of 0.1 to 24 hours.

If necessary, Lewis acid such as aluminum chloride or zinc chloride may be added in the reaction, and these compounds are usually used in the proportion of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

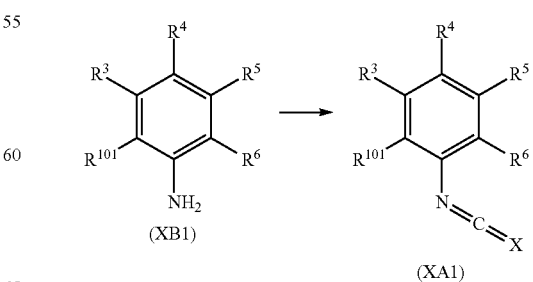

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time of the reaction is usually within a range of 0.1 to 24 hours.

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added in the reaction, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound (XA1) can be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

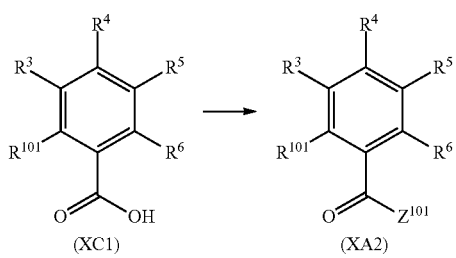

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, sulfuryl chloride, and the like.

In the reaction, the halogenating agent is usually used in the proportion within a range of 1 to 10 mols based on 1 mol of the compound (XC1).

The reaction temperature of the reaction is usually within a range of −20 to 150° C. The reaction time of the reaction is usually within a range of 0.1 to 24 hours.

The catalyst may be added in the reaction and dimethylformamide is used. The catalyst is usually used in the proportion within a range of 0.001 to 1 mol based on 1 mol of the compound (XC1).

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be used in the reaction, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

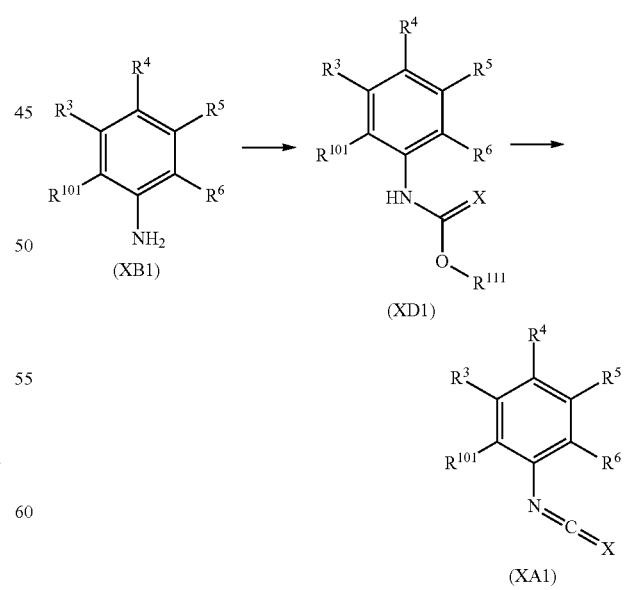

wherein $R^3$, $R^4$, $R^5$, $R^6$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on based on 1 mol of the compound (XB1).

The reaction temperature of the reaction is usually within a range of −20 to 150° C. The reaction time of the reaction is usually within a range of 0.1 to 24 hours.

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added in the reaction, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as carbon tetrachloride, chloroform or 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time of the reaction is usually within a range of 0.1 to 24 hours.

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added in the reaction, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2) can be produced by reacting a compound represented by formula (XE1) (hereinafter referred to as the compound (XE1)) with hydrogen in the presence of a catalyst:

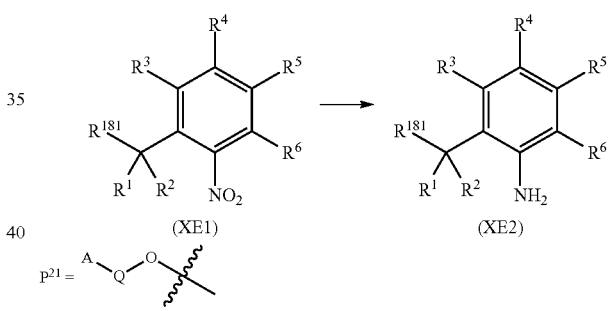

wherein $R^1$, $R^2$, $R^3$, $R^4$, $R^5$, $R^6$, A, and Q are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate, and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-supporting carbon (Pd/C), platinum-supporting carbon (Pt/C), osmium-supporting carbon (Os/C), ruthenium-supporting carbon (Ru/C), rhodium-supporting carbon (Rh/C), Raney nickel, and the like.

In the reaction, the catalyst is usually used in the proportion within a range of 0.0001 to 1 mol based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process F)

The compound (XE2) can be produced by reacting the compound (XE1) with a reducing agent in the presence of an acid:

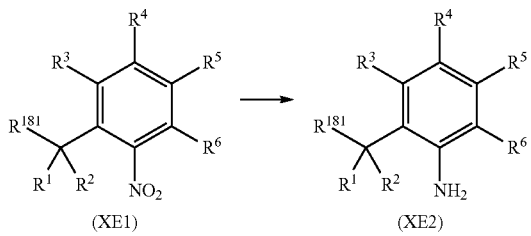

wherein symbols are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

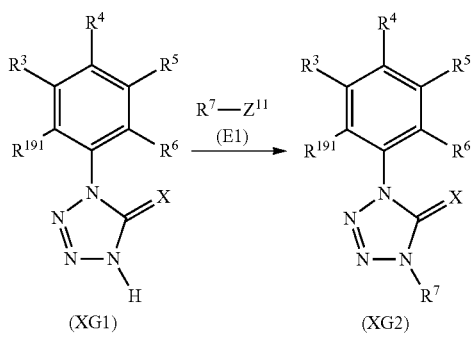

wherein $R^3$, $R^4$, $R^5$, $R^6$, $R^7$, X, and $Z^{11}$ are the same as defined above, and $R^{191}$ represents $P^{11}$ or $P^{12}$.

The reaction can be carried out in accordance with the reaction mentioned in Production Process E.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

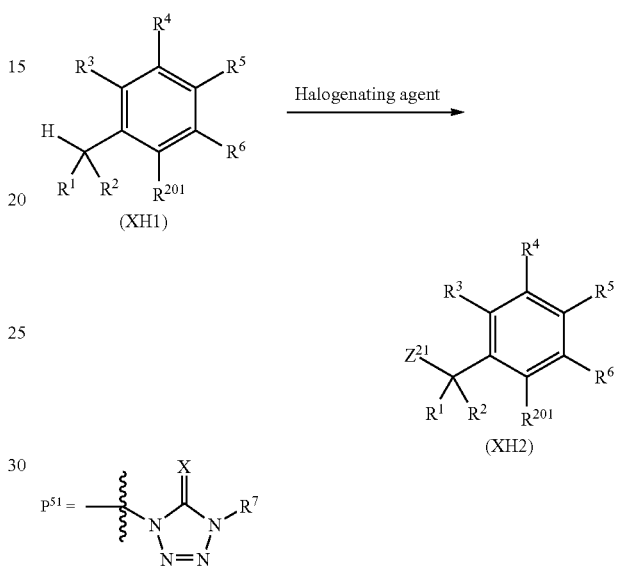

wherein $R^1$, $R^2$, $R^3$, $R^4$, $R^5$, $R^6$, $R^7$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, N-bromophthalimide, and the like.

It is also possible to use a radical initiator in the reaction.

Examples of the radical initiator to be used in the reaction include benzoyl peroxide, azobisisobutyronitrile (AIBN), diacyl peroxide, dialkyl peroxydicarbonate, tert-alkyl peroxyester, monoperoxycarbonate, di(tert-alkylperoxy)ketal and ketone peroxide, and the like.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

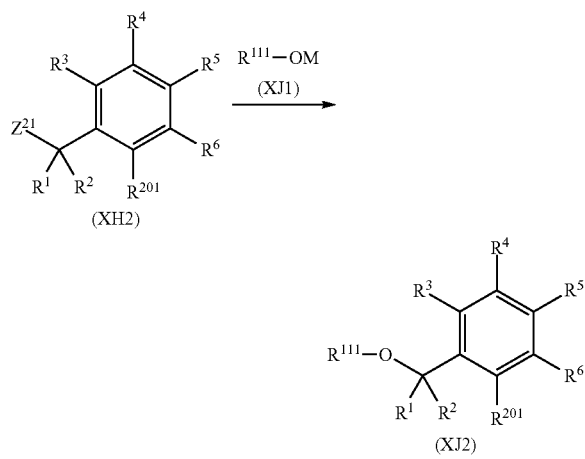

wherein $R^1$, $R^2$, $R^3$, $R^4$, $R^5$, $R^6$, $R^{201}$, $R^{111}$, and $Z^{21}$ are the same as defined above, and M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) to be usable in the reaction include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time of the reaction is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

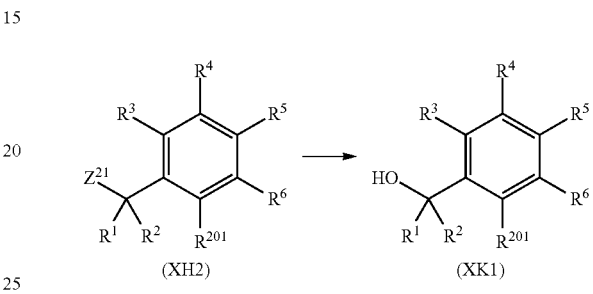

wherein symbols are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to a large excess based on 1 mol of the compound (XH2).

The reaction temperature of the reaction is usually within a range of −20 to 150° C. The reaction time of the reaction is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

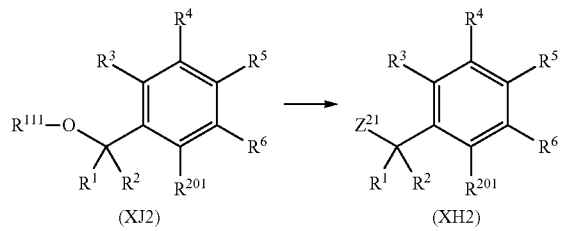

wherein symbols are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion within a range of 1 mol or more based on 1 mol of the compound (XJ2).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

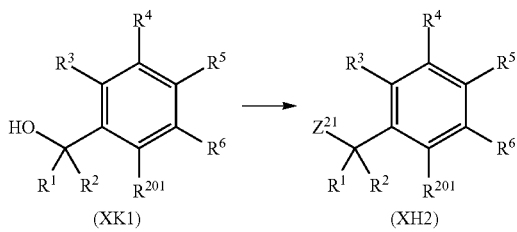

wherein symbols are the same as defined above.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

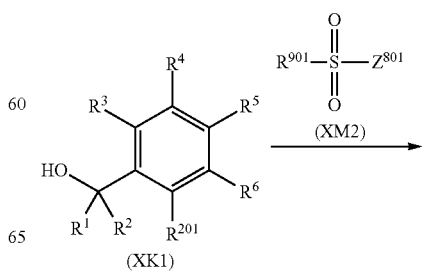

-continued

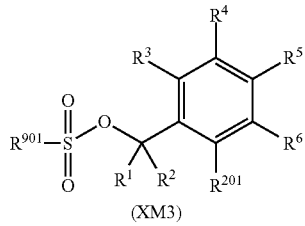

(XM3)

wherein $R^1$, $R^2$, $R^3$, $R^4$, $R^5$, $R^6$, $Z^{801}$, and $R^{201}$ are the same as defined above, and $R^{901}$ represents a C1-C6 alkyl group, a C1-C6 haloalkyl group, a C6-C16 aryl group, or a C6-C16 haloaryl group.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, and potassium hydroxide; alkali metal hydrides such as lithium hydride, sodium hydride, and potassium hydride; alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time of the reaction is usually within a range of 0.1 to 24 hours.

If necessary, sodium iodide, tetrabutylammonium iodide, and the like may be added in the reaction, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced in accordance with the reaction mentioned in Production Process B, using a compound represented by formula (XN11) (hereinafter referred to as the compound (XN11)) and the compound (G21):

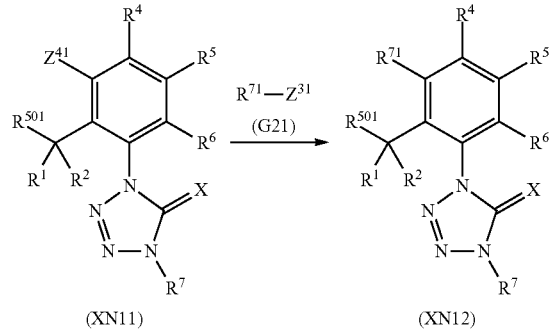

wherein $R^{501}$ represents a hydrogen atom or an $OR^{111}$ group, and $R^{111}$, $R^1$, $R^2$, $R^4$, $R^5$, $R^6$, $R^7$, $R^{71}$, X, $Z^{31}$, and $Z^{41}$ are the same as defined above.

A compound represented by formula (XN22) (hereinafter referred to as the compound (XN22)) can be produced in accordance with the reaction mentioned in Production Process B, using a compound represented by formula (XN21) (hereinafter referred to as the compound (XN21)) and the compound (G22):

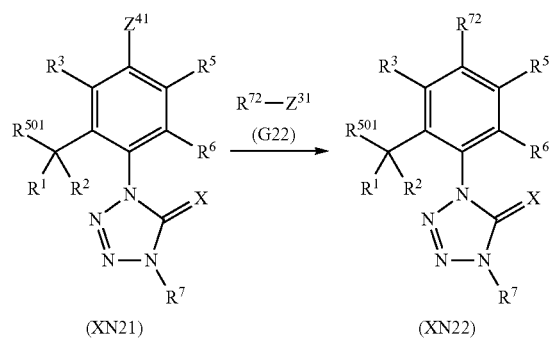

wherein symbols are the same as defined above.

A compound represented by formula (XN32) (hereinafter referred to as the compound (XN32)) can be produced in accordance with the reaction mentioned in Production Process B, using a compound represented by formula (XN31) (hereinafter referred to as the compound (XN31)) and the compound (G22):

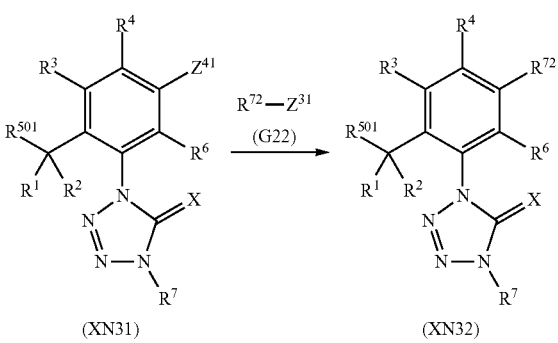

wherein symbols are the same as defined above.

A compound represented by formula (XN42) (hereinafter referred to as the compound (XN42)) can be produced in accordance with the reaction mentioned in Production Process B, using a compound represented by formula (XN41) (hereinafter referred to as the compound (XN41)) and the compound (G22):

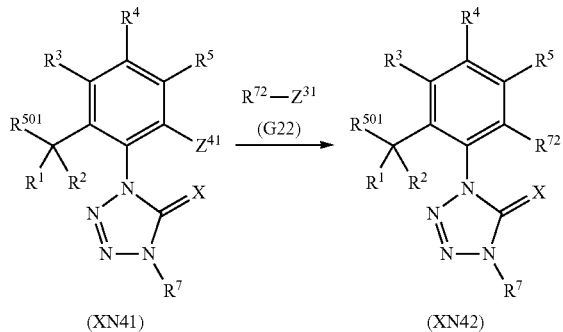

wherein symbols are the same as defined above.

The reaction can be carried out in accordance with the reaction mentioned in Production Process B.

In accordance with the reaction mentioned in Production Process B, it is possible to produce a compound in which two or more substituents selected from $R^3$, $R^4$, $R^5$, and $R^6$ are $R^{71}$ or $R^{72}$, among the group of compounds represented by formula (XN50):

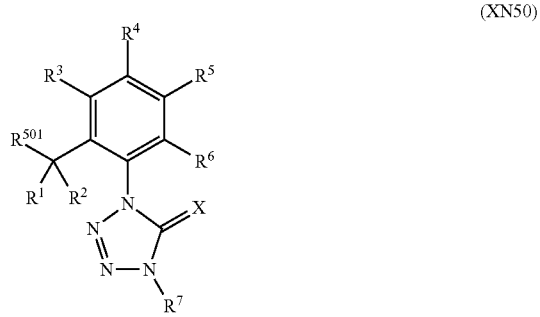

wherein symbols are the same as defined above.

Furthermore, the compound (XN50) can be produced by using the other known coupling reaction in place of the coupling reaction mentioned in Production Process B.

(Reference Production Process O)

A compound represented by formula (XW2) (hereinafter referred to as the compound (AXW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

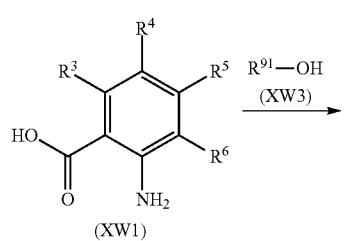

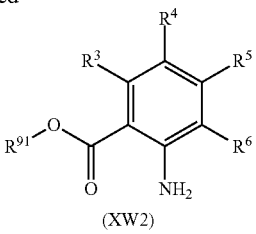

wherein symbols are the same as defined above.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) to be usable in the reaction include methyl alcohol, ethyl alcohol, propyl alcohol, isopropyl alcohol, n-butyl alcohol, and sec-butyl alcohol.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added in the reaction, and these compounds are usually used in the proportion within a range of 0.01 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and reacting the compound (XV1) with the compound (XW3):

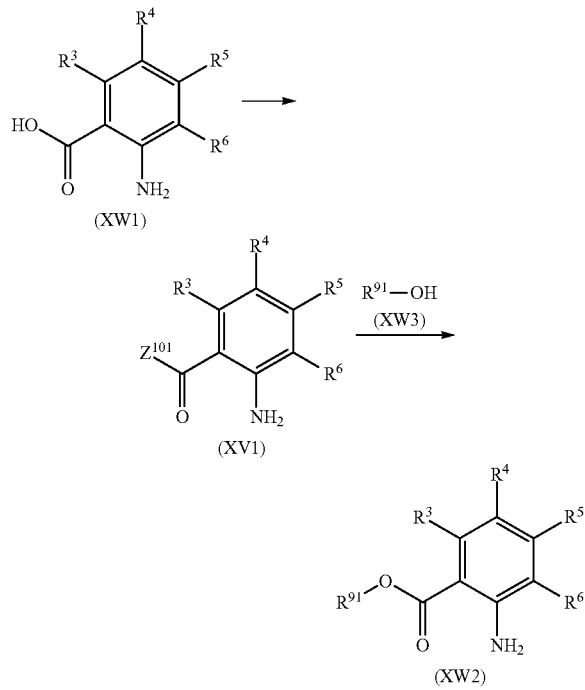

wherein $R^3$, $R^4$, $R^5$, $R^6$, $R^{91}$, and $Z^{101}$ are the same as defined above.

The process for producing the compound (XV1) by reacting the compound (XW1) with a halogenating agent can be carried out in accordance with the reaction mentioned in Reference Production Process C.

The process for producing the compound (XW2) from the compound (XV1) will be described below.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) to be usable in the reaction include methyl alcohol, ethyl alcohol, propyl alcohol, isopropyl alcohol, n-butyl alcohol, and sec-butyl alcohol.

In the reaction, an excess amount of the compound (XW3) is used based on the compound (XV1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

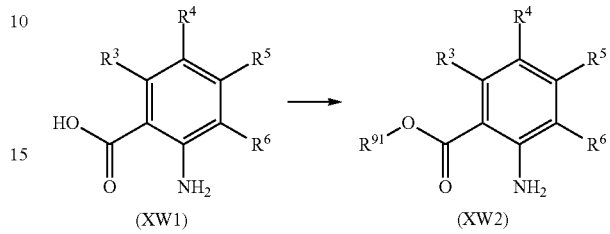

wherein symbols are the same as defined above.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent to be usable in the reaction include alkyl halides such as diazomethane, trimethylsilyldiazomethane, chlorodifluoromethane, methyl bromide, ethyl bromide, n-propyl bromide, methyl iodide, ethyl iodide, n-propyl bromide, allyl bromide, cyclopropyl bromide, benzyl bromide, and 1,1-difluoro-2-iodoethane; dialkyl sulfates such as dimethyl sulfate, diethyl sulfate, and di-n-propyl sulfate; and alkyl or arylsulfonic acid esters, such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

If necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; and quaternary ammonium salts such as tetra(n-butyl)ammonium hydroxide may be added in the reaction, and these compounds are usually used in the proportion within a range of 0.01 to 5 mols based on 1 mol of the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process R)

A compound represented by formula (XX2) (hereinafter referred to as the compound (XX2)) can be produced by reacting a compound represented by formula (XX1) (hereinafter referred to as the compound (XX1)) with a reducing agent:

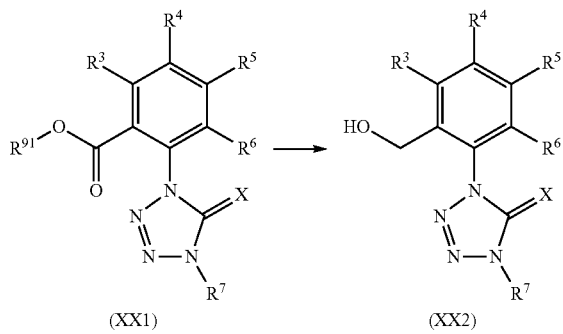

wherein symbols are the same as defined above.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; alcohols such as methanol, ethanol, propanol, and butanol; water; and mixtures thereof.

Examples of the reducing agent to be usable in the reaction include lithium triethylborohydride, aluminum diisobutylhydride, lithium aminoborohydride, lithium borohydride, sodium borohydride, borane, a borane dimethyl sulfide complex, and a borane tetrahydrofuran complex.

In the reaction, the reducing agent is usually used in the proportion within a range of 1 to 10 mols based on 1 mol of the compound (XX1).

The reaction temperature of the reaction is usually within a range of −78 to 100° C. The reaction time of the reaction is usually within a range of 0.1 to 24 hours.

After completion of the reaction, the compound (XX2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process S)

A compound represented by formula (XZ2) (hereinafter referred to as the compound (XZ2)) can be produced by reacting a compound represented by formula (XZ1) (hereinafter referred to as the compound (XZ1)) with a reducing agent:

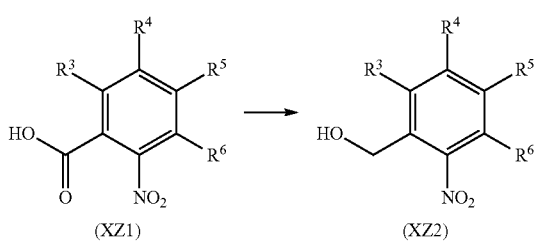

wherein symbols are the same as defined above.

The reaction is usually performed in a solvent.

Examples of the solvent to be used in the reaction include hydrocarbons such as n-hexane, cyclohexane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; alcohols such as methanol, ethanol, propanol, and butanol; water; and mixtures thereof.

Examples of the reducing agent to be usable in the reaction include borane, a borane tetrahydrofuran complex, and a borane dimethyl sulfide complex. It is also possible to use borane to be generated by mixing a borohydride such as sodium borohydride or potassium borohydride with an acid such as sulfuric acid, hydrochloric acid, methanesulfonic acid, or a boron trifluoride diethyl ether complex.

In the reaction, the reducing agent is usually used in the proportion within a range of 1 to 10 mols based on 1 mol of the compound (XZ1).

The reaction temperature of the reaction is usually within a range of −20 to 100° C. The reaction time of the reaction is usually within a range of 0.1 to 72 hours.

After completion of the reaction, the compound (XZ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

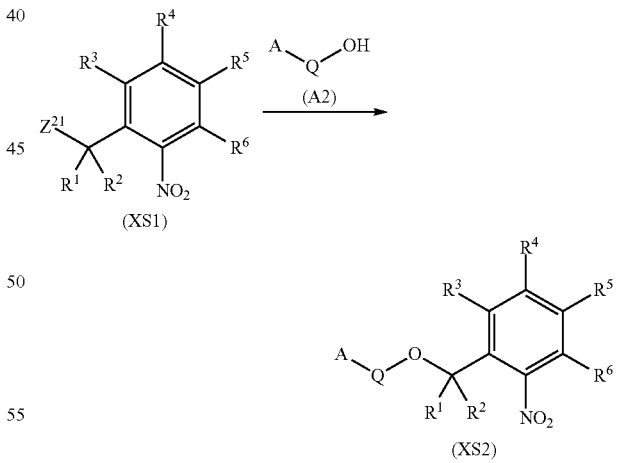

wherein symbols are the same as defined above.

The reaction can be carried out in accordance with the reaction mentioned in Production Process A.

(Reference Production Process U)

A compound represented by formula (XU2) (hereinafter referred to as the compound (XU2)) can be produced by subjecting a compound represented by formula (XU1) (hereinafter referred to as the compound (XU1)) and the compound (B2) to a coupling reaction in the presence of a base and a catalyst:

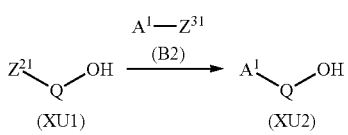

wherein symbols are the same as defined above.

The reaction can be carried out in accordance with the reaction mentioned in Production Process B.

(Reference Production Process V)

The compound (B1) can be produced by reacting a compound represented by formula (XO1) (hereinafter referred to as the compound (XO1)) with a compound represented by formula (XO2) (hereinafter referred to as the compound (XO2)) in the presence of a base:

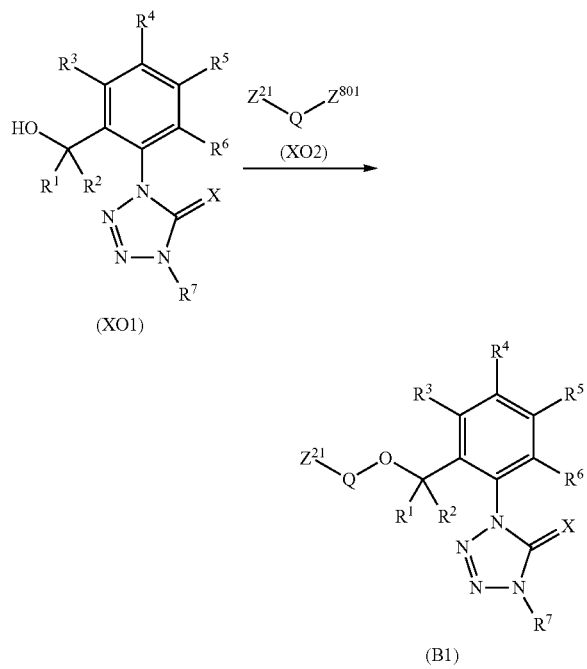

wherein symbols are the same as defined above.

The reaction can be carried out in accordance with the reaction mentioned in Production Process A.

(Reference Production Process W)

The compound (B1) can be produced by reacting the compound (A1) with the compound (XU1) in the presence of a base:

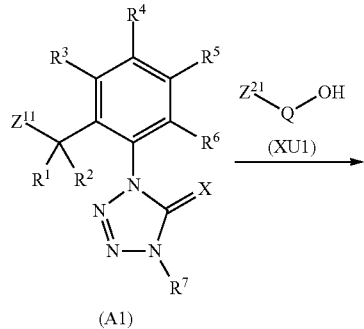

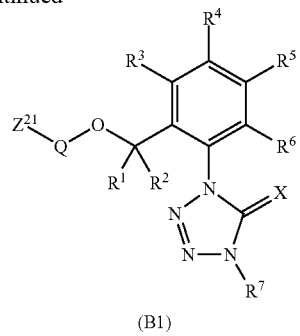

wherein symbols are the same as defined above.

The reaction can be carried out in accordance with the reaction mentioned in Production Process A.

Although a form used for the present compound may be the present compound as itself, the present compound is usually mixed with solid carriers, liquid carriers, surfactants, and the like, and optionally adding auxiliary agents for formulation, such as stickers, dispersers, and stabilizers to formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers, dispersers and stabilizers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present control compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The present control agent may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANGLE (registered trademark), and the like.

The present control agent can also be used as a mixture with or together with other fungicides, insecticides, acaricides, nematicides, and plant growth regulators.

Examples of these other fungicides include the followings:
(1) Azole fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, and ipconazole;
(2) Amine fungicides
such as fenpropimorph, tridemorph, fenpropidin, and spiroxamine;
(3) Benzimidazole fungicides
such as carbendazim, benomyl, thiabendazole, and thiophanate-methyl;
(4) Dicarboximide fungicides
such as procymidone, iprodione, and vinclozolin;
(5) Anilinopyridine fungicides
such as cyprodinil, pyrimethanil, and mepanipyrim;
(6) Phenylpyrrole fungicides
such as fenpiclonil and fludioxonil;
(7) Strobilurin fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, and mandestrobin;
(8) Phenylamide fungicides
such as metalaxyl, metalaxyl-M or mefenoxam, benalaxyl, and benalaxyl-M or kiralaxyl;
(9) Carboxylic acid amide fungicides
such as dimethomorph, iprovalicarb, benthivalicarb-isopropyl, mandipropamid, and valiphenal;
(10) Carboxamide fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, N-(1,1,3-trimethylindan-4-yl)-1-methyl-3-difluoromethylpyrazole-4-carboxylic acid amide (including racemate or enantiomer, a mixture of enantiomer of R form and enantiomer of S form at an optional ratio); and
(11) Other fungicides
such as diethofencarb, thiuram, fluazinam, mancozeb, chlorothalonil, captan, dichlofluanid, folpet, quinoxyfen, fenhexanid, fanoxadon, fenamidon, zoxamide, thaboxam, amisulbrom, cyazofamid, metrafenone, pyriofenone, cyflufenamid, proquinazid, flusulfamide, fluopicolide, fosetyl, cymoxanil, pencycuron, tolclofos-methyl, carpropamid, diclocymet, fenoxanil, tricyclazole, pyroquilon, probenazole, isotianil, tiadinil, tebufloquin, clomezine, kasugamycin, ferimzone, fthalide, validamycin, hydroxyisoxazole, iminoctadine acetate, isoprothiolane, oxolinic acid, oxytetracycline, streptomycin, copper oxychloride, copper hydroxide, copper hydroxide sulfate, organocopper, sulfur, ametoctradin, fenpyrazamine, oxathiapiprolin, 3-chloro-4-(2,6-difluorophenyl)-6-methyl-5-phenylpyridazine, and 3-cyano-4-(2,6-difluorophenyl)-6-methyl-5-phenylpyridazine.

Examples of these other insecticides include:
(1) Organophosphorus compounds
such as acephate, aluminium phosphide, butathiofos, cadusafos, chlorethoxyfos, chlorfenvinphos, chlorpyrifos, chlorpyrifos-methyl, cyanophos:CYAP, diazinon, dichlorodiisopropyl ether (DCIP), dichlofenthion:ECP, dichlorvos: DDVP, dimethoate, dimethylvinphos, disulfoton, EPN, ethion, ethoprophos, etrimfos, fenthion:MPP, fenitrothion: MEP, fosthiazate, formothion, hydrogen phosphide, isofenphos, isoxathion, malathion, mesulfenfos, methidathion:D-MTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, and cadusafos;
(2) Carbamate compounds
such as alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, and aldicarb;
(3) Synthetic pyrethroid compounds
such as acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxymethyl)benzyl(EZ)-(1RS,3RS;1RS,3SR)-2,2-dimethyl-3-prop-1-enylcyclopropanecarboxylate, 2,3,5,6-tetrafluoro-4-methylbenzyl(EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS;1RS,3SR)-2,2-dimethyl-3-(2-methyl-1-propenyl)cyclopropanecarboxylate;
(4) Nereistoxin compounds
such as cartap, bensultap, thiocyclam, monosultap, and bisultap;

(5) Neonicotinoid compounds
such as imidacloprid, nitenpyram, acetamiprid, thiamethoxam, thiacloprid, dinotefuran, and clothianidin;
(6) Benzoylurea compounds
such as chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron;
(7) Phenylpyrazole compounds
such as acetoprole, ethiprole, fipronil, vaniliprole, pyriprole, and pyrafluprole;
(8) Bt toxin insecticides
such as live spores derived from and crystal toxins produced from *Bacillus thuringiesis*, and a mixture thereof;
(9) Hydrazine compounds
such as chromafenozide, halofenozide, methoxyfenozide, and tebufenozide;
(10) Organochlorine compounds
such as aldrin, dieldrin, dienochlor, endosulfan, and methoxychlor;
(11) Natural insecticides
such as machine oil and nicotine-sulfate; and
(12) Other insecticides
such as avermectin-B, bromopropylate, buprofezin, chlorphenapyr, cyromazine, 1,3-dichloropropene (D-D), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, arsenic acid, benclothiaz, calcium cyanamide, calcium polysulfide, chlordane, DDT, DSP, flufenerim, flonicamid, flurimfen, formetanate, metam-ammonium, metamsodium, methyl bromide, potassium oleate, spiromesifen, sulfur, metaflumizone, spirotetramat, pyrifluquinazone, spinetoram, chlorantraniliprole, cyantraniliprole, cyclaniliprole, sulfoxaflor, and flupyradifurone.

Examples of these other acaricides (acaricidally active ingredients) include acequinocyl, amitraz, benzoximate, bifenaate, bromopropylate, chinomethionat, chlorobenzilate, chlorfenson (CPCBS), clofentezine, cyflumetofen, dicofol (kelthane), etoxazole, fenbutatin oxide, fenothiocarb, fenpyroximate, fluacrypyrim, fluproxyfen, hexythiazox, propargite:BPPS, polynactins, pyridaben, pyrimidifen, tebufenpyrad, tetradifon, spirodiclofen, spiromesifen, spirotetramat, amidoflumet, and cyenopyrafen.

Examples of these other nematicides (nematicidally active ingredients) include DCIP, fosthiazate, levamisole hydrochloride, methyisothiocyanate, morantel tartarate, imicyafos, fluensulfone, and the like.

Examples of these other plant growth regulators include: ethephon, chlormequat-chloride, mepiquat-chloride, gibberellin A typified by gibberellin A3, abscisic acid, kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, 5-(trifluoromethyl)benzo[b]thiophene-2-carboxylic acid, and the like.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The application dose varies depending on weather conditions, dosage forms, timing of application, methods of application, areas to be applied, target diseases, target crops, and the like, and is usually within a range of 1 to 500 g, and preferably 2 to 200 g, per 1,000 m² of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplanation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica*, colocasia, and the like;

Flowers:

Ornamental Foliage Plants:

Fruits: pomaceous fruits (for example, apple, pear, Japanese pear, Chinese quince, and quince), stone fruits (for example, peach, plum, nectarine, *Prunus mume*, cherry fruit, apricot, and prune), *citrus* fruits (for example, *Citrus unshiu*, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding blight caused by bacteria of the genus (*Rhizoctonia solani*), and take all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by bacteria of the genus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramuraria areola*), and *alternaria* leaf spot (*Alternaria macrospora, A. gossypii*); Coffee diseases: rust (*Hemileia vastatrix*); Rape seed diseases: *sclerotinia* rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), *alternaria* leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), *fusarium* wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: *alternaria* leaf spot (*Alternaria japonica*), white spot (*Cercosporella brassicae*), clubroot (*Plasmodiophora parasitica*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*); Kindney bean diseases: anthracnose (*Colletotrichum lindemthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and *verticillium* wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: cercospora leaf spot (*Cercospora beticola*), leaf blight (*Thanatephorus cucumeris*), root rot (*Thanatephorus cucumeris*), and *aphanomyces* root rot (*Aphanomyces sochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), graymold neck rot (*Botrytis slli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical *citrus* aphid (*Toxoptera* citricidus); stink bugs (Pentatomidae) such as green stink bug (Nezara antennata), bean bug (Riptortus clavetus), rice bug (Leptocorisa chinensis), white spotted spined bug (Eysarcoris parvus), stink bug (Halyomorpha mista), and tarnished plant bug (Lygus lineolaris); whiteflies (Aleyrodidae) such as greenhouse whitefly (Trialeurodes vaporariorum) and silverleaf whitefly (Bemisia argentifolii); scales (Coccidae) such as Calformia red scale (Aonidiella aurantii), San Jose scale (Comstockaspis perniciosa), citrus north scale (Unaspis citri), red wax scale (Ceroplastes rubens), and cottonycushion scale (Icerya purchasi); lace bugs (Tingidae); jumping plant lices (Homoptera, Psylloidea); and bed bugs (Cimex lectularius).

Lepidoptera: pyralid moths (Pyralidae) such as rice stem borer (Chilo suppressalis), yellow rice borer (Tryporyza incertulas), rice leafroller (Cnaphalocrocis medinalis), cotton leafroller (Notarcha derogata), Indian meal moth (Plodia interpunctella), oriental corn borer (Ostrinia furnacalis), cabbage webworm (Hellula undalis), and bluegrass webworm (Pediasia teterrellus); owlet moths (Noctuidae) such as common cutworm (Spodoptera litura), beet armyworm (Spodoptera exigua), armyworm (Pseudaletia separata), cabbage armyworm (Mamestra brassicae), black cutworm (Agrotis ipsilon), beet semi-looper (Plusia nigrisigna), Thoricoplusia spp., Heliothis spp., and Helicoverpa spp.; white butterflies (Pieridae) such as common white (Pieris rapae); tortricid moths (Tortricidae) such as Adoxophyes spp., oriental fruit moth (Grapholita molesta), soybean pod borer (Leguminivora glycinivorella), azuki bean podworm (Matsumuraeses azukivora), summer fruit tortrix (Adoxophyes orana fasciata), smaller tea tortrix (Adoxophyes sp.), oriental tea tortrix (Homona magnanima), apple tortrix (Archips fuscocupreanus), and codling moth (Cydia pomonella); leafblotch miners (Gracillariidae) such as tea leafroller (Caloptilia theivora), and apple leafminer (Phyllonorycter ringoneella); leaf miners (Gracillariidae) such as tea leafroller (Caloptilia theivora) and apple leafminer (Phyllonorycter ringoneella); codling moths (Carposimidae) such as peach fruit moth (Carposina niponensis); lyonetiid moths (Lyonetiidae) such as Lyonetia spp.; tussock moths (Lymantriidae) such as Lymantria spp. and Euproctis spp.; yponomeutid moths (Yponomeutidae) such as diamondback (Plutella xylostella); gelechild moths (Gelechiidae) such as pink bollworm (Pectinophora gossypiella) and potato tubeworm (Phthorimaea operculella); tiger moths and allies (Arctiidae) such as fall webworm (Hyphantria cunea); and tineid moths (Tineidae) such as casemaking clothes moth (Tinea translucens), and webbing clothes moth (Tineola bisselliella).

Thysanoptera: yellow citrus thrips (Frankliniella occidentalis), melon thrips (Thrips palmi), yellow tea thrips (Scirtothrips dorsalis), onion thrips (Thrips tabaci), flower thrips (Frankliniella intonsa), and tobacco thrips (Frankliniella fusca).

Diptera: houseflies (Musca domestica), common mosquito (Culex pipiens pallens), horsefly (Tabanus trigonus), onion maggot (Hylemya anitgua), seedcorn maggot (Hylemya platura), Anopheles sinensis, rice leafminer (Agromyza oryzae), rice leafminer (Hydrellia griseola), rice stem maggot (Chlorops oryzae), melon fly (Dacus cucurbitae), Mediterranean fruit fly (Ceratitis capitata), and legume leafminer (Liriomyza trifolii).

Coleoptera: twenty-eight-spotted ladybirds (Epilachna vigintioctopunctata), cucurbit leaf beetle (Aulacophora femoralis), yellow striped flea beetle (Phyllotreta striolata), rice leaf beetle (Oulema oryzae), rice curculio (Echinocnemus squameus), rice water weevil (Lissorhoptrus oryzophilus), boll weevil (Anthonomus grandis), azuki bean weevil (Callosobruchus chinensis), hunting billbug (Sphenophorus venatus), Japanese beetle (Popillia japonica), cupreous chafer (Anomala cuprea), corn root worms (Diabrotica spp.), Colorado beetle (Leptinotarsa decemlineata), click beetles (Agriotes spp.), cigarette beetle (Lasioderma serricorne), varied carper beetle (Anthrenus verbasci), red flour beetle (Tribolium castaneum), powder post beetle (Lyctus brunneus), white-spotted longicorn beetle (Anoplophora malasiaca), and pine shoot beetle (Tomicus piniperda).

Orthoptera: asiatic locusts (Locusta migratoria), African mole cricket (Gryllotalpa africana), rice grasshopper (Oxya yezoensis), and rice grasshopper (Oxya japonica).

Hymenoptera: cabbage sawflies (Athalia rosae), leaf-cutting ant (Acromyrmex spp.), and fire ant (Solenopsis spp.).

Nematodes: white-tip nematode (Aphelenchoides besseyi), strawberry bud nematode (Nothotylenchus acris), soybean cyst nematode (Heterodera glycines), southern root-knot nematode (Meloidogyne incognita), cobb's root-lesion nematode (Pratylenchus penetrans), and false root-knot nematode (Nacobbus aberrans).

Blattariae: German cockroach (Blattella germanica), smoky-brown cockroach (Periplaneta fuliginosa), American cockroach (Periplaneta America), brown cockroach (Periplaneta brunnea), and oriental cockroach (Blatta orientalis).

Acarina: Tetranychidae (for example, two-spotted spider mite (Tetranychus urticae), citrus red mite (Panonychus citri), and Oligonychus spp.); Eriophyidae (for example, pink citrus rust mite (Aculops pelekassi)); Tarsonemidae (for example, broad mite (Polyphagotarsonemus latus)); Tenuipalpidae; Tuckerellidae; Tuckerellidae Acaridae (for example, common grain mite (Tyrophagus putrescentiae)); Pyroglyphidae (for example, Americal house dust mite (Dermatophagoides farinae) and house dust mite (Dermatophagoides ptrenyssnus)); Cheyletidae (for example, cheyletid mite (Cheyletus eruditus), Cheyletus malaccensis, and Cheyletus moorei; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (Ixodes spp.) (for example, Ixodes scapularis), Boophilus spp. (for example, cattle tick (Boophilus microplus)), Amblyomma spp., Hyalomma spp., Rhipicephalus spp. (for example, kennel tick (Rhipicephalus sanguineus)), Haemaphysalis spp. (for example, Haemaphysalis longicornis), dermacentor spp., Ornithodoros spp. (for example, Ornithodoros moubata), red mite (Dermahyssus gallinae), ghost ant (Ornithonyssus sylviarum), Sarcoptes spp. (for example, Sarcoptes scabiei), Psoroptes spp., Chorioptes spp., Demodex spp., Eutrombicula spp., Ades spp. (for example, Asian tiger mosquito (Aedes albopictus)), Anopheles spp., Culex spp., Culicodes spp., Musca spp., Hypoderma spp., Gasterophilus spp., Haematobia spp., Tabanus spp., Simulium spp., Triatoma spp., lice (Phthiraptera) (for example, Damalinia spp.), Linognathus spp., Haematopinus spp., Ctenocephalides spp. (for example, cat flea (Ctenocephalides felis)) Xenosylla spp., Pharaoh's ant (monomorium pharaonic) and nematodes [for example, hairworm (for example, Nippostrongylus brasiliensis, Trichostrongylus axei, Trichostrongylus colubriformis), Trichinella spp. (for example, Trichinella spiriralis), barber pole worm (Haemonchus contortus),

*Nematodirus* spp. (for example, *Nematodirus battus*), *Ostertagia circumcincta, Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.40 g of AA1 mentioned in Synthesis Example 1, 0.19 g of phenylboronic acid, 0.68 g of tripotassium phosphate, 0.10 ml of water, 0.09 g of [1,1'-bis (diphenylphosphino)ferrocene]palladium(II) dichloride dichloromethane adduct, and 5 mL of dioxane was stirred with heating under reflux for 6 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.32 g of 1-methyl-4-[3-methyl-2-(6-phenylpyridin-2-yloxymethyl) phenyl]-1,4-dihydrotetrazol-5-one (hereinafter referred to as the present compound 1).

In the same manner as in Production Example 1, the present compounds 2 to 205 were synthesized.

Structural formulas of the present compounds and $^1$H-NMR data thereof are shown in Table 1 to Table 39.

TABLE 1

| Number of present compound | Structural formula | $^1$H-NMR data |
|---|---|---|
| 1 | 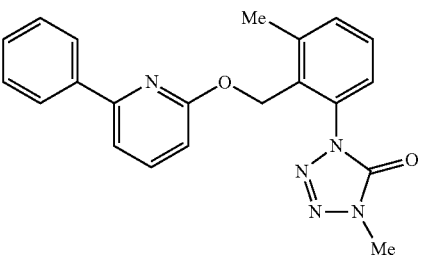 | $^1$H-NMR (DMSO-d$_6$) δ (ppm): 8.00-7.97 (2H, m), 7.59 (1H, dd, J = 8.0, 7.6 Hz), 7.48-7.44 (2H, m), 7.42-7.36 (3H, m), 7.33 (1H, d, J = 7.6 Hz), 7.26-7.22 (1H, m), 6.60 (1H, d, J = 8.0 Hz), 5.53 (2H, s), 3.49 (3H, s), 2.54 (3H, s). |
| 2 | 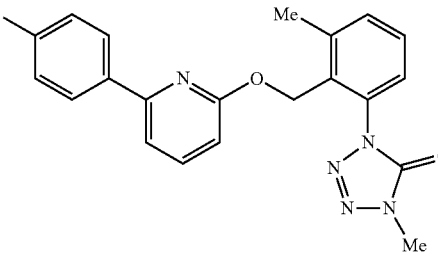 | $^1$H-NMR (CDCl$_3$) δ (ppm): 7.94-7.90 (2H, m), 7.60 (1H, t, J = 7.8 Hz), 7.44-7.39 (4H, m), 7.30 (1H, d, J = 7.3 Hz), 7.27-7.23 (1H, m), 6.62 (1H, d, J = 8.0 Hz), 5.51 (2H, s), 3.53 (3H, s), 2.54 (3H, s). |
| 3 | 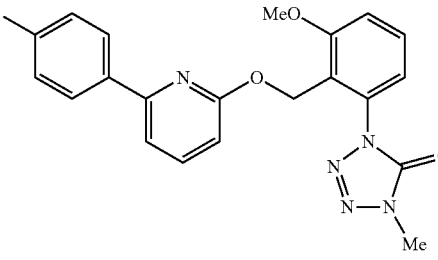 | $^1$H-NMR (CDCl$_3$) δ (ppm): 7.97-7.94 (2H, m), 7.57 (1H, t, J = 7.8 Hz), 7.47-7.40 (3H, m), 7.29-7.25 (1H, m), 7.10 (1H, d, J = 8.5 Hz), 7.02 (1H, d, J = 8.0 Hz), 6.54 (1H, d, J = 8.0 Hz), 5.65 (2H, s), 3.93 (3H, s), 3.48 (3H, s). |
| 4 | 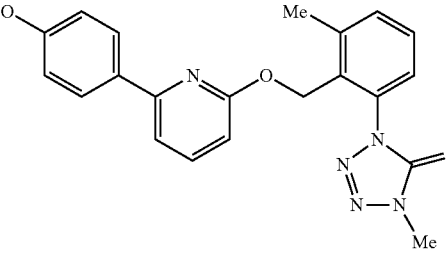 | $^1$H-NMR (CDCl$_3$) δ (ppm): 7.97-7.93 (2H, m), 7.57 (1H, t, J = 7.8 Hz), 7.42-7.37 (2H, m), 7.27-7.23 (2H, m), 7.01-6.97 (2H, m), 6.55 (1H, d, J = 8.2 Hz), 5.52 (2H, s), 3.87 (3H, s), 3.51 (3H, s), 2.54 (3H, s). |

TABLE 1-continued

| Number of present compound | Structural formula | ¹H-NMR data |
|---|---|---|
| 5 | [Structure: 4-fluorophenyl-pyridine-O-CH₂-(3-methylphenyl)-tetrazolinone with N-Me] | ¹H-NMR (CDCl₃) δ (ppm): 7.99-7.94 (2H, m), 7.59 (1H, t, J = 7.8 Hz), 7.40 (2H, d, J = 5.1 Hz), 7.28-7.24 (2H, m), 7.17-7.11 (2H, m), 6.60 (1H, d, J = 8.0 Hz), 5.51 (2H, s), 3.52 (3H, s), 2.53 (3H, s). |

TABLE 2

| Number of present compound | Structural formula | ¹H-NMR data |
|---|---|---|
| 6 | [Structure: 4-methylphenyl-pyridine-O-CH₂-(3-methylphenyl)-tetrazolinone with N-Me] | ¹H-NMR (CDCl₃) δ (ppm): 7.88 (2H, d, J = 8.3 Hz), 7.58 (1H, dd, J = 8.0, 7.6 Hz), 7.41-7.37 (2H, m), 7.31-7.22 (4H, m), 6.57 (1H, d, J = 8.3 Hz), 5.52 (2H, s), 3.50 (3H, s), 2.54 (3H, s), 2.41 (3H, s). |
| 7 | [Structure: 4-trifluoromethylphenyl-pyridine-O-CH₂-(3-methylphenyl)-tetrazolinone with N-Me] | ¹H-NMR (CDCl₃) δ (ppm): 8.08 (2H, d, J = 8.2 Hz), 7.72 (2H, d, J = 8.2 Hz), 7.64 (1H, t, J = 7.8 Hz), 7.41 (2H, d, J = 4.8 Hz), 7.37 (1H, d, J = 7.5 Hz), 7.28-7.25 (1H, m), 6.67 (1H, d, J = 8.2 Hz), 5.53 (2H, s), 3.53 (3H, s), 2.54 (3H, s). |
| 8 | [Structure: 3-fluorophenyl-pyridine-O-CH₂-(3-methylphenyl)-tetrazolinone with N-Me] | ¹H-NMR (CDCl₃) δ (ppm): 7.75 (1H, d, J = 7.7 Hz), 7.69 (1H, dt, J = 10.5, 2.1 Hz), 7.62 (1H, t, J = 7.8 Hz), 7.45-7.38 (3H, m), 7.31 (1H, d, J = 7.2 Hz), 7.27-7.24 (1H, m), 7.09 (1H, td, J = 8.3, 2.6 Hz), 6.64 (1H, d, J = 8.3 Hz), 5.52 (2H, s), 3.55 (3H, s), 2.55 (3H, s). |
| 9 | [Structure: 2-cyanophenyl-pyridine-O-CH₂-(3-methylphenyl)-tetrazolinone with N-Me] | ¹H-NMR (CDCl₃) δ (ppm): 7.80 (1H, dd, J = 7.7, 1.2 Hz), 7.77 (1H, dd, J = 8.0, 0.7 Hz), 7.71-7.64 (2H, m), 7.49 (1H, td, J = 7.7, 1.2 Hz), 7.42-7.38 (2H, m), 7.31 (1H, d, J = 7.7 Hz), 7.26-7.24 (1H, m), 6.77 (1H, d, J = 8.0 Hz), 5.51 (2H, s), 3.60 (3H, s), 2.53 (3H, s). |

TABLE 2-continued

| Number of present compound | Structural formula | ¹H-NMR data |
|---|---|---|
| 10 | NC—phenyl—pyridine—O—CH₂—(Me-phenyl)—tetrazolinone(Me) | ¹H-NMR (CDCl₃) δ (ppm): 8.09 (2H, d, J = 8.2 Hz), 7.75 (2H, d, J = 8.2 Hz), 7.66 (1H, t, J = 7.8 Hz), 7.44-7.37 (3H, m), 7.29-7.25 (1H, m), 6.70 (1H, d, J = 8.2 Hz), 5.51 (2H, s), 3.55 (3H, s), 2.54 (3H, s). |

TABLE 3

| Number of present compound | Structural formula | ¹H-NMR data |
|---|---|---|
| 11 | F₃CO—phenyl—pyridine—O—CH₂—(Me-phenyl)—tetrazolinone(Me) | ¹H-NMR (CDCl₃) δ (ppm): 8.03-7.99 (2H, m), 7.62 (1H, dd, J = 8.2, 7.5 Hz), 7.43-7.38 (2H, m), 7.32-7.24 (4H, m), 6.63 (1H, d, J = 8.2 Hz), 5.52 (2H, s), 3.52 (3H, s), 2.54 (3H, s). |
| 12 | MeS—phenyl—pyridine—O—CH₂—(Me-phenyl)—tetrazolinone(Me) | ¹H-NMR (CDCl₃) δ (ppm): 7.93-7.90 (2H, m), 7.58 (1H, dd, J = 8.2, 7.5 Hz), 7.41-7.36 (2H, m), 7.34-7.22 (4H, m), 6.58 (1H, d, J = 8.2 Hz), 5.52 (2H, s), 3.50 (3H, s), 2.54 (3H, s), 2.53 (3H, s). |
| 13 | MeO—phenyl—pyridine—O—CH₂—(cyclopropyl-phenyl)—tetrazolinone(Me) | ¹H-NMR (CDCl₃) δ (ppm): 7.98-7.95 (2H, m), 7.57 (1H, t, J = 7.8 Hz), 7.41 (1H, t, J = 7.8 Hz), 7.27-7.23 (3H, m), 7.01-6.97 (2H, m), 6.55 (1H, d, J = 8.2 Hz), 5.73 (2H, s), 3.87 (3H, s), 3.48 (3H, s), 2.26-2.18 (1H, m), 1.01-0.96 (2H, m), 0.80-0.76 (2H, m). |
| 14 | MeO—phenyl—pyridine—O—CH₂—(Et-phenyl)—tetrazolinone(Me) | ¹H-NMR (CDCl₃) δ (ppm): 7.98-7.94 (2H, m), 7.57 (1H, t, J = 7.8 Hz), 7.45 (2H, d, J = 4.8 Hz), 7.27-7.24 (2H, m), 7.01-6.97 (2H, m), 6.54 (1H, d, J = 8.2 Hz), 5.54 (2H, s), 3.87 (3H, s), 3.47 (3H, s), 2.90 (2H, q, J = 7.6 Hz), 1.30 (3H, t, J = 7.6 Hz). |

TABLE 3-continued

| Number of present compound | Structural formula | ¹H-NMR data |
|---|---|---|
| 15 | (3-methoxyphenyl)-pyridine linked via O-CH₂ to methyl-phenyl-tetrazolone structure | ¹H-NMR (CDCl₃) δ (ppm): 7.62-7.54 (3H, m), 7.41-7.32 (4H, m), 7.26-7.23 (1H, m), 6.96 (1H, ddd, J = 8.2, 2.8, 0.7 Hz), 6.61 (1H, dd, J = 8.2, 0.7 Hz), 5.54 (2H, s), 3.91 (3H, s), 3.49 (3H, s), 2.55 (3H, s). |

TABLE 4

| Number of present compound | Structural formula | ¹H-NMR data |
|---|---|---|
| 16 | (4-dimethylaminophenyl)-pyridine linked via O-CH₂ to methyl-phenyl-tetrazolone structure | ¹H-NMR (CDCl₃) δ (ppm): 7.93-7.90 (2H, m), 7.53 (1H, t, J = 7.8 Hz), 7.41-7.37 (2H, m), 7.25-7.22 (2H, m), 6.81-6.77 (2H, m), 6.48 (1H, d, J = 7.8 Hz), 5.52 (2H, s), 3.50 (3H, s), 3.03 (6H, s), 2.54 (3H, s). |
| 17 | (4-nitrophenyl)-pyridine linked via O-CH₂ to methyl-phenyl-tetrazolone structure | ¹H-NMR (CDCl₃) δ (ppm): 8.34-8.30 (2H, m), 8.15-8.12 (2H, m), 7.68 (1H, dd, J = 8.2, 7.3 Hz), 7.43-7.41 (3H, m), 7.30-7.23 (1H, m), 6.72 (1H, dd, J = 8.2, 0.7 Hz), 5.53 (2H, s), 3.56 (3H, s), 2.54 (3H, s). |
| 18 | (cyclohexenyl)-pyridine linked via O-CH₂ to methyl-phenyl-tetrazolone structure | ¹H-NMR (CDCl₃) δ (ppm): 7.48 (1H, dd, J = 8.1, 7.4 Hz), 7.39-7.38 (2H, m), 7.24 (1H, t, J = 4.8 Hz), 6.91 (1H, d, J = 7.4 Hz), 6.84-6.81 (1H, m), 6.49 (1H, d, J = 8.1 Hz), 5.40 (2H, s), 3.60 (3H, s), 2.50 (3H, s), 2.47-2.42 (2H, m), 2.30-2.24 (2H, m), 1.82-1.76 (2H, m), 1.70-1.64 (2H, m). |
| 19 | (2-methoxyphenyl)-pyridine linked via O-CH₂ to methyl-phenyl-tetrazolone structure | ¹H-NMR (CDCl₃) δ (ppm): 7.84 (1H, d, J = 7.8 Hz), 7.58-7.51 (2H, m), 7.39-7.34 (3H, m), 7.26-7.22 (1H, m), 7.08 (1H, t, J = 7.4 Hz), 7.00 (1H, d, J = 8.2 Hz), 6.58 (1H, d, J = 7.8 Hz), 5.47 (2H, s), 3.88 (3H, s), 3.55 (3H, s), 2.52 (3H, s). |

TABLE 4-continued

| Number of present compound | Structural formula | ¹H-NMR data |
|---|---|---|
| 20 | | ¹H-NMR (CDCl₃) δ (ppm): 8.72-8.70 (2H, m), 7.87-7.85 (2H, m), 7.67 (1H, t, J = 7.9 Hz), 7.43-7.41 (3H, m), 7.28-7.25 (1H, m), 6.72 (1H, d, J = 8.2 Hz), 5.53 (2H, s), 3.54 (3H, s), 2.55 (3H, s). |

TABLE 5

| Number of present compound | Structural formula | ¹H-NMR data |
|---|---|---|
| 21 | | ¹H-NMR (CDCl₃) δ (ppm): 9.17-9.16 (1H, m), 8.64 (1H, dd, J = 4.7, 1.7 Hz), 8.27 (1H, dt, J = 8.0, 1.9 Hz), 7.65 (1H, dd, J = 8.1, 7.4 Hz), 7.41-7.34 (4H, m), 7.27-7.25 (1H, m), 6.67 (1H, d, J = 8.2 Hz), 5.52 (2H, s), 3.56 (3H, s), 2.54 (3H, s). |
| 22 | | ¹H-NMR (CDCl₃) δ (ppm): 8.91 (1H, d, J = 2.3 Hz), 8.23 (1H, dd, J = 8.5, 2.5 Hz), 7.64 (1H, dd, J = 8.0, 7.6 Hz), 7.43-7.40 (3H, m), 7.32 (1H, d, J = 7.3 Hz), 7.28-7.25 (1H, m), 6.67 (1H, d, J = 8.2 Hz), 5.49 (2H, s), 3.58 (3H, s), 2.53 (3H, s). |
| 23 | | ¹H-NMR (CDCl₃) δ (ppm): 7.86-7.83 (2H, m), 7.60-7.56 (3H, m), 7.38 (2H, d, J = 5.1 Hz), 7.29-7.23 (2H, m), 6.61 (1H, d, J = 8.2 Hz), 5.51 (2H, s), 3.51 (3H, s), 2.53 (3H, s). |
| 24 | | ¹H-NMR (CDCl₃) δ (ppm): 8.69 (1H, d, J = 1.0 Hz), 7.97-7.93 (2H, m), 7.43-7.37 (2H, m), 7.28-7.25 (1H, m), 6.98-6.94 (3H, m), 5.47 (2H, s), 3.84 (3H, s), 3.67 (3H, s), 2.55 (3H, s). |

TABLE 5-continued

| Number of present compound | Structural formula | $^1$H-NMR data |
|---|---|---|
| 25 | | $^1$H-NMR (CDCl$_3$) δ (ppm): 8.77 (1H, s), 8.01-7.99 (2H, m), 7.47-7.38 (5H, m), 7.30-7.28 (1H, m), 7.05 (1H, s), 5.52 (2H, s), 3.68 (3H, s), 2.57 (3H, s). |

TABLE 6

| Number of present compound | Structural formula | $^1$H-NMR data |
|---|---|---|
| 26 | | $^1$H-NMR (CDCl$_3$) δ (ppm): 8.53 (1H, s), 8.01 (1H, s), 7.95-7.92 (2H, m), 7.45-7.40 (2H, m), 7.29-7.24 (1H, m), 7.04-7.00 (2H, m), 5.52 (2H, s), 3.88 (3H, s), 3.54 (3H, s), 2.55 (3H, s). |
| 27 | | $^1$H-NMR (CDCl$_3$) δ (ppm): 8.59 (1H, s), 8.08 (1H, s), 7.98-7.95 (2H, m), 7.52-7.40 (5H, m), 7.29-7.25 (1H, m), 5.55 (2H, s), 3.52 (3H, s), 2.55 (3H, s). |
| 28 | | $^1$H-NMR (CDCl$_3$) δ (ppm): 8.77 (1H, s), 8.09 (2H, d, J = 8.2 Hz), 7.76 (2H, d, J = 8.2 Hz), 7.45-7.39 (2H, m), 7.29-7.26 (1H, m), 7.06 (1H, s), 5.50 (2H, s), 3.70 (3H, s), 2.57 (3H, s). |
| 29 | | $^1$H-NMR (CDCl$_3$) δ (ppm): 8.07 (1H, d, J = 5.5 Hz), 7.55-7.52 (2H, m), 7.41-7.37 (2H, m), 7.28-7.24 (1H, m), 7.05 (1H, dd, J = 5.5, 1.6 Hz), 6.98-6.95 (2H, m), 6.83 (1H, d, J = 0.9 Hz), 5.40 (2H, s), 3.85 (3H, s), 3.65 (3H, s), 2.55 (3H, s). |

TABLE 6-continued

| Number of present compound | Structural formula | $^1$H-NMR data |
|---|---|---|
| 30 | | $^1$H-NMR (CDCl$_3$) δ (ppm): 8.11 (1H, d, J = 5.6 Hz), 7.59-7.56 (2H, m), 7.47-7.37 (5H, m), 7.28-7.25 (1H, m), 7.08 (1H, dd, J = 5.6, 1.6 Hz), 6.87 (1H, s), 5.42 (2H, s), 3.66 (3H, s), 2.56 (3H, s). |

TABLE 7

| Number of present compound | Structural formula | $^1$H-NMR data |
|---|---|---|
| 31 | | $^1$H-NMR (CDCl$_3$) δ (ppm): 8.10 (1H, dd, J = 5.4, 0.6 Hz), 7.51-7.48 (2H, m), 7.43-7.37 (4H, m), 7.27-7.24 (1H, m), 7.03 (1H, dd, J = 5.4, 1.4 Hz), 6.83 (1H, dd, J = 1.4, 0.6 Hz), 5.41 (2H, s), 3.66 (3H, s), 2.56 (3H, s). |
| 32 | | $^1$H-NMR (CDCl$_3$) δ (ppm): 8.07 (1H, d, J = 5.3 Hz), 7.40-7.24 (5H, m), 7.05-6.96 (3H, m), 6.84 (1H, s), 5.40 (2H, s), 3.81 (3H, s), 3.65 (3H, s), 2.55 (3H, s). |
| 33 | | $^1$H-NMR (CDCl$_3$) δ (ppm): 8.69 (1H, d, J = 1.0 Hz), 7.65-7.63 (1H, m), 7.55-7.46 (3H, m), 7.43-7.38 (2H, m), 7.28-7.24 (1H, m), 6.86 (1H, d, J = 1.0 Hz), 6.04 (1H, br s), 5.81 (1H, br s), 5.50 (2H, s), 3.72 (3H, s), 2.58 (3H, s). |
| 34 | | $^1$H-NMR (CDCl$_3$) δ (ppm): 7.50-7.43 (3H, m), 7.10-6.94 (7H, m), 5.35 (2H, s), 3.91 (3H, s), 3.85 (3H, s), 3.58 (3H, s), 2.01 (3H, s). |

TABLE 7-continued

| Number of present compound | Structural formula | ¹H-NMR data |
|---|---|---|
| 35 | | ¹H-NMR (CDCl$_3$) δ (ppm): 7.47-7.37 (5H, m), 7.12-7.06 (4H, m), 7.00 (1H, dd, J = 7.6, 1.6 Hz), 5.36 (2H, s), 3.92 (3H, s), 3.59 (3H, s), 2.01 (3H, s). |

TABLE 8

| Number of present compound | Structural formula | ¹H-NMR data |
|---|---|---|
| 36 | | ¹H-NMR (CDCl$_3$) δ (ppm): 7.54 (2H, d, J = 7.2 Hz), 7.47-7.40 (3H, m), 7.32 (1H, t, J = 7.4 Hz), 7.12-7.04 (5H, m), 5.36 (2H, s), 3.91 (3H, s), 3.58 (3H, s), 2.02 (3H, s). |
| 37 | | ¹H-NMR (CDCl$_3$) δ (ppm): 7.49-7.40 (3H, m), 7.35-7.26 (2H, m), 7.12-7.00 (5H, m), 5.39 (2H, s), 3.95 (3H, s), 3.62 (3H, s), 2.01 (3H, s). |
| 38 | | ¹H-NMR (CDCl$_3$) δ (ppm): 7.47-7.43 (2H, m), 7.33-7.23 (3H, m), 7.12-6.97 (4H, m), 6.91 (1H, dd, J = 7.6, 1.6 Hz), 5.29 (2H, s), 3.86 (3H, s), 3.61 (3H, s), 2.04 (3H, s). |
| 39 | | ¹H-NMR (CDCl$_3$) δ (ppm): 7.52-7.49 (2H, m), 7.44-7.38 (2H, m), 7.32-7.26 (2H, m), 7.15 (1H, d, J = 7.6 Hz), 7.05 (1H, t, J = 2.1 Hz), 6.98-6.95 (2H, m), 6.83-6.80 (1H, m), 5.08 (2H, s), 3.85 (3H, s), 3.58 (3H, s), 2.51 (3H, s). |

TABLE 8-continued

| Number of present compound | Structural formula | $^1$H-NMR data |
|---|---|---|
| 40 | | $^1$H-NMR (CDCl$_3$) δ (ppm): 7.58-7.56 (2H, m), 7.45-7.27 (7H, m), 7.21-7.18 (1H, m), 7.09 (1H, t, J = 2.1 Hz), 6.88-6.85 (1H, m), 5.09 (2H, s), 3.58 (3H, s), 2.52 (3H, s). |

TABLE 9

| Number of present compound | Structural formula | $^1$H-NMR data |
|---|---|---|
| 41 | | $^1$H-NMR (CDCl$_3$) δ (ppm): 7.61 (1H, d, J = 8.0 Hz), 7.52-7.37 (4H, m), 7.29 (1H, t, J = 7.9 Hz), 7.15 (1H, d, J = 7.9 Hz), 7.00-6.96 (3H, m), 6.77 (1H, dd, J = 8.1, 2.4 Hz), 5.36 (2H, s), 3.85 (3H, s), 3.55 (3H, s). |
| 42 | | $^1$H-NMR (CDCl$_3$) δ (ppm): 7.53-7.49 (2H, m), 7.43 (1H, t, J = 7.9 Hz), 7.33-7.26 (3H, m), 7.16-7.14 (1H, m), 7.06 (1H, t, J = 2.1 Hz), 6.99-6.95 (2H, m), 6.84 (1H, dd, J = 8.0, 2.5 Hz), 5.30 (2H, s), 3.85 (3H, s), 3.56 (3H, s), 2.17-2.10 (1H, m), 1.02-0.97 (2H, m), 0.79-0.75 (2H, m). |
| 43 | | $^1$H-NMR (CDCl$_3$) δ (ppm): 7.53-7.44 (4H, m), 7.34-7.26 (2H, m), 7.16 (1H, d, J = 7.8 Hz), 7.05 (1H, s), 6.97 (2H, d, J = 8.8 Hz), 6.84-6.81 (1H, m), 5.10 (2H, s), 3.86 (3H, s), 3.56 (3H, s), 2.85 (2H, q, J = 8.0 Hz), 1.30 (3H, t, J = 7.4 Hz). |
| 44 | | $^1$H-NMR (CDCl$_3$) δ (ppm): 7.51-7.44 (3H, m), 7.29-7.25 (1H, m), 7.12-7.06 (3H, m), 7.01 (1H, t, J = 1.9 Hz), 6.98-6.94 (2H, m), 6.78-6.75 (1H, m), 5.28 (2H, s), 3.92 (3H, s), 3.85 (3H, s), 3.55 (3H, s). |

TABLE 9-continued

| Number of present compound | Structural formula | ¹H-NMR data |
|---|---|---|
| 45 | (Et-biphenyl-O-CH₂-Me-phenyl-tetrazolone structure) | ¹H-NMR (CDCl₃) δ (ppm): 7.51-7.48 (2H, m), 7.45-7.39 (2H, m), 7.34-7.26 (4H, m), 7.20-7.17 (1H, m), 7.09 (1H, t, J = 2.1 Hz), 6.84 (1H, ddd, J = 8.1, 2.5, 0.8 Hz), 5.08 (2H, s), 3.59 (3H, s), 2.69 (2H, q, J = 7.6 Hz), 2.51 (3H, s), 1.28 (3H, t, J = 7.7 Hz). |

TABLE 10

| Number of present compound | Structural formula | ¹H-NMR data |
|---|---|---|
| 46 | (Me-biphenyl-O-CH₂-Me-phenyl-tetrazolone structure) | ¹H-NMR (CDCl₃) δ (ppm): 7.48-7.39 (4H, m), 7.34-7.17 (5H, m), 7.08 (1H, t, J = 2.1 Hz), 6.84 (1H, dd, J = 8.2, 2.5 Hz), 5.08 (2H, s), 3.58 (3H, s), 2.51 (3H, s), 2.39 (3H, s). |
| 47 | (MeS-biphenyl-O-CH₂-Me-phenyl-tetrazolone structure) | ¹H-NMR (CDCl₃) δ (ppm): 7.52-7.48 (2H, m), 7.45-7.39 (2H, m), 7.34-7.27 (4H, m), 7.18-7.16 (1H, m), 7.07 (1H, t, J = 1.9 Hz), 6.85 (1H, dd, J = 8.2, 2.5 Hz), 5.08 (2H, s), 3.58 (3H, s), 2.52 (3H, s), 2.51 (3H, s). |
| 48 | (F₃CO-biphenyl-O-CH₂-Me-phenyl-tetrazolone structure) | ¹H-NMR (CDCl₃) δ (ppm): 7.59-7.56 (2H, m), 7.45-7.40 (2H, m), 7.35 (1H, t, J = 7.9 Hz), 7.30-7.26 (3H, m), 7.17-7.14 (1H, m), 7.05 (1H, t, J = 1.9 Hz), 6.89 (1H, dd, J = 8.2, 2.5 Hz), 5.09 (2H, s), 3.59 (3H, s), 2.51 (3H, s). |
| 49 | (F₃C-biphenyl-O-CH₂-Me-phenyl-tetrazolone structure) | ¹H-NMR (CDCl₃) δ (ppm): 7.70-7.65 (4H, m), 7.46-7.35 (3H, m), 7.29 (1H, dd, J = 6.9, 2.3 Hz), 7.20 (1H, d, J = 7.6 Hz), 7.09 (1H, s), 6.92 (1H, dd, J = 8.2, 2.5 Hz), 5.10 (2H, s), 3.59 (3H, s), 2.52 (3H, s). |

TABLE 10-continued

| Number of present compound | Structural formula | ¹H-NMR data |
|---|---|---|
| 50 | (structure) | ¹H-NMR (CDCl₃) δ (ppm): 7.45-7.26 (5H, m), 7.20-7.15 (2H, m), 7.10-7.09 (2H, m), 6.91-6.86 (2H, m), 5.08 (2H, s), 3.86 (3H, s), 3.59 (3H, s), 2.51 (3H, s). |

TABLE 11

| Number of present compound | Structural formula | ¹H-NMR data |
|---|---|---|
| 51 | (structure) | ¹H-NMR (CDCl₃) δ (ppm): 7.50-7.47 (2H, m), 7.44-7.39 (2H, m), 7.31-7.26 (2H, m), 7.16 (1H, d, J = 7.8 Hz), 7.06 (1H, t, J = 1.9 Hz), 6.81-6.76 (3H, m), 5.07 (2H, s), 3.58 (3H, s), 2.99 (6H, s), 2.51 (3H, s). |
| 52 | (structure) | ¹H-NMR (CDCl₃) δ (ppm): 7.43-7.38 (2H, m), 7.34-7.25 (4H, m), 7.14-7.12 (1H, m), 7.07 (1H, t, J = 2.1 Hz), 7.04-7.00 (1H, m), 6.98 (1H, d, J = 7.8 Hz), 6.85 (1H, ddd, J = 8.2, 2.6, 0.8 Hz), 5.05 (2H, s), 3.81 (3H, s), 3.60 (3H, s), 2.50 (3H, s). |
| 53 | (structure) | ¹H-NMR (CDCl₃) δ (ppm): 7.47-7.26 (8H, m), 7.05 (1H, d, J = 6.6 Hz), 6.95 (1H, s), 6.90 (1H, d, J = 8.2 Hz), 5.07 (2H, s), 3.61 (3H, s), 2.51 (3H, s). |
| 54 | (structure) | ¹H-NMR (CDCl₃) δ (ppm): 8.83-8.82 (1H, m), 8.60-8.58 (1H, m), 7.87-7.83 (1H, m), 7.45-7.28 (5H, m), 7.20-7.17 (1H, m), 7.07 (1H, s), 6.92 (1H, dd, J = 8.2, 2.5 Hz), 5.10 (2H, s), 3.60 (3H, s), 2.52 (3H, s). |

TABLE 11-continued

| Number of present compound | Structural formula | ¹H-NMR data |
|---|---|---|
| 55 | | ¹H-NMR (CDCl₃) δ (ppm): 7.55-7.54 (1H, m), 7.45-7.28 (7H, m), 7.17-7.15 (1H, m), 7.05 (1H, dd, J = 2.4, 1.7 Hz), 6.90-6.87 (1H, m), 5.09 (2H, s), 3.60 (3H, s), 2.51 (3H, s). |

TABLE 12

| Number of present compound | Structural formula | ¹H-NMR data |
|---|---|---|
| 56 | | ¹H-NMR (CDCl₃) δ (ppm): 7.51-7.48 (2H, m), 7.45-7.38 (4H, m), 7.33 (1H, t, J = 8.0 Hz), 7.28 (1H, dd, J = 6.9, 2.3 Hz), 7.16-7.14 (1H, m), 7.04 (1H, t, J = 2.1 Hz), 6.89-6.86 (1H, m), 5.08 (2H, s), 3.59 (3H, s), 2.51 (3H, s). |
| 57 | | ¹H-NMR (CDCl₃) δ (ppm): 8.37 (1H, d, J = 2.5 Hz), 7.76 (1H, dd, J = 8.6, 2.6 Hz), 7.45-7.39 (2H, m), 7.34 (1H, t, J = 7.9 Hz), 7.29 (1H, dd, J = 6.9, 2.5 Hz), 7.14-7.11 (1H, m), 7.02 (1H, t, J = 2.1 Hz), 6.87 (1H, ddd, J = 8.2, 2.5, 0.7 Hz), 6.81 (1H, dd, J = 8.6, 0.7 Hz), 5.08 (2H, s), 3.98 (3H, s), 3.60 (3H, s), 2.51 (3H, s). |
| 58 | | ¹H-NMR (CDCl₃) δ (ppm): 7.55-7.50 (2H, m), 7.45-7.39 (2H, m), 7.35-7.27 (2H, m), 7.15-7.09 (3H, m), 7.04 (1H, t, J = 2.1 Hz), 6.86 (1H, dd, J = 8.2, 2.5 Hz), 5.08 (2H, s), 3.59 (3H, s), 2.51 (3H, s). |
| 59 | | ¹H-NMR (CDCl₃) δ (ppm): 7.45-7.39 (2H, m), 7.34 (1H, t, J = 8.0 Hz), 7.29 (1H, dd, J = 6.9, 2.3 Hz), 7.20-7.12 (2H, m), 7.08 (1H, d, J = 7.7 Hz), 6.97 (1H, t, J = 2.1 Hz), 6.90 (1H, dd, J = 8.2, 2.4 Hz), 5.08 (2H, s), 3.60 (3H, s), 2.51 (3H, s). |

TABLE 12-continued

| Number of present compound | Structural formula | $^1$H-NMR data |
|---|---|---|
| 60 | 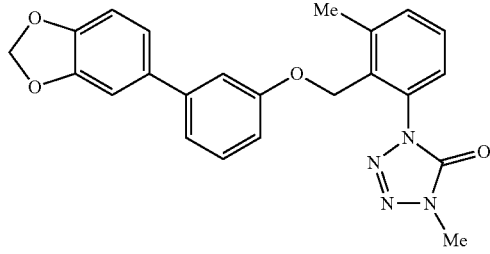 | $^1$H-NMR (CDCl$_3$) δ (ppm): 7.44-7.39 (2H, m), 7.32-7.27 (2H, m), 7.12-7.10 (1H, m), 7.05-7.01 (3H, m), 6.88-6.86 (1H, m), 6.83 (1H, ddd, J = 8.3, 2.6, 0.7 Hz), 5.99 (2H, s), 5.08 (2H, s), 3.59 (3H, s), 2.51 (3H, s). |

TABLE 13

| Number of present compound | Structural formula | $^1$H-NMR data |
|---|---|---|
| 61 | 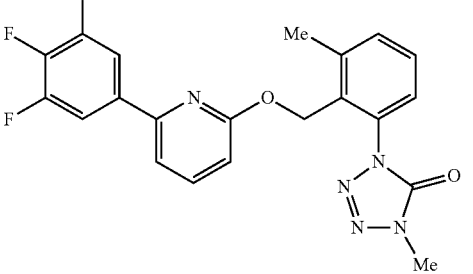 | $^1$H-NMR (CDCl$_3$) δ (ppm): 7.65-7.57 (3H, m), 7.41 (2H, d, J = 4.8 Hz), 7.28-7.23 (2H, m), 6.66 (1H, d, J = 8.0 Hz), 5.49 (2H, s), 3.60 (3H, s), 2.54 (3H, s). |
| 62 | 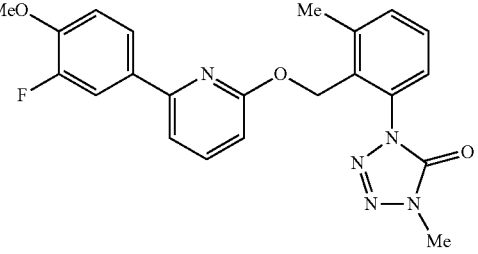 [SMILES: Cc1ccc(-c2cccc(OCc3c(C)cccc3-n3nnn(C)c3=O)n2)cc1] | $^1$H-NMR (CDCl$_3$) δ (ppm): 7.76-7.71 (2H, m), 7.58 (1H, t, J = 7.8 Hz), 7.42-7.38 (2H, m), 7.27-7.23 (2H, m), 7.03 (1H, t, J = 8.8 Hz), 6.58 (1H, d, J = 8.2 Hz), 5.50 (2H, s), 3.95 (3H, s), 3.55 (3H, s), 2.54 (3H, s). |
| 63 | 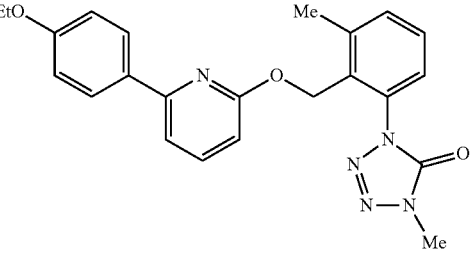 [SMILES: Cc1cccc(-n2nnn(C)c2=O)c1COc1cccc(-c2ccc(Br)cc2)n1] | $^1$H-NMR (CDCl$_3$) δ (ppm): 7.96-7.92 (2H, m), 7.57 (1H, t, J = 8.2 Hz), 7.42-7.39 (2H, m), 7.27-7.23 (2H, m), 7.00-6.96 (2H, m), 6.55 (1H, d, J = 8.2 Hz), 5.52 (2H, s), 4.10 (2H, q, J = 7.0 Hz), 3.51 (3H, s), 2.54 (3H, s), 1.46 (3H, t, J = 7.0 Hz). |
| 64 | 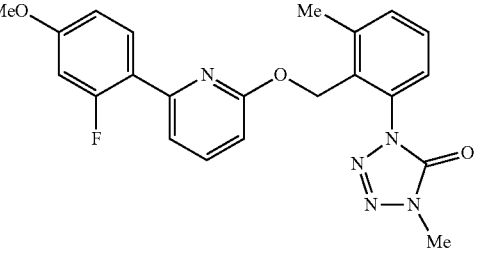 | $^1$H-NMR (CDCl$_3$) δ (ppm): 7.90 (1H, t, J = 8.2 Hz), 7.60 (1H, t, J = 7.9 Hz), 7.43-7.38 (3H, m), 7.27-7.23 (1H, m), 7.07 (1H, d, J = 7.9 Hz), 6.97 (1H, d, J = 12.4 Hz), 6.61 (1H, d, J = 8.2 Hz), 5.49 (2H, s), 3.55 (3H, s), 2.53 (3H, s), 2.40 (3H, s). |

TABLE 13-continued

| Number of present compound | Structural formula | ¹H-NMR data |
|---|---|---|
| 65 | | ¹H-NMR (CDCl₃) δ (ppm): 8.00-7.95 (2H, m), 7.59 (1H, t, J = 7.8 Hz), 7.47-7.43 (2H, m), 7.28-7.23 (2H, m), 7.17-7.11 (2H, m), 6.59 (1H, d, J = 8.2 Hz), 5.54 (2H, s), 3.47 (3H, s), 2.89 (2H, q, J = 7.6 Hz), 1.29 (3H, t, J = 7.6 Hz). |

TABLE 14

| Number of present compound | Structural formula | ¹H-NMR data |
|---|---|---|
| 66 | | ¹H-NMR (CDCl₃) δ (ppm): 8.01-7.96 (2H, m), 7.59 (1H, t, J = 7.8 Hz), 7.41 (1H, t, J = 7.8 Hz), 7.28-7.23 (3H, m), 7.17-7.11 (2H, m), 6.60 (1H, d, J = 8.2 Hz), 5.73 (2H, s), 3.49 (3H, s), 2.21 (1H, tt, J = 8.6, 3.8 Hz), 1.01-0.96 (2H, m), 0.80-0.76 (2H, m). |
| 67 | | ¹H-NMR (CDCl₃) δ (ppm): 7.99-7.95 (2H, m), 7.62 (1H, dd, J = 8.2, 1.2 Hz), 7.56 (1H, t, J = 7.8 Hz), 7.43 (1H, t, J = 8.0 Hz), 7.34 (1H, dd, J = 8.0, 1.2 Hz), 7.27-7.26 (1H, m), 7.00-6.96 (2H, m), 6.49 (1H, d, J = 8.0 Hz), 5.74 (2H, s), 3.87 (3H, s), 3.47 (3H, s). |
| 68 | | ¹H-NMR (CDCl₃) δ (ppm): 8.02-7.96 (2H, m), 7.63-7.57 (2H, m), 7.44 (1H, t, J = 8.0 Hz), 7.35 (1H, dd, J = 8.0, 1.0 Hz), 7.28 (1H, d, J = 7.2 Hz), 7.17-7.11 (2H, m), 6.55 (1H, d, J = 8.2 Hz), 5.73 (2H, s), 3.50 (3H, s). |
| 69 | | ¹H-NMR (CDCl₃) δ (ppm): 8.00-7.96 (2H, m), 7.53 (1H, dd, J = 8.2, 7.6 Hz), 7.44 (1H, t, J = 8.1 Hz), 7.24 (1H, dd, J = 7.6, 0.7 Hz), 7.09 (1H, d, J = 8.5 Hz), 7.03-6.96 (3H, m), 6.48 (1H, dd, J = 8.2, 0.7 Hz), 5.65 (2H, s), 3.93 (3H, s), 3.87 (3H, s), 3.45 (3H, s). |

TABLE 14-continued

| Number of present compound | Structural formula | ¹H-NMR data |
|---|---|---|
| 70 | (structure) | ¹H-NMR (CDCl₃) δ (ppm): 8.03-7.98 (2H, m), 7.56 (1H, dd, J = 8.2, 7.6 Hz), 7.45 (1H, t, J = 8.1 Hz), 7.25 (1H, d, J = 7.1 Hz), 7.16-7.08 (3H, m), 7.02 (1H, dd, J = 7.9, 0.8 Hz), 6.53 (1H, d, J = 8.2 Hz), 5.64 (2H, s), 3.92 (3H, s), 3.48 (3H, s). |

TABLE 15

| Number of present compound | Structural formula | ¹H-NMR data |
|---|---|---|
| 71 | (structure) | ¹H-NMR (CDCl₃) δ (ppm): 7.96-7.92 (2H, m), 7.57 (1H, dd, J = 8.0, 7.6 Hz), 7.42-7.37 (2H, m), 7.27-7.24 (2H, m), 7.00-6.96 (2H, m), 6.55 (1H, dd, J = 8.0, 0.5 Hz), 5.52 (2H, s), 3.99 (2H, t, J = 6.5 Hz), 3.51 (3H, s), 2.54 (3H, s), 1.89-1.80 (2H, m), 1.07 (3H, t, J = 7.4 Hz). |
| 72 | (structure) | ¹H-NMR (CDCl₃) δ (ppm): 7.99-7.95 (2H, m), 7.59 (1H, t, J = 7.8 Hz), 7.41-7.35 (4H, m), 7.30-7.24 (2H, m), 7.16-7.13 (1H, m), 7.11-7.06 (4H, m), 6.59 (1H, d, J = 8.0 Hz), 5.51 (2H, s), 3.54 (3H, s), 2.54 (3H, s). |
| 73 | (structure) | ¹H-NMR (CDCl₃) δ (ppm): 7.95-7.91 (2H, m), 7.56 (1H, t, J = 7.9 Hz), 7.41-7.37 (2H, m), 7.27-7.22 (2H, m), 6.98-6.95 (2H, m), 6.54 (1H, d, J = 8.2 Hz), 5.51 (2H, s), 4.68-4.58 (1H, m), 3.51 (3H, s), 2.54 (3H, s), 1.38 (6H, d, J = 6.2 Hz). |
| 74 | (structure) | ¹H-NMR (CDCl₃) δ (ppm): 7.58-7.49 (3H, m), 7.42-7.37 (2H, m), 7.27-7.21 (2H, m), 6.91-6.88 (1H, m), 6.56 (1H, dd, J = 8.1, 0.6 Hz), 6.02 (2H, s), 5.50 (2H, s), 3.55 (3H, s), 2.54 (3H, s). |

TABLE 15-continued

| Number of present compound | Structural formula | ¹H-NMR data |
|---|---|---|
| 75 | 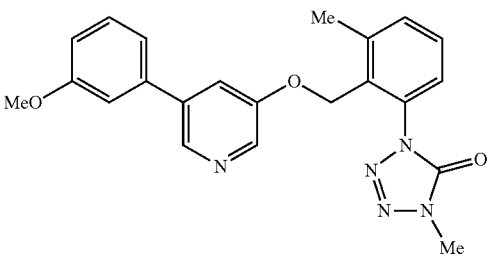 [SMILES: COc1cccc(-c2cncc(OCc3c(C)cccc3-n3nnn(C)c3=O)c2)c1] | ¹H-NMR (CDCl₃) δ (ppm): 8.47 (1H, d, J = 1.6 Hz), 8.26 (1H, d, J = 2.7 Hz), 7.47-7.29 (5H, m), 7.15 (1H, d, J = 7.8 Hz), 7.08 (1H, t, J = 2.1 Hz), 6.95 (1H, dd, J = 8.2, 2.5 Hz), 5.14 (2H, s), 3.87 (3H, s), 3.63 (3H, s), 2.52 (3H, s). |

TABLE 16

| Number of present compound | Structural formula | ¹H-NMR data |
|---|---|---|
| 76 | 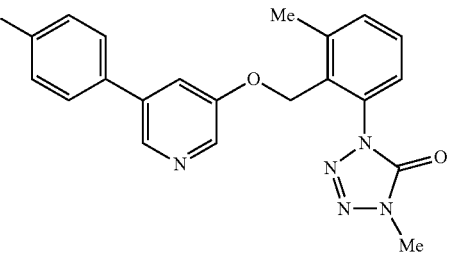 | ¹H-NMR (CDCl₃) δ (ppm): 8.43 (1H, d, J = 1.8 Hz), 8.26 (1H, d, J = 2.7 Hz), 7.55-7.50 (2H, m), 7.48-7.41 (2H, m), 7.32-7.30 (2H, m), 7.20-7.14 (2H, m), 5.14 (2H, s), 3.63 (3H, s), 2.52 (3H, s). |
| 77 | 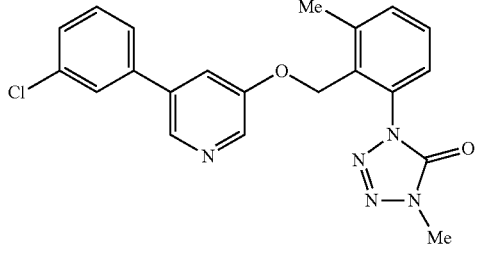 [SMILES: Cc1cccc(-n2nnn(C)c2=O)c1COc1cncc(-c2cccc(Cl)c2)c1] | ¹H-NMR (CDCl₃) δ (ppm): 8.45 (1H, d, J = 1.8 Hz), 8.28 (1H, d, J = 2.7 Hz), 7.55-7.54 (1H, m), 7.48-7.37 (5H, m), 7.32-7.30 (2H, m), 5.14 (2H, s), 3.64 (3H, s), 2.53 (3H, s). |
| 78 | 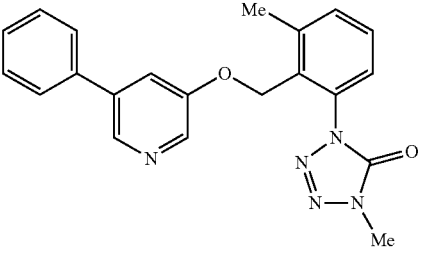 [SMILES: Cc1cccc(-n2nnn(C)c2=O)c1COc1cncc(-c2ccccc2)c1] | ¹H-NMR (CDCl₃) δ (ppm): 8.48 (1H, d, J = 1.8 Hz), 8.26 (1H, d, J = 2.7 Hz), 7.58-7.55 (2H, m), 7.50-7.39 (5H, m), 7.36 (1H, dd, J = 2.7, 1.8 Hz), 7.31 (1H, dd, J = 7.2, 1.9 Hz), 5.14 (2H, s), 3.63 (3H, s), 2.52 (3H, s). |
| 79 | 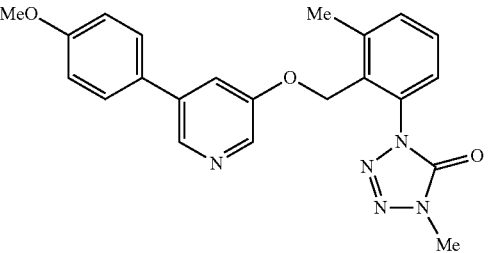 | ¹H-NMR (CDCl₃) δ (ppm): 8.45 (1H, s), 8.21 (1H, d, J = 2.7 Hz), 7.52-7.49 (2H, m), 7.47-7.41 (2H, m), 7.31-7.29 (2H, m), 7.02-6.99 (2H, m), 5.13 (2H, s), 3.86 (3H, s), 3.62 (3H, s), 2.52 (3H, s). |

TABLE 16-continued

| Number of present compound | Structural formula | ¹H-NMR data |
|---|---|---|
| 80 | 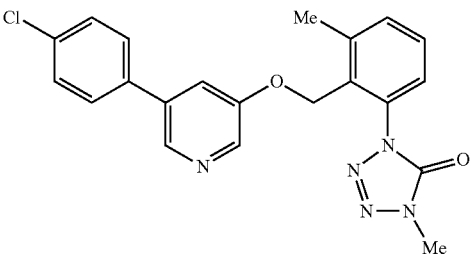 [SMILES: Cc1cccc(-n2nnn(C)c2=O)c1COc1cncc(-c2ccc(Cl)cc2)c1] | ¹H-NMR (CDCl₃) δ (ppm): 8.44 (1H, d, J = 1.8 Hz), 8.27 (1H, d, J = 2.7 Hz), 7.51-7.41 (6H, m), 7.32-7.29 (2H, m), 5.14 (2H, s), 3.63 (3H, s), 2.52 (3H, s). |

TABLE 17

| Number of present compound | Structural formula | ¹H-NMR data |
|---|---|---|
| 81 | 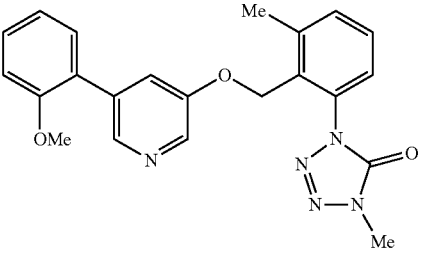 [SMILES: COc1ccccc1-c1cncc(OCc2c(C)cccc2-n2nnn(C)c2=O)c1] | ¹H-NMR (CDCl₃) δ (ppm): 8.40 (1H, d, J = 1.6 Hz), 8.22 (1H, d, J = 2.7 Hz), 7.47-7.29 (6H, m), 7.06 (1H, t, J = 7.6 Hz), 7.01 (1H, d, J = 8.2 Hz), 5.11 (2H, s), 3.83 (3H, s), 3.63 (3H, s), 2.52 (3H, s). |
| 82 | 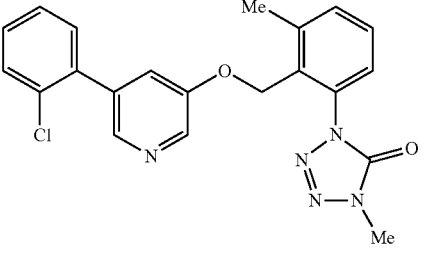 [SMILES: Cc1cccc(-n2nnn(C)c2=O)c1COc1cncc(-c2ccccc2Cl)c1] | ¹H-NMR (CDCl₃) δ (ppm): 8.48 (1H, d, J = 1.8 Hz), 8.30 (1H, d, J = 2.7 Hz), 7.50-7.43 (6H, m), 7.38-7.30 (2H, m), 5.15 (2H, s), 3.62 (3H, s), 2.52 (3H, s). |
| 83 | 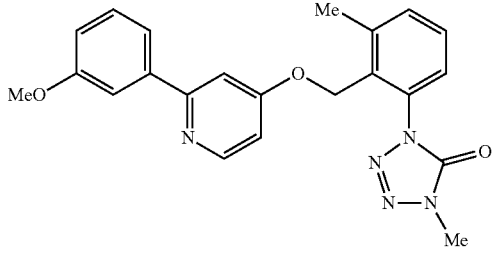 [SMILES: COc1cccc(-c2cc(OCc3c(C)cccc3-n3nnn(C)c3=O)ccn2)c1] | ¹H-NMR (CDCl₃) δ (ppm): 8.51 (1H, d, J = 5.7 Hz), 7.54 (1H, dd, J = 2.5, 1.6 Hz), 7.51-7.41 (3H, m), 7.37 (1H, t, J = 8.0 Hz), 7.31 (1H, dd, J = 7.4, 1.6 Hz), 7.20 (1H, d, J = 2.3 Hz), 6.98-6.95 (1H, m), 6.76 (1H, dd, J = 5.7, 2.3 Hz), 5.15 (2H, s), 3.89 (3H, s), 3.61 (3H, s), 2.51 (3H, s). |
| 84 | 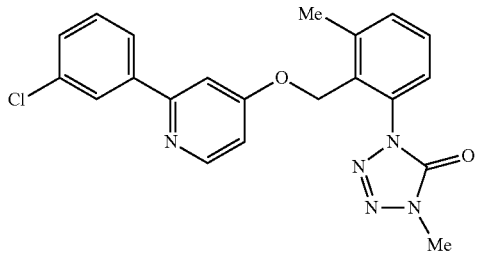 [SMILES: Cc1cccc(-n2nnn(C)c2=O)c1COc1ccnc(-c2cccc(Cl)c2)c1] | ¹H-NMR (CDCl₃) δ (ppm): 8.51 (1H, d, J = 5.7 Hz), 7.97 (1H, s), 7.82-7.79 (1H, m), 7.48-7.38 (4H, m), 7.32 (1H, dd, J = 7.6, 1.6 Hz), 7.18 (1H, d, J = 2.3 Hz), 6.78 (1H, dd, J = 5.7, 2.3 Hz), 5.15 (2H, s), 3.62 (3H, s), 2.51 (3H, s). |

TABLE 17-continued

| Number of present compound | Structural formula | $^1$H-NMR data |
|---|---|---|
| 85 | | $^1$H-NMR (CDCl$_3$) δ (ppm): 8.49 (1H, d, J = 5.7 Hz), 7.96-7.90 (2H, m), 7.48-7.41 (2H, m), 7.31 (1H, dd, J = 7.6, 1.6 Hz), 7.16-7.12 (3H, m), 6.75 (1H, dd, J = 5.7, 2.3 Hz), 5.14 (2H, s), 3.61 (3H, s), 2.51 (3H, s). |

TABLE 18

| Number of present compound | Structural formula | $^1$H-NMR data |
|---|---|---|
| 86 | | $^1$H-NMR (CDCl$_3$) δ (ppm): 8.47 (1H, d, J = 5.7 Hz), 7.92-7.89 (2H, m), 7.48-7.42 (2H, m), 7.31 (1H, dd, J = 7.2, 1.7 Hz), 7.14 (1H, d, J = 2.3 Hz), 7.00-6.97 (2H, m), 6.71 (1H, dd, J = 5.7, 2.3 Hz), 5.14 (2H, s), 3.86 (3H, s), 3.61 (3H, s), 2.51 (3H, s). |
| 87 | | $^1$H-NMR (CDCl$_3$) δ (ppm): 8.50 (1H, d, J = 5.7 Hz), 7.91-7.88 (2H, m), 7.49-7.42 (4H, m), 7.32 (1H, dd, J = 7.6, 1.6 Hz), 7.17 (1H, d, J = 2.3 Hz), 6.77 (1H, dd, J = 5.7, 2.3 Hz), 5.15 (2H, s), 3.61 (3H, s), 2.51 (3H, s). |
| 88 | | $^1$H-NMR (CDCl$_3$) δ (ppm): 8.51 (1H, d, J = 5.7 Hz), 7.76 (1H, dd, J = 7.6, 1.6 Hz), 7.47-7.29 (5H, m), 7.07 (1H, t, J = 7.4 Hz), 7.00 (1H, d, J = 8.2 Hz), 6.74 (1H, dd, J = 5.7, 2.5 Hz), 5.12 (2H, s), 3.87 (3H, s), 3.61 (3H, s), 2.50 (3H, s). |
| 89 | | $^1$H-NMR (CDCl$_3$) δ (ppm): 8.52 (1H, d, J = 5.7 Hz), 7.96-7.93 (2H, m), 7.49-7.39 (5H, m), 7.31 (1H, dd, J = 7.3, 1.8 Hz), 7.21 (1H, d, J = 2.3 Hz), 6.76 (1H, dd, J = 5.7, 2.3 Hz), 5.15 (2H, s), 3.61 (3H, s), 2.51 (3H, s). |

TABLE 18-continued

| Number of present compound | Structural formula | ¹H-NMR data |
|---|---|---|
| 90 | | ¹H-NMR (CDCl₃) δ (ppm): 8.50 (1H, d, J = 5.7 Hz), 8.42-8.37 (2H, m), 7.51-7.49 (3H, m), 7.46-7.41 (2H, m), 7.29-7.25 (1H, m), 6.57 (1H, d, J = 5.7 Hz), 5.60 (2H, s), 3.51 (3H, s), 2.55 (3H, s). |

TABLE 19

| Number of present compound | Structural formula | ¹H-NMR data |
|---|---|---|
| 91 | | ¹H-NMR (CDCl₃) δ (ppm): 8.47 (1H, d, J = 5.7 Hz), 8.43-8.38 (2H, m), 7.46-7.41 (2H, m), 7.30-7.27 (1H, m), 7.19-7.14 (2H, m), 6.56 (1H, d, J = 5.7 Hz), 5.58 (2H, s), 3.53 (3H, s), 2.54 (3H, s). |
| 92 | | ¹H-NMR (CDCl₃) δ (ppm): 8.45 (1H, d, J = 5.7 Hz), 8.37-8.34 (2H, m), 7.45-7.41 (2H, m), 7.29-7.25 (1H, m), 7.02-6.98 (2H, m), 6.50 (1H, d, J = 5.7 Hz), 5.58 (2H, s), 3.89 (3H, s), 3.52 (3H, s), 2.55 (3H, s). |
| 93 | | ¹H-NMR (CDCl₃) δ (ppm): 8.48 (1H, d, J = 5.7 Hz), 8.35-8.32 (2H, m), 7.48-7.43 (4H, m), 7.30-7.26 (1H, m), 6.58 (1H, d, J = 5.7 Hz), 5.58 (2H, s), 3.53 (3H, s), 2.54 (3H, s). |
| 94 | | ¹H-NMR (CDCl₃) δ (ppm): 8.53 (1H, d, J = 5.7 Hz), 7.70 (1H, dd, J = 7.7, 1.7 Hz), 7.45-7.38 (3H, m), 7.28-7.24 (1H, m), 7.08-7.03 (2H, m), 6.57 (1H, d, J = 5.7 Hz), 5.52 (2H, s), 3.89 (3H, s), 3.56 (3H, s), 2.52 (3H, s). |

TABLE 19-continued

| Number of present compound | Structural formula | ¹H-NMR data |
|---|---|---|
| 95 | | ¹H-NMR (CDCl₃) δ (ppm): 8.54 (1H, d, J = 5.7 Hz), 7.77-7.73 (1H, m), 7.52-7.48 (1H, m), 7.44-7.36 (4H, m), 7.28-7.24 (1H, m), 6.64 (1H, d, J = 5.7 Hz), 5.53 (2H, s), 3.59 (3H, s), 2.52 (3H, s). |

TABLE 20

| Number of present compound | Structural formula | ¹H-NMR data |
|---|---|---|
| 96 | | ¹H-NMR (CDCl₃) δ (ppm): 8.49 (1H, d, J = 5.7 Hz), 8.01-7.96 (2H, m), 7.46-7.39 (3H, m), 7.29-7.25 (1H, m), 7.07-7.04 (1H, m), 6.57 (1H, d, J = 5.7 Hz), 5.61 (2H, s), 3.92 (3H, s), 3.50 (3H, s), 2.55 (3H, s). |
| 97 | | ¹H-NMR (CDCl₃) δ (ppm): 8.50 (1H, d, J = 5.7 Hz), 8.36 (1H, t, J = 1.8 Hz), 8.28 (1H, dt, J = 7.4, 1.5 Hz), 7.48-7.40 (4H, m), 7.30-7.26 (1H, m), 6.59 (1H, d, J = 5.7 Hz), 5.58 (2H, s), 3.56 (3H, s), 2.56 (3H, s). |
| 98 | | ¹H-NMR (CDCl₃) δ (ppm): 8.46 (1H, d, J = 5.0 Hz), 7.62-7.57 (2H, m), 7.41-7.37 (3H, m), 7.30 (1H, d, J = 5.3 Hz), 7.26-7.24 (1H, m), 7.04 (1H, dd, J = 8.1, 1.7 Hz), 5.55 (2H, s), 3.89 (3H, s), 3.61 (3H, s), 2.60 (3H, s). |
| 99 | | ¹H-NMR (CDCl₃) δ (ppm): 8.46 (1H, d, J = 5.3 Hz), 8.05-8.02 (2H, m), 7.50-7.45 (3H, m), 7.41-7.37 (2H, m), 7.32 (1H, d, J = 5.3 Hz), 7.27-7.24 (1H, m), 5.55 (2H, s), 3.61 (3H, s), 2.60 (3H, s). |

TABLE 20-continued

| Number of present compound | Structural formula | ¹H-NMR data |
|---|---|---|
| 100 | | ¹H-NMR (CDCl₃) δ (ppm): 8.40 (1H, d, J = 5.3 Hz), 8.04-8.01 (2H, m), 7.41-7.37 (2H, m), 7.26-7.24 (2H, m), 7.00-6.97 (2H, m), 5.52 (2H, s), 3.88 (3H, s), 3.62 (3H, s), 2.60 (3H, s). |

TABLE 21

| Number of present compound | Structural formula | ¹H-NMR data |
|---|---|---|
| 101 | | ¹H-NMR (CDCl₃) δ (ppm): 8.39 (1H, d, J = 5.3 Hz), 7.95 (1H, dd, J = 7.8, 1.8 Hz), 7.58 (1H, d, J = 5.3 Hz), 7.45-7.36 (3H, m), 7.26-7.23 (1H, m), 7.09-7.05 (1H, m), 7.00 (1H, d, J = 8.5 Hz), 5.51 (2H, s), 3.89 (3H, s), 3.63 (3H, s), 2.59 (3H, s). |
| 102 | | ¹H-NMR (CDCl₃) δ (ppm): 7.43-7.38 (2H, m), 7.30-7.26 (1H, m), 7.20 (1H, t, J = 7.9 Hz), 6.99 (1H, dt, J = 8.0, 1.3 Hz), 6.88 (1H, t, J = 2.2 Hz), 6.74 (1H, ddd, J = 8.0, 2.5, 0.7 Hz), 6.12-6.10 (1H, m), 5.02 (2H, s), 3.61 (3H, s), 2.49 (3H, s), 2.39-2.34 (2H, m), 2.22-2.17 (2H, m), 1.80-1.74 (2H, m), 1.68-1.62 (2H, m). |
| 103 | | ¹H-NMR (CDCl₃) δ (ppm): 8.47 (1H, d, J = 5.3 Hz), 8.00-7.96 (2H, m), 7.47-7.44 (2H, m), 7.40-7.37 (2H, m), 7.28 (1H, d, J = 5.3 Hz), 7.26-7.24 (1H, m), 5.53 (2H, s), 3.64 (3H, s), 2.60 (3H, s). |
| 104 | | ¹H-NMR (CDCl₃) δ (ppm): 8.09-8.04 (4H, m), 7.64 (1H, t, J = 7.8 Hz), 7.42-7.38 (3H, m), 7.28-7.24 (1H, m), 6.67 (1H, d, J = 8.2 Hz), 5.53 (2H, s), 3.53 (3H, s), 2.66 (3H, s), 2.55 (3H, s). |

TABLE 22

| Number of present compound | Structural formula | ¹H-NMR data |
|---|---|---|
| 105 | | ¹H-NMR (CDCl₃) δ (ppm): 10.08 (1H, s), 8.16-8.13 (2H, m), 7.99-7.96 (2H, m), 7.65 (1H, dd, J = 8.1, 7.4 Hz), 7.43-7.38 (3H, m), 7.28-7.24 (1H, m), 6.69 (1H, dd, J = 8.1, 0.5 Hz), 5.54 (2H, s), 3.53 (3H, s), 2.54 (3H, s). |
| 106 | | ¹H-NMR (CDCl₃) δ (ppm): 8.14-8.11 (2H, m), 8.06-8.03 (2H, m), 7.64 (1H, t, J = 7.8 Hz), 7.42-7.38 (3H, m), 7.28-7.23 (1H, m), 6.66 (1H, d, J = 8.0 Hz), 5.54 (2H, s), 3.96 (3H, s), 3.52 (3H, s), 2.55 (3H, s). |
| 107 | | ¹H-NMR (CDCl₃) δ (ppm): 8.17-8.14 (2H, m), 8.05-8.02 (2H, m), 7.67 (1H, t, J = 7.8 Hz), 7.44-7.39 (3H, m), 7.29-7.25 (1H, m), 6.71 (1H, d, J = 8.2 Hz), 5.52 (2H, s), 3.56 (3H, s), 3.11 (3H, s), 2.54 (3H, s). |
| 108 | | ¹H-NMR (CDCl₃) δ (ppm): 8.00-7.96 (2H, m), 7.61 (1H, dd, J = 8.0, 7.6 Hz), 7.43-7.38 (2H, m), 7.32-7.25 (4H, m), 6.65 (1H, br s), 6.61 (1H, d, J = 8.2 Hz), 5.51 (2H, s), 3.55 (3H, s), 3.06 (3H, s), 2.53 (3H, s). |

TABLE 23

| Number of present compound | Structural formula | $^1$H-NMR data |
|---|---|---|
| 109 | | $^1$H-NMR (CDCl$_3$) δ (ppm): 8.78 (1H, s), 8.43-8.39 (2H, m), 7.44-7.36 (2H, m), 7.28-7.26 (1H, m), 7.00-6.96 (2H, m), 5.58 (2H, s), 3.89 (3H, s), 3.64 (3H, s), 2.59 (3H, s). |
| 110 | | $^1$H-NMR (CDCl$_3$) δ (ppm): 7.53-7.50 (2H, m), 7.45-7.34 (5H, m), 7.30-7.26 (1H, m), 7.09-7.01 (2H, m), 6.92 (1H, td, J = 7.7, 2.0 Hz), 5.16 (2H, s), 3.63 (3H, s), 2.55 (3H, s). |
| 111 | | $^1$H-NMR (CDCl$_3$) δ (ppm): 7.44-7.26 (4H, m), 7.11-7.01 (4H, m), 6.94-6.90 (2H, m), 5.16 (2H, s), 3.84 (3H, s), 3.63 (3H, s), 2.55 (3H, s). |
| 112 | | $^1$H-NMR (CDCl$_3$) δ (ppm): 7.47-7.38 (6H, m), 7.30-7.26 (1H, m), 7.07 (1H, td, J = 7.9, 1.3 Hz), 7.00-6.91 (2H, m), 5.16 (2H, s), 3.63 (3H, s), 2.55 (3H, s). |
| 113 | | $^1$H-NMR (CDCl$_3$) δ (ppm): 8.32-8.30 (1H, m), 7.75 (1H, ddd, J = 8.6, 2.5, 1.8 Hz), 7.44-7.38 (2H, m), 7.31-7.26 (1H, m), 7.08 (1H, td, J = 7.8, 1.3 Hz), 7.00-6.96 (1H, m), 6.93 (1H, td, J = 7.8, 1.6 Hz), 6.81 (1H, dd, J = 8.7, 0.7 Hz), 5.16 (2H, s), 3.98 (3H, s), 3.64 (3H, s), 2.55 (3H, s). |

TABLE 24

| Number of present compound | Structural formula | ¹H-NMR data |
|---|---|---|
| 114 | | ¹H-NMR (CDCl₃) δ (ppm): 7.51-7.46 (2H, m), 7.44-7.38 (2H, m), 7.30-7.27 (1H, m), 7.15-7.04 (3H, m), 7.00-6.96 (1H, m), 6.92 (1H, td, J = 7.8, 1.8 Hz), 5.16 (2H, s), 3.63 (3H, s), 2.55 (3H, s). |
| 115 | | ¹H-NMR (CDCl₃) δ (ppm): 7.43-7.34 (3H, m), 7.30-7.24 (2H, m), 7.07-6.92 (5H, m), 5.15 (2H, s), 3.80 (3H, s), 3.64 (3H, s), 2.54 (3H, s). |
| 116 | | ¹H-NMR (CDCl₃) δ (ppm): 7.43-7.38 (2H, m), 7.32 (1H, t, J = 7.9 Hz), 7.29-7.25 (1H, m), 7.16-7.13 (1H, m), 6.90-6.84 (3H, m), 6.80-6.77 (2H, m), 5.01 (2H, s), 3.83 (3H, s), 3.61 (3H, s), 2.49 (3H, s), 2.20 (3H, s). |
| 117 | | ¹H-NMR (CDCl₃) δ (ppm): 7.43-7.25 (8H, m), 7.15 (1H, d, J = 7.7 Hz), 6.80-6.77 (2H, m), 5.01 (2H, s), 3.61 (3H, s), 2.49 (3H, s), 2.19 (3H, s). |
| 118 | | ¹H-NMR (CDCl₃) δ (ppm): 8.12 (1H, dd, J = 2.5, 0.7 Hz), 7.54 (1H, dd, J = 8.4, 2.5 Hz), 7.43-7.38 (2H, m), 7.30-7.26 (1H, m), 7.16 (1H, d, J = 8.4 Hz), 6.81-6.79 (2H, m), 6.73 (1H, d, J = 2.5 Hz), 5.02 (2H, s), 3.98 (3H, s), 3.62 (3H, s), 2.49 (3H, s), 2.19 (3H, s). |

TABLE 25

| Number of present compound | Structural formula | ¹H-NMR data |
|---|---|---|
| 119 | | ¹H-NMR (CDCl$_3$) δ (ppm): 7.43-7.37 (2H, m), 7.29-7.24 (3H, m), 7.14 (1H, d, J = 8.4 Hz), 7.12-7.06 (2H, m), 6.79 (1H, dd, J = 8.4, 2.7 Hz), 6.73 (1H, d, J = 2.7 Hz), 5.01 (2H, s), 3.61 (3H, s), 2.49 (3H, s), 2.17 (3H, s). |
| 120 | | ¹H-NMR (CDCl$_3$) δ (ppm): 7.43-7.38 (2H, m), 7.29-7.22 (3H, m), 7.15-7.12 (1H, m), 6.96-6.93 (2H, m), 6.78-6.75 (2H, m), 5.01 (2H, s), 3.85 (3H, s), 3.61 (3H, s), 2.49 (3H, s), 2.20 (3H, s). |
| 121 | | ¹H-NMR (CDCl$_3$) δ (ppm): 7.42-7.32 (3H, m), 7.28-7.24 (1H, m), 7.15-7.12 (2H, m), 7.01 (1H, t, J = 7.4 Hz), 6.96 (1H, d, J = 8.2 Hz), 6.79 (1H, dd, J = 8.2, 2.7 Hz), 6.74 (1H, d, J = 2.7 Hz), 4.99 (2H, s), 3.77 (3H, s), 3.61 (3H, s), 2.49 (3H, s), 2.05 (3H, s). |
| 122 | | ¹H-NMR (CDCl$_3$) δ (ppm): 7.44-7.36 (4H, m), 7.29-7.22 (3H, m), 7.14 (1H, d, J = 8.2 Hz), 6.79 (1H, dd, J = 8.2, 2.7 Hz), 6.72 (1H, d, J = 2.7 Hz), 5.01 (2H, s), 3.61 (3H, s), 2.49 (3H, s), 2.17 (3H, s). |
| 123 | | ¹H-NMR (CDCl$_3$) δ (ppm): 7.43-7.26 (6H, m), 7.09-6.98 (4H, m), 5.16 (2H, s), 3.81 (3H, s), 3.62 (3H, s), 2.55 (3H, s). |

TABLE 26

| Number of present compound | Structural formula | ¹H-NMR data |
|---|---|---|
| 124 | (structure) | ¹H-NMR (CDCl₃) δ (ppm): 7.48-7.39 (4H, m), 7.31-7.26 (1H, m), 7.15-7.04 (5H, m), 5.19 (2H, s), 3.63 (3H, s), 2.55 (3H, s). |
| 125 | (structure) | ¹H-NMR (CDCl₃) δ (ppm): 7.44-7.39 (2H, m), 7.35 (1H, t, J = 8.0 Hz), 7.30-7.26 (1H, m), 7.13-7.06 (4H, m), 7.02 (1H, t, J = 2.1 Hz), 6.91-6.88 (1H, m), 5.19 (2H, s), 3.87 (3H, s), 3.62 (3H, s), 2.55 (3H, s). |
| 126 | (structure) | ¹H-NMR (CDCl₃) δ (ppm): 7.52-7.49 (2H, m), 7.45-7.39 (4H, m), 7.37-7.33 (1H, m), 7.31-7.26 (1H, m), 7.14-7.07 (3H, m), 5.19 (2H, s), 3.62 (3H, s), 2.55 (3H, s). |
| 127 | (structure) | ¹H-NMR (CDCl₃) δ (ppm): 8.29 (1H, d, J = 2.6 Hz), 7.70 (1H, dd, J = 8.6, 2.6 Hz), 7.44-7.39 (2H, m), 7.31-7.26 (1H, m), 7.13-7.03 (3H, m), 6.81 (1H, dd, J = 8.6, 0.7 Hz), 5.19 (2H, s), 3.98 (3H, s), 3.64 (3H, s), 2.55 (3H, s). |
| 128 | (structure) | ¹H-NMR (CDCl₃) δ (ppm): 7.53-7.50 (2H, m), 7.46-7.35 (6H, m), 7.29 (1H, dd, J = 6.9, 2.5 Hz), 7.12 (1H, dd, J = 8.1, 1.9 Hz), 7.08 (1H, d, J = 1.9 Hz), 5.23 (2H, s), 3.62 (3H, s), 2.56 (3H, s). |

TABLE 27

| Number of present compound | Structural formula | ¹H-NMR data |
|---|---|---|
| 129 | | ¹H-NMR (CDCl₃) δ (ppm): 7.45-7.36 (7H, m), 7.29 (1H, dd, J = 7.1, 2.1 Hz), 7.07 (1H, dd, J = 8.1, 1.9 Hz), 7.02 (1H, d, J = 1.9 Hz), 5.23 (2H, s), 3.63 (3H, s), 2.56 (3H, s). |
| 130 | | ¹H-NMR (CDCl₃) δ (ppm): 7.44-7.31 (4H, m), 7.29-7.26 (2H, m), 7.09-6.98 (4H, m), 5.16 (2H, s), 3.81 (3H, s), 3.63 (3H, s), 2.55 (3H, s). |
| 131 | | ¹H-NMR (CDCl₃) δ (ppm): 7.45-7.38 (4H, m), 7.30-7.26 (1H, m), 7.10-7.06 (3H, m), 6.98-6.94 (2H, m), 5.18 (2H, s), 3.85 (3H, s), 3.62 (3H, s), 2.55 (3H, s). |
| 132 | | ¹H-NMR (CDCl₃) δ (ppm): 7.49-7.35 (5H, m), 7.30 (1H, dd, J = 7.1, 1.9 Hz), 7.16-7.10 (2H, m), 7.06 (1H, dd, J = 8.2, 2.0 Hz), 7.01 (1H, d, J = 2.0 Hz), 5.23 (2H, s), 3.63 (3H, s), 2.56 (3H, s). |
| 133 | | ¹H-NMR (CDCl₃) δ (ppm): 7.43-7.38 (2H, m), 7.35-7.31 (1H, m), 7.30-7.25 (2H, m), 7.15-7.12 (1H, m), 7.10-6.97 (4H, m), 5.13 (2H, s), 3.81 (3H, s), 3.63 (3H, s), 2.54 (3H, s). |

TABLE 28
| Number of present compound | Structural formula | ¹H-NMR data |
|---|---|---|
| 134 | 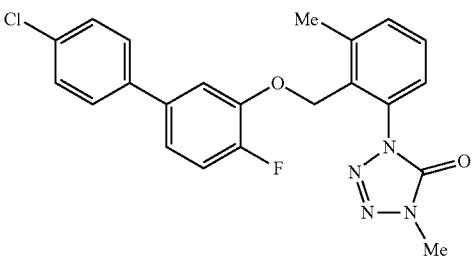 [SMILES: Cc1cccc(-n2nnn(C)c2=O)c1COc1cc(-c2ccc(Cl)cc2)ccc1F] | ¹H-NMR (CDCl₃) δ (ppm): 7.44-7.38 (6H, m), 7.30-7.26 (1H, m), 7.12-7.06 (3H, m), 5.19 (2H, s), 3.62 (3H, s), 2.54 (3H, s). |
| 135 | 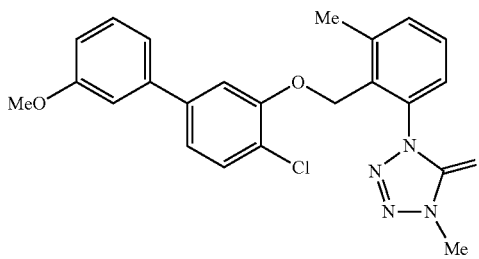 | ¹H-NMR (CDCl₃) δ (ppm): 7.45-7.34 (4H, m), 7.30 (1H, dd, J = 6.9, 2.3 Hz), 7.13-7.09 (2H, m), 7.07 (1H, d, J = 2.1 Hz), 7.03 (1H, t, J = 2.2 Hz), 6.92 (1H, ddd, J = 8.2, 2.5, 0.7 Hz), 5.23 (2H, s), 3.87 (3H, s), 3.63 (3H, s), 2.56 (3H, s). |
| 136 | 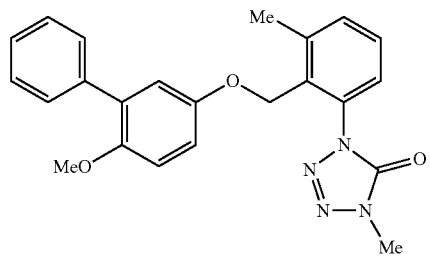 [SMILES: COc1ccc(OCc2c(C)cccc2-n2nnn(C)c2=O)cc1-c1ccccc1] | ¹H-NMR (CDCl₃) δ (ppm): 7.52-7.49 (2H, m), 7.43-7.38 (4H, m), 7.35-7.26 (2H, m), 6.89-6.80 (3H, m), 5.01 (2H, s), 3.75 (3H, s), 3.60 (3H, s), 2.50 (3H, s). |
| 137 | 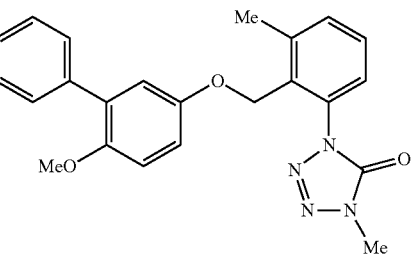 | ¹H-NMR (CDCl₃) δ (ppm): 7.46-7.35 (6H, m), 7.28-7.26 (1H, m), 6.89-6.80 (3H, m), 5.01 (2H, s), 3.75 (3H, s), 3.60 (3H, s), 2.50 (3H, s). |
| 138 | 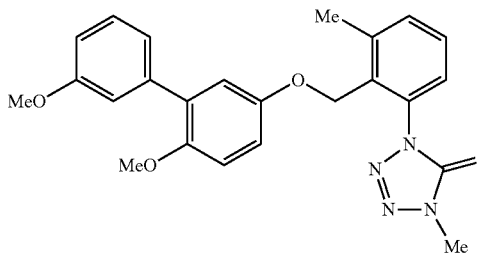 | ¹H-NMR (CDCl₃) δ (ppm): 7.43-7.38 (2H, m), 7.32 (1H, t, J = 7.9 Hz), 7.29-7.25 (1H, m), 7.11-7.06 (2H, m), 6.90-6.86 (3H, m), 6.82 (1H, dd, J = 8.8, 2.9 Hz), 5.01 (2H, s), 3.84 (3H, s), 3.75 (3H, s), 3.61 (3H, s), 2.50 (3H, s). |

TABLE 29

| Number of present compound | Structural formula | ¹H-NMR data |
|---|---|---|
| 139 | (structure) | ¹H-NMR (CDCl₃) δ (ppm): 8.30 (1H, dd, J = 2.5, 0.7 Hz), 7.75 (1H, dd, J = 8.6, 2.5 Hz), 7.44-7.38 (2H, m), 7.30-7.26 (1H, m), 6.89-6.81 (3H, m), 6.78 (1H, dd, J = 8.6, 0.7 Hz), 5.01 (2H, s), 3.97 (3H, s), 3.76 (3H, s), 3.62 (3H, s), 2.50 (3H, s). |
| 140 | (structure) | ¹H-NMR (CDCl₃) δ (ppm): 7.47-7.38 (4H, m), 7.29-7.26 (1H, m), 6.97-6.94 (2H, m), 6.87-6.85 (2H, m), 6.80-6.77 (1H, m), 5.01 (2H, s), 3.84 (3H, s), 3.75 (3H, s), 3.60 (3H, s), 2.50 (3H, s). |
| 141 | (structure) | ¹H-NMR (CDCl₃) δ (ppm): 7.50-7.45 (2H, m), 7.43-7.37 (2H, m), 7.29-7.26 (1H, m), 7.11-7.06 (2H, m), 6.89-6.80 (3H, m), 5.01 (2H, s), 3.75 (3H, s), 3.60 (3H, s), 2.50 (3H, s). |
| 142 | (structure) | ¹H-NMR (CDCl₃) δ (ppm): 7.51-7.48 (2H, m), 7.44-7.39 (2H, m), 7.30-7.26 (1H, m), 6.98-6.95 (3H, m), 6.86 (1H, s), 6.65 (1H, s), 5.05 (2H, s), 3.84 (3H, s), 3.60 (3H, s), 2.51 (3H, s), 2.37 (3H, s). |
| 143 | (structure) | ¹H-NMR (CDCl₃) δ (ppm): 7.57-7.54 (2H, m), 7.44-7.38 (4H, m), 7.36-7.31 (1H, m), 7.30-7.27 (1H, m), 7.02 (1H, m), 6.90 (1H, t, J = 1.7 Hz), 6.69 (1H, br s), 5.06 (2H, s), 3.60 (3H, s), 2.51 (3H, s), 2.38 (3H, s). |

TABLE 30

| Number of present compound | Structural formula | ¹H-NMR data |
|---|---|---|
| 144 | | ¹H-NMR (CDCl₃) δ (ppm): 7.42-7.37 (2H, m), 7.35-7.31 (1H, m), 7.28-7.22 (2H, m), 7.02-6.96 (2H, m), 6.89-6.81 (3H, m), 4.98 (2H, s), 3.78 (3H, s), 3.71 (3H, s), 3.62 (3H, s), 2.49 (3H, s). |
| 145 | | ¹H-NMR (CDCl₃) δ (ppm): 7.50-7.46 (2H, m), 7.45-7.37 (4H, m), 7.31-7.27 (1H, m), 6.97 (1H, br s), 6.85 (1H, t, J = 1.8 Hz), 6.70 (1H, br s), 5.06 (2H, s), 3.60 (3H, s), 2.51 (3H, s), 2.37 (3H, s). |
| 146 | | ¹H-NMR (CDCl₃) δ (ppm): 7.43-7.38 (2H, m), 7.33-7.26 (3H, m), 7.03-6.96 (2H, m), 6.94-6.93 (1H, m), 6.88-6.87 (1H, m), 6.68-6.67 (1H, m), 5.02 (2H, s), 3.80 (3H, s), 3.62 (3H, s), 2.50 (3H, s), 2.36 (3H, s). |
| 147 | | ¹H-NMR (CDCl₃) δ (ppm): 7.53-7.48 (2H, m), 7.44-7.38 (2H, m), 7.31-7.27 (1H, m), 7.13-7.07 (2H, m), 6.96 (1H, br s), 6.85-6.84 (1H, m), 6.68 (1H, br s), 5.06 (2H, s), 3.60 (3H, s), 2.51 (3H, s), 2.37 (3H, s). |
| 148 | | ¹H-NMR (CDCl₃) δ (ppm): 7.44-7.39 (2H, m), 7.33 (1H, t, J = 8.1 Hz), 7.30-7.27 (1H, m), 7.15-7.13 (1H, m), 7.09-7.08 (1H, m), 7.01 (1H, br s), 6.90-6.87 (2H, m), 6.69 (1H, br s), 5.06 (2H, s), 3.86 (3H, s), 3.60 (3H, s), 2.51 (3H, s), 2.38 (3H, s). |

TABLE 31
| Number of present compound | Structural formula | ¹H-NMR data |
|---|---|---|
| 149 | 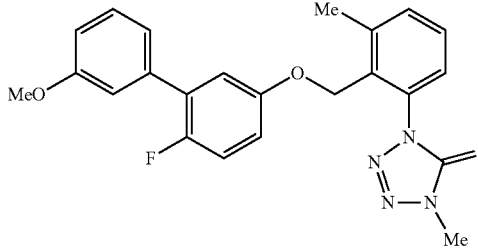 | ¹H-NMR (CDCl₃) δ (ppm): 7.45-7.39 (2H, m), 7.37 (1H, t, J = 8.0 Hz), 7.32-7.27 (1H, m), 7.14-7.03 (3H, m), 6.95-6.92 (2H, m), 6.83-6.79 (1H, m), 5.04 (2H, s), 3.86 (3H, s), 3.62 (3H, s), 2.51 (3H, s). |
| 150 | 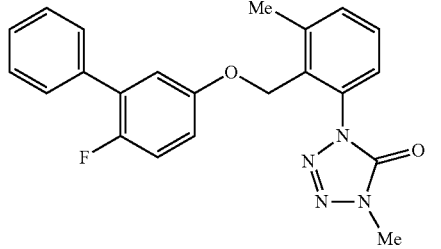 [SMILES: Cc1cccc(-n2nnn(C)c2=O)c1COc1ccc(F)c(-c2ccccc2)c1] | ¹H-NMR (CDCl₃) δ (ppm): 7.54-7.51 (2H, m), 7.46-7.35 (5H, m), 7.28 (1H, dd, J = 6.9, 2.3 Hz), 7.04 (1H, dd, J = 9.8, 8.9 Hz), 6.92 (1H, dd, J = 6.4, 3.2 Hz), 6.79 (1H, dt, J = 8.9, 3.4 Hz), 5.03 (2H, s), 3.60 (3H, s), 2.50 (3H, s). |
| 151 | 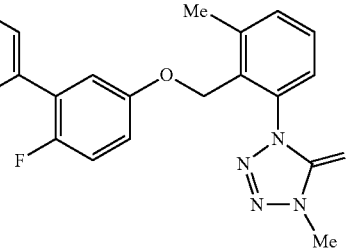 | ¹H-NMR (CDCl₃) δ (ppm): 8.32-8.31 (1H, m), 7.76-7.73 (1H, m), 7.44-7.38 (2H, m), 7.28 (1H, dd, J = 7.1, 2.1 Hz), 7.05 (1H, dd, J = 9.8, 8.9 Hz), 6.87 (1H, dd, J = 6.2, 3.2 Hz), 6.83-6.78 (2H, m), 5.03 (2H, s), 3.98 (3H, s), 3.61 (3H, s), 2.50 (3H, s). |
| 152 | 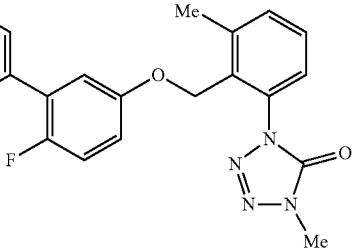 | ¹H-NMR (CDCl₃) δ (ppm): 7.47-7.44 (2H, m), 7.43-7.38 (4H, m), 7.28 (1H, dd, J = 7.2, 2.2 Hz), 7.04 (1H, dd, J = 9.8, 8.9 Hz), 6.87 (1H, dd, J = 6.3, 3.1 Hz), 6.80 (1H, dt, J = 8.9, 3.4 Hz), 5.03 (2H, s), 3.61 (3H, s), 2.50 (3H, s). |
| 153 | 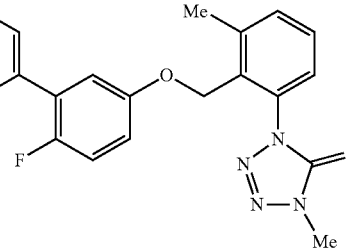 | ¹H-NMR (CDCl₃) δ (ppm): 7.51-7.47 (2H, m), 7.46-7.40 (2H, m), 7.29 (1H, dd, J = 6.9, 2.3 Hz), 7.06-6.97 (3H, m), 6.91 (1H, dd, J = 6.4, 3.2 Hz), 6.79-6.75 (1H, m), 5.04 (2H, s), 3.87 (3H, s), 3.62 (3H, s), 2.52 (3H, s). |

TABLE 32

| Number of present compound | Structural formula | ¹H-NMR data |
|---|---|---|
| 154 | | ¹H-NMR (CDCl₃) δ (ppm): 7.53-7.49 (2H, m), 7.46-7.40 (2H, m), 7.32-7.28 (1H, m), 7.17-7.11 (2H, m), 7.06 (1H, dd, J = 10.0, 9.0 Hz), 6.90-6.88 (1H, m), 6.83-6.79 (1H, m), 5.05 (2H, s), 3.62 (3H, s), 2.52 (3H, s). |
| 155 | | ¹H-NMR (CDCl₃) δ (ppm): 7.45-7.36 (3H, m), 7.30-7.26 (2H, m), 7.06-7.00 (3H, m), 6.88-6.80 (2H, m), 5.02 (2H, s), 3.83 (3H, s), 3.63 (3H, s), 2.51 (3H, s). |
| 156 | | ¹H-NMR (CDCl₃) δ (ppm): 8.39 (1H, d, J = 1.4 Hz), 8.16 (1H, s), 8.10 (1H, dd, J = 8.7, 1.6 Hz), 7.68-7.63 (2H, m), 7.44-7.38 (3H, m), 7.30-7.26 (1H, m), 6.65 (1H, dd, J = 8.2, 0.7 Hz), 5.56 (2H, s), 3.56 (3H, s), 2.57 (3H, s). |
| 157 | | ¹H-NMR (CDCl₃) δ (ppm): 8.93 (1H, dd, J = 4.2, 1.7 Hz), 8.23 (1H, dd, J = 8.2, 0.9 Hz), 8.18 (1H, d, J = 8.7 Hz), 8.01-7.96 (2H, m), 7.47-7.39 (4H, m), 7.35-7.30 (2H, m), 7.24-7.23 (1H, m), 6.95-6.92 (1H, m), 5.14 (2H, s), 3.60 (3H, s), 2.55 (3H, s). |
| 158 | | ¹H-NMR (CDCl₃) δ (ppm): 8.94 (1H, dd, J = 4.2, 1.7 Hz), 8.46 (1H, d, J = 2.1 Hz), 8.35 (1H, dd, J = 8.8, 1.9 Hz), 8.31-8.28 (1H, m), 8.19 (1H, d, J = 8.8 Hz), 7.67 (1H, dd, J = 8.0, 7.6 Hz), 7.50-7.39 (4H, m), 7.28-7.26 (1H, m), 6.67 (1H, d, J = 8.0 Hz), 5.60 (2H, s), 3.49 (3H, s), 2.57 (3H, s). |

TABLE 33

| Number of present compound | Structural formula | ¹H-NMR data |
|---|---|---|
| 159 | | ¹H-NMR (CDCl₃) δ (ppm): 8.13 (1H, s), 7.96 (1H, s), 7.65-7.58 (2H, m), 7.45-7.40 (2H, m), 7.38-7.34 (1H, m), 7.32-7.28 (1H, m), 7.22 (1H, d, J = 7.1 Hz), 7.12 (1H, s), 6.89 (1H, d, J = 8.2 Hz), 5.11 (2H, s), 3.60 (3H, s), 2.52 (3H, s). |
| 166 | | ¹H-NMR (CDCl₃) δ (ppm): 7.43-7.38 (2H, m), 7.29-7.26 (1H, m), 7.24-7.22 (1H, m), 7.16-7.13 (1H, m), 7.09 (1H, d, J = 3.6 Hz), 7.05-7.04 (1H, m), 6.77-6.74 (1H, m), 6.71-6.70 (1H, m), 5.06 (2H, s), 3.59 (3H, s), 2.50 (3H, s), 2.49 (3H, s). |
| 167 | | ¹H-NMR (CDCl₃) δ (ppm): 7.42-7.39 (2H, m), 7.29-7.25 (4H, m), 7.22-7.20 (1H, m), 7.11-7.10 (1H, m), 7.07-7.04 (1H, m), 6.81-6.78 (1H, m), 5.07 (2H, s), 3.57 (3H, s), 2.49 (3H, s). |
| 168 | | ¹H-NMR (CDCl₃) δ (ppm): 7.45-7.35 (5H, m), 7.31-7.27 (2H, m), 7.21-7.18 (1H, m), 7.10-7.09 (1H, m), 6.83-6.80 (1H, m), 5.07 (2H, s), 3.57 (3H, s), 2.50 (3H, s). |

TABLE 34

| Number of present compound | Structural formula | ¹H-NMR data |
|---|---|---|
| 169 | | ¹H-NMR (CDCl₃) δ (ppm): 7.86-7.82 (1H, m), 7.58-7.54 (1H, m), 7.49-7.47 (1H, m), 7.39-7.38 (2H, m), 7.26-7.23 (1H, m), 6.81-6.76 (1H, m), 6.73-6.70 (1H, m), 6.58-6.56 (1H, m), 5.46 (2H, s), 3.87 (3H, s), 3.56 (3H, s), 2.51 (3H, s). |

TABLE 34-continued

| Number of present compound | Structural formula | $^1$H-NMR data |
|---|---|---|
| 170 | (structure) | $^1$H-NMR (CDCl$_3$) δ (ppm): 8.32 (1H, d, J = 8.4 Hz), 7.65 (1H, d, J = 7.5 Hz), 7.57-7.53 (1H, m), 7.39-7.37 (2H, m), 7.26-7.23 (1H, m), 6.54-6.52 (1H, m), 6.46 (1H, d, J = 8.4 Hz), 5.46 (2H, s), 4.04 (3H, s), 3.98 (3H, s), 3.55 (3H, s), 2.51 (3H, s). |
| 171 | (structure) | $^1$H-NMR (CDCl$_3$) δ (ppm): 8.29 (1H, dd, J = 7.5, 2.0 Hz), 8.20 (1H, dd, J = 4.9, 1.9 Hz), 7.70-7.68 (1H, m), 7.61-7.57 (1H, m), 7.40-7.38 (2H, m), 7.26-7.24 (1H, m), 7.04 (1H, dd, J = 7.5, 5.0 Hz), 6.62-6.60 (1H, m), 5.48 (2H, s), 4.05 (3H, s), 3.54 (3H, s), 2.52 (3H, s). |
| 172 | (structure) | $^1$H-NMR (CDCl$_3$) δ (ppm): 7.79 (1H, d, J = 8.4 Hz), 7.58-7.54 (1H, m), 7.50-7.48 (1H, m), 7.39-7.37 (2H, m), 7.26-7.22 (1H, m), 7.06 (1H, dd, J = 8.3, 1.9 Hz), 6.98-6.97 (1H, m), 6.59-6.57 (1H, m), 5.46 (2H, s), 3.87 (3H, s), 3.55 (3H, s), 2.51 (3H, s). |

TABLE 35

| Number of present compound | Structural formula | $^1$H-NMR data |
|---|---|---|
| 173 | (structure) | $^1$H-NMR (CDCl$_3$) δ (ppm): 7.56-7.51 (2H, m), 7.39-7.38 (2H, m), 7.37-7.35 (1H, m), 7.25-7.21 (2H, m), 7.10-7.07 (1H, m), 6.52 (1H, d, J = 8.2 Hz), 5.48 (2H, s), 3.55 (3H, s), 2.55 (3H, s). |
| 174 | (structure) | $^1$H-NMR (CDCl$_3$) δ (ppm): 7.88-7.87 (1H, m), 7.62-7.60 (1H, m), 7.57-7.53 (1H, m), 7.40-7.36 (3H, m), 7.25-7.23 (1H, m), 7.19 (1H, dd, J = 7.5, 0.7 Hz), 6.55 (1H, dd, J = 8.2, 0.7 Hz), 5.50 (2H, s), 3.51 (3H, s), 2.54 (3H, s). |

TABLE 35-continued

| Number of present compound | Structural formula | ¹H-NMR data |
|---|---|---|
| 175 | | ¹H-NMR (CDCl₃) δ (ppm): 7.62-7.58 (1H, m), 7.50 (1H, d, J = 2.1 Hz), 7.41-7.40 (2H, m), 7.27-7.24 (1H, m), 7.18 (1H, d, J = 7.6 Hz), 6.63 (1H, d, J = 8.2 Hz), 6.58 (1H, d, J = 2.1 Hz), 5.43 (2H, s), 4.23 (3H, s), 3.53 (3H, s), 2.52 (3H, s). |
| 176 | | ¹H-NMR (CDCl₃) δ (ppm): 7.51-7.47 (1H, m), 7.39-7.35 (3H, m), 7.25-7.23 (1H, m), 7.14-7.13 (1H, m), 6.74 (1H, dd, J = 3.5, 1.0 Hz), 6.48 (1H, d, J = 7.6 Hz), 5.46 (2H, s), 3.56 (3H, s), 2.54 (3H, s), 2.51 (3H, s). |
| 177 | | ¹H-NMR (CDCl₃) δ (ppm): 7.51-7.50 (1H, m), 7.43-7.41 (2H, m), 7.36-7.34 (1H, m), 7.30-7.26 (1H, m), 7.01 (1H, d, J = 6.3 Hz), 6.93-6.91 (2H, m), 6.30-6.29 (1H, m), 5.07 (2H, s), 3.88 (3H, s), 3.60 (3H, s), 2.51 (3H, s). |
| 178 | | ¹H-NMR (CDCl₃) δ (ppm): 7.87 (1H, d, J = 8.7 Hz), 7.55-7.50 (2H, m), 7.39-7.35 (2H, m), 7.24-7.21 (1H, m), 6.62 (1H, dd, J = 8.7, 2.3 Hz), 6.55 (1H, d, J = 2.3 Hz), 6.52 (1H, dd, J = 7.1, 1.8 Hz), 5.47 (2H, s), 3.859 (3H, s), 3.857 (3H, s), 3.54 (3H, s), 2.51 (3H, s). |
| 179 | | ¹H-NMR (CDCl₃) δ (ppm): 7.56 (1H, d, J = 7.9 Hz), 7.43-7.40 (2H, m), 7.31-7.26 (2H, m), 7.14-7.12 (1H, m), 7.07-7.06 (1H, m), 6.84-6.81 (1H, m), 6.38 (1H, d, J = 8.2 Hz), 5.05 (2H, s), 3.959 (3H, s), 3.956 (3H, s), 3.60 (3H, s), 2.50 (3H, s). |

TABLE 36

| Number of present compound | Structural formula | ¹H-NMR data |
|---|---|---|
| 180 | | ¹H-NMR (CDCl₃) δ (ppm): 7.41-7.36 (2H, m), 7.30-7.22 (3H, m), 7.07 (1H, d, J = 7.7 Hz), 7.02-7.00 (1H, m), 6.85-6.83 (1H, m), 6.73-6.67 (2H, m), 5.05 (2H, s), 3.77 (3H, s), 3.57 (3H, s), 2.49 (3H, s). |
| 181 | | ¹H-NMR (CDCl₃) δ (ppm): 7.42-7.37 (2H, m), 7.31-7.26 (2H, m), 7.22 (1H, d, J = 8.2 Hz), 7.08-7.06 (1H, m), 7.02-6.98 (2H, m), 6.95 (1H, d, J = 2.0 Hz), 6.87-6.84 (1H, m), 5.05 (2H, s), 3.79 (3H, s), 3.58 (3H, s), 2.49 (3H, s). |
| 182 | | ¹H-NMR (CDCl₃) δ (ppm): 7.59-7.55 (2H, m), 7.47 (1H, dd, J = 7.4, 0.8 Hz), 7.40-7.38 (2H, m), 7.26-7.23 (1H, m), 6.80 (1H, d, J = 8.9 Hz), 6.57 (1H, dd, J = 8.1, 0.8 Hz), 5.47 (2H, s), 3.93 (3H, s), 3.92 (3H, s), 3.82 (3H, s), 3.54 (3H, s), 2.52 (3H, s). |
| 183 | | ¹H-NMR (CDCl₃) δ (ppm): 7.59-7.54 (3H, m), 7.37-7.35 (2H, m), 7.24-7.22 (1H, m), 7.03-6.98 (1H, m), 6.90-6.87 (1H, m), 6.58 (1H, dd, J = 6.6, 2.3 Hz), 5.49 (2H, s), 3.81 (3H, s), 3.56 (3H, s), 2.51 (3H, s). |
| 184 | | ¹H-NMR (CDCl₃) δ (ppm): 7.62-7.55 (2H, m), 7.48-7.46 (1H, m), 7.39-7.38 (2H, m), 7.26-7.23 (1H, m), 7.14-7.11 (2H, m), 6.64-6.62 (1H, m), 5.47 (2H, s), 3.85 (3H, s), 3.55 (3H, s), 2.52 (3H, s). |

TABLE 36-continued

| Number of present compound | Structural formula | ¹H-NMR data |
| --- | --- | --- |
| 185 | | ¹H-NMR (CDCl₃) δ (ppm): 7.60-7.56 (1H, m), 7.38-7.33 (3H, m), 7.25-7.22 (1H, m), 6.99-6.93 (3H, m), 6.62-6.60 (1H, m), 5.41 (2H, s), 3.54 (3H, s), 2.49 (3H, s), 2.38 (3H, s). |
| 186 | | ¹H-NMR (CDCl₃) δ (ppm): 7.81-7.77 (1H, m), 7.64-7.60 (1H, m), 7.38-7.37 (2H, m), 7.26-7.22 (1H, m), 6.97 (1H, d, J = 7.3 Hz), 6.84 (1H, dd, J = 8.2, 4.1 Hz), 6.65 (1H, d, J = 8.2 Hz), 5.43 (2H, s), 3.58 (3H, s), 2.55 (3H, s), 2.51 (3H, s). |

TABLE 37

| Number of present compound | Structural formula | ¹H-NMR data |
| --- | --- | --- |
| 187 | | ¹H-NMR (CDCl₃) δ (ppm): 7.85-7.82 (1H, m), 7.79-7.76 (2H, m), 7.56-7.52 (1H, m), 7.38-7.31 (5H, m), 7.26-7.23 (1H, m), 6.58 (1H, d, J = 8.2 Hz), 5.53 (2H, s), 3.52 (3H, s), 2.54 (3H, s). |
| 188 | | ¹H-NMR (CDCl₃) δ (ppm): 8.47 (1H, d, J = 8.2 Hz), 7.90 (1H, d, J = 7.2 Hz), 7.77 (1H, s), 7.63-7.59 (1H, m), 7.47-7.37 (4H, m), 7.27-7.23 (2H, m), 6.64 (1H, d, J = 8.4 Hz), 5.53 (2H, s), 3.45 (3H, s), 2.52 (3H, s). |
| 189 | | ¹H-NMR (CDCl₃) δ (ppm): 7.60-7.56 (1H, m), 7.51-7.49 (1H, m), 7.39-7.37 (3H, m), 7.25-7.23 (1H, m), 7.17-7.13 (1H, m), 6.96 (1H, dd, J = 8.0, 1.6 Hz), 6.62-6.60 (1H, m), 5.48 (2H, s), 3.91 (3H, s), 3.74 (3H, s), 3.53 (3H, s), 2.52 (3H, s). |

TABLE 37-continued

| Number of present compound | Structural formula | ¹H-NMR data |
|---|---|---|
| 190 | (structure) | ¹H-NMR (CDCl₃) δ (ppm): 7.60-7.56 (1H, m), 7.37-7.35 (2H, m), 7.31 (1H, d, J = 8.2 Hz), 7.27-7.26 (1H, m), 7.25-7.22 (2H, m), 6.93 (1H, dd, J = 7.3, 0.7 Hz), 6.61 (1H, dd, J = 8.2, 0.7 Hz), 5.41 (2H, s), 3.53 (3H, s), 2.49 (3H, s), 2.36 (3H, s). |
| 191 | (structure) | ¹H-NMR (CDCl₃) δ (ppm): 8.96 (1H, s), 7.59-7.50 (2H, m), 7.37 (2H, d, J = 4.6 Hz), 7.27-7.23 (1H, m), 6.59 (1H, d, J = 8.0 Hz), 5.47 (2H, s), 4.08 (3H, s), 4.06 (3H, s), 3.60 (3H, s), 2.51 (3H, s). |
| 192 | (structure) | ¹H-NMR (CDCl₃) δ (ppm): 7.79-7.77 (1H, m), 7.66-7.62 (1H, m), 7.58 (1H, s), 7.41-7.39 (2H, m), 7.27-7.24 (1H, m), 6.73-6.71 (1H, m), 5.46 (2H, s), 4.17 (3H, s), 4.12 (3H, s), 3.59 (3H, s), 2.52 (3H, s). |
| 193 | (structure) | ¹H-NMR (CDCl₃) δ (ppm): 8.01 (1H, d, J = 6.6 Hz), 7.78-7.76 (1H, m), 7.59-7.55 (1H, m), 7.38-7.37 (2H, m), 7.25-7.20 (2H, m), 6.99-6.96 (1H, m), 6.56 (1H, d, J = 8.2 Hz), 5.50 (2H, s), 4.65 (2H, t, J = 8.8 Hz), 3.52 (3H, s), 3.24 (2H, t, J = 8.8 Hz), 2.52 (3H, s). |

TABLE 38

| Number of present compound | Structural formula | ¹H-NMR data |
|---|---|---|
| 194 | (structure) | ¹H-NMR (CDCl₃) δ (ppm): 7.90-7.85 (1H, m), 7.56-7.53 (2H, m), 7.39-7.37 (2H, m), 7.26-7.23 (1H, m), 6.79-6.74 (1H, m), 6.69 (1H, dd, J = 11.1, 2.5 Hz), 6.58-6.54 (1H, m), 5.46 (2H, s), 4.07 (2H, q, J = 6.9 Hz), 3.55 (3H, s), 2.51 (3H, s), 1.44 (3H, t, J = 6.9 Hz). |

TABLE 38-continued
| Number of present compound | Structural formula | $^1$H-NMR data |
|---|---|---|
| 195 | 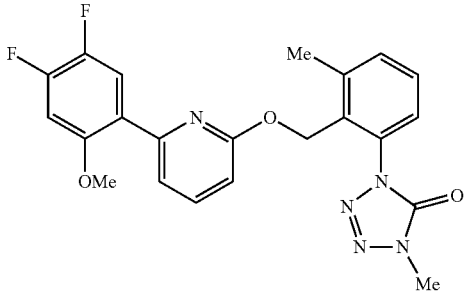 [SMILES: COc1cc(F)c(F)cc1-c1cccc(OCc2c(C)cccc2-n2nnn(C)c2=O)n1] | $^1$H-NMR (CDCl$_3$) δ (ppm): 7.73-7.68 (1H, m), 7.58-7.52 (2H, m), 7.39-7.36 (2H, m), 7.26-7.22 (1H, m), 6.82-6.77 (1H, m), 6.58 (1H, dd, J = 7.2, 1.6 Hz), 5.46 (2H, s), 3.83 (3H, s), 3.59 (3H, s), 2.52 (3H, s). |
| 196 | 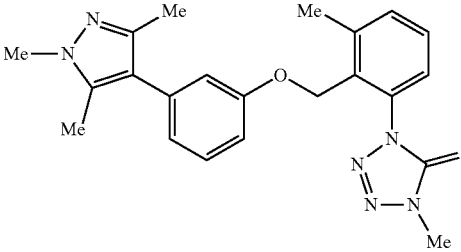 | $^1$H-NMR (CDCl$_3$) δ (ppm): 7.43-7.38 (2H, m), 7.32-7.26 (2H, m), 6.86-6.84 (1H, m), 6.82-6.79 (1H, m), 6.75-6.74 (1H, m), 5.05 (2H, s), 3.77 (3H, s), 3.60 (3H, s), 2.50 (3H, s), 2.24 (3H, s), 2.23 (3H, s). |
| 197 | 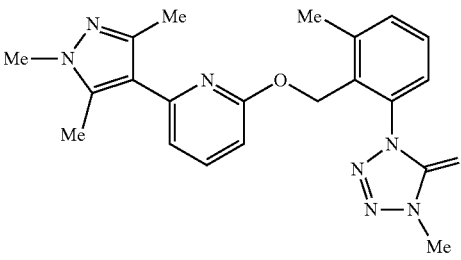 | $^1$H-NMR (CDCl$_3$) δ (ppm): 7.58-7.54 (1H, m), 7.42-7.39 (2H, m), 7.30-7.24 (1H, m), 6.89 (1H, d, J = 7.5 Hz), 6.52 (1H, d, J = 8.2 Hz), 5.39 (2H, s), 3.79 (3H, s), 3.55 (3H, s), 2.51 (3H, s), 2.45 (3H, s), 2.40 (3H, s). |
| 198 | 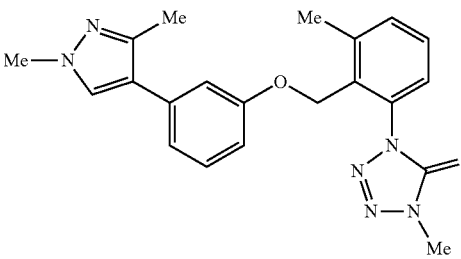 | $^1$H-NMR (CDCl$_3$) δ (ppm): 7.43-7.38 (3H, m), 7.28-7.25 (2H, m), 6.99 (1H, d, J = 7.7 Hz), 6.89-6.87 (1H, m), 6.77 (1H, dd, J = 8.4, 2.5 Hz), 5.05 (2H, s), 3.85 (3H, s), 3.58 (3H, s), 2.50 (3H, s), 2.38 (3H, s). |
| 199 | 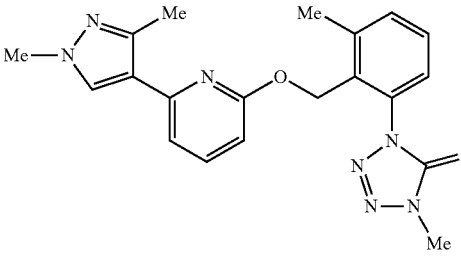 | $^1$H-NMR (CDCl$_3$) δ (ppm): 7.77 (1H, s), 7.54-7.50 (1H, m), 7.42-7.39 (2H, m), 7.27-7.24 (1H, m), 6.99 (1H, d, J = 7.2 Hz), 6.48 (1H, d, J = 8.2 Hz), 5.42 (2H, s), 3.88 (3H, s), 3.54 (3H, s), 2.55 (3H, s), 2.51 (3H, s). |

TABLE 39

| Number of present compound | Structural formula | ¹H-NMR data |
|---|---|---|
| 200 | | ¹H-NMR (CDCl₃) δ (ppm): 7.51-7.49 (1H, m), 7.43-7.38 (2H, m), 7.28-7.25 (1H, m), 7.02-6.98 (1H, m), 6.87 (1H, dd, J = 5.9, 3.2 Hz), 6.80-6.76 (1H, m), 6.38 (1H, d, J = 8.2 Hz), 5.00 (2H, s), 3.96 (3H, s), 3.94 (3H, s), 3.61 (3H, s), 2.49 (3H, s). |
| 201 | | ¹H-NMR (CDCl₃) δ (ppm): 7.50 (1H, d, J = 8.0 Hz), 7.41-7.36 (2H, m), 7.28-7.26 (1H, m), 7.12 (1H, d, J = 8.7 Hz), 7.06-7.04 (2H, m), 6.38 (1H, d, J = 8.0 Hz), 5.15 (2H, s), 3.952 (3H, s), 3.951 (3H, s), 3.62 (3H, s), 2.53 (3H, s). |
| 202 | | ¹H-NMR (CDCl₃) δ (ppm): 7.53 (1H, d, J = 8.0 Hz), 7.41-7.36 (2H, m), 7.27-7.24 (1H, m), 6.93-6.88 (2H, m), 6.65 (1H, s), 6.38-6.33 (1H, m), 5.03 (2H, s), 3.95 (3H, s), 3.94 (3H, s), 3.60 (3H, s), 2.49 (3H, s), 2.34 (3H, s). |
| 203 | | ¹H-NMR (CDCl₃) δ (ppm): 7.41-7.35 (3H, m), 7.27-7.24 (1H, m), 7.13 (1H, d, J = 8.4 Hz), 6.79 (1H, dd, J = 8.3, 2.8 Hz), 6.71-6.70 (1H, m), 6.37 (1H, d, J = 7.9 Hz), 4.99 (2H, s), 3.96 (3H, s), 3.91 (3H, s), 3.60 (3H, s), 2.48 (3H, s), 2.07 (3H, s). |
| 204 | | ¹H-NMR (CDCl₃) δ (ppm): 7.48 (1H, d, J = 8.0 Hz), 7.40-7.35 (2H, m), 7.27-7.24 (1H, m), 6.85-6.81 (3H, m), 6.36 (1H, d, J = 8.0 Hz), 4.99 (2H, s), 3.94 (3H, s), 3.91 (3H, s), 3.71 (3H, s), 3.60 (3H, s), 2.49 (3H, s). |

TABLE 39-continued

| Number of present compound | Structural formula | ¹H-NMR data |
|---|---|---|
| 205 | 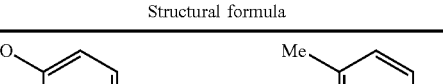 | ¹H-NMR (CDCl₃) δ (ppm): 7.51 (1H, d, J = 8.2 Hz), 7.42-7.34 (2H, m), 7.32-7.26 (2H, m), 7.08-7.04 (2H, m), 6.39 (1H, d, J = 8.0 Hz), 5.18 (2H, s), 3.96-3.95 (6H, m), 3.62 (3H, s), 2.54 (3H, s). |

Production Example 160

A mixture of 0.51 g of AA1 mentioned in Synthesis Example 1, 0.41 g of 1-methylpiperazine, 0.38 g of potassium carbonate, and 5 mL of N,N-dimethylformamide was stirred at 130° C. for 15 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.38 g of 1-methyl-4-{3-methyl-2-[2-(4-methylpiperazin-1-yl)-pyridin-6-yloxymethyl]phenyl}-1,4-dihydrotetrazol-5-one (hereinafter referred to as the present compound 160).

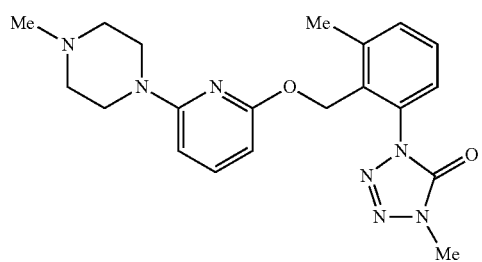 [SMILES: Cc1cccc(-n2nnn(C)c2=O)c1COc1cccc(N2CCN(C)CC2)n1]

¹H-NMR (CDCl₃) δ (ppm): 7.40-7.35 (3H, m), 7.25-7.22 (1H, m), 6.15 (1H, d, J=8.2 Hz), 6.01 (1H, d, J=7.7 Hz), 5.30 (2H, s), 3.62 (3H, s), 3.50 (4H, t, J=5.1 Hz), 2.52 (4H, t, J=5.1 Hz), 2.49 (3H, s), 2.35 (3H, s).

Production Example 161

A mixture of 0.49 g of AA1 mentioned in Synthesis Example 1, 0.34 g of morpholine, 0.36 g of potassium carbonate, and 4 mL of N,N-dimethylformamide was stirred at 130° C. for 15 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.21 g of 1-methyl-4-[3-methyl-2-(2-morpholin-4-yl-pyridin-6-yloxymethyl)phenyl]-1,4-dihydrotetrazol-5-one (hereinafter referred to as the present compound 161).

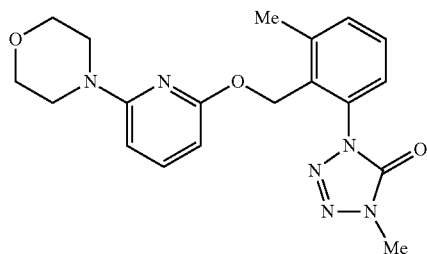 [SMILES: Cc1cccc(-n2nnn(C)c2=O)c1COc1cccc(N2CCOCC2)n1]

¹H-NMR (CDCl₃) δ (ppm): 7.41-7.37 (3H, m), 7.26-7.23 (1H, m), 6.13 (1H, d, J=7.8 Hz), 6.05 (1H, d, J=8.0 Hz), 5.30 (2H, s), 3.81 (4H, t, J=4.6 Hz), 3.62 (3H, s), 3.44 (4H, t, J=4.6 Hz), 2.48 (3H, s).

Production Example 162

A mixture of 0.50 g of AA1 mentioned in Synthesis Example 1, 0.34 g of piperidine, 0.37 g of potassium carbonate, and 5 mL of N,N-dimethylformamide was stirred at 120° C. for 10 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.41 g of 1-methyl-4-[3-methyl-2-(2-piperidin-1-yl-pyridin-6-yloxymethyl)-phenyl]-1,4-dihydrotetrazol-5-one (hereinafter referred to as the present compound 162).

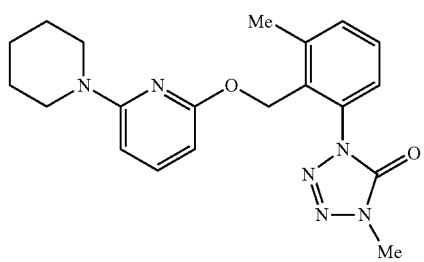 [SMILES: Cc1cccc(-n2nnn(C)c2=O)c1COc1cccc(N2CCCCC2)n1]

¹H-NMR (CDCl₃) δ (ppm): 7.40-7.36 (2H, m), 7.34 (1H, t, J=8.0 Hz), 7.26-7.21 (1H, m), 6.15 (1H, d, J=8.0 Hz), 5.94 (1H, d, J=8.0 Hz), 5.30 (2H, s), 3.62 (3H, s), 3.48-3.46 (4H, m), 2.49 (3H, s), 1.63 (6H, br s).

Production Example 206

A mixture of 0.20 g of AA1 mentioned in Synthesis Example 1, 0.11 g of pyrazole, 0.18 g of potassium tert-butoxide, and 5 mL of dimethyl sulfoxide was stirred at 100° C. for 2 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.09 g of 1-methyl-4-{3-methyl-2-[2-(1H-pyrazol-1-yl)-pyridin-6-yloxymethyl]-phenyl}-1,4-dihydrotetrazol-5-one (hereinafter referred to as the present compound 206).

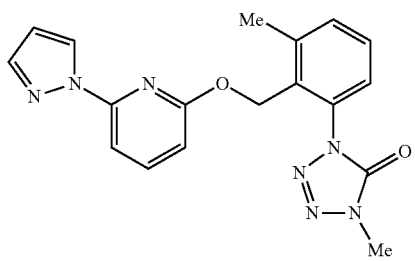 [SMILES: Cc1cccc(-n2nnn(C)c2=O)c1COc1cccc(-n2cccn2)n1]

$^1$H-NMR (CDCl$_3$) δ (ppm): 8.46-8.44 (1H, m), 7.73-7.72 (1H, m), 7.66-7.64 (1H, m), 7.52 (1H, d, J=7.8 Hz), 7.41-7.40 (2H, m), 7.27-7.25 (1H, m), 6.55 (1H, dd, J=8.0, 0.7 Hz), 6.46-6.45 (1H, m), 5.45 (2H, s), 3.53 (3H, s), 2.53 (3H, s).

Production Example 207

A mixture of 0.20 g of AA1 mentioned in Synthesis Example 1, 0.15 g of 3,5-dimethyl-1H-pyrazole, 0.18 g of potassium tert-butoxide, and 5 mL of dimethyl sulfoxide was stirred at 100° C. for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.05 g of 1-methyl-4-{3-methyl-2-[2-(3,5-dimethyl-1H-pyrazol-1-yl)pyridin-6-yloxymethyl]phenyl}-1,4-dihydrotetrazol-5-one (hereinafter referred to as the present compound 207).

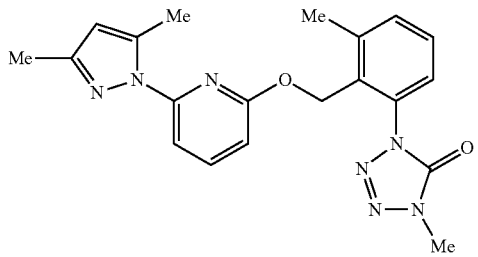 [SMILES: Cc1cc(C)n(-c2cccc(OCc3c(C)cccc3-n3nnn(C)c3=O)n2)n1]

$^1$H-NMR (CDCl$_3$) δ (ppm): 7.67-7.63 (1H, m), 7.45-7.41 (3H, m), 7.28-7.26 (1H, m), 6.54 (1H, d, J=8.2 Hz), 6.00 (1H, s), 5.33 (2H, s), 3.56 (3H, s), 2.66 (3H, s), 2.50 (3H, s), 2.30 (3H, s).

Production Example 163

A mixture of 0.30 g of CA25 mentioned in Reference Production Example 25, 0.16 g of 2-chloro-5-methoxypyrimidine, 0.45 g of tripotassium phosphate, 1.00 ml of water, 0.06 g of [1,1'-bis(diphenylphosphino)ferrocene]palladium(II) dichloride dichloromethane adduct, and 10 mL of dimethoxyethane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.10 g of 1-{2-[3-(5-methoxypyrimidin-2-yl)phenoxymethyl]-3-methylphenyl}-4-methyl-1,4-dihydrotetrazol-5-one (hereinafter referred to as the present compound 163).

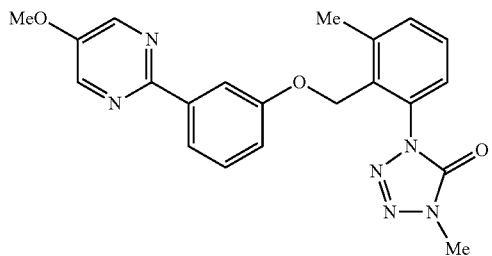 [SMILES: COc1cnc(-c2cccc(OCc3c(C)cccc3-n3nnn(C)c3=O)c2)nc1]

$^1$H-NMR (CDCl$_3$) δ (ppm): 8.47 (2H, s), 7.96 (1H, dt, J=7.7, 1.2 Hz), 7.91-7.90 (1H, m), 7.45-7.40 (2H, m), 7.36 (1H, t, J=7.9 Hz), 7.29 (1H, dd, J=6.7, 2.4 Hz), 6.96-6.93 (1H, m), 5.13 (2H, s), 3.97 (3H, s), 3.62 (3H, s), 2.52 (3H, s).

Production Example 164

A mixture of 0.30 g of CA25 mentioned in Reference Production Example 25, 0.12 g of 2-chloropyridine, 0.45 g of tripotassium phosphate, 1.00 ml of water, 0.06 g of [1,1'-bis(diphenylphosphino)ferrocene]palladium(II) dichloride dichloromethane adduct, and 10 mL of dimethoxyethane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.10 g of 1-methyl-4-[3-methyl-2-(3-pyridin-2-yl-phenoxymethyl)phenyl]-1,4-dihydrotetrazol-5-one (hereinafter referred to as the present compound 164).

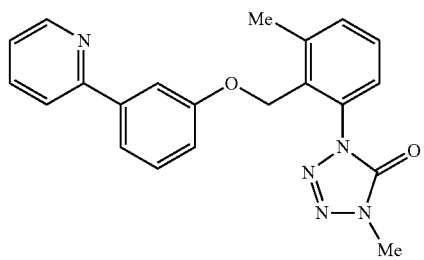 [SMILES: Cc1cccc(-n2nnn(C)c2=O)c1COc1cccc(-c2ccccn2)c1]

¹H-NMR (CDCl₃) δ (ppm): 8.69-8.67 (1H, m), 7.77-7.69 (2H, m), 7.57-7.55 (2H, m), 7.44-7.22 (5H, m), 6.95-6.92 (1H, m), 5.11 (2H, s), 3.60 (3H, s), 2.51 (3H, s).

Production Example 165

A mixture of 0.30 g of CA25 mentioned in Reference Production Example 25, 0.16 g of 3-chloro-6-methoxypyridazine, 0.45 g of tripotassium phosphate, 1.00 ml of water, 0.06 g of [1,1'-bis(diphenylphosphino)ferrocene]palladium(II) dichloride dichloromethane adduct, and 10 mL of dimethoxyethane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.23 g of 1-{2-[3-(3-methoxypyridazin-6-yl)phenoxymethyl]-3-methylphenyl}-4-methyl-1,4-dihydrotetrazol-5-one (hereinafter referred to as the present compound 165).

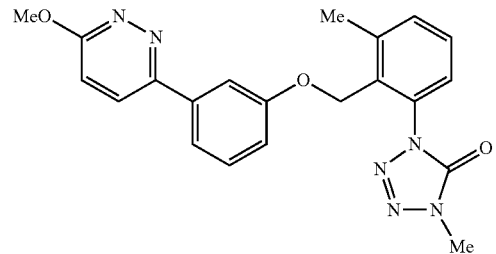 [SMILES: COc1ccc(-c2cccc(OCc3c(C)cccc3-n3nnn(C)c3=O)c2)nn1]

¹H-NMR (CDCl₃) δ (ppm): 7.77 (1H, d, J=9.4 Hz), 7.64-7.63 (1H, m), 7.56-7.54 (1H, m), 7.45-7.36 (3H, m), 7.30-7.28 (1H, m), 7.05 (1H, d, J=9.2 Hz), 6.98-6.95 (1H, m), 5.11 (2H, s), 4.19 (3H, s), 3.61 (3H, s), 2.51 (3H, s).

In the same manner as in Production Examples 163, 164, and 165, the present compounds 208 to 214 were synthesized.

Structural formulas of the present compounds and ¹H-NMR data thereof are shown in Table 40.

TABLE 40

| Number of present compound | Structural formula | ¹H-NMR data |
|---|---|---|
| 208 | | ¹H-NMR (CDCl₃) δ (ppm): 7.43-7.36 (4H, m), 7.33-7.32 (1H, m), 7.30-7.26 (2H, m), 6.81 (1H, dd, J = 7.7, 2.3 Hz), 6.51 (1H, d, J = 2.3 Hz), 5.07 (2H, s), 3.94 (3H, s), 3.60 (3H, s), 2.50 (3H, s). |
| 209 | | ¹H-NMR (CDCl₃) δ (ppm): 7.43-7.39 (2H, m), 7.30-7.24 (2H, m), 7.11-7.09 (1H, m), 7.05 (1H, d, J = 3.9 Hz), 7.00-6.99 (1H, m), 6.88 (1H, d, J = 3.9 Hz), 6.81 (1H, dd, J = 7.8, 2.1 Hz), 5.06 (2H, s), 3.60 (3H, s), 2.50 (3H, s). |
| 210 | | ¹H-NMR (CDCl₃) δ (ppm): 7.74 (1H, s), 7.59 (1H, s), 7.42-7.39 (2H, m), 7.29-7.23 (2H, m), 7.08-7.06 (1H, m), 6.97-6.95 (1H, m), 6.74 (1H, dd, J = 8.2, 2.5 Hz), 5.05 (2H, s), 3.92 (3H, s), 3.58 (3H, s), 2.50 (3H, s). |

TABLE 40-continued

| Number of present compound | Structural formula | ¹H-NMR data |
|---|---|---|
| 211 | | ¹H-NMR (CDCl₃) δ (ppm): 7.85 (1H, d, J = 3.2 Hz), 7.54-7.53 (2H, m), 7.44-7.38 (2H, m), 7.34-7.26 (3H, m), 6.95-6.92 (1H, m), 5.10 (2H, s), 3.60 (3H, s), 2.50 (3H, s). |
| 212 | | ¹H-NMR (CDCl₃) δ (ppm): 7.49-7.44 (3H, m), 7.42-7.38 (2H, m), 7.32-7.26 (2H, m), 6.91-6.88 (1H, m), 5.09 (2H, s), 3.60 (3H, s), 2.49 (6H, s). |
| 213 | | ¹H-NMR (CDCl₃) δ (ppm): 8.84 (1H, d, J = 2.1 Hz), 7.52-7.48 (3H, m), 7.41-7.36 (2H, m), 7.33-7.28 (2H, m), 6.86 (1H, dd, J = 8.2, 1.6 Hz), 5.09 (2H, s), 3.56 (3H, s), 2.48 (3H, s). |
| 214 | | ¹H-NMR (CDCl₃) δ (ppm): 8.75 (1H, s), 8.06 (1H, s), 7.45-7.40 (2H, m), 7.33-7.26 (2H, m), 7.18 (1H, d, J = 7.7 Hz), 7.08-7.06 (1H, m), 6.88-6.85 (1H, m), 5.07 (2H, s), 3.61 (3H, s), 2.51 (3H, s). |

Production Example 215

A mixture of 0.3 g of CA29 mentioned in Reference Production Example 30, 0.28 g of 4-bromo-1-methyl-1H-pyrazole, 0.37 g of tripotassium phosphate, 0.5 mL of water, 0.07 g of [1,1'-bis(diphenylphosphino)ferrocene]palladium (II) dichloride dichloromethane adduct, and 5 mL of dimethoxyethane was stirred with heating under reflux for 2 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.07 g of 1-methyl-4-{3-methyl-2-[6-(1-methyl-1H-pyrazol-4-yl)pyridin-2-yloxymethyl]-phenyl}-1,4-dihydrotetrazol-5-one (hereinafter referred to as the present compound 215).

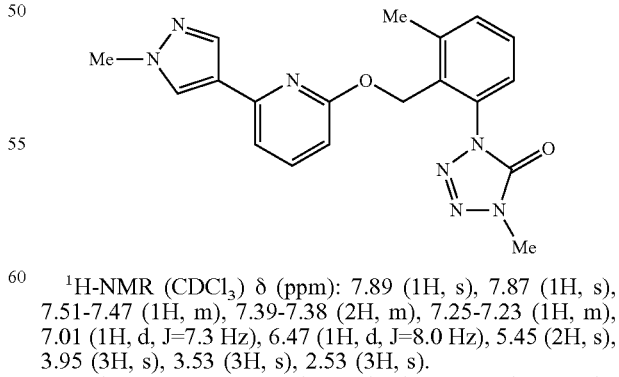

¹H-NMR (CDCl₃) δ (ppm): 7.89 (1H, s), 7.87 (1H, s), 7.51-7.47 (1H, m), 7.39-7.38 (2H, m), 7.25-7.23 (1H, m), 7.01 (1H, d, J=7.3 Hz), 6.47 (1H, d, J=8.0 Hz), 5.45 (2H, s), 3.95 (3H, s), 3.53 (3H, s), 2.53 (3H, s).

In the same manner as in Production Example 215, the present compounds 216 to 221 were synthesized.

Structural formulas of the present compound and ¹H-NMR data are shown in Table 41.

TABLE 41

| Number of present compound | Structural formula | ¹H-NMR data |
|---|---|---|
| 216 | | ¹H-NMR (CDCl₃) δ (ppm): 7.59-7.51 (2H, m), 7.40-7.38 (3H, m), 7.25-7.23 (1H, m), 6.84 (1H, d, J = 2.3 Hz), 6.57 (1H, dd, J = 7.9, 1.1 Hz), 5.49 (2H, s), 3.96 (3H, s), 3.54 (3H, s), 2.54 (3H, s). |
| 217 | | ¹H-NMR (CDCl₃) δ (ppm): 7.54-7.50 (1H, m), 7.40-7.38 (2H, m), 7.29 (1H, d, J = 3.9 Hz), 7.26-7.23 (1H, m), 7.13-7.12 (1H, m), 6.89 (1H, d, J = 3.9 Hz), 6.52 (1H, dd, J = 8.2, 0.7 Hz), 5.44 (2H, s), 3.59 (3H, s), 2.54 (3H, s). |
| 218 | | ¹H-NMR (CDCl₃) δ (ppm): 7.89 (1H, d, J = 3.2 Hz), 7.77 (1H, d, J = 7.6 Hz), 7.67-7.64 (1H, m), 7.42-7.40 (3H, m), 7.27-7.25 (1H, m), 6.70 (1H, d, J = 8.2 Hz), 5.49 (2H, s), 3.57 (3H, s), 2.55 (3H, s). |
| 219 | | ¹H-NMR (CDCl₃) δ (ppm): 7.71-7.69 (1H, m), 7.64-7.60 (1H, m), 7.54-7.53 (1H, m), 7.41-7.39 (2H, m), 7.26-7.24 (1H, m), 6.67-6.65 (1H, m), 5.47 (2H, s), 3.57 (3H, s), 2.54 (3H, s), 2.52 (3H, s). |
| 220 | | ¹H-NMR (CDCl₃) δ (ppm): 8.86 (1H, d, J = 2.0 Hz), 8.08 (1H, d, J = 2.0 Hz), 7.76-7.74 (1H, m), 7.65-7.63 (1H, m), 7.41-7.40 (2H, m), 7.27-7.25 (1H, m), 6.65-6.63 (1H, m), 5.50 (2H, s), 3.52 (3H, s), 2.54 (3H, s). |

| Number of present compound | Structural formula | ¹H-NMR data |
|---|---|---|
| 221 | | ¹H-NMR (CDCl₃) δ (ppm): 8.81 (1H, s), 8.31 (1H, s), 7.60-7.56 (1H, m), 7.41-7.40 (2H, m), 7.27-7.25 (2H, m), 6.59 (1H, d, J = 8.4 Hz), 5.46 (2H, s), 3.58 (3H, s), 2.55 (3H, s). |

Next, with respect to the production of the present tetrazolinone compound X, Synthesis Examples are shown.

Synthesis Example 1

To a mixture of 4.68 g of CA20 mentioned in Reference Production Example 20 and 100 mL of tetrahydrofuran, 1.02 g of 55% sodium hydride was added under ice cooling, followed by stirring for 30 minutes. To the reaction mixture, 5.03 g of 2,6-dibromopyridine was added under ice cooling. The temperature of the mixture was raised to room temperature, followed by stirring for 13 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 6.99 g of 1-[2-(2-bromopyridin-6-yloxymethyl)-3-methylphenyl]-4-methyl-1,4-dihydrotetrazol-5-one (referred to as AA1).

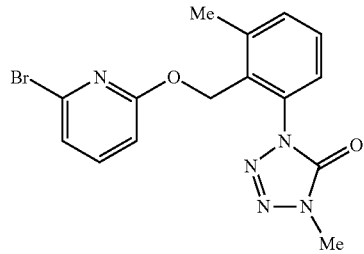

¹H-NMR (CDCl₃) δ (ppm): 7.41-7.35 (3H, m), 7.25-7.23 (1H, m), 7.03 (1H, d, J=7.3 Hz), 6.59 (1H, d, J=8.2 Hz), 5.39 (2H, s), 3.69 (3H, s), 2.56 (3H, s).

Synthesis Example 2

To a mixture of 2.72 g of CA22 mentioned in Reference Production Example 22 and 50 mL of tetrahydrofuran, 0.53 g of 55% sodium hydride was added under ice cooling, followed by stirring for 30 minutes. To the reaction mixture, 2.62 g of 2,6-dibromopyridine was added under ice cooling. The temperature of the mixture was raised to room temperature, followed by stirring for 4 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.96 g of 1-[2-(2-bromopyridin-6-yloxymethyl)-3-cyclopropylphenyl]-4-methyl-1,4-dihydrotetrazol-5-one.

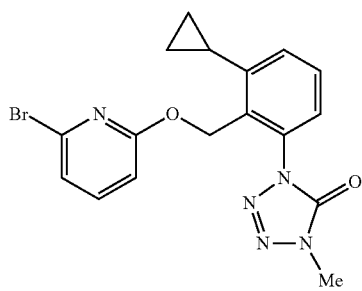 [SMILES: Cn1nnn(-c2cccc(C3CC3)c2COc2cccc(Br)n2)c1=O]

¹H-NMR (CDCl₃) δ (ppm): 7.43-7.36 (2H, m), 7.26-7.23 (2H, m), 7.04 (1H, dd, J=7.4, 0.6 Hz), 6.60 (1H, dd, J=8.2, 0.6 Hz), 5.59 (2H, s), 3.68 (3H, s), 2.28-2.21 (1H, m), 1.04-0.99 (2H, m), 0.79-0.75 (2H, m).

Synthesis Example 3

To a mixture of 2.58 g of CA21 mentioned in Reference Production Example 21 and 50 mL of tetrahydrofuran, 0.53 g of 55% sodium hydride was added under ice cooling, followed by stirring for 30 minutes. To the reaction mixture, 2.61 g of 2,6-dibromopyridine was added under ice cooling. The temperature of the mixture was raised to room temperature, followed by stirring for 4 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 3.64 g of 1-[2-(2-bromopyridin-6-yloxymethyl)-3-ethylphenyl]-4-methyl-1,4-dihydrotetrazol-5-one.

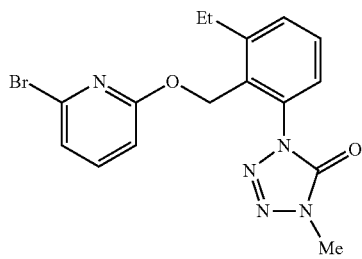

¹H-NMR (CDCl₃) δ (ppm): 7.47-7.42 (2H, m), 7.38 (1H, t, J=7.8 Hz), 7.26-7.24 (1H, m), 7.04 (1H, d, J=7.2 Hz), 6.59

(1H, d, J=8.2 Hz), 5.39 (2H, s), 3.68 (3H, s), 2.91 (2H, q, J=7.6 Hz), 1.29 (3H, t, J=7.6 Hz).

Synthesis Example 4

To a mixture of 2.00 g of CA24 mentioned in Reference Production Example 24 and 40 mL of tetrahydrofuran, 0.40 g of 55% sodium hydride was added under ice cooling, followed by stirring for 30 minutes. To the reaction mixture, 1.97 g of 2,6-dibromopyridine was added under ice cooling. The temperature of the mixture was raised to room temperature, followed by stirring for 12 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 1.92 g of 1-[2-(2-bromopyridin-6-yloxymethyl)-3-chlorophenyl]-4-methyl-1,4-dihydrotetrazol-5-one.

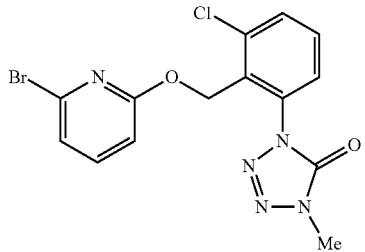

$^1$H-NMR (CDCl$_3$) δ (ppm): 7.61 (1H, dd, J=8.2, 1.2 Hz), 7.46 (1H, t, J=8.0 Hz), 7.41-7.35 (2H, m), 7.05 (1H, d, J=7.5 Hz), 6.60 (1H, d, J=8.0 Hz), 5.54 (2H, s), 3.68 (3H, s).

Synthesis Example 5

To a mixture of 2.00 g of CA23 mentioned in Reference Production Example 23 and 40 mL of tetrahydrofuran, 0.41 g of 55% sodium hydride was added under ice cooling, followed by stirring for 30 minutes. To the reaction mixture, 2.00 g of 2,6-dibromopyridine was added under ice cooling. The temperature of the mixture was raised to room temperature, followed by stirring for 12 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.93 g of 1-[2-(2-bromopyridin-6-yloxymethyl)-3-methoxyphenyl]-4-methyl-1,4-dihydrotetrazol-5-one.

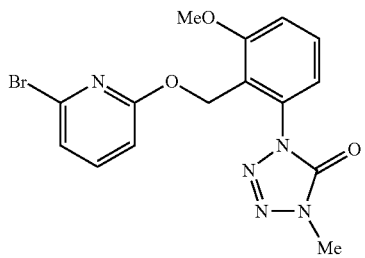

$^1$H-NMR (CDCl$_3$) δ (ppm): 7.46 (1H, t, J=8.2 Hz), 7.36 (1H, t, J=7.8 Hz), 7.09 (1H, d, J=8.0 Hz), 7.05-7.01 (2H, m), 6.57 (1H, d, J=8.2 Hz), 5.46 (2H, s), 3.93 (3H, s), 3.66 (3H, s).

Synthesis Example 6

To a mixture of 1.54 g of CA20 mentioned in Reference Production Example 20 and 35 mL of tetrahydrofuran, 0.34 g of 55% sodium hydride was added under ice cooling, followed by stirring for 30 minutes. To the reaction mixture, 1.04 g of 4,6-dichloropyrimidine was added under ice cooling. The temperature of the mixture was raised to room temperature, followed by stirring for 14 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.13 g of 1-[2-(4-chloropyrimidin-6-yloxymethyl)-3-methylphenyl]-4-methyl-1,4-dihydrotetrazol-5-one.

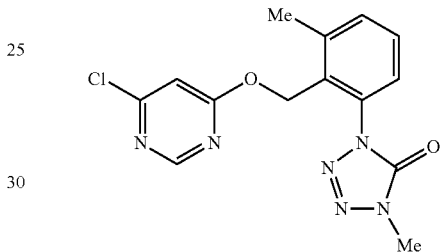

$^1$H-NMR (CDCl$_3$) δ (ppm): 8.48 (1H, s), 7.44-7.38 (2H, m), 7.27-7.25 (1H, m), 6.69 (1H, s), 5.45 (2H, s), 3.71 (3H, s), 2.53 (3H, s).

Synthesis Example 7

To a mixture of 1.54 g of CA20 mentioned in Reference Production Example 20 and 35 mL of N,N-dimethylformamide, 0.34 g of 55% sodium hydride was added under ice cooling, followed by stirring for 30 minutes. To the reaction mixture, 1.04 g of 2,6-dichloropyrazine was added under ice cooling. The temperature of the mixture was raised to room temperature, followed by stirring for 14 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.17 g of 1-[2-(2-chloropyrazin-6-yloxymethyl)-3-methylphenyl]-4-methyl-1,4-dihydrotetrazol-5-one.

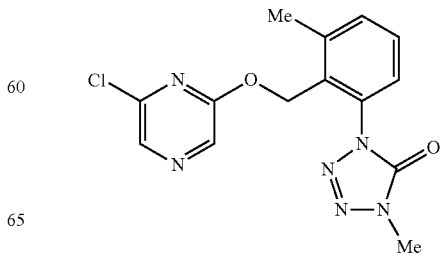

$^1$H-NMR (CDCl$_3$) δ (ppm): 8.13 (1H, s), 8.04 (1H, s), 7.44-7.39 (2H, m), 7.30-7.26 (1H, m), 5.43 (2H, s), 3.71 (3H, s), 2.56 (3H, s).

Synthesis Example 8

To a mixture of 1.23 g of CA20 mentioned in Reference Production Example 20, 0.98 g of 4-bromo-2-fluoropyridine, and 10 mL of tetrahydrofuran, 0.63 g of potassium tert-butoxide was added under ice cooling, followed by stirring for 30 minutes. The temperature of the reaction mixture was raised to room temperature, followed by stirring for 30 minutes. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 1.86 g of 1-[2-(4-bromopyridin-2-yloxymethyl)-3-methylphenyl]-4-methyl-1,4-dihydrotetrazol-5-one.

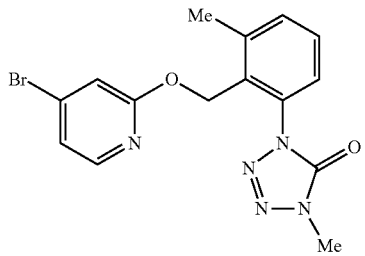

$^1$H-NMR (CDCl$_3$) δ (ppm): 7.88 (1H, d, J=5.6 Hz), 7.41-7.36 (2H, m), 7.26-7.23 (1H, m), 6.99 (1H, dd, J=5.6, 1.7 Hz), 6.86 (1H, d, J=1.7 Hz), 5.36 (2H, s), 3.69 (3H, s), 2.53 (3H, s).

Synthesis Example 9

A mixture of 2.99 g of CA7 mentioned in Reference Production Example 7, 1.87 g of 5-bromo-2-methylphenol, 2.76 g of potassium carbonate, and 40 mL of acetonitrile was stirred with heating under reflux for 2 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 3.49 g of 1-[2-(3-bromo-6-methylphenoxymethyl)-3-methoxyphenyl]-4-methyl-1,4-dihydrotetrazol-5-one.

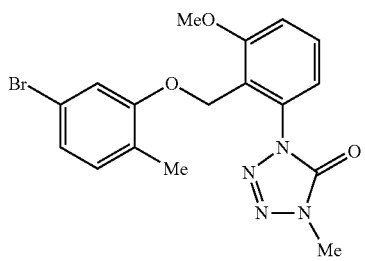 [SMILES: COc1cccc(-n2nnn(C)c2=O)c1COc1cc(Br)ccc1C]

$^1$H-NMR (CDCl$_3$) δ (ppm): 7.47 (1H, t, J=8.1 Hz), 7.10-7.03 (3H, m), 6.95-6.89 (2H, m), 5.25 (2H, s), 3.95 (3H, s), 3.63 (3H, s), 1.92 (3H, s).

Synthesis Example 10

A mixture of 7.00 g of CA14 mentioned in Reference Production Example 14, 4.49 g of 3-bromophenol, 4.44 g of potassium carbonate, and 100 mL of acetonitrile was stirred with heating under reflux for 3 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 8.22 g of 1-[2-(3-bromophenoxymethyl)-3-methylphenyl]-4-methyl-1,4-dihydrotetrazol-5-one.

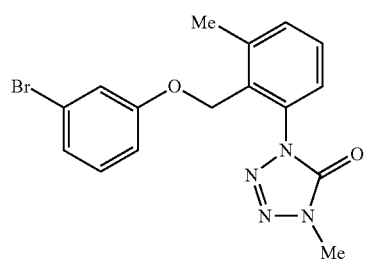 [SMILES: Cc1cccc(-n2nnn(C)c2=O)c1COc1ccnc(Cl)c1]

$^1$H-NMR (CDCl$_3$) δ (ppm): 7.45-7.39 (2H, m), 7.28 (1H, dd, J=7.2, 1.9 Hz), 7.15-7.03 (3H, m), 6.80 (1H, dt, J=7.6, 1.9 Hz), 5.00 (2H, s), 3.64 (3H, s), 2.48 (3H, s).

Synthesis Example 11

To a mixture of 2.83 g of CA14 mentioned in Reference Production Example 14 and 50 mL of N,N-dimethylformamide, 0.48 g of 55% sodium hydride was added under ice cooling, followed by stirring for 30 minutes. To the reaction mixture, 1.91 g of 5-bromopyridin-3-ol was added under ice cooling. The temperature of the mixture was raised to room temperature, followed by stirring for 20 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.81 g of 1-[2-(3-bromopyridin-5-yloxymethyl)-3-methylphenyl]-4-methyl-1,4-dihydrotetrazol-5-one.

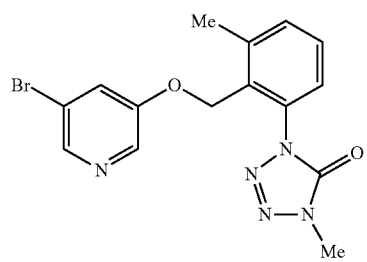

$^1$H-NMR (CDCl$_3$) δ (ppm): 8.31 (1H, d, J=1.9 Hz), 8.20 (1H, d, J=2.4 Hz), 7.48-7.41 (2H, m), 7.36-7.35 (1H, m), 7.30 (1H, dd, J=7.4, 1.6 Hz), 5.06 (2H, s), 3.67 (3H, s), 2.49 (3H, s).

Synthesis Example 12

To a mixture of 5.66 g of CA14 mentioned in Reference Production Example 14 and 100 mL of N,N-dimethylformamide, 0.96 g of 55% sodium hydride was added under ice cooling, followed by stirring for 30 minutes. To the reaction mixture, 2.84 g of 2-chloropyridin-4-ol was added under ice cooling. The temperature of the mixture was raised to room temperature, followed by stirring for 24 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 5.10 g of 1-[2-(2-chloropyridin-4-yloxymethyl)-3-methylphenyl]-4-methyl-1,4-dihydrotetrazol-5-one.

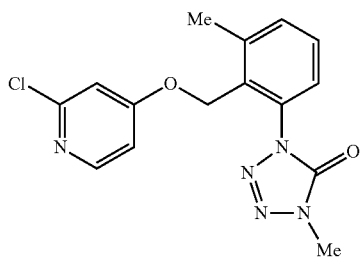

$^1$H-NMR (CDCl$_3$) δ (ppm): 8.19 (1H, d, J=5.7 Hz), 7.48-7.41 (2H, m), 7.31 (1H, dd, J=7.6, 1.1 Hz), 6.84 (1H, d, J=2.3 Hz), 6.73 (1H, dd, J=5.7, 2.3 Hz), 5.07 (2H, s), 3.66 (3H, s), 2.48 (3H, s).

Synthesis Example 13

To a mixture of 2.64 g of CA20 mentioned in Reference Production Example 20 and 60 mL of tetrahydrofuran, 0.58 g of 55% sodium hydride was added under ice cooling, followed by stirring for 30 minutes. To the reaction mixture, under ice cooling, 1.79 g of 2,4-dichloropyrimidine was added. The temperature of the mixture was raised to room temperature, followed by stirring for 14 hours. Water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 2.62 g of 1-[2-(2-chloropyrimidin-4-yloxymethyl)-3-methylphenyl]-4-methyl-1,4-dihydrotetrazol-5-one and 1.43 g of 1-[2-(4-chloropyrimidin-2-yloxymethyl)-3-methylphenyl]-4-methyl-1,4-dihydrotetrazol-5-one.

1-[2-(2-Chloropyrimidin-4-yloxymethyl)-3-methylphenyl]-4-methyl-1,4-dihydrotetrazol-5-one

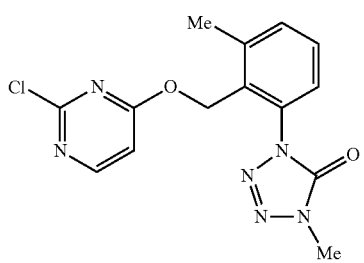 [SMILES: Cc1cccc(-n2nnn(C)c2=O)c1COc1ccnc(Cl)n1]

$^1$H-NMR (CDCl$_3$) δ (ppm): 8.26 (1H, d, J=5.7 Hz), 7.45-7.39 (2H, m), 7.28-7.26 (1H, m), 6.59 (1H, d, J=5.7 Hz), 5.48 (2H, s), 3.72 (3H, s), 2.56 (3H, s).

1-[2-(4-Chloropyrimidin-2-yloxymethyl)-3-methylphenyl]-4-methyl-1,4-dihydrotetrazol-5-one

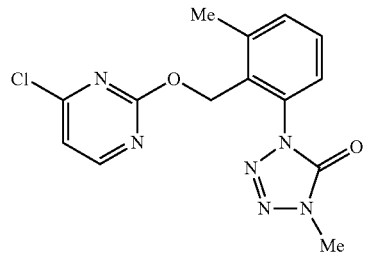 [SMILES: Cc1cccc(-n2nnn(C)c2=O)c1COc1nccc(Cl)n1]

$^1$H-NMR (CDCl$_3$) δ (ppm): 8.28 (1H, d, J=5.3 Hz), 7.41-7.36 (2H, m), 7.27-7.24 (1H, m), 6.93 (1H, d, J=5.3 Hz), 5.48 (2H, s), 3.73 (3H, s), 2.59 (3H, s).

Synthesis Example 14

To a mixture of 2.64 g of CA20 mentioned in Reference Production Example 20 and 60 mL of tetrahydrofuran, 0.58 g of 55% sodium hydride was added under ice cooling, followed by stirring for 30 minutes. To the reaction mixture, 1.80 g of 2,4-dichloro-1,3,5-triazine was added under ice cooling. The temperature of the mixture was raised to room temperature, followed by stirring for 12 hours and further stirring at 50° C. for 4 hours. After standing to cool, water was poured into the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.24 g of 1-[2-(4-chloro-1,3,5-triazin-2-yloxymethyl)-3-methylphenyl]-4-methyl-1,4-dihydrotetrazol-5-one.

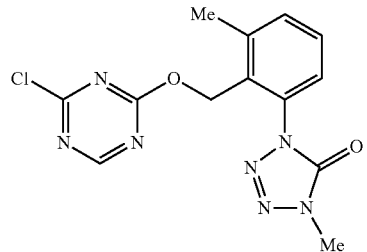 [SMILES: Cc1cccc(-n2nnn(C)c2=O)c1COc1ncnc(Cl)n1]

$^1$H-NMR (CDCl$_3$) δ (ppm): 8.64 (1H, s), 7.46-7.37 (2H, m), 7.29-7.27 (1H, m), 5.56 (2H, s), 3.74 (3H, s), 2.58 (3H, s).

Synthesis Example 15

A mixture of 1.48 g of CA14 mentioned in Reference Production Example 14, 1.00 g of 3-bromo-2-fluorophenol, 1.08 g of potassium carbonate, and 30 mL of acetonitrile was stirred with heating under reflux for 3 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.9 g of 1-[2-(3-bromo-2-fluorophenoxymethyl)-3-methylphenyl]-4-methyl-1,4-dihydrotetrazol-5-one.

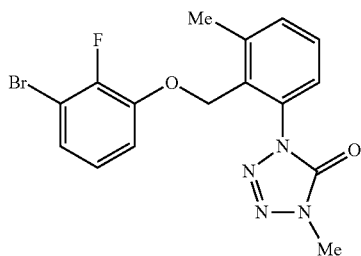

¹H-NMR (CDCl₃) δ (ppm): 7.44-7.39 (2H, m), 7.31-7.26 (1H, m), 7.16-7.12 (1H, m), 6.93-6.85 (2H, m), 5.12 (2H, s), 3.68 (3H, s), 2.52 (3H, s).

Synthesis Example 16

A mixture of 7.20 g of CA14 mentioned in Reference Production Example 14, 5.00 g of 3-bromo-4-methylphenol, 5.30 g of potassium carbonate, and 150 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 10.1 g of 1-[2-(3-bromo-4-methylphenoxymethyl)-3-methylphenyl]-4-methyl-1,4-dihydrotetrazol-5-one.

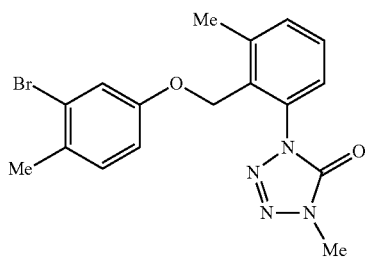 [SMILES: Cc1ccc(OCc2c(C)cccc2-n2nnn(C)c2=O)cc1Br]

¹H-NMR (CDCl₃) δ (ppm): 7.44-7.38 (2H, m), 7.30-7.26 (1H, m), 7.11-7.07 (2H, m), 6.72 (1H, dd, J=8.4, 2.6 Hz), 4.97 (2H, s), 3.65 (3H, s), 2.48 (3H, s), 2.31 (3H, s).

Synthesis Example 17

A mixture of 1.30 g of CA14 mentioned in Reference Production Example 14, 1.00 g of 5-bromo-2-chlorophenol, 0.95 g of potassium carbonate, and 30 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.60 g of 1-[2-(5-bromo-2-chlorophenoxymethyl)-3-methylphenyl]-4-methyl-1,4-dihydrotetrazol-5-one.

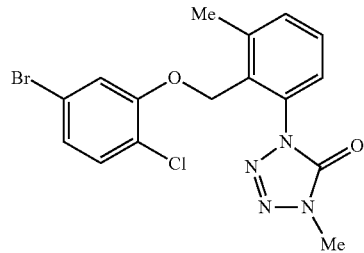 [SMILES: Cc1cccc(-n2nnn(C)c2=O)c1COc1cc(Br)ccc1Cl]

¹H-NMR (CDCl₃) δ (ppm): 7.45-7.39 (2H, m), 7.31-7.29 (1H, m), 7.19-7.17 (1H, m), 7.05-7.02 (2H, m), 5.13 (2H, s), 3.68 (3H, s), 2.53 (3H, s).

Synthesis Example 18

A mixture of 7.06 g of CA14 mentioned in Reference Production Example 14, 5.00 g of 5-bromo-2-fluorophenol, 5.16 g of potassium carbonate, and 150 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 10.0 g of 1-[2-(5-bromo-2-fluorophenoxymethyl)-3-methylphenyl]-4-methyl-1,4-dihydrotetrazol-5-one.

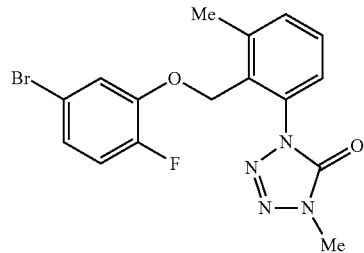 [SMILES: Cc1cccc(-n2nnn(C)c2=O)c1COc1cc(Br)ccc1F]

¹H-NMR (CDCl₃) δ (ppm): 7.45-7.38 (2H, m), 7.28 (1H, dd, J=7.3, 1.8 Hz), 7.08-7.02 (2H, m), 6.92 (1H, dd, J=10.8, 8.7 Hz), 5.09 (2H, s), 3.68 (3H, s), 2.52 (3H, s).

Synthesis Example 19

A mixture of 6.64 g of CA14 mentioned in Reference Production Example 14, 5.00 g of 3-bromo-4-methoxyphenol, 4.87 g of potassium carbonate, and 100 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 9.17 g of 1-[2-(3-bromo-4-methoxyphenoxymethyl)-3-methylphenyl]-4-methyl-1,4-dihydrotetrazol-5-one.

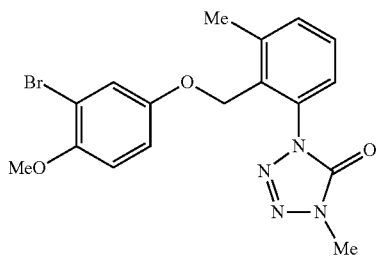 [SMILES: COc1ccc(OCc2c(C)cccc2-n2nnn(C)c2=O)cc1Br]

¹H-NMR (CDCl₃) δ (ppm): 7.45-7.38 (2H, m), 7.28-7.26 (1H, m), 7.11-7.10 (1H, m), 6.83-6.76 (2H, m), 4.96 (2H, s), 3.83 (3H, s), 3.65 (3H, s), 2.48 (3H, s).

Synthesis Example 20

A mixture of 1.44 g of CA14 mentioned in Reference Production Example 14, 1.00 g of 3-bromo-5-methylphenol, 1.06 g of potassium carbonate, and 30 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.80 g of 1-[2-(3-bromo-5-methylphenoxymethyl)-3-methylphenyl]-4-methyl-1,4-dihydrotetrazol-5-one.

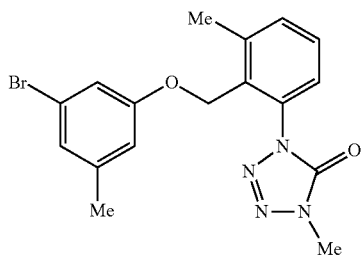

¹H-NMR (CDCl₃) δ (ppm): 7.45-7.38 (2H, m), 7.31-7.26 (1H, m), 6.93 (1H, br s), 6.84-6.83 (1H, m), 6.61 (1H, br s), 4.97 (2H, s), 3.65 (3H, s), 2.48 (3H, s), 2.28 (3H, s).

Synthesis Example 21

A mixture of 7.06 g of CA14 mentioned in Reference Production Example 14, 5.00 g of 3-bromo-4-fluorophenol, 5.16 g of potassium carbonate, and 150 mL of acetonitrile was stirred with heating under reflux for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 9.93 g of 1-[2-(3-bromo-4-fluorophenoxymethyl)-3-methylphenyl]-4-methyl-1,4-dihydrotetrazol-5-one.

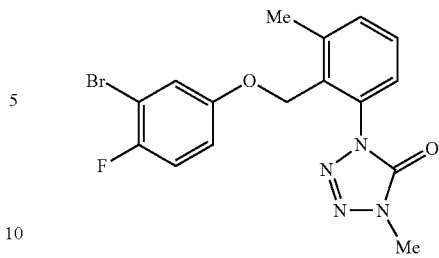

¹H-NMR (CDCl₃) δ (ppm): 7.45-7.39 (2H, m), 7.29-7.27 (1H, m), 7.06-6.99 (2H, m), 6.78-6.74 (1H, m), 4.97 (2H, s), 3.65 (3H, s), 2.48 (3H, s).

Regarding the production of intermediates for producing the above-mentioned present compounds, Reference Production Examples will be shown below.

Reference Production Example 1

Anhydrous aluminum chloride (21.9 g) was added to 250 mL of N,N-dimethylformamide under ice cooling, followed by stirring for 15 minutes. To this was added 10.7 g of sodium azide and the mixture was stirred for 15 minutes, followed by the addition of 25.0 g of 1-chloro-3-isocyanato-2-methylbenzene and further heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one (referred to as CA1).

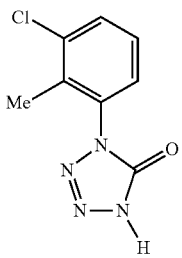

¹H-NMR (CDCl₃) δ (ppm): 2.32 (3H, s), 7.28-7.36 (2H, m), 7.57 (1H, dd, J=6.8, 2.2 Hz), 13.08 (1H, s).

Reference Production Example 2

To a mixture of 10.00 g of CA1 mentioned in Reference Production Example 1 and 100 mL of N,N-dimethylformamide, 2.30 g of 60% sodium hydride was added under ice cooling. The temperature of the mixture was raised to room temperature, followed by stirring for 14 hours. To the reaction mixture, 3.2 mL of methyl iodide was added under ice cooling. The temperature of the mixture was raised to room temperature, followed by stirring for 14 hours. Water was poured into the reaction mixture and the mixture was extracted with ethyl acetate. The organic layer were washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one (referred to as CA2).

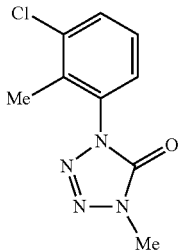

$^1$H-NMR (CDCl$_3$) δ (ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 3

A mixture of 1.56 g of CA2 mentioned in Reference Production Example 2, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one (referred to as CA3).

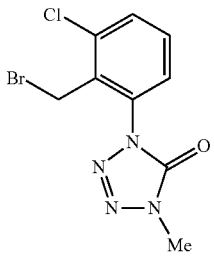

$^1$H-NMR (CDCl$_3$) δ (ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. After standing to cool, the reaction mixture was concentrated under reduced pressure to obtain 17.0 g of 1-methoxy-3-isocyanato-2-methylbenzene (referred to as CA4).

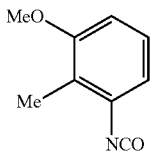

$^1$H-NMR (CDCl$_3$) δ (ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 5

Anhydrous aluminum chloride (16.0 g) was added to 180 mL of N,N-dimethylformamide under ice cooling, followed by stirring for 15 minutes. To this was added 7.8 g of sodium azide and the mixture was stirred for 15 minutes, followed by the addition of 17.0 g of CA4 mentioned in Reference Production Example 4 and further heating at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (referred to as CA5).

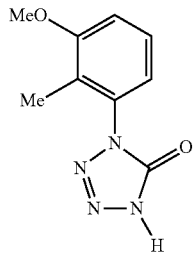 [SMILES: COc1cccc(-n2nn[nH]c2=O)c1C]

$^1$H-NMR (DMSO-d$_6$) δ (ppm): 1.99 (3H, s), 3.87 (3H, s), 7.01 (1H, d, J=8.1 Hz), 7.17 (1H, d, J=8.1 Hz), 7.36 (1H, t, J=8.3 Hz), 14.63 (1H, s).

Reference Production Example 6

To a mixture of 10.00 g of CA5 mentioned in Reference Production Example 5 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one (referred to as CA6).

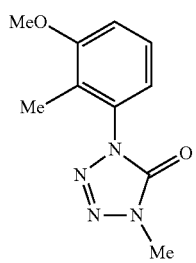

$^1$H-NMR (CDCl$_3$) δ (ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz).

Reference Production Example 7

A mixture of 2.19 g of CA6 mentioned in Reference Production Example 6, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one (referred to as CA7).

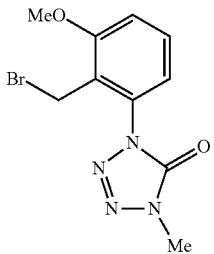

$^1$H-NMR (CDCl$_3$) δ (ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. After standing to cool, the reaction mixture was concentrated under reduced pressure to obtain 30.3 g of 1-bromo-3-isocyanato-2-methylbenzene (referred to as CA8).

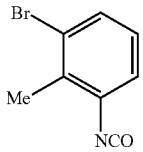

$^1$H-NMR (CDCl$_3$) δ (ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 9

Anhydrous aluminum chloride (19.7 g) was added to 220 mL of N,N-dimethylformamide under ice cooling, followed by stirring for 15 minutes. To this was added 9.6 g of sodium azide and the mixture was stirred for 15 minutes, followed by the addition of 30.3 g of CA8 mentioned in Reference Production Example 8 and further heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (referred to as CA9).

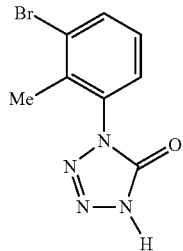 [SMILES: Cc1c(Br)cccc1-n1nn[nH]c1=O]

$^1$H-NMR (DMSO-d$_6$) δ (ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 10

To a mixture of 31.4 g of CA9 mentioned in Reference Production Example 9 and 250 mL of N,N-dimethylformamide, 5.90 g of 60% sodium hydride under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (referred to as CA10).

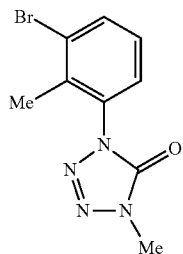 [SMILES: Cc1c(Br)cccc1-n1nnn(C)c1=O]

$^1$H-NMR (CDCl$_3$) δ (ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 11

A mixture of 8.47 g of CA10 mentioned in Reference Production Example 10, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate.

The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one (referred to as CA11).

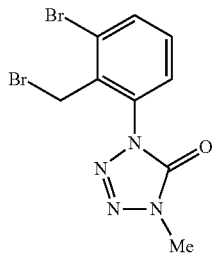 [SMILES: Cn1nnn(-c2cccc(Br)c2CBr)c1=O]

$^1$H-NMR (CDCl$_3$) δ (ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 12

A mixture of 45.0 g of CA11 mentioned in Reference Production Example 11, 37.4 g of sodium methoxide, and 600 mL of tetrahydrofuran was stirred at room temperature for 3 hours. Saturated sodium bicarbonate water was poured into the reaction mixture, followed by extraction with ethyl acetate. The organic layer was washed with saturated sodium bicarbonate water and dried over anhydrous sodium sulfate. After concentration under reduced pressure, 36.2 g of 1-(2-methoxymethyl-3-bromophenyl)-4-methyl-1,4-dihydrotetrazol-5-one (referred to as CA12) was obtained.

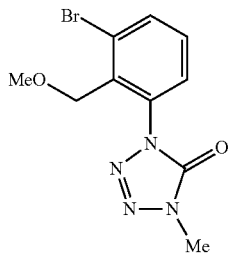 [SMILES: COCc1c(Br)cccc1-n1nnn(C)c1=O]

$^1$H-NMR (CDCl$_3$) δ (ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 13

A mixture of 36.2 g of CA12 mentioned in Reference Production Example 12, 23.2 g of methylboronic acid, 66.7 g of cesium fluoride, 10.6 g of [1,1'-bis(diphenylphosphino)ferrocene]palladium(II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1,4-dihydrotetrazol-5-one (referred to as CA13).

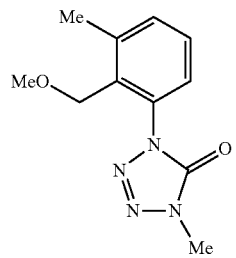 [SMILES: COCc1c(C)cccc1-n1nnn(C)c1=O]

$^1$H-NMR (CDCl$_3$) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 14

A mixture of 25.6 g of CA13 mentioned in Reference Production Example 13, 50 mL of acetic acid, and 50 mL of a 25% hydrogen bromide-acetic acid solution was stirred at 65° C. for 1 hour. A saturated saline solution was poured into the reaction mixture, followed by extraction with ethyl acetate. The organic layer was washed with saturated sodium bicarbonate water and dried over anhydrous sodium sulfate. After concentration under reduced pressure, 27.9 g of 1-(2-bromomethyl-3-methylphenyl)-4-methyl-1,4-dihydrotetrazol-5-one (referred to as CA14) was obtained.

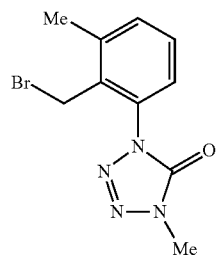 [SMILES: Cc1cccc(-n2nnn(C)c2=O)c1CBr]

$^1$H-NMR (CDCl$_3$) δ (ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of CA12 mentioned in Reference Production Example 12, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one (referred to as CA15).

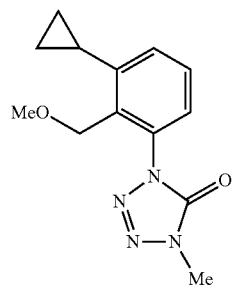 [SMILES: COCc1c(C2CC2)cccc1-n1nnn(C)c1=O]

¹H-NMR (CDCl₃) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of CA15 mentioned in Reference Production Example 15, 40 mL of acetic acid, and 40 mL of a 25% hydrogen bromide-acetic acid solution was stirred at 65° C. for 2 hours. A saturated saline solution was poured into the reaction mixture, followed by extraction with ethyl acetate. The organic layer was washed with saturated sodium bicarbonate water and dried over anhydrous sodium sulfate. After concentration under reduced pressure, 30.8 g of 1-(2-bromomethyl-3-cyclopropylphenyl)-4-methyl-1,4-dihydrotetrazol-5-one (referred to as CA16) was obtained.

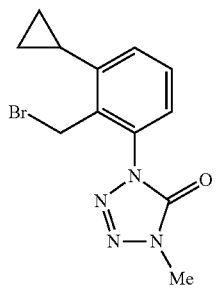 [SMILES: Cn1nnn(-c2cccc(C3CC3)c2CBr)c1=O]

¹H-NMR (CDCl₃) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 29.8 g of CA12 mentioned in Reference Production Example 12, 35.2 g of tributylvinyltin, 11.6 g of tetrakistriphenylphosphinepalladium, and 500 mL of toluene was stirred with heating under reflux for 14 hours. After cooling, a saturated aqueous ammonium chloride solution was poured into the reaction solution, followed by extraction with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one (referred to as CA17).

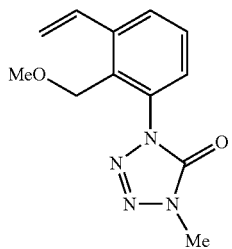 [SMILES: C=Cc1cccc(-n2nnn(C)c2=O)c1COC]

¹H-NMR (CDCl₃) δ (ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 18

A mixture of 19.7 g of CA17 mentioned in Reference Production Example 17, 3.02 g of a palladium-fibroin composite, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one (referred to as CA18).

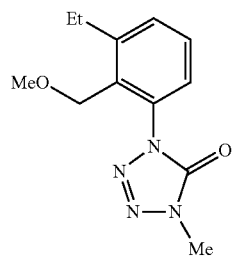 [SMILES: CCc1cccc(-n2nnn(C)c2=O)c1COC]

¹H-NMR (CDCl₃) δ (ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 19

A mixture of 19.3 g of CA18 mentioned in Reference Production Example 18, 40 mL of acetic acid, and 40 mL of a 25% hydrogen bromide-acetic acid solution was stirred at 65° C. for 1.5 hours. A saturated saline solution was poured into the reaction mixture, followed by extraction with ethyl acetate. The organic layer was washed with saturated sodium bicarbonate water and dried over anhydrous sodium sulfate. After concentration under reduced pressure, 23.3 g of 1-(2-bromomethyl-3-ethylphenyl)-4-methyl-1,4-dihydrotetrazol-5-one (referred to as CA19) was obtained.

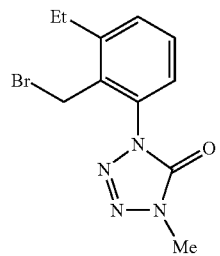 [SMILES: CCc1cccc(-n2nnn(C)c2=O)c1CBr]

¹H-NMR (CDCl₃) δ (ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 20

Under ice cooling, a mixture of 7.00 g of CA14 mentioned in Reference Production Example 14, 9.90 g of calcium carbonate, 80 ml of dioxane, and 80 ml of water was stirred with heating under reflux for 7 hours. After cooling, water was poured into the reaction solution and the mixture was extracted with ethyl acetate. The organic layer was washed with water and a saturated saline solution, and then dried over anhydrous magnesium sulfate. After concentration under reduced pressure, 4.68 g of 1-(2-hydroxymethyl-3-methylphenyl)-4-methyl-1,4-dihydrotetrazol-5-one (referred to as CA20) was obtained.

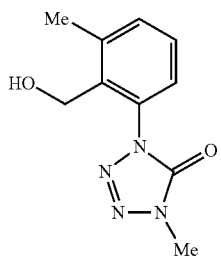 [SMILES: Cc1cccc(-n2nnn(C)c2=O)c1CO]

¹H-NMR (CDCl₃) δ (ppm): 7.39-7.34 (2H, m), 7.23-7.18 (1H, m), 4.48 (2H, d, J=7.1 Hz), 3.75 (3H, s), 2.56 (3H, s).

Reference Production Example 21

Under ice cooling, a mixture of 3.00 g of CA19 mentioned in Reference Production Example 19, 4.00 g of calcium carbonate, 50 ml of dioxane, and 50 ml of water was stirred with heating under reflux for 6 hours. After cooling, water was poured into the reaction solution and the mixture was extracted with ethyl acetate. The organic layer was washed with water and a saturated saline solution, and then dried over anhydrous magnesium sulfate. After concentration under reduced pressure, 2.58 g of 1-(2-hydroxymethyl-3-ethylphenyl)-4-methyl-1,4-dihydrotetrazol-5-one (referred to as CA21) was obtained.

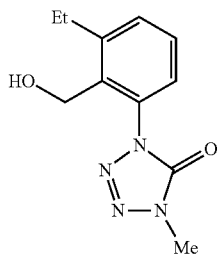 [SMILES: CCc1cccc(-n2nnn(C)c2=O)c1CO]

¹H-NMR (CDCl₃) δ (ppm): 7.44-7.39 (2H, m), 7.23-7.19 (1H, m), 4.49 (2H, d, J=7.2 Hz), 3.75 (3H, s), 2.93 (2H, q, J=7.6 Hz), 1.31 (3H, t, J=7.6 Hz).

Reference Production Example 22

Under ice cooling, a mixture of 3.00 g of CA16 mentioned in Reference Production Example 16, 3.90 g of calcium carbonate, 50 ml of dioxane, and 50 ml of water was stirred with heating under reflux for 6 hours. After cooling, water was poured into the reaction solution and the mixture was extracted with ethyl acetate. The organic layer was washed with water and a saturated saline solution, and then dried over anhydrous magnesium sulfate. After concentration under reduced pressure, 2.72 g of 1-(2-hydroxymethyl-3-cyclopropylphenyl)-4-methyl-1,4-dihydrotetrazol-5-one (referred to as CA22) was obtained.

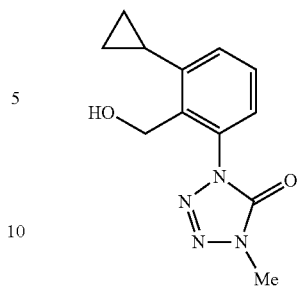

¹H-NMR (CDCl₃) δ (ppm): 7.38 (1H, t, J=7.8 Hz), 7.20 (1H, d, J=8.0 Hz), 7.16 (1H, d, J=7.7 Hz), 4.68 (2H, d, J=7.0 Hz), 3.76 (3H, s), 2.39-2.32 (1H, m), 1.10-1.05 (2H, m), 0.79-0.75 (2H, m).

Reference Production Example 23

Under ice cooling, 3.00 g of CA7 mentioned in Reference Production Example 7, 4.02 g of calcium carbonate, 50 ml of dioxane, and 50 ml of water was stirred with heating under reflux for 5 hours. After cooling, water was poured into the reaction solution and the mixture was extracted with ethyl acetate. The organic layer was washed with water and a saturated saline solution, and then dried over anhydrous magnesium sulfate. After concentration under reduced pressure, 1.70 g of 1-(2-hydroxymethyl-3-methoxyphenyl)-4-methyl-1,4-dihydrotetrazol-5-one (referred to as CA23) was obtained.

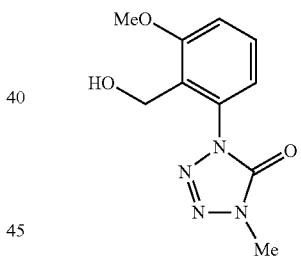

¹H-NMR (CDCl₃) δ (ppm): 7.44 (1H, t, J=8.2 Hz), 7.07 (1H, d, J=8.5 Hz), 7.01 (1H, d, J=8.0 Hz), 4.55 (2H, d, J=7.0 Hz), 3.95 (3H, s), 3.74 (3H, s).

Reference Production Example 24

Under ice cooling, a mixture of 4.87 g of CA3 mentioned in Reference Production Example 3, 6.42 g of calcium carbonate, 50 ml of dioxane, and 50 ml of water was stirred with heating under reflux for 7 hours. After cooling, water was poured into the reaction solution and the mixture was extracted with ethyl acetate. The organic layer was washed with water and a saturated saline solution, and then dried over anhydrous magnesium sulfate. After concentration under reduced pressure, 2.00 g of 1-(2-hydroxymethyl-3-chlorophenyl)-4-methyl-1,4-dihydrotetrazol-5-one (referred to as CA24) was obtained.

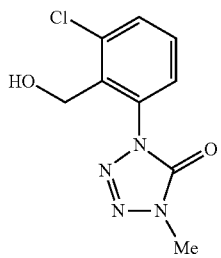 [SMILES: Cn1nnn(-c2cccc(Cl)c2CO)c1=O]

¹H-NMR (CDCl₃) δ (ppm): 7.61 (1H, dd, J=8.0, 1.1 Hz), 7.43 (1H, t, J=8.0 Hz), 7.34 (1H, dd, J=8.0, 1.1 Hz), 4.64 (2H, d, J=7.3 Hz), 3.76 (3H, s).

Reference Production Example 25

A mixture of 10.0 g of 1-[2-(3-bromophenoxymethyl)-3-methylphenyl]-4-methyl-1,4-dihydrotetrazol-5-one mentioned in Synthesis Example 10, 8.12 g of bis(pinacolato)diboron, 7.86 g of potassium acetate, 2.18 g of [1,1'-bis(diphenylphosphino)ferrocene]palladium(II) dichloride dichloromethane adduct, and 200 mL of dimethyl sulfoxide was stirred at 90° C. for 5 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 9.68 g of 1-methyl-4-{3-methyl-2-[3-(4,4,5,5-tetramethyl-[1,3,2]dioxaborolan-2-yl)-phenoxymethyl]-phenyl}-1,4-dihydrotetrazol-5-one (referred to as CA25).

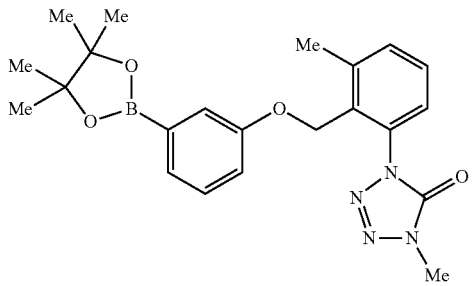 [SMILES: Cc1cccc(-n2nnn(C)c2=O)c1COc1cccc(B2OC(C)(C)C(C)(C)O2)c1]

¹H-NMR (CDCl₃) δ (ppm): 7.44-7.39 (3H, m), 7.31-7.23 (3H, m), 6.98-6.95 (1H, m), 5.03 (2H, s), 3.63 (3H, s), 2.49 (3H, s), 1.35 (12H, s).

Reference Production Example 26

A mixture of 8.10 g of (2-amino-6-methylphenyl)methanol produced by the method mentioned in WO 2010/58314 A, 6.94 g of concentrated sulfuric acid, and 450 mL of methanol was stirred at 50° C. for 2 hours. After the reaction mixture was cooled to 0° C., 5.66 g of sodium hydroxide was added and the mixture was concentrated under reduced pressure. To the residue thus obtained, saturated sodium bicarbonate water was added, followed by extraction with toluene. The organic layer was washed with water and saturated sodium bicarbonate water, dried over anhydrous sodium sulfate, and then concentrated under reduced pressure to obtain 8.62 g of 3-methyl-2-methoxymethyl-1-aminobenzene (referred to as CA26).

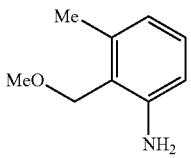

¹H-NMR (CDCl₃) δ (ppm): 2.33 (3H, s), 3.36 (3H, s), 4.12 (2H, s), 4.54 (2H, s), 6.55 (1H, d, J=8.0 Hz), 6.58 (1H, d, J=7.3 Hz), 7.00 (1H, t, J=7.7 Hz).

Reference Production Example 27

A mixture of 6.35 g of CA26 mentioned in Reference Production Example 26, 4.36 g of triphosgene, 150 mL of saturated sodium bicarbonate water, and 150 mL of ethyl acetate was stirred for 1 hour under ice cooling. The organic layer of the reaction mixture was washed with a saturated saline solution and then concentrated under reduced pressure to obtain 6.30 g of 3-methyl-2-methoxymethyl-1-isocyanatobenzene (referred to as CA27).

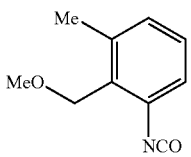

¹H-NMR (CDCl₃) δ (ppm): 2.40 (3H, s), 3.42 (3H, s), 4.51 (2H, s), 6.97 (1H, d, J=8.0 Hz), 7.03 (1H, d, J=7.6 Hz), 7.16 (1H, t, J=7.8 Hz).

Reference Production Example 28

Under ice cooling, 6.16 g of anhydrous aluminum chloride was added to 100 mL of N,N-dimethylformamide, followed by stirring for 30 minutes. To this was added 3.00 g of sodium azide, followed by stirring for 30 minutes, the addition of 6.30 g of CA27 mentioned in Reference Production Example 27, and further heating at 80° C. for 10 hours. After cooling, the reaction solution was added in a mixture of 4.62 g of sodium nitrite, 100 mL of water, and 100 g of ice while stirring. The mixture was acidified with 10% hydrochloric acid and then extracted with ethyl acetate. The organic layer was washed with water and an aqueous 10% sodium hydrogen sulfate solution, dried over anhydrous sodium sulfate, and then concentrated under reduced pressure to obtain 7.00 g of 1-(2-methoxymethyl-3-methylphenyl)-1,4-dihydrotetrazol-5-one (referred to as CA28).

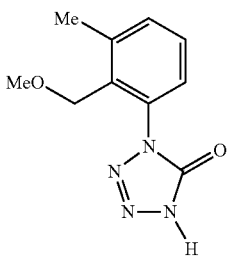 [SMILES: COCc1c(C)cccc1-n1nn[nH]c1=O]

¹H-NMR (CDCl₃) δ (ppm): 2.49 (3H, s), 3.25 (3H, s), 4.45 (2H, s), 7.24 (1H, t, J=4.9 Hz), 7.39 (2H, d, J=4.9 Hz), 13.00 (1H, s).

Reference Production Example 29

A mixture of 7.20 g of CA28 mentioned in Reference Production Example 28, 13.56 g of potassium carbonate, 3.72 mL of dimethylsulfuric acid, and 150 mL of N,N-dimethylformamide was stirred at room temperature for 1 hour. Water was poured into the reaction mixture and the mixture was extracted with ethyl acetate. The organic layer was washed with water and a saturated saline solution, dried over anhydrous magnesium sulfate, and then concentrated under reduced pressure to obtain 6.90 g of CA13 mentioned in Reference Production Example 13. $^1$H-NMR data matched with the values mentioned in Reference Production Example 13.

Reference Production Example 30

A mixture of 3.0 g of 1-[2-(6-bromopyridin-2-yloxymethyl)-3-methylphenyl]-4-methyl-1,4-dihydrotetrazol-5-one mentioned in Synthesis Example 1, 4.1 g of bis(pinacolato) diboron, 2.4 g of potassium acetate, 0.65 g of [1,1'-bis(diphenylphosphino)ferrocene]palladium(II) dichloride dichloromethane adduct, and 20 mL of dimethyl sulfoxide was stirred at 90° C. for 3 hours. After standing to cool, water was poured into the reaction mixture and the mixture was extracted with ethyl acetate. The organic layer was washed with water and a saturated saline solution, dried over anhydrous magnesium sulfate, and then concentrated under reduced pressure to obtain 3.9 g of 1-methyl-4-{3-methyl-2-[6-(4,4,5,5-tetramethyl-[1,3,2]dioxaborolan-2-yl)-pyridin-2-yloxymethyl]-phenyl}-1,4-dihydrotetrazol-5-one (referred to as CA29).

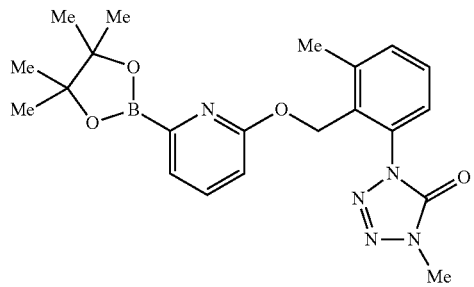 [SMILES: Cc1cccc(-n2nnn(C)c2=O)c1COc1cccc(B2OC(C)(C)C(C)(C)O2)n1]

$^1$H-NMR (CDCl$_3$) δ (ppm): 7.91-7.86 (1H, m), 7.62 (1H, d, J=7.2 Hz), 7.46-7.40 (2H, m), 7.31-7.28 (1H, m), 6.85 (1H, d, J=8.6 Hz), 5.41 (2H, s), 3.66 (3H, s), 2.56 (3H, s), 1.21 (12H, s).

According to the above-mentioned processes, the following compounds can be obtained:
compounds Q1A-001 to Q1A-558, Q1B-001 to Q1B-558, Q1C-001 to Q1C-558, Q1D-001 to Q1D-558, Q1E-001 to Q1E-558, Q1F-001 to Q1F-558, Q1G-001 to Q1G-558, Q1H-001 to Q1H-558, Q1I-001 to Q1I-558, Q1J-001 to Q1J-558, Q1K-001 to Q1K-558, Q2A-001 to Q2A-558, Q2B-001 to Q2B-558, Q2C-001 to Q2C-558, Q2D-001 to Q2D-558, Q2E-001 to Q2E-558, Q2F-001 to Q2F-558, Q2G-001 to Q2G-558, Q2H-001 to Q2H-558, Q2I-001 to Q2I-558, Q2J-001 to Q2J-558, Q2K-001 to Q2K-558, Q3A-001 to Q3A-558, Q3B-001 to Q3B-558, Q3C-001 to Q3C-558, Q3D-001 to Q3D-558, Q3E-001 to Q3E-558, Q3F-001 to Q3F-558, Q3G-001 to Q3G-558, Q3H-001 to Q3H-558, Q3I-001 to Q3I-558, Q3J-001 to Q3J-558, Q3K-001 to Q3K-558, Q4A-001 to Q4A-558, Q4B-001 to Q4B-558, Q4C-001 to Q4C-558, Q4D-001 to Q4D-558, Q4E-001 to Q4E-558, Q4F-001 to Q4F-558, Q4G-001 to Q4G-558, Q4H-001 to Q4H-558, Q4I-001 to Q4I-558, Q4J-001 to Q4J-558, Q4K-001 to Q4K-558, Q5A-001 to Q5A-558, Q5B-001 to Q5B-558, Q5C-001 to Q5C-558, Q5D-001 to Q5D-558, Q5E-001 to Q5E-558, Q5F-001 to Q5F-558, Q5G-001 to Q5G-558, Q5H-001 to Q5H-558, Q5I-001 to Q5I-558, Q5J-001 to Q5J-558, Q5K-001 to Q5K-558, Q6A-001 to Q6A-558, Q6B-001 to Q6B-558, Q6C-001 to Q6C-558, Q6D-001 to Q6D-558, Q6E-001 to Q6E-558, Q6F-001 to Q6F-558, Q6G-001 to Q6G-558, Q6H-001 to Q6H-558, Q6I-001 to Q6I-558, Q6J-001 to Q6J-558, Q6K-001 to Q6K-558, Q7A-001 to Q7A-558, Q7B-001 to Q7B-558, Q7C-001 to Q7C-558, Q7D-001 to Q7D-558, Q7E-001 to Q7E-558, Q7F-001 to Q7F-558, Q7G-001 to Q7G-558, Q7H-001 to Q7H-558, Q7I-001 to Q7I-558, Q7J-001 to Q7J-558, Q7K-001 to Q7K-558, Q8A-001 to Q8A-558, Q8B-001 to Q8B-558, Q8C-001 to Q8C-558, Q8D-001 to Q8D-558, Q8E-001 to Q8E-558, Q8F-001 to Q8F-558, Q8G-001 to Q8G-558, Q8H-001 to Q8H-558, Q8I-001 to Q8I-558, Q8J-001 to Q8J-558, Q8K-001 to Q8K-558, Q9A-001 to Q9A-558, Q9B-001 to Q9B-558, Q9C-001 to Q9C-558, Q9D-001 to Q9D-558, Q9E-001 to Q9E-558, Q9F-001 to Q9F-558, Q9G-001 to Q9G-558, Q9H-001 to Q9H-558, Q9I-001 to Q9I-558, Q9J-001 to Q9J-558, Q9K-001 to Q9K-558, Q10A-001 to Q10A-558, Q10B-001 to Q10B-558, Q10C-001 to Q10C-558, Q10D-001 to Q10D-558, Q10E-001 to Q10E-558, Q10E-001 to Q10E-558, Q10G-001 to Q10G-558, Q10H-001 to Q10H-558, Q10I-001 to Q10I-558, Q10J-001 to Q10J-558, Q10K-001 to Q10K-558, Q11A-001 to Q11A-558, Q11B-001 to Q11B-558, Q11C-001 to Q11C-558, Q11D-001 to Q11D-558, Q11E-001 to Q11E-558, Q11F-001 to Q11F-558, Q11G-001 to Q11G-558, Q11H-001 to Q11H-558, Q11I-001 to Q11I-558, Q11J-001 to Q11J-558, Q11K-001 to Q11K-558, Q12A-001 to Q12A-558, Q12B-001 to Q12B-558, Q12C-001 to Q12C-558, Q12D-001 to Q12D-558, Q12E-001 to Q12E-558, Q12F-001 to Q12F-558, Q12G-001 to Q12G-558, Q12H-001 to Q12H-558, Q12I-001 to Q12I-558, Q12J-001 to Q12J-558, and Q12K-001 to Q12K-558.

The compounds Q1A-001 to Q12K-558 have structures shown below:

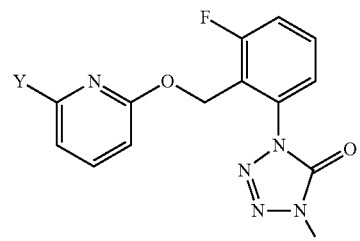

(Q1A)

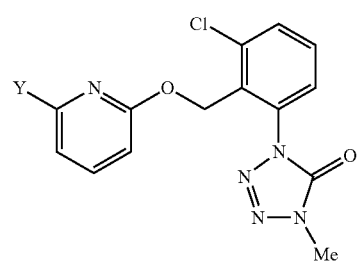

(Q1B)

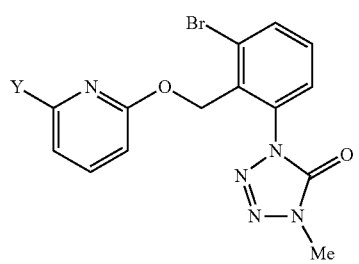 (Q1C)
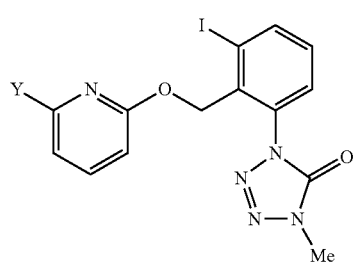 (Q1D)
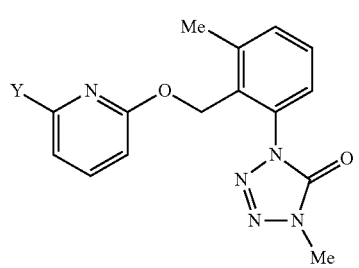 (Q1E)
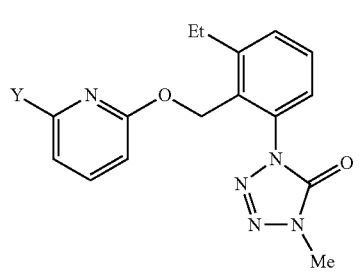 (Q1F)
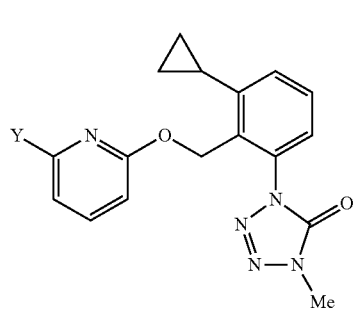 (Q1G)
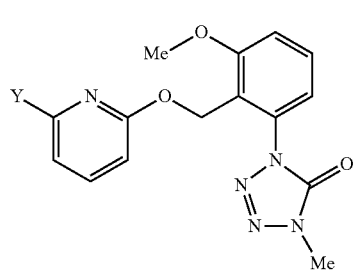 (Q1H)
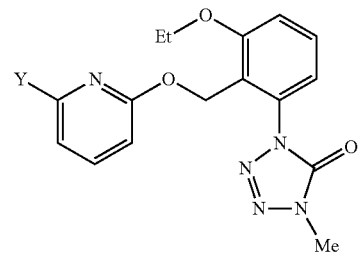 (Q1I)
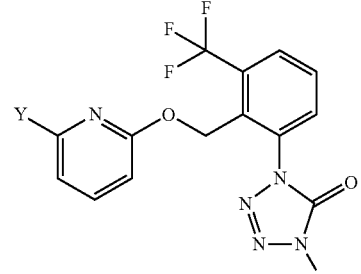 (Q1J)
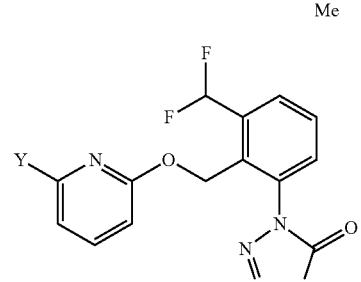 (Q1K)
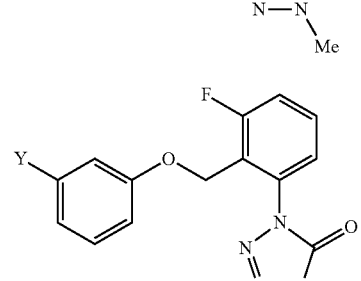 (Q2A)
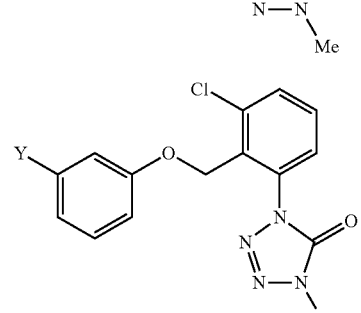 (Q2B)
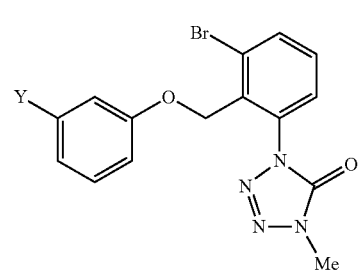 (Q2C)

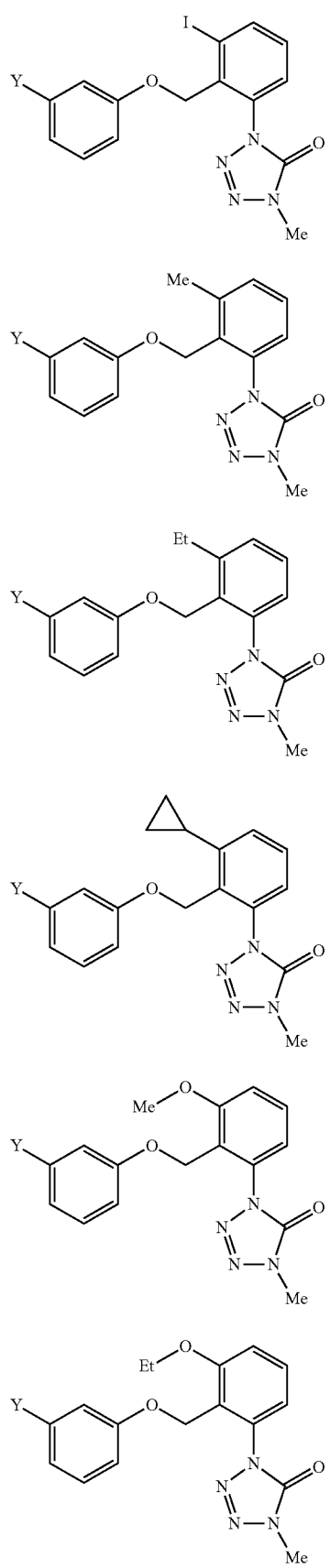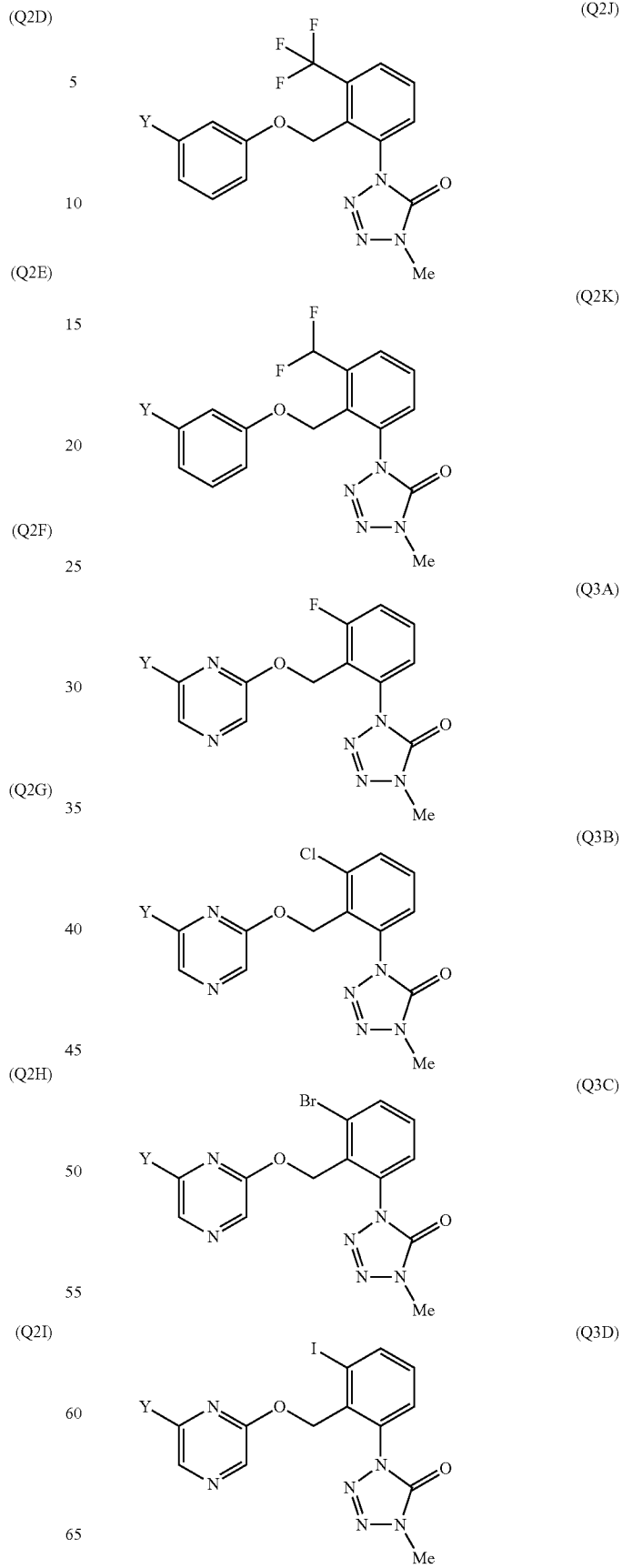

-continued
(Q3E)
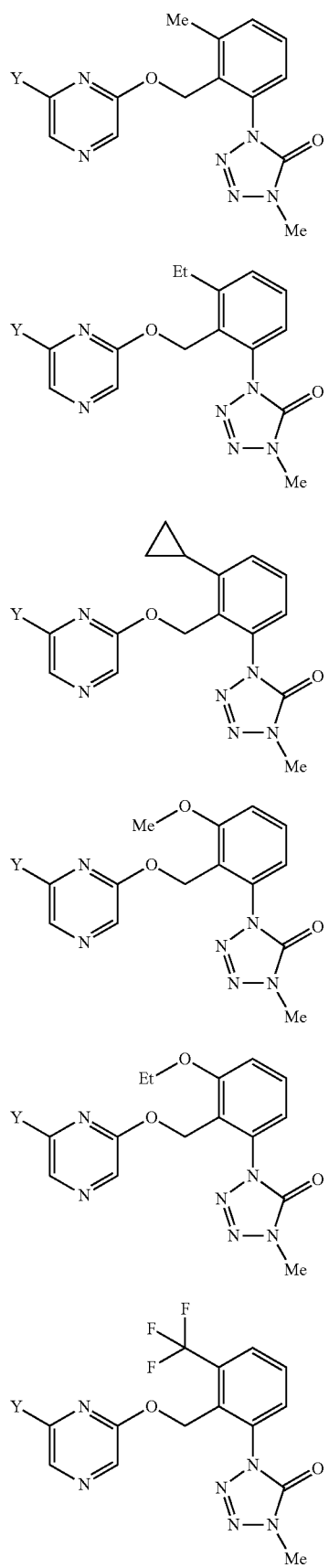
(Q3F)
(Q3G)
(Q3H)
(Q3I)
(Q3J)
-continued
(Q3K)
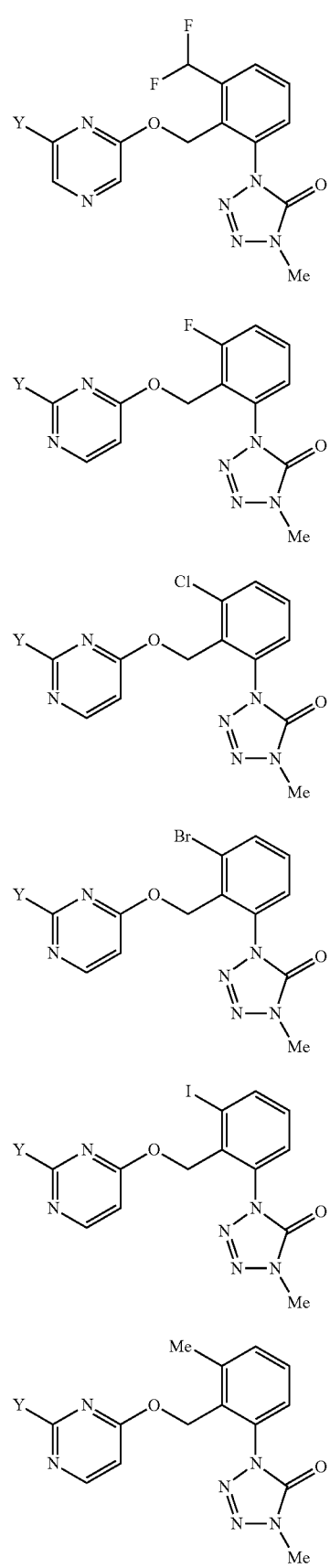
(Q4A)
(Q4B)
(Q4C)
(Q4D)
(Q4E)

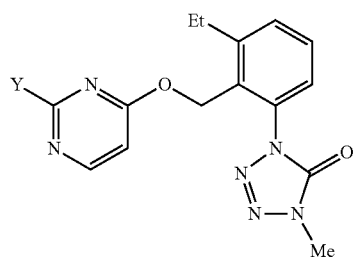
(Q4F)
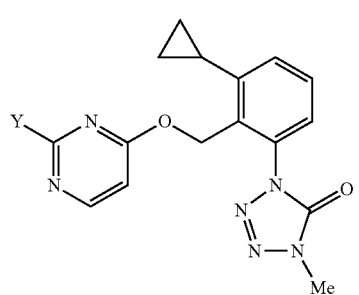
(Q4G)
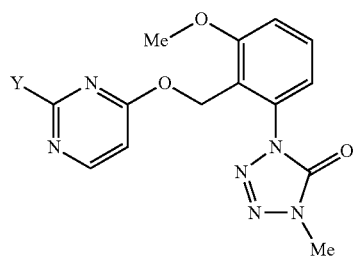
(Q4H)
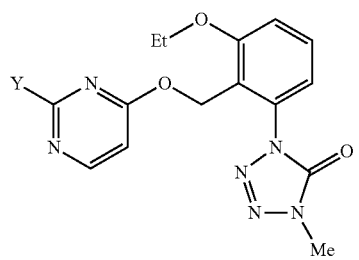
(Q4I)
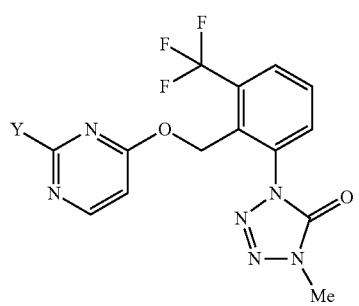
(Q4J)
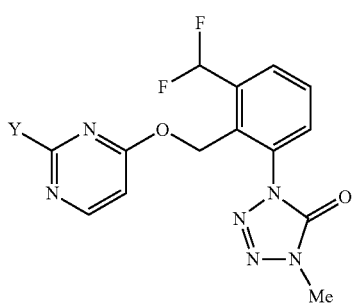
(Q4K)
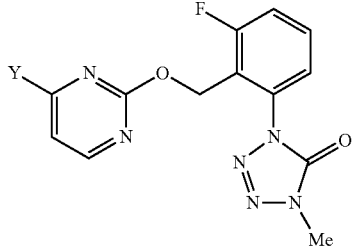
(Q5A)
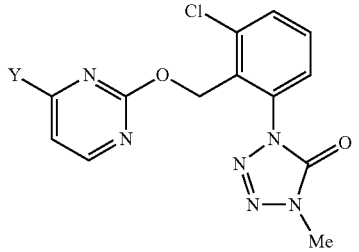
(Q5B)
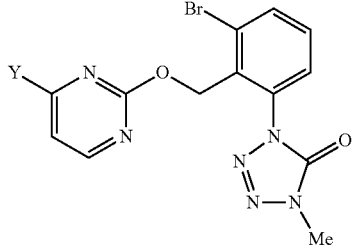
(Q5C)
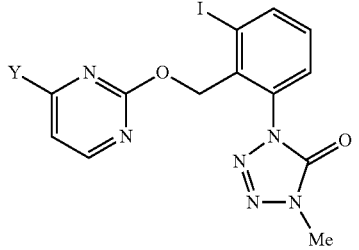
(Q5D)
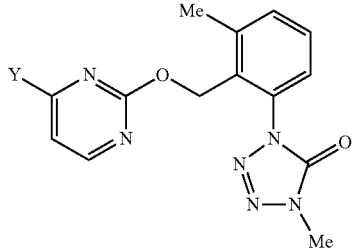
(Q5E)

(Q5F)
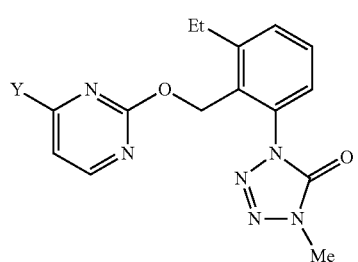
(Q5G)
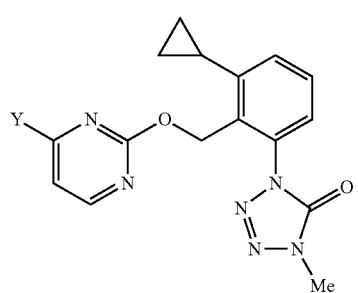
(Q5H)
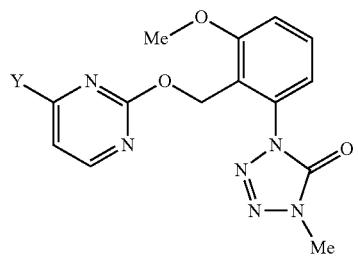
(Q5I)
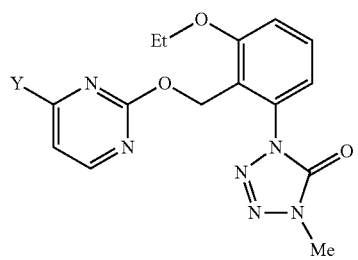
(Q5J)
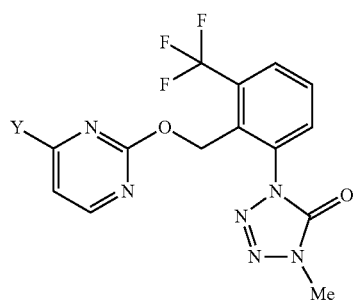
(Q5K)
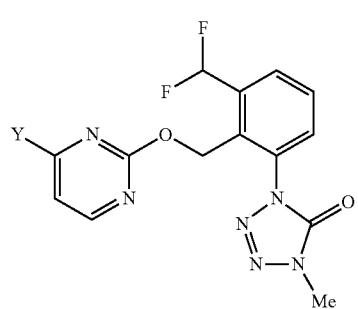
(Q6A)
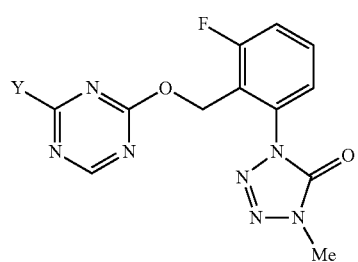
(Q6B)
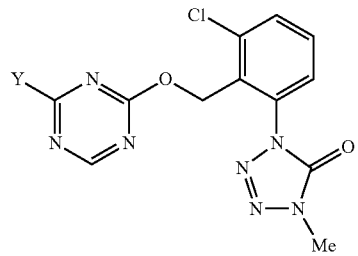
(Q6C)
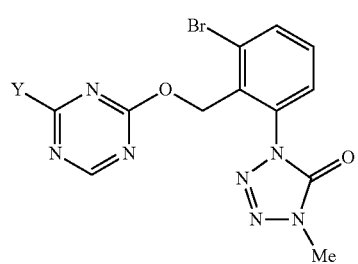
(Q6D)
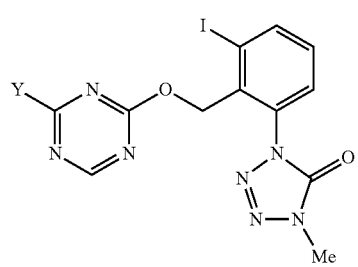
(Q6E)
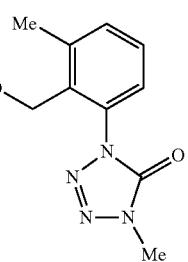

(Q6F) 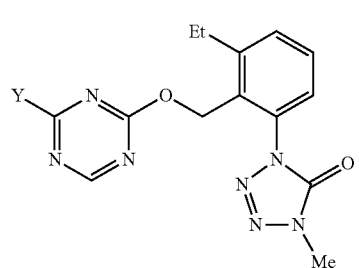
(Q6G) 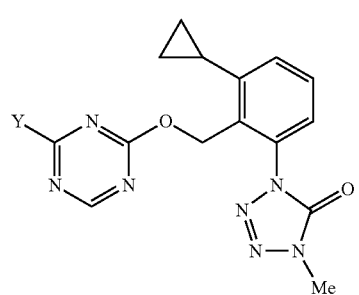
(Q6H) 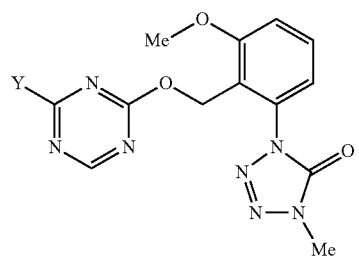
(Q6I) 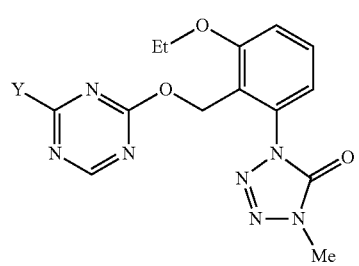
(Q6J) 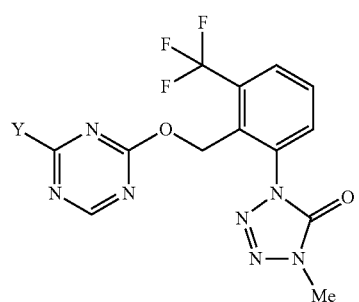
(Q6K) 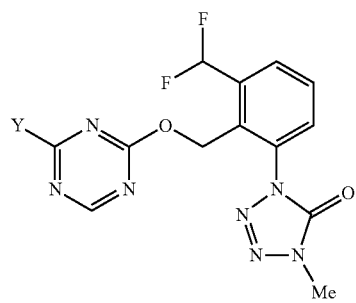
(Q7A) 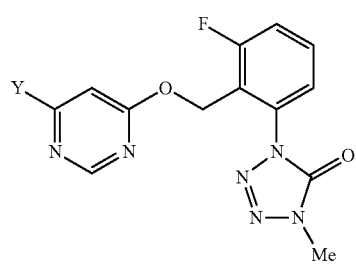
(Q7B) 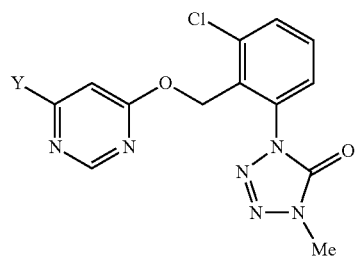
(Q7C) 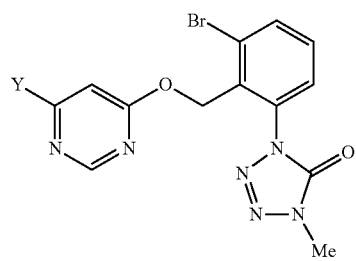
(Q7D) 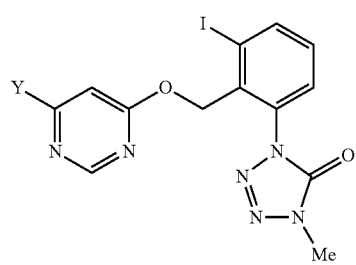
(Q7E) 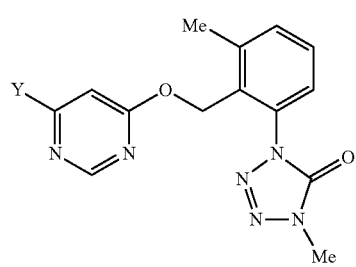

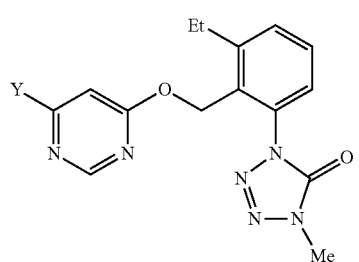
(Q7F)
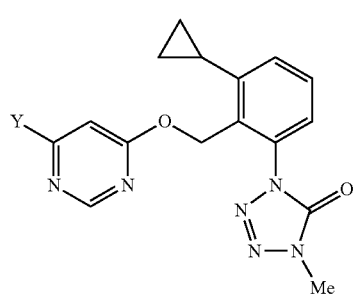
(Q7G)
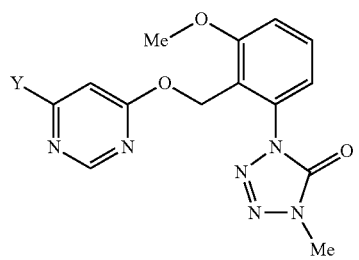
(Q7H)
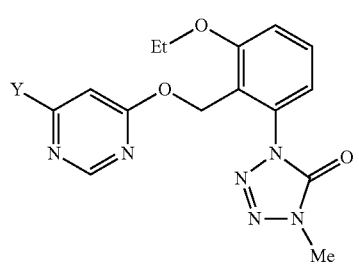
(Q7I)
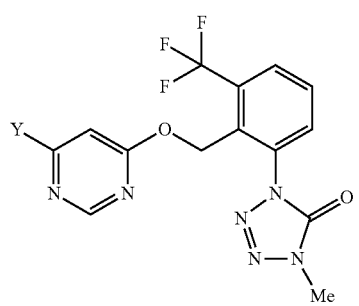
(Q7J)
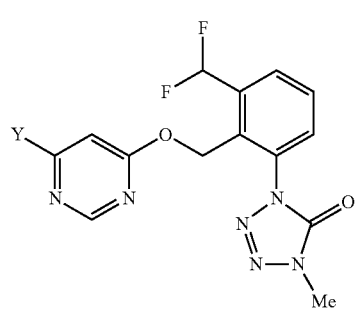
(Q7K)
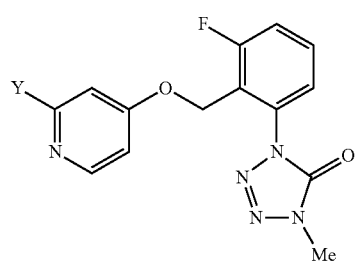
(Q8A)
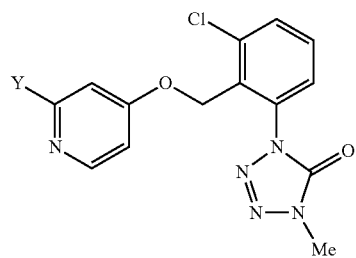
(Q8B)
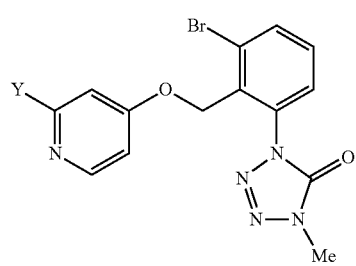
(Q8C)
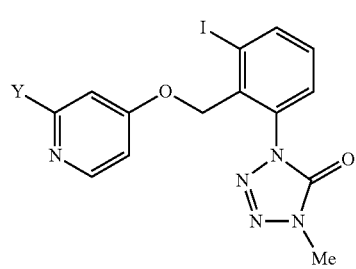
(Q8D)
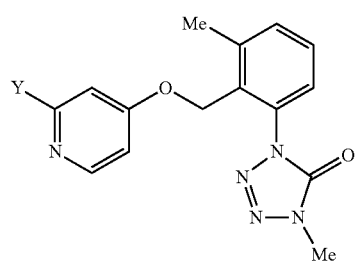
(Q8E)

(Q8F) 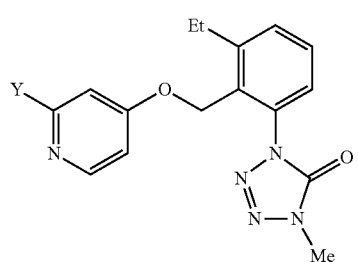
(Q8G) 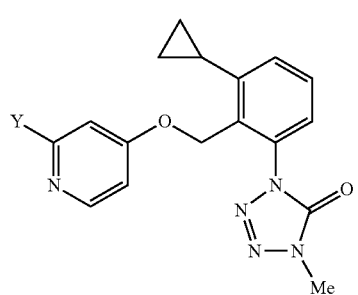
(Q8H) 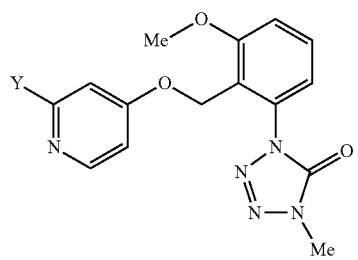
(Q8I) 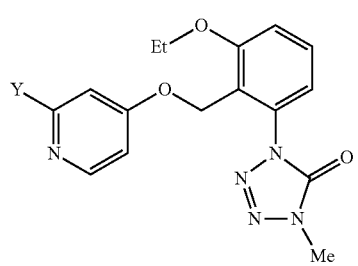
(Q8J) 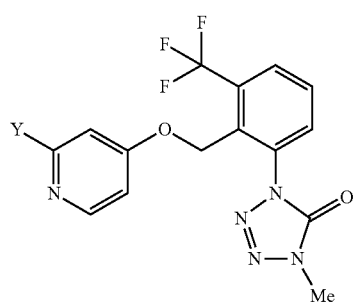
(Q8K) 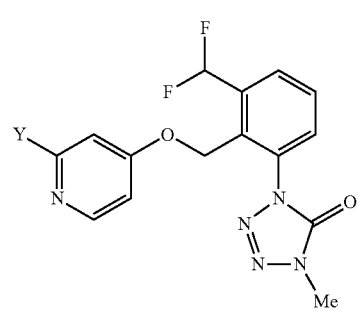
(Q9A) 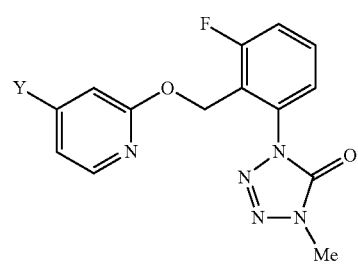
(Q9B) 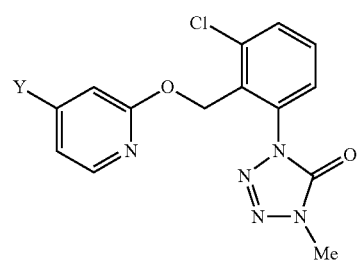
(Q9C) 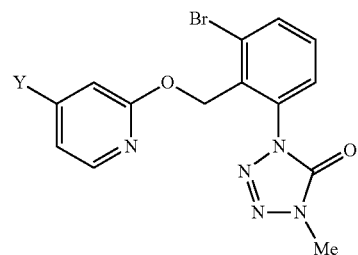
(Q9D) 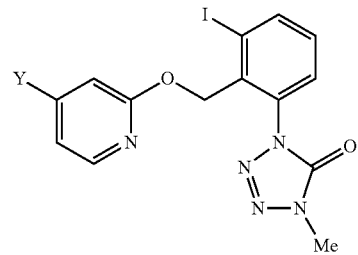
(Q9E) 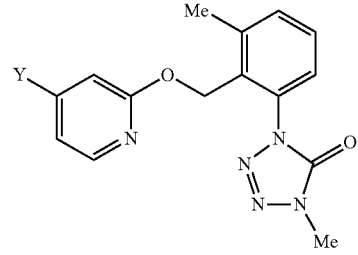

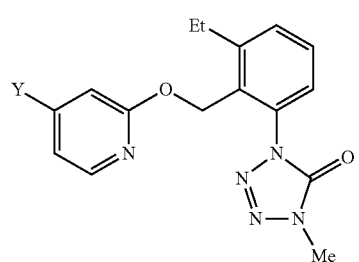
(Q9F)
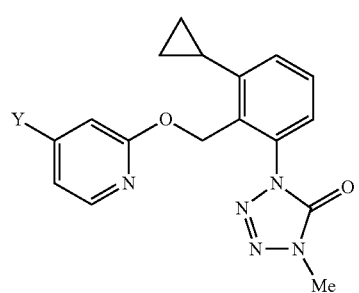
(Q9G)
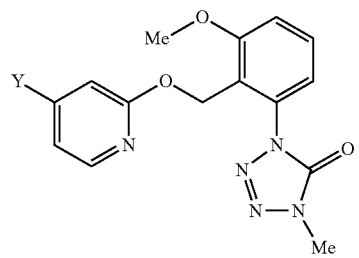
(Q9H)
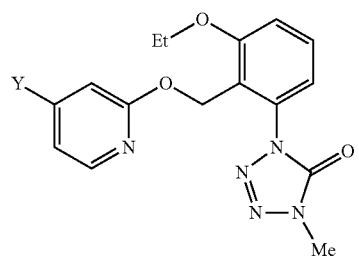
(Q9I)
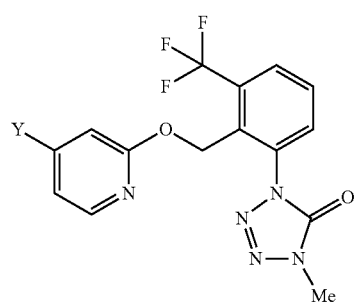
(Q9J)
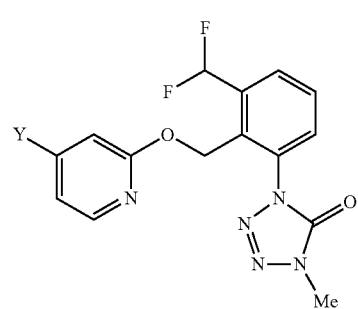
(Q9K)
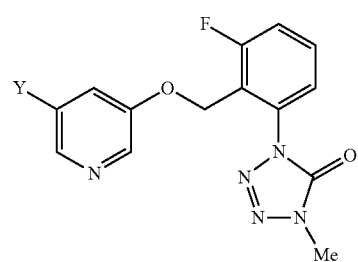
(Q10A)
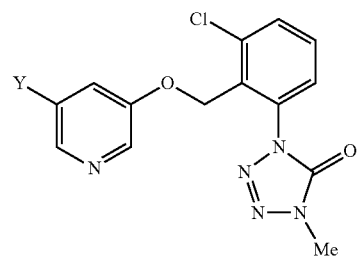
(Q10B)
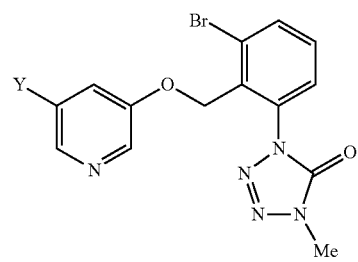
(Q10C)
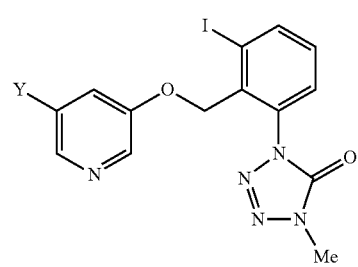
(Q10D)
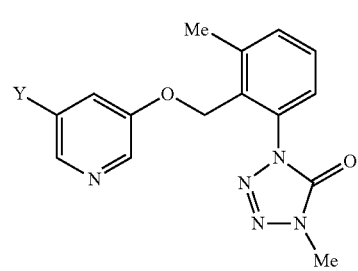
(Q10E)

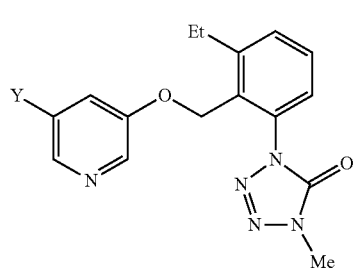 (Q10F)
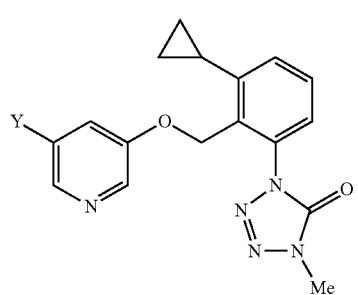 (Q10G)
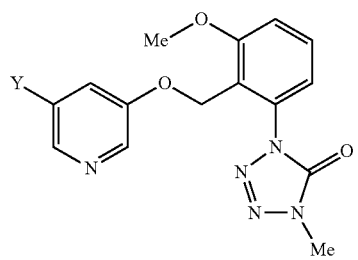 (Q10H)
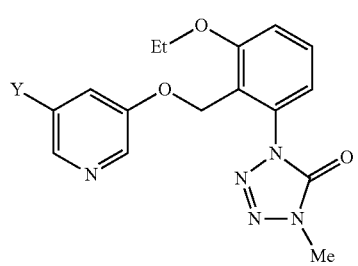 (Q10I)
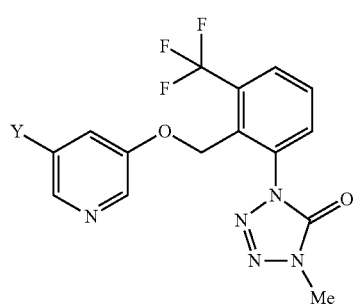 (Q10J)
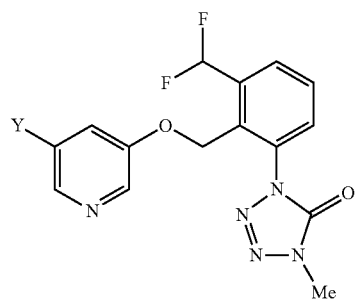 (Q10K)
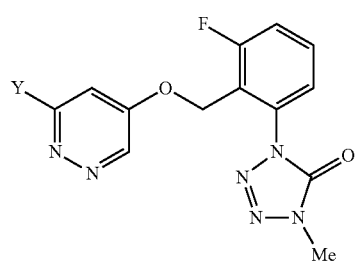 (Q11A)
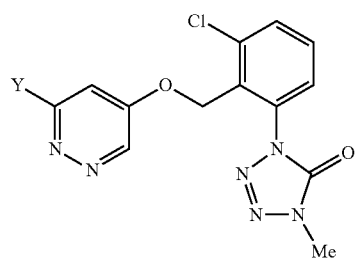 (Q11B)
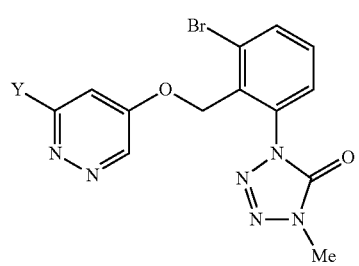 (Q11C)
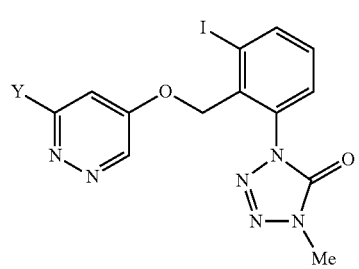 (Q11D)
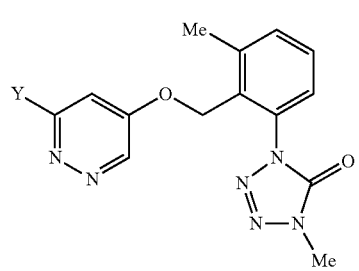 (Q11E)

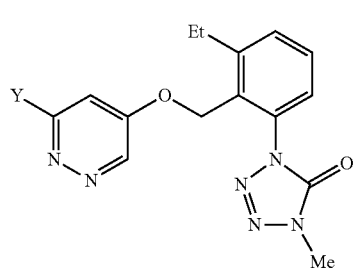
(Q11F)
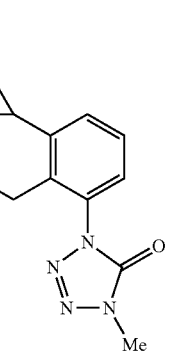
(Q11G)
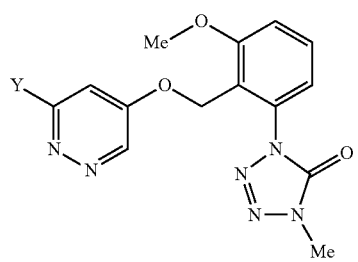
(Q11H)
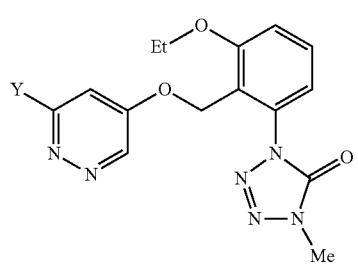
(Q11I)
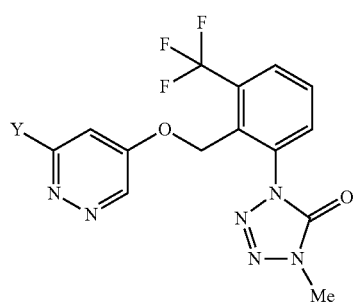
(Q11J)
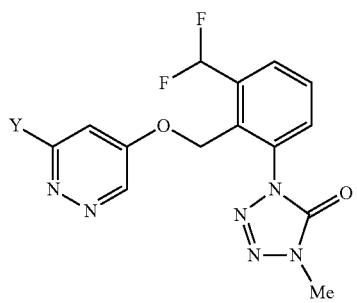
(Q11K)
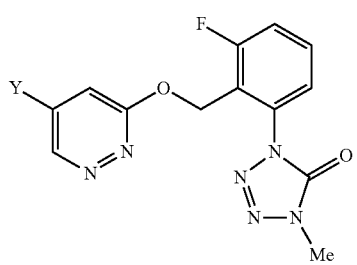
(Q12A)
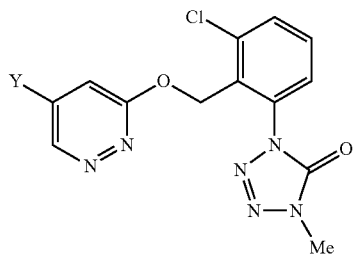
(Q12B)
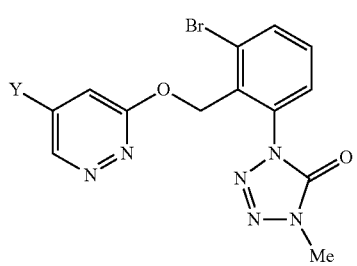
(Q12C)
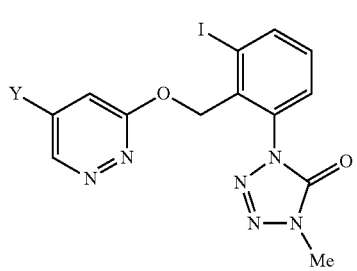
(Q12D)
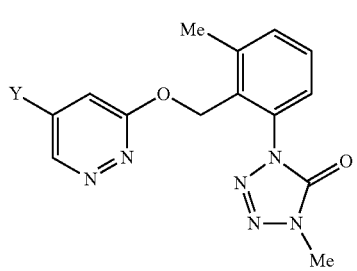
(Q12E)

-continued (Q12F)

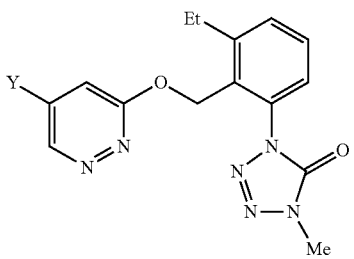

(Q12G)

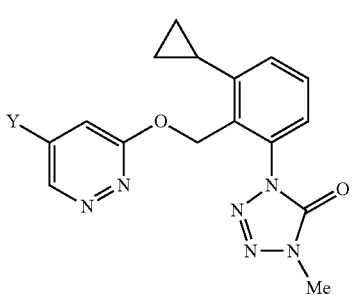

(Q12H)

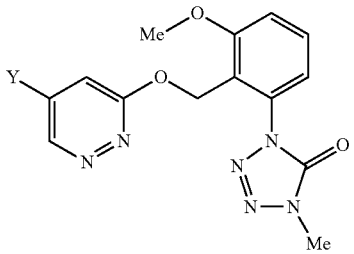

(Q12I)

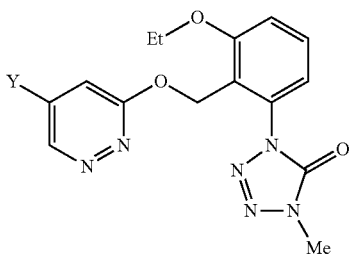

(Q12J)

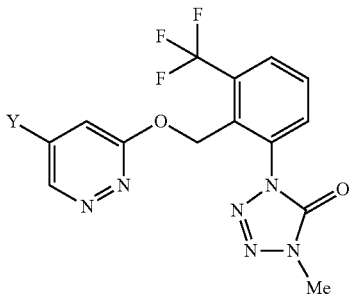

-continued (Q12K)

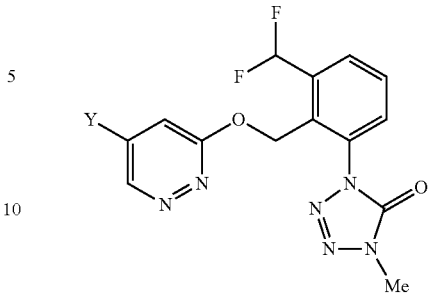

wherein Me represents methyl, Et represents ethyl, and Y represents a substituent corresponding to each of substituent numbers 1 to 558 shown below.

For example, Q1A-001 represents a compound represented by formula (Q1A) in which Y is a substituent 001, and is represented by the following formula:

(Q1A-001)

[substituent number; Y], [001; phenyl group], [002; 2-fluorophenyl group], [003; 3-fluorophenyl group], [004; 4-fluorophenyl group], [005; 2,3-difluorophenyl group], [006; 2,4-difluorophenyl group], [007; 2,5-difluorophenyl group], [008; 2,6-difluorophenyl group], [009; 3,4-difluorophenyl group], [010; 3,5-difluorophenyl group], [011; 2,3,4-trifluorophenyl group], [012; 2,3,5-trifluorophenyl group], [013; 2,3,6-trifluorophenyl group], [014; 2,4,5-trifluorophenyl group], [015; 2,4,6-trifluorophenyl group], [016; 3,4,5-trifluorophenyl group], [017; 2,3,4,6-tetrafluorophenyl group], [018; 2,3,5,6-tetrafluorophenyl group], [019; 2,3,4,5,6-pentafluorophenyl group], [020; 2-chlorophenyl group], [021; 3-chlorophenyl group], [022; 4-chlorophenyl group], [023; 2,3-dichlorophenyl group], [024; 2,4-dichlorophenyl group], [025; 2,5-dichlorophenyl group], [026; 2,6-dichlorophenyl group], [027; 3,4-dichlorophenyl group], [028; 3,5-dichlorophenyl group], [029; 2,3,4-trichlorophenyl group]

[substituent number; Y], [030; 2,3,5-trichlorophenyl group], [031; 2,3,6-trichlorophenyl group], [032; 2,4,5-trichlorophenyl group], [033; 2,4,6-trichlorophenyl group], [034; 3,4,5-trichlorophenyl group], [035; 2,3,4,6-tetrachlorophenyl group], [036; 2,3,5,6-tetrachlorophenyl group], [037; 2,3,4,5,6-pentachlorophenyl group], [038; 2-bromophenyl group], [039; 3-bromophenyl group], [040; 4-bromophenyl group], [041; 2,4-dibromophenyl group], [042; 2,5-dibromophenyl group], [043; 2,6-dibromophenyl group], [044; 2,4,6-tribromophenyl group], [045; 2,3,4,5,6-pentabromophenyl group], [046; 2-iodophenyl group], [047; 3-iodophenyl group], [048; 4-iodophenyl group], [049; 2,4-diiodophenyl group], [050; 2-chloro-3-fluorophenyl group], [051; 2-chloro-4-fluorophenyl group], [052; 2-chloro-5-fluorophenyl group], [053; 2-chloro-6-fluorophenyl group], [054; 2-chloro-3-bromophenyl group], [055; 2-chloro-4-bromophenyl group], [056; 2-chloro-5-bromophenyl group], [057; 2-chloro-6-bromophenyl group], [058; 2-bromo-3-chlorophenyl group]

[substituent number; Y], [059; 2-bromo-4-chlorophenyl group], [060; 2-bromo-5-chlorophenyl group], [061; 2-bromo-3-fluorophenyl group], [062; 2-bromo-4-fluorophenyl group], [063; 2-bromo-5-fluorophenyl group], [064; 2-bromo-6-fluorophenyl group], [065; 2-fluoro-3-chlorophenyl group], [066; 2-fluoro-4-chlorophenyl group], [067; 2-fluoro-5-chlorophenyl group], [068; 2-fluoro-4-bromophenyl group], [069; 3-chloro-4-fluorophenyl group], [070; 3-chloro-5-fluorophenyl group], [071; 3-chloro-4-bromophenyl group], [072; 3-chloro-5-bromophenyl group], [073; 3-fluoro-4-chlorophenyl group], [074; 3-fluoro-4-bromophenyl group], [075; 3-bromo-4-chlorophenyl group], [076; 3-bromo-4-fluorophenyl group], [077; 2,6-dichloro-4-bromophenyl group], [078; 2,3-difluoro-4-chlorophenyl group], [079; 2,6-difluoro-4-chlorophenyl group], [080; 2,5-difluoro-4-chlorophenyl group], [081; 3,5-difluoro-4-chlorophenyl group], [082; 2,3,5-trifluoro-4-chlorophenyl group], [083; 2,3,6-trifluoro-4-chlorophenyl group], [084; 2,3,5,6-tetrafluoro-4-chlorophenyl group], [085; 2,3-difluoro-4-bromophenyl group], [086; 2,6-difluoro-4-bromophenyl group], [087; 2,5-difluoro-4-bromophenyl group]

[substituent number; Y], [088; 3,5-difluoro-4-bromophenyl group], [089; 2,3,5-trifluoro-4-bromophenyl group], [090; 2,3,6-trifluoro-4-bromophenyl group], [091; 2,3,5,6-tetrafluoro-4-bromophenyl group], [092; 2-fluoro-4-iodophenyl group], [093; 3-fluoro-4-iodophenyl group], [094; 2,3-difluoro-4-iodophenyl group], [095; 2,6-difluoro-4-iodophenyl group], [096; 2,5-difluoro-4-iodophenyl group], [097; 3,5-difluoro-4-iodophenyl group], [098; 2,3,5-trifluoro-4-iodophenyl group], [099; 2,3,6-trifluoro-4-iodophenyl group], [100; 2,3,5,6-tetrafluoro-4-iodophenyl group], [101; 2-methylphenyl group], [102; 3-methylphenyl group], [103; 4-methylphenyl group], [104; 2,3-dimethylphenyl group], [105; 2,4-dimethylphenyl group], [106; 2,5-dimethylphenyl group], [107; 2,6-dimethylphenyl group], [108; 3,4-dimethylphenyl group], [109; 3,5-dimethylphenyl group], [110; 2,3,5-trimethylphenyl group], [111; 2,3,4-trimethylphenyl group], [112; 2,3,6-trimethylphenyl group], [113; 2,4,5-trimethylphenyl group], [114; 2,4,6-trimethylphenyl group], [115; 3,4,5-trimethylphenyl group], [116; 2,3,4,6-tetramethylphenyl group]

[substituent number; Y], [117; 2,3,5,6-tetramethylphenyl group], [118; 2,3,4,5,6-pentamethylphenyl group], [119; 2-ethylphenyl group], [120; 3-ethylphenyl group], [121; 4-ethylphenyl group], [122; 2,4-diethylphenyl group], [123; 2,6-diethylphenyl group], [124; 3,5-diethylphenyl group], [125; 2,4,6-triethylphenyl group], [126; 2-n-propylphenyl group], [127; 3-n-propylphenyl group], [128; 4-n-propylphenyl group], [129; 2-isopropylphenyl group], [130; 3-isopropylphenyl group], [131; 4-isopropylphenyl group], [132; 2,4-diisopropylphenyl group], [133; 2,6-diisopropylphenyl group], [134; 3,5-diisopropylphenyl group], [135; 2-s-butylphenyl group], [136; 3-s-butylphenyl group], [137; 4-s-butylphenyl group], [138; 2-t-butylphenyl group], [139; 3-t-butylphenyl group], [140; 4-t-butylphenyl group], [141; 4-n-butylphenyl group], [142; 4-n-nonylphenyl group], [143; 2-methyl-4-t-butylphenyl group], [144; 2-methyl-6-t-butylphenyl group], [145; 2-methyl-4-isopropylphenyl group]

[substituent number; Y], [146; 2-methyl-5-isopropylphenyl group], [147; 3-methyl-4-isopropylphenyl group], [148; 2-cyclopropylphenyl group], [149; 3-cyclopropylphenyl group], [150; 4-cyclopropylphenyl group], [151; 4-cyclobutylphenyl group], [152; 4-cyclopentylphenyl group], [153; 4-hydroxylphenyl group], [154; 2-methoxyphenyl group], [155; 3-methoxyphenyl group], [156; 4-methoxyphenyl group], [157; 2-ethoxyphenyl group], [158; 3-ethoxyphenyl group], [159; 4-ethoxyphenyl group], [160; 2-n-propyloxyphenyl group], [161; 3-n-propyloxyphenyl group], [162; 4-n-propyloxyphenyl group], [163; 2-isopropyloxyphenyl group], [164; 3-isopropyloxyphenyl group], [165; 4-isopropyloxyphenyl group], [166; 2-n-hexyloxyphenyl group], [167; 3-n-hexyloxyphenyl group], [168; 4-n-hexyloxyphenyl group], [169; 2-benzyloxyphenyl group], [170; 3-benzyloxyphenyl group], [171; 4-benzyloxyphenyl group], [172; 2,3-dimethoxyphenyl group], [173; 2,4-dimethoxyphenyl group], [174; 2,5-dimethoxyphenyl group]

[substituent number; Y], [175; 2,6-dimethoxyphenyl group], [176; 3,4-dimethoxyphenyl group], [177; 3,5-dimethoxyphenyl group], [178; 2-t-butoxyphenyl group], [179; 3-t-butoxyphenyl group], [180; 4-t-butoxyphenyl group], [181; 2-trifluoromethoxyphenyl group], [182; 3-trifluoromethoxyphenyl group], [183; 4-trifluoromethoxyphenyl group], [184; 2-pentafluoroethoxyphenyl group], [185; 3-pentafluoroethoxyphenyl group], [186; 4-pentafluoroethoxyphenyl group], [187; 2-phenoxyphenyl group], [188; 3-phenoxyphenyl group], [189; 4-phenoxyphenyl group], [190; 4-(2'-fluorophenoxy)phenyl group], [191; 4-(3'-chlorophenoxy)phenyl group], [192; 4-(4'-chlorophenoxy)phenyl group], [193; 2,3,6-trimethyl-4-fluorophenyl group], [194; 2,3,6-trimethyl-4-chlorophenyl group], [195; 2,3,6-trimethyl-4-bromophenyl group], [196; 2,4-dimethyl-6-fluorophenyl group], [197; 2,4-dimethyl-6-chlorophenyl group], [198; 2,4-dimethyl-6-bromophenyl group], [199; 2-isopropyl-4-chloro-5-methylphenyl group], [200; 2-methyl-5-isopropyl-4-chlorophenyl group], [201; 3-fluoro-2-methoxyphenyl group], [202; 4-fluoro-2-methoxyphenyl group], [203; 5-fluoro-2-methoxyphenyl group]

[substituent number; Y], [204; 6-fluoro-2-methoxyphenyl group], [205; 2-fluoro-3-methoxyphenyl group], [206; 4-fluoro-3-methoxyphenyl group], [207; 5-fluoro-3-methoxyphenyl group], [208; 6-fluoro-3-methoxyphenyl group], [209; 2-fluoro-4-methoxyphenyl group], [210; 3-fluoro-4-methoxyphenyl group], [211; 3,4-difluoro-2-methoxyphenyl group], [212; 3,5-difluoro-2-methoxyphenyl group], [213; 3,6-difluoro-2-methoxyphenyl group], [214; 4,5-difluoro-2-methoxyphenyl group], [215; 4,6-difluoro-2-methoxyphenyl group], [216; 5,6-difluoro-2-methoxyphenyl group], [217; 2,4-difluoro-3-methoxyphenyl group], [218; 2,5-difluoro-3-methoxyphenyl group], [219; 2,6-difluoro-3-methoxyphenyl group], [220; 4,5-difluoro-3-methoxyphenyl group], [221; 4,6-difluoro-3-methoxyphenyl group], [222; 5,6-difluoro-3-methoxyphenyl group], [223; 2,3-difluoro-4-methoxyphenyl group], [224; 2,5-difluoro-4-methoxyphenyl group], [225; 2,6-difluoro-4-methoxyphenyl group], [226; 3,5-difluoro-4-methoxyphenyl group], [227; 3,6-difluoro-4-methoxyphenyl group], [228; 2,3,5-trifluoro-4-methoxyphenyl group], [229; 2,3,5,6-tetrafluoro-4-methoxyphenyl group], [230; 3-chloro-2-methoxyphenyl group], [231; 4-chloro-2-methoxyphenyl group], [232; 5-chloro-2-methoxyphenyl group]

[substituent number; Y], [233; 6-chloro-2-methoxyphenyl group], [234; 2-chloro-3-methoxyphenyl group], [235; 4-chloro-3-methoxyphenyl group], [236; 5-chloro-3-methoxyphenyl group], [237; 6-chloro-3-methoxyphenyl group], [238; 2-chloro-4-methoxyphenyl group], [239; 3-chloro-4-methoxyphenyl group], [240; 3,4-dichloro-2-methoxyphenyl group], [241; 3,5-dichloro-2-methoxyphenyl group], [242; 3,6-dichloro-2-methoxyphenyl group],

[243; 4,5-dichloro-2-methoxyphenyl group], [244; 4,6-dichloro-2-methoxyphenyl group], [245; 5,6-dichloro-2-methoxyphenyl group], [246; 2,4-dichloro-3-methoxyphenyl group], [247; 2,5-dichloro-3-methoxyphenyl group], [248; 2,6-dichloro-3-methoxyphenyl group], [249; 4,5-dichloro-3-methoxyphenyl group], [250; 4,6-dichloro-3-methoxyphenyl group], [251; 5,6-dichloro-3-methoxyphenyl group], [252; 2,3-dichloro-4-methoxyphenyl group], [253; 2,5-dichloro-4-methoxyphenyl group], [254; 2,6-dichloro-4-methoxyphenyl group], [255; 3,5-dichloro-4-methoxyphenyl group], [256; 3,6-dichloro-4-methoxyphenyl group], [257; 3-fluoro-2-trifluoromethoxyphenyl group], [258; 4-fluoro-2-trifluoromethoxyphenyl group], [259; 5-fluoro-2-trifluoromethoxyphenyl group], [260; 6-fluoro-2-trifluoromethoxyphenyl group], [261; 2-fluoro-3-trifluoromethoxyphenyl group]

[substituent number; Y], [262; 4-fluoro-3-trifluoromethoxyphenyl group], [263; 5-fluoro-3-trifluoromethoxyphenyl group], [264; 6-fluoro-3-trifluoromethoxyphenyl group], [265; 2-fluoro-4-trifluoromethoxyphenyl group], [266; 3-fluoro-4-trifluoromethoxyphenyl group], [267; 3,4-difluoro-2-trifluoromethoxyphenyl group], [268; 3,5-difluoro-2-trifluoromethoxyphenyl group], [269; 3,6-difluoro-2-trifluoromethoxyphenyl group], [270; 4,5-difluoro-2-trifluoromethoxyphenyl group], [271; 4,6-difluoro-2-trifluoromethoxyphenyl group], [272; 5,6-difluoro-2-trifluoromethoxyphenyl group], [273; 2,4-difluoro-3-trifluoromethoxyphenyl group], [274; 2,5-difluoro-3-trifluoromethoxyphenyl group], [275; 2,6-difluoro-3-trifluoromethoxyphenyl group], [276; 4,5-difluoro-3-trifluoromethoxyphenyl group], [277; 4,6-difluoro-3-trifluoromethoxyphenyl group], [278; 5,6-difluoro-3-trifluoromethoxyphenyl group], [279; 2,3-difluoro-4-trifluoromethoxyphenyl group], [280; 2,5-difluoro-4-trifluoromethoxyphenyl group], [281; 2,6-difluoro-4-trifluoromethoxyphenyl group], [282; 3,5-difluoro-4-trifluoromethoxyphenyl group], [283; 3,6-difluoro-4-trifluoromethoxyphenyl group], [284; 2,3,5-trifluoro-4-trifluoromethoxyphenyl group], [285; 2,3,5,6-tetrafluoro-4-trifluoromethoxyphenyl group], [286; 3-chloro-2-trifluoromethoxyphenyl group], [287; 4-chloro-2-trifluoromethoxyphenyl group], [288; 5-chloro-2-trifluoromethoxyphenyl group], [289; 6-chloro-2-trifluoromethoxyphenyl group], [290; 2-chloro-3-trifluoromethoxyphenyl group]

[substituent number; Y], [291; 4-chloro-3-trifluoromethoxyphenyl group], [292; 5-chloro-3-trifluoromethoxyphenyl group], [293; 6-chloro-3-trifluoromethoxyphenyl group], [294; 2-chloro-4-trifluoromethoxyphenyl group], [295; 3-chloro-4-trifluoromethoxyphenyl group], [296; 3,4-dichloro-2-trifluoromethoxyphenyl group], [297; 3,5-dichloro-2-trifluoromethoxyphenyl group], [298; 3,6-dichloro-2-trifluoromethoxyphenyl group], [299; 4,5-dichloro-2-trifluoromethoxyphenyl group], [300; 4,6-dichloro-2-trifluoromethoxyphenyl group], [301; 5,6-dichloro-2-trifluoromethoxyphenyl group], [302; 2,4-dichloro-3-trifluoromethoxyphenyl group], [303; 2,5-dichloro-3-trifluoromethoxyphenyl group], [304; 2,6-dichloro-3-trifluoromethoxyphenyl group], [305; 4,5-dichloro-3-trifluoromethoxyphenyl group], [306; 4,6-dichloro-3-trifluoromethoxyphenyl group], [307; 5,6-dichloro-3-trifluoromethoxyphenyl group], [308; 2,3-dichloro-4-trifluoromethoxyphenyl group], [309; 2,5-dichloro-4-trifluoromethoxyphenyl group], [310; 2,6-dichloro-4-trifluoromethoxyphenyl group], [311; 3,5-dichloro-4-trifluoromethoxyphenyl group], [312; 3,6-dichloro-4-trifluoromethoxyphenyl group], [313; 2-carbamoylphenyl group], [314; 3-carbamoylphenyl group], [315; 4-carbamoylphenyl group], [316; 2-(N-methylaminocarbonyl)phenyl group], [317; 3-(N-methylaminocarbonyl)phenyl group], [318; 4-(N-methylaminocarbonyl)phenyl group], [319; 2-(N,N-dimethylaminocarbonyl)phenyl group]

[substituent number; Y], [320; 3-(N,N-dimethylaminocarbonyl)phenyl group], [321; 4-(N,N-dimethylaminocarbonyl)phenyl group], [322; 2-methoxycarbonylphenyl group], [323; 3-methoxycarbonylphenyl group], [324; 4-methoxycarbonylphenyl group], [325; 4-acetoxyphenyl group], [326; 2-methoxymethylphenyl group], [327; 3-methoxymethylphenyl group], [3], [8; 4-methoxymethylphenyl group], [329; 2-formylphenyl group], [330; 3-formylphenyl group], [331; 4-formylphenyl group], [332; 2-methyl-5-bromophenyl group], [333; 2-methyl-6-bromophenyl group], [334; 2-chloro-3-methylphenyl group], [335; 2-chloro-4-methylphenyl group], [336; 2-chloro-5-methylphenyl group], [337; 2-fluoro-3-methylphenyl group], [338; 2-fluoro-4-methylphenyl group], [339; 2-fluoro-5-methylphenyl group], [340; 2-bromo-3-methylphenyl group], [341; 2-bromo-4-methylphenyl group], [342; 2-bromo-5-methylphenyl group], [343; 3-methyl-4-chlorophenyl group], [344; 3-methyl-5-chlorophenyl group], [345; 3-methyl-4-fluorophenyl group], [346; 3-methyl-5-fluorophenyl group], [347; 3-methyl-4-bromophenyl group], [348; 3-methyl-5-bromophenyl group]

[substituent number; Y], [349; 3-fluoro-4-methylphenyl group], [350; 3-chloro-4-methylphenyl group], [351; 3-bromo-4-methylphenyl group], [352; 2-chloro-4,5-dimethylphenyl group], [353; 2-bromo-4,5-dimethylphenyl group], [354; 2-chloro-3,5-dimethylphenyl group], [355; 2-bromo-3,5-dimethylphenyl group], [356; 2,6-dibromo-4-methylphenyl group], [357; 2,4-dichloro-6-methylphenyl group], [358; 2,4-difluoro-6-methylphenyl group], [359; 2,4-dibromo-6-methylphenyl group], [360; 2,6-dimethyl-4-fluorophenyl group], [361; 2,6-dimethyl-4-chlorophenyl group], [362; 2,6-dimethyl-4-bromophenyl group], [363; 3,5-dimethyl-4-fluorophenyl group], [364; 3,5-dimethyl-4-chlorophenyl group], [365; 3,5-dimethyl-4-bromophenyl group], [366; 2,3-difluoro-4-methylphenyl group], [367; 2,5-difluoro-4-methylphenyl group], [368; 3,5-difluoro-4-methylphenyl group], [369; 2,3,5-trifluoro-4-methylphenyl group], [370; 2,3,6-trifluoro-4-methylphenyl group], [371; 2,3,5,6-tetrafluoro-4-methylphenyl group], [372; 2-fluoro-4-ethylphenyl group], [373; 3-fluoro-4-ethylphenyl group], [374; 2,3-difluoro-4-ethylphenyl group], [375; 2,6-difluoro-4-ethylphenyl group], [376; 2,5-difluoro-4-ethylphenyl group], [377; 3,5-difluoro-4-ethylphenyl group]

[substituent number; Y], [378; 2,3,5-trifluoro-4-ethylphenyl group], [379; 2,3,6-trifluoro-4-ethylphenyl group], [380; 2,3,5,6-tetrafluoro-4-ethylphenyl group], [381; 2-trifluoromethylphenyl group], [382; 3-trifluoromethylphenyl group], [383; 4-trifluoromethylphenyl group], [384; 4-(2,2,2-trifluoro-1-trifluoromethyl-ethyl)phenyl group], [385; 4-(2,2-difluoroethoxy)phenyl group], [386; 4-(2,2,2-trifluoroethoxy)phenyl group], [387; 2-nitrophenyl group 388; 3-nitrophenyl group], [389; 4-nitrophenyl group], [390; 2-cyanophenyl group], [391; 3-cyanophenyl group], [392; 4-cyanophenyl group], [393; 2-methyl-3-chlorophenyl group], [394; 2-methyl-4-chlorophenyl group], [395; 2-methyl-5-chlorophenyl group], [396; 2-methyl-6-chlorophenyl group], [397; 2-methyl-3-fluorophenyl group], [398; 2-methyl-4-fluorophenyl group], [399; 2-methyl-5-fluorophenyl group], [400; 2-methyl-6-fluorophenyl group], [401; 2-methyl-3-bromophenyl group], [402; 2-methyl-4-bromophenyl group], [403; 4-methylthiophenyl group], [404;

4-methylsulfonylphenyl group], [405; 4-methylsulfinylphenyl group], [406; 4-trifluoromethylthiophenyl group]
[substituent number; Y], [407; 4-ethynylphenyl group], [408; 4-(1-propynyl)phenyl group], [409; 4-vinylphenyl group], [410; 4-(2,2-dichlorovinyl)phenyl group], [411; 4-(2,2-difluorovinyl)phenyl group], [412; cyclohexyl group], [413; 2-chlorocyclohexyl group], [414; 3-chlorocyclohexyl group], [415; 4-chlorocyclohexyl group], [416; 4,4-dichlorocyclohexyl group], [417; 2-bromocyclohexyl group], [418; 3-bromocyclohexyl group], [419; 4-bromocyclohexyl group], [420; 4,4-dibromocyclohexyl group], [421; 2-iodocyclohexyl group], [422; 3-iodocyclohexyl group], [423; 4-iodocyclohexyl group], [424; 2-fluorocyclohexyl group], [425; 3-fluorocyclohexyl group], [426; 4-fluorocyclohexyl group], [427; 4,4-difluorocyclohexyl group], [428; 4-methylcyclohexyl group], [429; 4-ethylcyclohexyl group], [430; 4-methoxycyclohexyl group], [431; 4-ethoxycyclohexyl group], [432; 4-trifluoromethoxycyclohexyl group], [433; 1-cyclohexenyl group], [434; 2-cyclohexenyl group], [435; 3-cyclohexenyl group]
[substituent number; Y], [436; 4-fluoro-1-cyclohexenyl group], [437; 4-fluoro-2-cyclohexenyl group], [438; 4-fluoro-3-cyclohexenyl group 439; 2-chloro-1-cyclohexenyl group], [440; 3-chloro-1-cyclohexenyl group], [441; 4-chloro-1-cyclohexenyl group], [442; 5-chloro-1-cyclohexenyl group], [443; 6-chloro-1-cyclohexenyl group], [444; 1-chloro-2-cyclohexenyl group], [445; 2-chloro-2-cyclohexenyl group], [446; 3-chloro-2-cyclohexenyl group], [447; 4-chloro-2-cyclohexenyl group], [448; 5-chloro-2-cyclohexenyl group], [449; 6-chloro-2-cyclohexenyl group], [450; 1-chloro-3-cyclohexenyl group], [451; 2-chloro-3-cyclohexenyl group], [452; 3-chloro-3-cyclohexenyl group], [453; 4-chloro-3-cyclohexenyl group], [454; 5-chloro-3-cyclohexenyl group], [455; 6-chloro-3-cyclohexenyl group], [456; 4-bromo-1-cyclohexenyl group], [457; 4-bromo-2-cyclohexenyl group], [458; 4-bromo-3-cyclohexenyl group], [459; 4-methyl-1-cyclohexenyl group], [460; 4-methyl-2-cyclohexenyl group], [461; 4-methyl-3-cyclohexenyl group], [462; 4-ethyl-1-cyclohexenyl group], [463; 4-ethyl-2-cyclohexenyl group], [464; 4-ethyl-3-cyclohexenyl group]
[substituent number; Y], [465; 4-methoxy-1-cyclohexenyl group], [466; 4-methoxy-2-cyclohexenyl group], [467; 4-trifluoromethoxy-1-cyclohexenyl group], [468; 4-trifluoromethoxy-2-cyclohexenyl group], [469; morpholino group], [470; thiomorpholino group], [471; piperidino group], [472; 4-methoxypiperidino group], [473; piperazinyl group], [474; N-methylpiperazinyl group], [475; pyrrolyl group], [476; imidazolyl group], [477; pyrazolyl group], [478; 4-methyl-pyrazol-1-yl group], [479; 4,5-dimethyl-pyrazol-1-yl group], [480; 3-methyl-pyrazol-1-yl group], [481; 3,4-dimethyl-pyrazol-1-yl group], [482; 4-methoxy-3,5-dimethyl-pyrazol-1-yl group], [483; 1-methyl-1H-pyrazol-3-yl group], [484; 1,4,5-trimethyl-1H-pyrazol-3-yl group], [485; 1,4-dimethyl-5-methoxy-1H-pyrazol-3-yl group], [486; 2-pyridyl group], [487; 3-pyridyl group], [488; 4-pyridyl group], [489; 5-methoxy-2-pyridyl group], [490; 5-trifluoromethoxy-2-pyridyl group], [491; 5-fluoro-2-pyridyl group], [492; 5-chloro-2-pyridyl group], [493; 6-methoxy-3-pyridyl group]
[substituent number; Y], [494; 6-trifluoromethoxy-3-pyridyl group], [495; 6-fluoro-3-pyridyl group], [496; 6-chloro-3-pyridyl group], [497; 5-methoxy-2-pyrazinyl group], [498; 5-trifluoromethoxy-2-pyrazinyl group], [499; 5-fluoro-2-pyrazinyl group], [500; 5-chloro-2-pyrazinyl group], [501; 5-methoxy-2-pyrimidinyl group], [502; 5-trifluoromethoxy-2-pyrimidinyl group], [503; 5-fluoro-2-pyrimidinyl group], [504; 5-chloro-2-pyrimidinyl group], [505; 6-methoxy-3-pyridazinyl group], [506; 6-trifluoromethoxy-3-pyridazinyl group], [507; 6-fluoro-3-pyridazinyl group], [508; 6-chloro-3-pyridazinyl group], [509; 1-naphthyl group], [510; 2-naphthyl group], [511; 2-quinolyl group], [512; 3-quinolyl group], [513; 4-quinolyl group], [514; 5-quinolyl group], [515; 6-quinolyl group], [516; 7-quinolyl group], [517; 8-quinolyl group], [518; 3-isoquinolyl group], [519; 6-isoquinolyl group], [520; 7-isoquinolyl group], [521; 3,4-methylenedioxyphenyl group]
[substituent number; Y], [522; 2-ethoxy-4-methoxyphenyl group], [523; 2-isopropyloxy-4-methoxyphenyl group], [524; 4-ethoxy-2-methoxyphenyl group], [525; 4-isopropyloxy-2-methoxyphenyl group], [526; 4-fluoro-2-isopropyloxyphenyl group], [527; 4-chloro-2-isopropyloxyphenyl group], [528; 4-bromo-2-isopropyloxyphenyl group], [529; 4-fluoro-2-ethoxyphenyl group], [530; 4-chloro-2-ethoxyphenyl group], [531; 4-bromo-2-ethoxyphenyl group], [532; 4-cyano-2-methoxyphenyl group], [533; 4-cyano-2-ethoxyphenyl group], [534; 4-cyano-2-isopropyloxyphenyl group], [535; 2-methoxy-3-pyridyl group], [536; 6-chloro-2-methoxy-3-pyridyl group], [537; 6-fluoro-2-methoxy-3-pyridyl group], [538; 6-bromo-2-methoxy-3-pyridyl group], [539; 6-ethoxy-2-methoxy-3-pyridyl group], [540; 2,6-dimethoxy-3-pyridyl group], [541; 6-trifluoromethyl-2-methoxy-3-pyridyl group], [542; 6-cyano-2-methoxy-3-pyridyl group]
[543; 2-ethoxy-3-pyridyl group], [544; 6-chloro-2-ethoxy-3-pyridyl group], [545; 6-fluoro-2-ethoxy-3-pyridyl group], [546; 6-bromo-2-ethoxy-3-pyridyl group], [547; 2-ethoxy-6-methoxy-3-pyridyl group], [548; 2,6-diethoxy-3-pyridyl group], [549; 6-trifluoromethyl-2-ethoxy-3-pyridyl group], [550; 6-cyano-2-ethoxy-3-pyridyl group], [551; 2-isopropyloxy-3-pyridyl group], [552; 6-chloro-2-isopropyloxy-3-pyridyl group], [553; 6-fluoro-2-isopropyloxy-3-pyridyl group], [554; 6-bromo-2-isopropyloxy-3-pyridyl group], [555; 2-isopropyloxy-6-methoxy-3-pyridyl group], [556; 2,6-diisopropyloxy-3-pyridyl group], [557; 6-trifluoromethyl-2-isopropyloxy-3-pyridyl group], [558; 6-cyano-2-isopropyloxy-3-pyridyl group]

In accordance with the above process, it is possible to obtain compounds THF-Q1-001 to THCFF-Q12-558.

The compounds THF-Q1-001 to THCFF-Q12-558 are compounds represented by the following formulas:

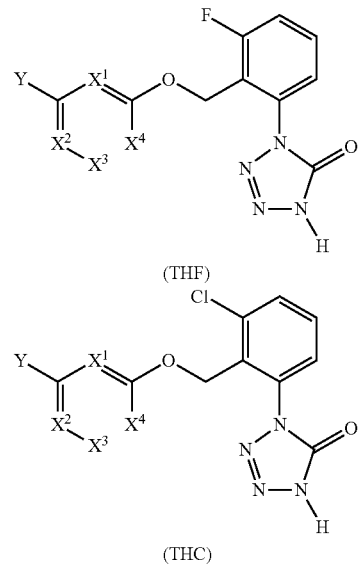

(THF)

(THC)

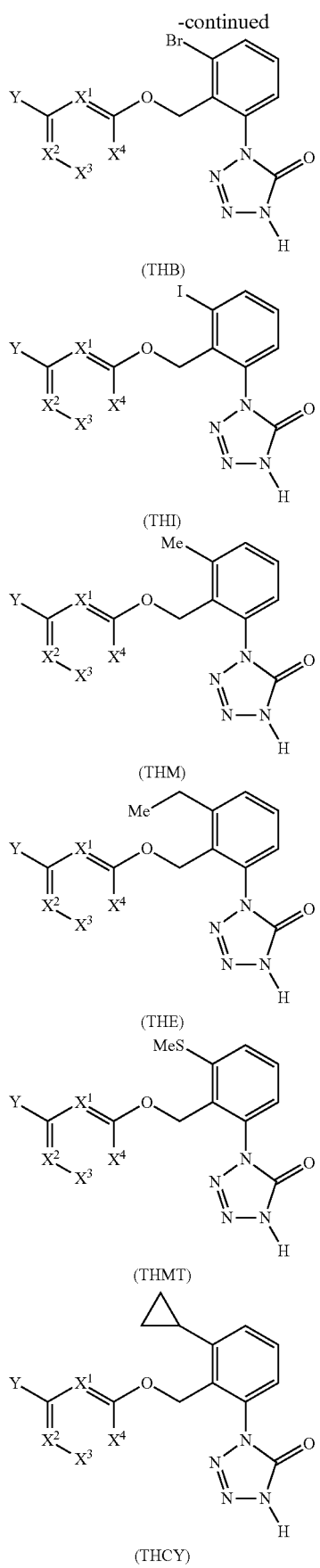

(THB)
(THI)
(THM)
(THE)
(THMT)
(THCY)

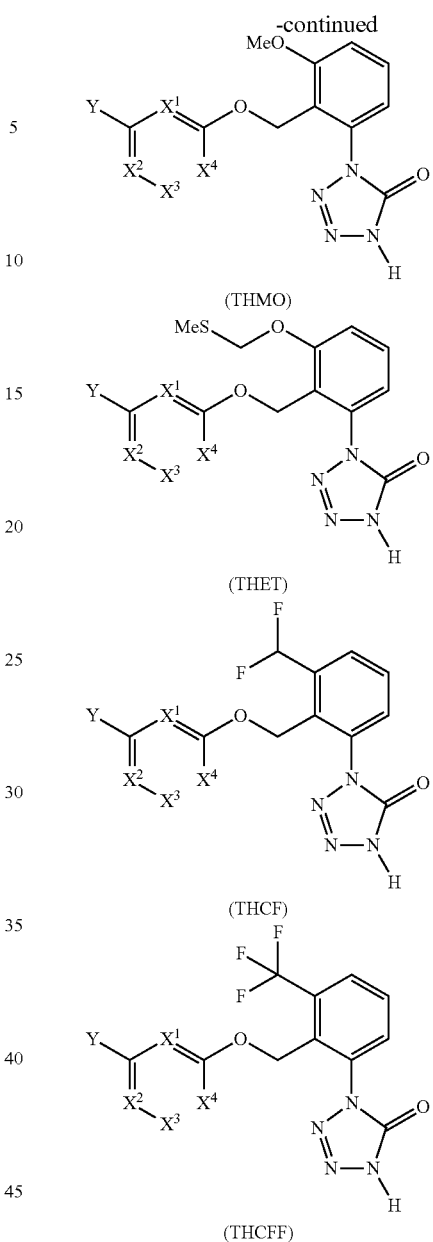

(THMO)
(THET)
(THCF)
(THCFF)

wherein $X^1$, $X^2$, $X^3$, and $X^4$ represent any one of combinations Q1 to Q12 shown in Table 42, and Y represents a substituent corresponding to each of substituent numbers 1 to 558.

TABLE 42

| Combination | $X^1$, $X^2$, $X^3$, $X^4$ |
|---|---|
| Q1 | $X^1$ = N, $X^2$ = CH, $X^3$ = CH, $X^4$ = CH |
| Q2 | $X^1$ = CH, $X^2$ = CH, $X^3$ = CH, $X^4$ = CH |
| Q3 | $X^1$ = N, $X^2$ = CH, $X^3$ = N, $X^4$ = CH |
| Q4 | $X^1$ = N, $X^2$ = N, $X^3$ = CH, $X^4$ = CH |
| Q5 | $X^1$ = N, $X^2$ = CH, $X^3$ = CH, $X^4$ = N |
| Q6 | $X^1$ = N, $X^2$ = N, $X^3$ = CH, $X^4$ = N |
| Q7 | $X^1$ = CH, $X^2$ = N, $X^3$ = CH, $X^4$ = N |
| Q8 | $X^1$ = CH, $X^2$ = N, $X^3$ = CH, $X^4$ = CH |
| Q9 | $X^1$ = CH, $X^2$ = CH, $X^3$ = CH, $X^4$ = N |
| Q10 | $X^1$ = CH, $X^2$ = CH, $X^3$ = N, $X^4$ = CH |
| Q11 | $X^1$ = CH, $X^2$ = N, $X^3$ = N, $X^4$ = CH |
| Q12 | $X^1$ = CH, $X^2$ = CH, $X^3$ = N, $X^4$ = N |

A tetrazolinone compound in which $X^1$, $X^2$, $X^3$, and $X^4$ are Q1 shown in Table 42, and the substituent Y is any one of substituent numbers 1 to 558 in a compound represented by formula (THF) (referred to as the compound THF).

A tetrazolinone compound in which $X^1$, $X^2$, $X^3$, and $X^4$ are Q2 shown in Table 42, and the substituent Y is any one of substituent numbers 1 to 558 in the compound THF.

A tetrazolinone compound in which $X^1$, $X^2$, $X^3$, and $X^4$ are Q3 shown in Table 42, and the substituent Y is any one of substituent numbers 1 to 558 in the compound THF.

A tetrazolinone compound in which $X^1$, $X^2$, $X^3$, and $X^4$ are Q4 shown in Table 42, and the substituent Y is any one of substituent numbers 1 to 558 in the compound THF.

A tetrazolinone compound in which $X^1$, $X^2$, $X^3$, and $X^4$ are Q5 shown in Table 42, and the substituent Y is any one of substituent numbers 1 to 558 in the compound THF.

A tetrazolinone compound in which $X^1$, $X^2$, $X^3$, and $X^4$ are Q6 shown in Table 42, and the substituent Y is any one of substituent numbers 1 to 558 in the compound THF.

A tetrazolinone compound in which $X^1$, $X^2$, $X^3$, and $X^4$ are Q7 shown in Table 42, and the substituent Y is any one of substituent numbers 1 to 558 in the compound THF.

A tetrazolinone compound in which $X^1$, $X^2$, $X^3$, and $X^4$ are Q8 shown in Table 42, and the substituent Y is any one of substituent numbers 1 to 558 in the compound THF.

A tetrazolinone compound in which $X^1$, $X^2$, $X^3$, and $X^4$ are Q9 shown in Table 42, and the substituent Y is any one of substituent numbers 1 to 558 in the compound THF.

A tetrazolinone compound in which $X^1$, $X^2$, $X^3$, and $X^4$ are Q10 shown in Table 42, and the substituent Y is any one of substituent numbers 1 to 558 in the compound THF.

A tetrazolinone compound in which $X^1$, $X^2$, $X^3$, and $X^4$ are Q11 shown in Table 42, and the substituent Y is any one of substituent numbers 1 to 558 in the compound THF.

A tetrazolinone compound in which $X^1$, $X^2$, $X^3$, and $X^4$ are Q12 shown in Table 42, and the substituent Y is any one of substituent numbers 1 to 558 in the compound THF.

A tetrazolinone compound in which $X^1$, $X^2$, $X^3$, and $X^4$ are Q1 shown in Table 42, and the substituent Y is any one of substituent numbers 1 to 558 in a compound represented by formula (THC) (referred to as the compound THC).

A tetrazolinone compound in which $X^1$, $X^2$, $X^3$, and $X^4$ are Q2 shown in Table 42, and the substituent Y is any one of substituent numbers 1 to 558 in the compound THC.

A tetrazolinone compound in which $X^1$, $X^2$, $X^3$, and $X^4$ are Q3 shown in Table 42, and the substituent Y is any one of substituent numbers 1 to 558 in the compound THC.

A tetrazolinone compound in which $X^1$, $X^2$, $X^3$, and $X^4$ are Q4 shown in Table 42, and the substituent Y is any one of substituent numbers 1 to 558 in the compound THC.

A tetrazolinone compound in which $X^1$, $X^2$, $X^3$, and $X^4$ are Q5 shown in Table 42, and the substituent Y is any one of substituent numbers 1 to 558 in the compound THC.

A tetrazolinone compound in which $X^1$, $X^2$, $X^3$, and $X^4$ are Q6 shown in Table 42, and the substituent Y is any one of substituent numbers 1 to 558 in the compound THC.

A tetrazolinone compound in which $X^1$, $X^2$, $X^3$, and $X^4$ are Q7 shown in Table 42, and the substituent Y is any one of substituent numbers 1 to 558 in the compound THC.

A tetrazolinone compound in which $X^1$, $X^2$, $X^3$, and $X^4$ are Q8 shown in Table 42, and the substituent Y is any one of substituent numbers 1 to 558 in the compound THC.

A tetrazolinone compound in which $X^1$, $X^2$, $X^3$, and $X^4$ are Q9 shown in Table 42, and the substituent Y is any one of substituent numbers 1 to 558 in the compound THC.

A tetrazolinone compound in which $X^1$, $X^2$, $X^3$, and $X^4$ are Q10 shown in Table 42, and the substituent Y is any one of substituent numbers 1 to 558 in the compound THC.

A tetrazolinone compound in which $X^1$, $X^2$, $X^3$, and $X^4$ are Q11 shown in Table 42, and the substituent Y is any one of substituent numbers 1 to 558 in the compound THC.

A tetrazolinone compound in which $X^1$, $X^2$, $X^3$, and $X^4$ are Q12 shown in Table 42, and the substituent Y is any one of substituent numbers 1 to 558 in the compound THC.

A tetrazolinone compound in which $X^1$, $X^2$, $X^3$, and $X^4$ are Q1 shown in Table 42, and the substituent Y is any one of substituent numbers 1 to 558 in a compound represented by formula (THB) (referred to as the compound THB).

A tetrazolinone compound in which $X^1$, $X^2$, $X^3$, and $X^4$ are Q2 shown in Table 42, and the substituent Y is any one of substituent numbers 1 to 558 in the compound THB.

A tetrazolinone compound in which $X^1$, $X^2$, $X^3$, and $X^4$ are Q3 shown in Table 42, and the substituent Y is any one of substituent numbers 1 to 558 in the compound THB.

A tetrazolinone compound in which $X^1$, $X^2$, $X^3$, and $X^4$ are Q4 shown in Table 42, and the substituent Y is any one of substituent numbers 1 to 558 in the compound THB.

A tetrazolinone compound in which $X^1$, $X^2$, $X^3$, and $X^4$ are Q5 shown in Table 42, and the substituent Y is any one of substituent numbers 1 to 558 in the compound THB.

A tetrazolinone compound in which $X^1$, $X^2$, $X^3$, and $X^4$ are Q6 shown in Table 42, and the substituent Y is any one of substituent numbers 1 to 558 in the compound THB.

A tetrazolinone compound in which $X^1$, $X^2$, $X^3$, and $X^4$ are Q7 shown in Table 42, and the substituent Y is any one of substituent numbers 1 to 558 in the compound THB.

A tetrazolinone compound in which $X^1$, $X^2$, $X^3$, and $X^4$ are Q8 shown in Table 42, and the substituent Y is any one of substituent numbers 1 to 558 in the compound THB.

A tetrazolinone compound in which $X^1$, $X^2$, $X^3$, and $X^4$ are Q9 shown in Table 42, and the substituent Y is any one of substituent numbers 1 to 558 in the compound THB.

A tetrazolinone compound in which $X^1$, $X^2$, $X^3$, and $X^4$ are Q10 shown in Table 42, and the substituent Y is any one of substituent numbers 1 to 558 in the compound THB.

A tetrazolinone compound in which $X^1$, $X^2$, $X^3$, and $X^4$ are Q11 shown in Table 42, and the substituent Y is any one of substituent numbers 1 to 558 in the compound THB.

A tetrazolinone compound in which $X^1$, $X^2$, $X^3$, and $X^4$ are Q12 shown in Table 42, and the substituent Y is any one of substituent numbers 1 to 558 in the compound THB.

A tetrazolinone compound in which $X^1$, $X^2$, $X^3$, and $X^4$ are Q1 shown in Table 42, and the substituent Y is any one of substituent numbers 1 to 558 in a compound represented by formula (THI) (referred to as the compound THI).

A tetrazolinone compound in which $X^1$, $X^2$, $X^3$, and $X^4$ are Q2 shown in Table 42, and the substituent Y is any one of substituent numbers 1 to 558 in the compound THI.

A tetrazolinone compound in which $X^1$, $X^2$, $X^3$, and $X^4$ are Q3 shown in Table 42, and the substituent Y is any one of substituent numbers 1 to 558 in the compound THI.

A tetrazolinone compound in which $X^1$, $X^2$, $X^3$, and $X^4$ are Q4 shown in Table 42, and the substituent Y is any one of substituent numbers 1 to 558 in the compound THI.

A tetrazolinone compound in which $X^1$, $X^2$, $X^3$, and $X^4$ are Q5 shown in Table 42, and the substituent Y is any one of substituent numbers 1 to 558 in the compound THI.

A tetrazolinone compound in which $X^1$, $X^2$, $X^3$, and $X^4$ are Q6 shown in Table 42, and the substituent Y is any one of substituent numbers 1 to 558 in the compound THI.

A tetrazolinone compound in which $X^1$, $X^2$, $X^3$, and $X^4$ are Q7 shown in Table 42, and the substituent Y is any one of substituent numbers 1 to 558 in the compound THI.

A tetrazolinone compound in which $X^1$, $X^2$, $X^3$, and $X^4$ are Q8 shown in Table 42, and the substituent Y is any one of substituent numbers 1 to 558 in the compound THI.

A tetrazolinone compound in which $X^1$, $X^2$, $X^3$, and $X^4$ are Q9 shown in Table 42, and the substituent Y is any one of substituent numbers 1 to 558 in the compound THI.

A tetrazolinone compound in which $X^1$, $X^2$, $X^3$, and $X^4$ are Q10 shown in Table 42, and the substituent Y is any one of substituent numbers 1 to 558 in the compound THI.

A tetrazolinone compound in which $X^1$, $X^2$, $X^3$, and $X^4$ are Q11 shown in Table 42, and the substituent Y is any one of substituent numbers 1 to 558 in the compound THI.

A tetrazolinone compound in which $X^1$, $X^2$, $X^3$, and $X^4$ are Q12 shown in Table 42, and the substituent Y is any one of substituent numbers 1 to 558 in the compound THI.

A tetrazolinone compound in which $X^1$, $X^2$, $X^3$, and $X^4$ are Q1 shown in Table 42, and the substituent Y is any one of substituent numbers 1 to 558 in a compound represented by formula (THM) (referred to as the compound THM).

A tetrazolinone compound in which $X^1$, $X^2$, $X^3$, and $X^4$ are Q2 shown in Table 42, and the substituent Y is any one of substituent numbers 1 to 558 in the compound THM.

A tetrazolinone compound in which $X^1$, $X^2$, $X^3$, and $X^4$ are Q3 shown in Table 42, and the substituent Y is any one of substituent numbers 1 to 558 in the compound THM.

A tetrazolinone compound in which $X^1$, $X^2$, $X^3$, and $X^4$ are Q4 shown in Table 42, and the substituent Y is any one of substituent numbers 1 to 558 in the compound THM.

A tetrazolinone compound in which $X^1$, $X^2$, $X^3$, and $X^4$ are Q5 shown in Table 42, and the substituent Y is any one of substituent numbers 1 to 558 in the compound THM.

A tetrazolinone compound in which $X^1$, $X^2$, $X^3$, and $X^4$ are Q6 shown in Table 42, and the substituent Y is any one of substituent numbers 1 to 558 in the compound THM.

A tetrazolinone compound in which $X^1$, $X^2$, $X^3$, and $X^4$ are Q7 shown in Table 42, and the substituent Y is any one of substituent numbers 1 to 558 in the compound THM.

A tetrazolinone compound in which $X^1$, $X^2$, $X^3$, and $X^4$ are Q8 shown in Table 42, and the substituent Y is any one of substituent numbers 1 to 558 in the compound THM.

A tetrazolinone compound in which $X^1$, $X^2$, $X^3$, and $X^4$ are Q9 shown in Table 42, and the substituent Y is any one of substituent numbers 1 to 558 in the compound THM.

A tetrazolinone compound in which $X^1$, $X^2$, $X^3$, and $X^4$ are Q10 shown in Table 42, and the substituent Y is any one of substituent numbers 1 to 558 in the compound THM.

A tetrazolinone compound in which $X^1$, $X^2$, $X^3$, and $X^4$ are Q11 shown in Table 42, and the substituent Y is any one of substituent numbers 1 to 558 in the compound THM.

A tetrazolinone compound in which $X^1$, $X^2$, $X^3$, and $X^4$ are Q12 shown in Table 42, and the substituent Y is any one of substituent numbers 1 to 558 in the compound THM.

A tetrazolinone compound in which $X^1$, $X^2$, $X^3$, and $X^4$ are Q1 shown in Table 42, and the substituent Y is any one of substituent numbers 1 to 558 in a compound represented by formula (THE) (referred to as the compound THE).

A tetrazolinone compound in which $X^1$, $X^2$, $X^3$, and $X^4$ are Q2 shown in Table 42, and the substituent Y is any one of substituent numbers 1 to 558 in the compound THE.

A tetrazolinone compound in which $X^1$, $X^2$, $X^3$, and $X^4$ are Q3 shown in Table 42, and the substituent Y is any one of substituent numbers 1 to 558 in the compound THE.

A tetrazolinone compound in which $X^1$, $X^2$, $X^3$, and $X^4$ are Q4 shown in Table 42, and the substituent Y is any one of substituent numbers 1 to 558 in the compound THE.

A tetrazolinone compound in which $X^1$, $X^2$, $X^3$, and $X^4$ are Q5 shown in Table 42, and the substituent Y is any one of substituent numbers 1 to 558 in the compound THE A tetrazolinone compound in which $X^1$, $X^2$, $X^3$, and $X^4$ are Q6 shown in Table 42, and the substituent Y is any one of substituent numbers 1 to 558 in the compound THE.

A tetrazolinone compound in which $X^1$, $X^2$, $X^3$, and $X^4$ are Q7 shown in Table 42, and the substituent Y is any one of substituent numbers 1 to 558 in the compound THE.

A tetrazolinone compound in which $X^1$, $X^2$, $X^3$, and $X^4$ are Q8 shown in Table 42, and the substituent Y is any one of substituent numbers 1 to 558 in the compound THE.

A tetrazolinone compound in which $X^1$, $X^2$, $X^3$, and $X^4$ are Q9 shown in Table 42, and the substituent Y is any one of substituent numbers 1 to 558 in the compound THE.

A tetrazolinone compound in which $X^1$, $X^2$, $X^3$, and $X^4$ are Q10 shown in Table 42, and the substituent Y is any one of substituent numbers 1 to 558 in the compound THE.

A tetrazolinone compound in which $X^1$, $X^2$, $X^3$, and $X^4$ are Q11 shown in Table 42, and the substituent Y is any one of substituent numbers 1 to 558 in the compound THE.

A tetrazolinone compound in which $X^1$, $X^2$, $X^3$, and $X^4$ are Q12 shown in Table 42, and the substituent Y is any one of substituent numbers 1 to 558 in the compound THE.

A tetrazolinone compound in which $X^1$, $X^2$, $X^3$, and $X^4$ are Q1 shown in Table 42, and the substituent Y is any one of substituent numbers 1 to 558 in a compound represented by formula (THMT) (referred to as the compound THMT).

A tetrazolinone compound in which $X^1$, $X^2$, $X^3$, and $X^4$ are Q2 shown in Table 42, and the substituent Y is any one of substituent numbers 1 to 558 in the compound THMT.

A tetrazolinone compound in which $X^1$, $X^2$, $X^3$, and $X^4$ are Q3 shown in Table 42, and the substituent Y is any one of substituent numbers 1 to 558 in the compound THMT.

A tetrazolinone compound in which $X^1$, $X^2$, $X^3$, and $X^4$ are Q4 shown in Table 42, and the substituent Y is any one of substituent numbers 1 to 558 in the compound THMT.

A tetrazolinone compound in which $X^1$, $X^2$, $X^3$, and $X^4$ are Q5 shown in Table 42, and the substituent Y is any one of substituent numbers 1 to 558 in the compound THMT.

A tetrazolinone compound in which $X^1$, $X^2$, $X^3$, and $X^4$ are Q6 shown in Table 42, and the substituent Y is any one of substituent numbers 1 to 558 in the compound THMT.

A tetrazolinone compound in which $X^1$, $X^2$, $X^3$, and $X^4$ are Q7 shown in Table 42, and the substituent Y is any one of substituent numbers 1 to 558 in the compound THMT.

A tetrazolinone compound in which $X^1$, $X^2$, $X^3$, and $X^4$ are Q8 shown in Table 42, and the substituent Y is any one of substituent numbers 1 to 558 in the compound THMT.

A tetrazolinone compound in which $X^1$, $X^2$, $X^3$, and $X^4$ are Q9 shown in Table 42, and the substituent Y is any one of substituent numbers 1 to 558 in the compound THMT.

A tetrazolinone compound in which $X^1$, $X^2$, $X^3$, and $X^4$ are Q10 shown in Table 42, and the substituent Y is any one of substituent numbers 1 to 558 in the compound THMT.

A tetrazolinone compound in which $X^1$, $X^2$, $X^3$, and $X^4$ are Q11 shown in Table 42, and the substituent Y is any one of substituent numbers 1 to 558 in the compound THMT.

A tetrazolinone compound in which $X^1$, $X^2$, $X^3$, and $X^4$ are Q12 shown in Table 42, and the substituent Y is any one of substituent numbers 1 to 558 in the compound THMT.

A tetrazolinone compound in which $X^1$, $X^2$, $X^3$, and $X^4$ are Q1 shown in Table 42, and the substituent Y is any one of substituent numbers 1 to 558 in a compound represented by formula (THCY) (referred to as the compound THCY).

A tetrazolinone compound in which $X^1$, $X^2$, $X^3$, and $X^4$ are Q2 shown in Table 42, and the substituent Y is any one of substituent numbers 1 to 558 in the compound THCY.

A tetrazolinone compound in which $X^1$, $X^2$, $X^3$, and $X^4$ are Q3 shown in Table 42, and the substituent Y is any one of substituent numbers 1 to 558 in the compound THCY.

A tetrazolinone compound in which $X^1$, $X^2$, $X^3$, and $X^4$ are Q4 shown in Table 42, and the substituent Y is any one of substituent numbers 1 to 558 in the compound THCY.

A tetrazolinone compound in which $X^1$, $X^2$, $X^3$, and $X^4$ are Q5 shown in Table 42, and the substituent Y is any one of substituent numbers 1 to 558 in the compound THCY.

A tetrazolinone compound in which $X^1$, $X^2$, $X^3$, and $X^4$ are Q6 shown in Table 42, and the substituent Y is any one of substituent numbers 1 to 558 in the compound THCY.

A tetrazolinone compound in which $X^1$, $X^2$, $X^3$, and $X^4$ are Q7 shown in Table 42, and the substituent Y is any one of substituent numbers 1 to 558 in the compound THCY.

A tetrazolinone compound in which $X^1$, $X^2$, $X^3$, and $X^4$ are Q8 shown in Table 42, and the substituent Y is any one of substituent numbers 1 to 558 in the compound THCY.

A tetrazolinone compound in which $X^1$, $X^2$, $X^3$, and $X^4$ are Q9 shown in Table 42, and the substituent Y is any one of substituent numbers 1 to 558 in the compound THCY.

A tetrazolinone compound in which $X^1$, $X^2$, $X^3$, and $X^4$ are Q10 shown in Table 42, and the substituent Y is any one of substituent numbers 1 to 558 in the compound THCY.

A tetrazolinone compound in which $X^1$, $X^2$, $X^3$, and $X^4$ are Q11 shown in Table 42, and the substituent Y is any one of substituent numbers 1 to 558 in the compound THCY.

A tetrazolinone compound in which $X^1$, $X^2$, $X^3$, and $X^4$ are Q12 shown in Table 42, and the substituent Y is any one of substituent numbers 1 to 558 in the compound THCY.

A tetrazolinone compound in which $X^1$, $X^2$, $X^3$, and $X^4$ are Q1 shown in Table 42, and the substituent Y is any one of substituent numbers 1 to 558 in a compound represented by formula (THMO) (referred to as the compound THMO).

A tetrazolinone compound in which $X^1$, $X^2$, $X^3$, and $X^4$ are Q2 shown in Table 42, and the substituent Y is any one of substituent numbers 1 to 558 in the compound THMO.

A tetrazolinone compound in which $X^1$, $X^2$, $X^3$, and $X^4$ are Q3 shown in Table 42, and the substituent Y is any one of substituent numbers 1 to 558 in the compound THMO.

A tetrazolinone compound in which $X^1$, $X^2$, $X^3$, and $X^4$ are Q4 shown in Table 42, and the substituent Y is any one of substituent numbers 1 to 558 in the compound THMO.

A tetrazolinone compound in which $X^1$, $X^2$, $X^3$, and $X^4$ are Q5 shown in Table 42, and the substituent Y is any one of substituent numbers 1 to 558 in the compound THMO.

A tetrazolinone compound in which $X^1$, $X^2$, $X^3$, and $X^4$ are Q6 shown in Table 42, and the substituent Y is any one of substituent numbers 1 to 558 in the compound THMO.

A tetrazolinone compound in which $X^1$, $X^2$, $X^3$, and $X^4$ are Q7 shown in Table 42, and the substituent Y is any one of substituent numbers 1 to 558 in the compound THMO.

A tetrazolinone compound in which $X^1$, $X^2$, $X^3$, and $X^4$ are Q8 shown in Table 42, and the substituent Y is any one of substituent numbers 1 to 558 in the compound THMO.

A tetrazolinone compound in which $X^1$, $X^2$, $X^3$, and $X^4$ are Q9 shown in Table 42, and the substituent Y is any one of substituent numbers 1 to 558 in the compound THMO.

A tetrazolinone compound in which $X^1$, $X^2$, $X^3$, and $X^4$ are Q10 shown in Table 42, and the substituent Y is any one of substituent numbers 1 to 558 in the compound THMO.

A tetrazolinone compound in which $X^1$, $X^2$, $X^3$, and $X^4$ are Q11 shown in Table 42, and the substituent Y is any one of substituent numbers 1 to 558 in the compound THMO.

A tetrazolinone compound in which $X^1$, $X^2$, $X^3$, and $X^4$ are Q12 shown in Table 42, and the substituent Y is any one of substituent numbers 1 to 558 in the compound THMO.

A tetrazolinone compound in which $X^1$, $X^2$, $X^3$, and $X^4$ are Q1 shown in Table 42, and the substituent Y is any one of substituent numbers 1 to 558 in a compound represented by formula (THET) (referred to as the compound THET).

A tetrazolinone compound in which $X^1$, $X^2$, $X^3$, and $X^4$ are Q2 shown in Table 42, and the substituent Y is any one of substituent numbers 1 to 558 in the compound THET.

A tetrazolinone compound in which $X^1$, $X^2$, $X^3$, and $X^4$ are Q3 shown in Table 42, and the substituent Y is any one of substituent numbers 1 to 558 in the compound THET.

A tetrazolinone compound in which $X^1$, $X^2$, $X^3$, and $X^4$ are Q4 shown in Table 42, and the substituent Y is any one of substituent numbers 1 to 558 in the compound THET.

A tetrazolinone compound in which $X^1$, $X^2$, $X^3$, and $X^4$ are Q5 shown in Table 42, and the substituent Y is any one of substituent numbers 1 to 558 in the compound THET.

A tetrazolinone compound in which $X^1$, $X^2$, $X^3$, and $X^4$ are Q6 shown in Table 42, and the substituent Y is any one of substituent numbers 1 to 558 in the compound THET.

A tetrazolinone compound in which $X^1$, $X^2$, $X^3$, and $X^4$ are Q7 shown in Table 42, and the substituent Y is any one of substituent numbers 1 to 558 in the compound THET.

A tetrazolinone compound in which $X^1$, $X^2$, $X^3$, and $X^4$ are Q8 shown in Table 42, and the substituent Y is any one of substituent numbers 1 to 558 in the compound THET.

A tetrazolinone compound in which $X^1$, $X^2$, $X^3$, and $X^4$ are Q9 shown in Table 42, and the substituent Y is any one of substituent numbers 1 to 558 in the compound THET.

A tetrazolinone compound in which $X^1$, $X^2$, $X^3$, and $X^4$ are Q10 shown in Table 42, and the substituent Y is any one of substituent numbers 1 to 558 in the compound THET.

A tetrazolinone compound in which $X^1$, $X^2$, $X^3$, and $X^4$ are Q11 shown in Table 42, and the substituent Y is any one of substituent numbers 1 to 558 in the compound THET.

A tetrazolinone compound in which $X^1$, $X^2$, $X^3$, and $X^4$ are Q12 shown in Table 42, and the substituent Y is any one of substituent numbers 1 to 558 in the compound THET.

A tetrazolinone compound in which $X^1$, $X^2$, $X^3$, and $X^4$ are Q1 shown in Table 42, and the substituent Y is any one of substituent numbers 1 to 558 in a compound represented by formula (THCF) (referred to as the compound THCF).

A tetrazolinone compound in which $X^1$, $X^2$, $X^3$, and $X^4$ are Q2 shown in Table 42, and the substituent Y is any one of substituent numbers 1 to 558 in the compound THCF.

A tetrazolinone compound in which $X^1$, $X^2$, $X^3$, and $X^4$ are Q3 shown in Table 42, and the substituent Y is any one of substituent numbers 1 to 558 in the compound THCF.

A tetrazolinone compound in which $X^1$, $X^2$, $X^3$, and $X^4$ are Q4 shown in Table 42, and the substituent Y is any one of substituent numbers 1 to 558 in the compound THCF.

A tetrazolinone compound in which $X^1$, $X^2$, $X^3$, and $X^4$ are Q5 shown in Table 42, and the substituent Y is any one of substituent numbers 1 to 558 in the compound THCF.

A tetrazolinone compound in which $X^1$, $X^2$, $X^3$, and $X^4$ are Q6 shown in Table 42, and the substituent Y is any one of substituent numbers 1 to 558 in the compound THCF.

A tetrazolinone compound in which $X^1$, $X^2$, $X^3$, and $X^4$ are Q7 shown in Table 42, and the substituent Y is any one of substituent numbers 1 to 558 in the compound THCF.

A tetrazolinone compound in which $X^1$, $X^2$, $X^3$, and $X^4$ are Q8 shown in Table 42, and the substituent Y is any one of substituent numbers 1 to 558 in the compound THCF.

A tetrazolinone compound in which $X^1$, $X^2$, $X^3$, and $X^4$ are Q9 shown in Table 42, and the substituent Y is any one of substituent numbers 1 to 558 in the compound THCF.

A tetrazolinone compound in which $X^1$, $X^2$, $X^3$, and $X^4$ are Q10 shown in Table 42, and the substituent Y is any one of substituent numbers 1 to 558 in the compound THCF.

A tetrazolinone compound in which $X^1$, $X^2$, $X^3$, and $X^4$ are Q11 shown in Table 42, and the substituent Y is any one of substituent numbers 1 to 558 in the compound THCF.

A tetrazolinone compound in which $X^1$, $X^2$, $X^3$, and $X^4$ are Q12 shown in Table 42, and the substituent Y is any one of substituent numbers 1 to 558 in the compound THCF.

A tetrazolinone compound in which $X^1$, $X^2$, $X^3$, and $X^4$ are Q1 shown in Table 42, and the substituent Y is any one of substituent numbers 1 to 558 in a compound represented by formula (THCFF) (referred to as the compound THCFF).

A tetrazolinone compound in which $X^1$, $X^2$, $X^3$, and $X^4$ are Q2 shown in Table 42, and the substituent Y is any one of substituent numbers 1 to 558 in the compound THCFF.

A tetrazolinone compound in which $X^1$, $X^2$, $X^3$, and $X^4$ are Q3 shown in Table 42, and the substituent Y is any one of substituent numbers 1 to 558 in the compound THCFF.

A tetrazolinone compound in which $X^1$, $X^2$, $X^3$, and $X^4$ are Q4 shown in Table 42, and the substituent Y is any one of substituent numbers 1 to 558 in the compound THCFF.

A tetrazolinone compound in which $X^1$, $X^2$, $X^3$, and $X^4$ are Q5 shown in Table 42, and the substituent Y is any one of substituent numbers 1 to 558 in the compound THCFF.

A tetrazolinone compound in which $X^1$, $X^2$, $X^3$, and $X^4$ are Q6 shown in Table 42, and the substituent Y is any one of substituent numbers 1 to 558 in the compound THCFF.

A tetrazolinone compound in which $X^1$, $X^2$, $X^3$, and $X^4$ are Q7 shown in Table 42, and the substituent Y is any one of substituent numbers 1 to 558 in the compound THCFF.

A tetrazolinone compound in which $X^1$, $X^2$, $X^3$, and $X^4$ are Q8 shown in Table 42, and the substituent Y is any one of substituent numbers 1 to 558 in the compound THCFF.

A tetrazolinone compound in which $X^1$, $X^2$, $X^3$, and $X^4$ are Q9 shown in Table 42, and the substituent Y is any one of substituent numbers 1 to 558 in the compound THCFF.

A tetrazolinone compound in which $X^1$, $X^2$, $X^3$, and $X^4$ are Q10 shown in Table 42, and the substituent Y is any one of substituent numbers 1 to 558 in the compound THCFF.

A tetrazolinone compound in which $X^1$, $X^2$, $X^3$, and $X^4$ are Q11 shown in Table 42, and the substituent Y is any one of substituent numbers 1 to 558 in the compound THCFF.

A tetrazolinone compound in which $X^1$, $X^2$, $X^3$, and $X^4$ are Q12 shown in Table 42, and the substituent Y is any one of substituent numbers 1 to 558 in the compound THCFF.

For example, a compound in which $X^1$, $X^2$, $X^3$, and $X^4$ are Q1 shown in Table 42, and Y is a substituent numbers 1 in formula (THF) represent the following compound.

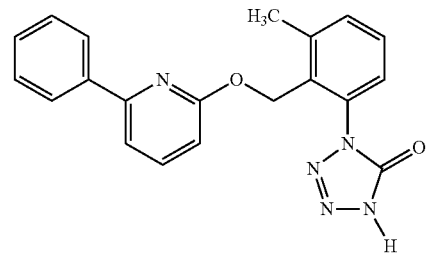

(THF-Q1-001)

In accordance with the above method, it is possible to obtain intermediates TZF-T01 to TZCFF-T12.

The intermediates TZF-T01 to TZCFF-T12 are compounds represented by the following formulas:

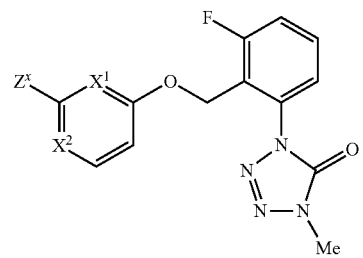

(TZF)

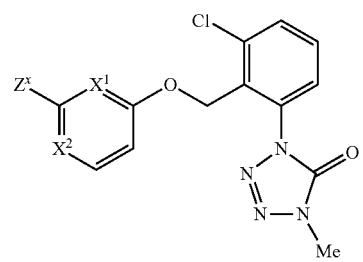

(TZC)

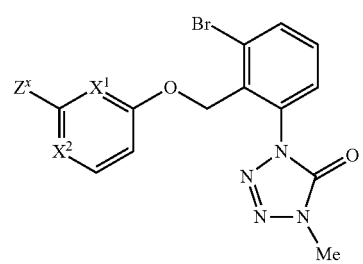

(TZB)

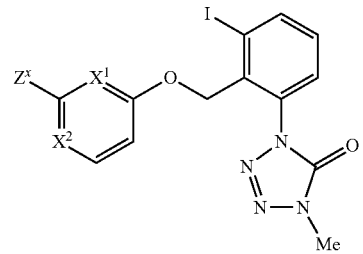

(TZI)

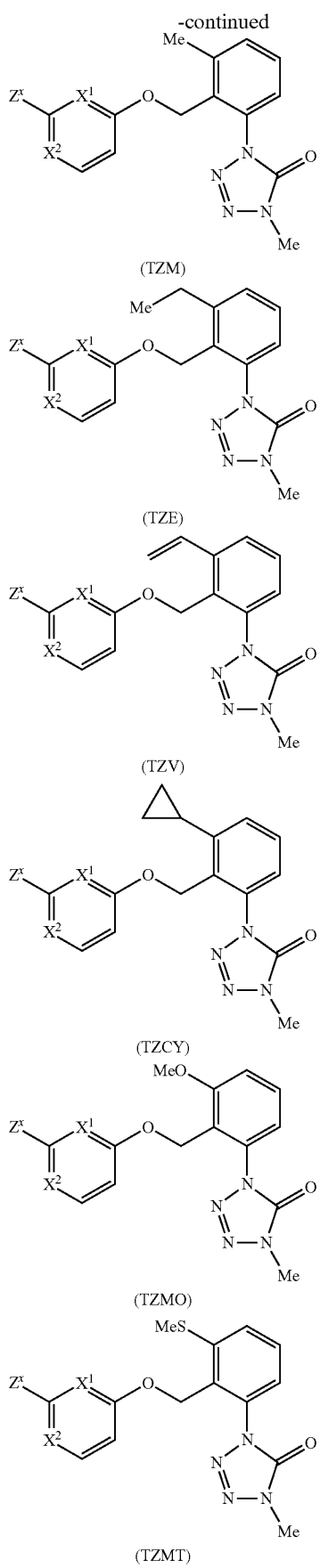

(TZM)

(TZE)

(TZV)

(TZCY)

(TZMO)

(TZMT)

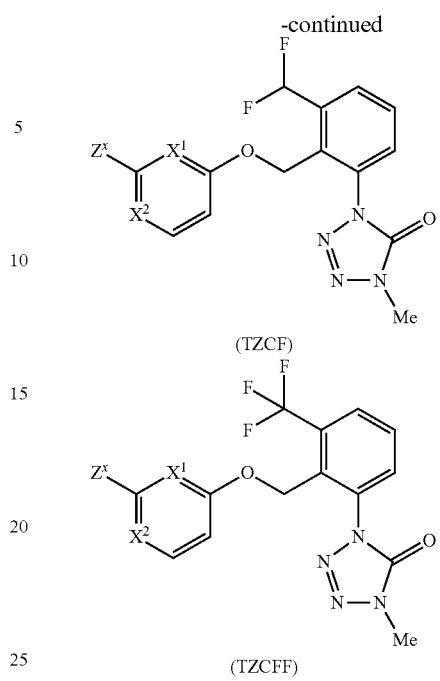

(TZCF)

(TZCFF)

wherein $X^1$, $X^2$, and $Z^X$ represent any one of combinations T1 to T12 shown in Table 43.

TABLE 43

| Combination | $X^1$, $X^2$, $Z^X$ |
|---|---|
| T1 | $X^1 = N$, $X^2 = CH$, $Z^X = F$ |
| T2 | $X^1 = N$, $X^2 = CH$, $Z^X = Cl$ |
| T3 | $X^1 = N$, $X^2 = CH$, $Z^X = Br$ |
| T4 | $X^1 = N$, $X^2 = CH$, $Z^X = I$ |
| T5 | $X^1 = CH$, $X^2 = CH$, $Z^X = F$ |
| T6 | $X^1 = CH$, $X^2 = CH$, $Z^X = Cl$ |
| T7 | $X^1 = CH$, $X^2 = CH$, $Z^X = Br$ |
| T8 | $X^1 = CH$, $X^2 = CH$, $Z^X = I$ |
| T9 | $X^1 = N$, $X^2 = N$, $Z^X = F$ |
| T10 | $X^1 = N$, $X^2 = N$, $Z^X = Cl$ |
| T11 | $X^1 = N$, $X^2 = N$, $Z^X = Br$ |
| T12 | $X^1 = N$, $X^2 = N$, $Z^X = I$ |

In Table 43, F represents a fluorine atom, Cl represents a chlorine atom, Br represents a bromine atom, and I represents an iodine atom.

For example, a compound in which $X^1$, $X^2$, and $Z^X$ are T1 shown in Table 43 in formula (TZF) represent the following compound.

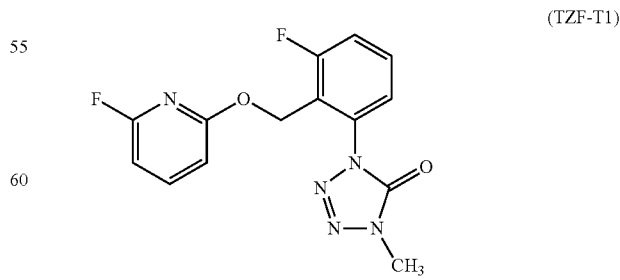

(TZF-T1)

In accordance with the above method, it is possible to obtain compounds TF-L001-1 to TCFF-L057-558.

The compounds TF-L001-1 to TCFF-L057-558 are compounds represented by the following formulas:

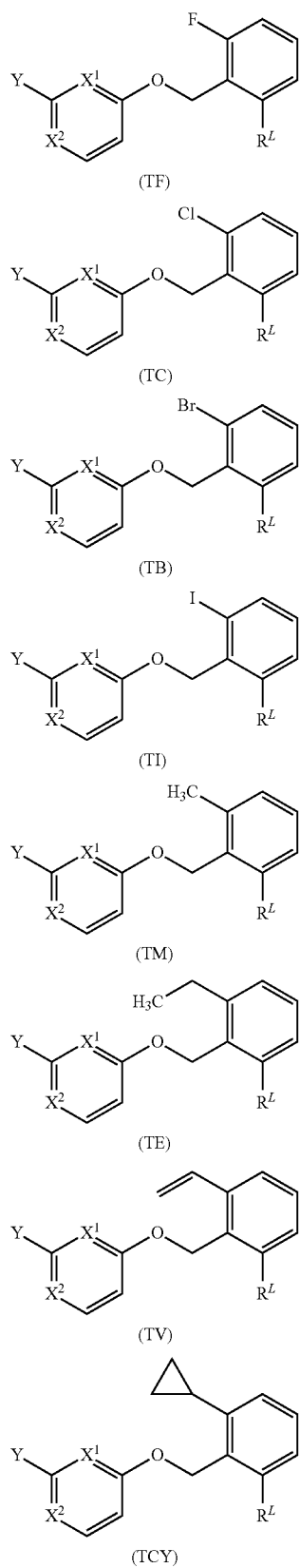

(TF)
(TC)
(TB)
(TI)
(TM)
(TE)
(TV)
(TCY)

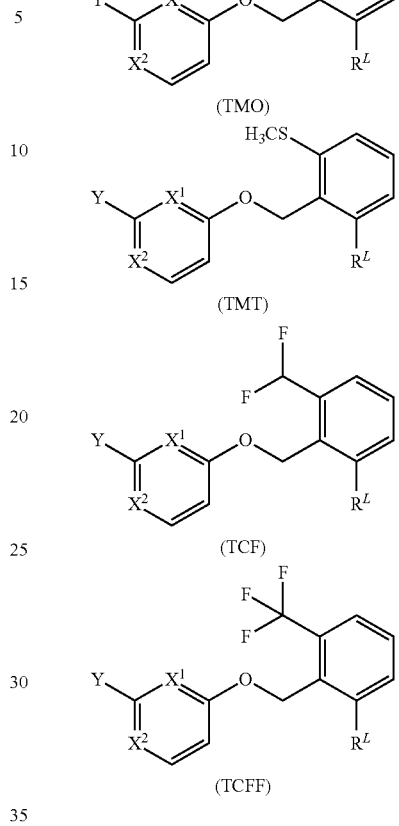

(TMO)
(TMT)
(TCF)
(TCFF)

wherein $X^1$, $X^2$, and $R^L$ represent any one of combinations L1 to L57 shown in Table 44 and Table 45, and Y represents a substituent corresponding to each of substituent numbers 1 to 558.

TABLE 44

| Combination | $X^1$, $X^2$, $R^L$ |
|---|---|
| L1 | $X^1$ = N, $X^2$ = CH, $R^L$ = $NO_2$ |
| L2 | $X^1$ = N, $X^2$ = CH, $R^L$ = $NH_2$ |
| L3 | $X^1$ = N, $X^2$ = CH, $R^L$ = NCO |
| L4 | $X^1$ = N, $X^2$ = CH, $R^L$ = $CO_2H$ |
| L5 | $X^1$ = N, $X^2$ = CH, $R^L$ = $CO_2CH_3$ |
| L6 | $X^1$ = N, $X^2$ = CH, $R^L$ = $CO_2CH_2CH_3$ |
| L7 | $X^1$ = N, $X^2$ = CH, $R^L$ = $CO_2(CH_2)_2CH_3$ |
| L8 | $X^1$ = N, $X^2$ = CH, $R^L$ = $CO_2CH(CH_3)_2$ |
| L9 | $X^1$ = N, $X^2$ = CH, $R^L$ = Cl |
| L10 | $X^1$ = N, $X^2$ = CH, $R^L$ = Br |
| L11 | $X^1$ = N, $X^2$ = CH, $R^L$ = I |
| L12 | $X^1$ = N, $X^2$ = CH, $R^L$ = COCl |
| L13 | $X^1$ = N, $X^2$ = CH, $R^L$ = COBr |
| L14 | $X^1$ = N, $X^2$ = CH, $R^L$ = NSO |
| L15 | $X^1$ = N, $X^2$ = CH, $R^L$ = $CON_3$ |
| L16 | $X^1$ = N, $X^2$ = CH, $R^L$ = $CONH_2$ |
| L17 | $X^1$ = N, $X^2$ = CH, $R^L$ = CONHCl |
| L18 | $X^1$ = N, $X^2$ = CH, $R^L$ = CONHBr |
| L19 | $X^1$ = N, $X^2$ = CH, $R^L$ = CONHOH |
| L20 | $X^1$ = CH, $X^2$ = CH, $R^L$ = $NO_2$ |
| L21 | $X^1$ = CH, $X^2$ = CH, $R^L$ = $NH_2$ |
| L22 | $X^1$ = CH, $X^2$ = CH, $R^L$ = NCO |
| L23 | $X^1$ = CH, $X^2$ = CH, $R^L$ = $CO_2H$ |
| L24 | $X^1$ = CH, $X^2$ = CH, $R^L$ = $CO_2CH_3$ |
| L25 | $X^1$ = CH, $X^2$ = CH, $R^L$ = $CO_2CH_2CH_3$ |
| L26 | $X^1$ = CH, $X^2$ = CH, $R^L$ = $CO_2(CH_2)_2CH_3$ |
| L27 | $X^1$ = CH, $X^2$ = CH, $R^L$ = $CO_2CH(CH_3)_2$ |

TABLE 44-continued

| Combination | $X^1$, $X^2$, $R^L$ |
| --- | --- |
| L28 | $X^1$ = CH, $X^2$ = CH, $R^L$ = Cl |
| L29 | $X^1$ = CH, $X^2$ = CH, $R^L$ = Br |

TABLE 45

| Combination | $X^1$, $X^2$, $R^L$ |
| --- | --- |
| L30 | $X^1$ = CH, $X^2$ = CH, $R^L$ = I |
| L31 | $X^1$ = CH, $X^2$ = CH, $R^L$ = COCl |
| L32 | $X^1$ = CH, $X^2$ = CH, $R^L$ = COBr |
| L33 | $X^1$ = CH, $X^2$ = CH, $R^L$ = NSO |
| L34 | $X^1$ = CH, $X^2$ = CH, $R^L$ = CON$_3$ |
| L35 | $X^1$ = CH, $X^2$ = CH, $R^L$ = CONH$_2$ |
| L36 | $X^1$ = CH, $X^2$ = CH, $R^L$ = CONHCl |
| L37 | $X^1$ = CH, $X^2$ = CH, $R^L$ = CONHBr |
| L38 | $X^1$ = CH, $X^2$ = CH, $R^L$ = CONHOH |
| L39 | $X^1$ = N, $X^2$ = N, $R^L$ = NO$_2$ |
| L40 | $X^1$ = N, $X^2$ = N, $R^L$ = NH$_2$ |
| L41 | $X^1$ = N, $X^2$ = N, $R^L$ = NCO |
| L42 | $X^1$ = N, $X^2$ = N, $R^L$ = CO$_2$H |
| L43 | $X^1$ = N, $X^2$ = N, $R^L$ = CO$_2$CH$_3$ |
| L44 | $X^1$ = N, $X^2$ = N, $R^L$ = CO$_2$CH$_2$CH$_3$ |
| L45 | $X^1$ = N, $X^2$ = N, $R^L$ = CO$_2$(CH$_2$)$_2$CH$_3$ |
| L46 | $X^1$ = N, $X^2$ = N, $R^L$ = CO$_2$CH(CH$_3$)$_2$ |
| L47 | $X^1$ = N, $X^2$ = N, $R^L$ = Cl |
| L48 | $X^1$ = N, $X^2$ = N, $R^L$ = Br |
| L49 | $X^1$ = N, $X^2$ = N, $R^L$ = I |
| L50 | $X^1$ = N, $X^2$ = N, $R^L$ = COCl |
| L51 | $X^1$ = N, $X^2$ = N, $R^L$ = COBr |
| L52 | $X^1$ = N, $X^2$ = N, $R^L$ = NSO |
| L53 | $X^1$ = N, $X^2$ = N, $R^L$ = CON$_3$ |
| L54 | $X^1$ = N, $X^2$ = N, $R^L$ = CONH$_2$ |
| L55 | $X^1$ = N, $X^2$ = N, $R^L$ = CONHCl |
| L56 | $X^1$ = N, $X^2$ = N, $R^L$ = CONHBr |
| L57 | $X^1$ = N, $X^2$ = N, $R^L$ = CONHOH |

In Table 44 and Table 45, NO$_2$ represents a nitro group, NH$_2$ represents an amino group, NCO represents an isocyanate group, CO$_2$H represents a carboxyl group, CO$_2$CH$_3$ represents a methoxycarbonyl group, CO$_2$CH$_2$CH$_3$ represents an ethoxycarbonyl group, CO$_2$(CH$_2$)$_2$CH$_3$ represents a propyloxycarbonyl group, CO$_2$CH(CH$_3$)$_2$ represents an isopropyloxycarbonyl group, F represents a fluorine atom, Cl represents a chlorine atom, Br represents a bromine atom, I represents an iodine atom, COCl represents a formyl chloride group, and COBr represents a formyl bromide group.

A tetrazolinone compound in which $X^1$, $X^2$, and $R^L$ are L1 shown in Table 44, and the substituent Y is any one of substituent numbers 1 to 558 in a compound represented by formula (TF) (referred to as the compound TF).

A tetrazolinone compound in which $X^1$, $X^2$, and $R^L$ are L2 shown in Table 44, and the substituent Y is any one of substituent numbers 1 to 558 in the compound TF.

A tetrazolinone compound in which $X^1$, $X^2$, and $R^L$ are L3 shown in Table 44, and the substituent Y is any one of substituent numbers 1 to 558 in the compound TF.

A tetrazolinone compound in which $X^1$, $X^2$, and $R^L$ are L4 shown in Table 44, and the substituent Y is any one of substituent numbers 1 to 558 in the compound TF.

A tetrazolinone compound in which $X^1$, $X^2$, and $R^L$ are L5 shown in Table 44, and the substituent Y is any one of substituent numbers 1 to 558 in the compound TF.

A tetrazolinone compound in which $X^1$, $X^2$, and $R^L$ are L6 shown in Table 44, and the substituent Y is any one of substituent numbers 1 to 558 in the compound TF.

A tetrazolinone compound in which $X^1$, $X^2$, and $R^L$ are L7 shown in Table 44, and the substituent Y is any one of substituent numbers 1 to 558 in the compound TF.

A tetrazolinone compound in which $X^1$, $X^2$, and $R^L$ are L8 shown in Table 44, and the substituent Y is any one of substituent numbers 1 to 558 in the compound TF.

A tetrazolinone compound in which $X^1$, $X^2$, and $R^L$ are L9 shown in Table 44, and the substituent Y is any one of substituent numbers 1 to 558 in the compound TF.

A tetrazolinone compound in which $X^1$, $X^2$, and $R^L$ are L10 shown in Table 44, and the substituent Y is any one of substituent numbers 1 to 558 in the compound TF.

A tetrazolinone compound in which $X^1$, $X^2$, and $R^L$ are L11 shown in Table 44, and the substituent Y is any one of substituent numbers 1 to 558 in the compound TF.

A tetrazolinone compound in which $X^1$, $X^2$, and $R^L$ are L12 shown in Table 44, and the substituent Y is any one of substituent numbers 1 to 558 in the compound TF.

A tetrazolinone compound in which $X^1$, $X^2$, and $R^L$ are L13 shown in Table 44, and the substituent Y is any one of substituent numbers 1 to 558 in the compound TF.

A tetrazolinone compound in which $X^1$, $X^2$, and $R^L$ are L14 shown in Table 44, and the substituent Y is any one of substituent numbers 1 to 558 in the compound TF.

A tetrazolinone compound in which $X^1$, $X^2$, and $R^L$ are L15 shown in Table 44, and the substituent Y is any one of substituent numbers 1 to 558 in the compound TF.

A tetrazolinone compound in which $X^1$, $X^2$, and $R^L$ are L16 shown in Table 44, and the substituent Y is any one of substituent numbers 1 to 558 in the compound TF.

A tetrazolinone compound in which $X^1$, $X^2$, and $R^L$ are L17 shown in Table 44, and the substituent Y is any one of substituent numbers 1 to 558 in the compound TF.

A tetrazolinone compound in which $X^1$, $X^2$, and $R^L$ are L18 shown in Table 44, and the substituent Y is any one of substituent numbers 1 to 558 in the compound TF.

A tetrazolinone compound in which $X^1$, $X^2$, and $R^L$ are L19 shown in Table 44, and the substituent Y is any one of substituent numbers 1 to 558 in the compound TF.

A tetrazolinone compound in which $X^1$, $X^2$, and $R^L$ are L20 shown in Table 44, and the substituent Y is any one of substituent numbers 1 to 558 in the compound TF.

A tetrazolinone compound in which $X^1$, $X^2$, and $R^L$ are L21 shown in Table 44, and the substituent Y is any one of substituent numbers 1 to 558 in the compound TF.

A tetrazolinone compound in which $X^1$, $X^2$, and $R^L$ are L22 shown in Table 44, and the substituent Y is any one of substituent numbers 1 to 558 in the compound TF.

A tetrazolinone compound in which $X^1$, $X^2$, and $R^L$ are L23 shown in Table 44, and the substituent Y is any one of substituent numbers 1 to 558 in the compound TF.

A tetrazolinone compound in which $X^1$, $X^2$, and $R^L$ are L24 shown in Table 44, and the substituent Y is any one of substituent numbers 1 to 558 in the compound TF.

A tetrazolinone compound in which $X^1$, $X^2$, and $R^L$ are L25 shown in Table 44, and the substituent Y is any one of substituent numbers 1 to 558 in the compound TF.

A tetrazolinone compound in which $X^1$, $X^2$, and $R^L$ are L26 shown in Table 44, and the substituent Y is any one of substituent numbers 1 to 558 in the compound TF.

A tetrazolinone compound in which $X^1$, $X^2$, and $R^L$ are L27 shown in Table 44, and the substituent Y is any one of substituent numbers 1 to 558 in the compound TF.

A tetrazolinone compound in which $X^1$, $X^2$, and $R^L$ are L28 shown in Table 44, and the substituent Y is any one of substituent numbers 1 to 558 in the compound TF.

A tetrazolinone compound in which $X^1$, $X^2$, and $R^L$ are L29 shown in Table 44, and the substituent Y is any one of substituent numbers 1 to 558 in the compound TF.

A tetrazolinone compound in which $X^1$, $X^2$, and $R^L$ are L30 shown in Table 45, and the substituent Y is any one of substituent numbers 1 to 558 in the compound TF.

A tetrazolinone compound in which $X^1$, $X^2$, and $R^L$ are L31 shown in Table 45, and the substituent Y is any one of substituent numbers 1 to 558 in the compound TF.

A tetrazolinone compound in which $X^1$, $X^2$, and $R^L$ are L32 shown in Table 45, and the substituent Y is any one of substituent numbers 1 to 558 in the compound TF.

A tetrazolinone compound in which $X^1$, $X^2$, and $R^L$ are L33 shown in Table 45, and the substituent Y is any one of substituent numbers 1 to 558 in the compound TF.

A tetrazolinone compound in which $X^1$, $X^2$, and $R^L$ are L34 shown in Table 45, and the substituent Y is any one of substituent numbers 1 to 558 in the compound TF.

A tetrazolinone compound in which $X^1$, $X^2$, and $R^L$ are L35 shown in Table 45, and the substituent Y is any one of substituent numbers 1 to 558 in the compound TF.

A tetrazolinone compound in which $X^1$, $X^2$, and $R^L$ are L36 shown in Table 45, and the substituent Y is any one of substituent numbers 1 to 558 in the compound TF.

A tetrazolinone compound in which $X^1$, $X^2$, and $R^L$ are L37 shown in Table 45, and the substituent Y is any one of substituent numbers 1 to 558 in the compound TF.

A tetrazolinone compound in which $X^1$, $X^2$, and $R^L$ are L38 shown in Table 45, and the substituent Y is any one of substituent numbers 1 to 558 in the compound TF.

A tetrazolinone compound in which $X^1$, $X^2$, and $R^L$ are L39 shown in Table 45, and the substituent Y is any one of substituent numbers 1 to 558 in the compound TF.

A tetrazolinone compound in which $X^1$, $X^2$, and $R^L$ are L40 shown in Table 45, and the substituent Y is any one of substituent numbers 1 to 558 in the compound TF.

A tetrazolinone compound in which $X^1$, $X^2$, and $R^L$ are L41 shown in Table 45, and the substituent Y is any one of substituent numbers 1 to 558 in the compound TF.

A tetrazolinone compound in which $X^1$, $X^2$, and $R^L$ are L42 shown in Table 45, and the substituent Y is any one of substituent numbers 1 to 558 in the compound TF.

A tetrazolinone compound in which $X^1$, $X^2$, and $R^L$ are L43 shown in Table 45, and the substituent Y is any one of substituent numbers 1 to 558 in the compound TF.

A tetrazolinone compound in which $X^1$, $X^2$, and $R^L$ are L44 shown in Table 45, and the substituent Y is any one of substituent numbers 1 to 558 in the compound TF.

A tetrazolinone compound in which $X^1$, $X^2$, and $R^L$ are L45 shown in Table 45, and the substituent Y is any one of substituent numbers 1 to 558 in the compound TF.

A tetrazolinone compound in which $X^1$, $X^2$, and $R^L$ are L46 shown in Table 45, and the substituent Y is any one of substituent numbers 1 to 558 in the compound TF.

A tetrazolinone compound in which $X^1$, $X^2$, and $R^L$ are L47 shown in Table 45, and the substituent Y is any one of substituent numbers 1 to 558 in the compound TF.

A tetrazolinone compound in which $X^1$, $X^2$, and $R^L$ are L48 shown in Table 45, and the substituent Y is any one of substituent numbers 1 to 558 in the compound TF.

A tetrazolinone compound in which $X^1$, $X^2$, and $R^L$ are L49 shown in Table 45, and the substituent Y is any one of substituent numbers 1 to 558 in the compound TF.

A tetrazolinone compound in which $X^1$, $X^2$, and $R^L$ are L50 shown in Table 45, and the substituent Y is any one of substituent numbers 1 to 558 in the compound TF.

A tetrazolinone compound in which $X^1$, $X^2$, and $R^L$ are L51 shown in Table 45, and the substituent Y is any one of substituent numbers 1 to 558 in the compound TF.

A tetrazolinone compound in which $X^1$, $X^2$, and $R^L$ are L52 shown in Table 45, and the substituent Y is any one of substituent numbers 1 to 558 in the compound TF.

A tetrazolinone compound in which $X^1$, $X^2$, and $R^L$ are L53 shown in Table 45, and the substituent Y is any one of substituent numbers 1 to 558 in the compound TF.

A tetrazolinone compound in which $X^1$, $X^2$, and $R^L$ are L54 shown in Table 45, and the substituent Y is any one of substituent numbers 1 to 558 in the compound TF.

A tetrazolinone compound in which $X^1$, $X^2$, and $R^L$ are L55 shown in Table 45, and the substituent Y is any one of substituent numbers 1 to 558 in the compound TF.

A tetrazolinone compound in which $X^1$, $X^2$, and $R^L$ are L56 shown in Table 45, and the substituent Y is any one of substituent numbers 1 to 558 in the compound TF.

A tetrazolinone compound in which $X^1$, $X^2$, and $R^L$ are L57 shown in Table 45, and the substituent Y is any one of substituent numbers 1 to 558 in the compound TF.

A tetrazolinone compound in which $X^1$, $X^2$, and $R^L$ are L1 shown in Table 44, and the substituent Y is any one of substituent numbers 1 to 558 in a compound represented by formula (TC) (referred to as the compound TC).

A tetrazolinone compound in which $X^1$, $X^2$, and $R^L$ are L2 shown in Table 44, and the substituent Y is any one of substituent numbers 1 to 558 in the compound TC.

A tetrazolinone compound in which $X^1$, $X^2$, and $R^L$ are L3 shown in Table 44, and the substituent Y is any one of substituent numbers 1 to 558 in the compound TC.

A tetrazolinone compound in which $X^1$, $X^2$, and $R^L$ are L4 shown in Table 44, and the substituent Y is any one of substituent numbers 1 to 558 in the compound TC.

A tetrazolinone compound in which $X^1$, $X^2$, and $R^L$ are L5 shown in Table 44, and the substituent Y is any one of substituent numbers 1 to 558 in the compound TC.

A tetrazolinone compound in which $X^1$, $X^2$, and $R^L$ are L6 shown in Table 44, and the substituent Y is any one of substituent numbers 1 to 558 in the compound TC.

A tetrazolinone compound in which $X^1$, $X^2$, and $R^L$ are L7 shown in Table 44, and the substituent Y is any one of substituent numbers 1 to 558 in the compound TC.

A tetrazolinone compound in which $X^1$, $X^2$, and $R^L$ are L8 shown in Table 44, and the substituent Y is any one of substituent numbers 1 to 558 in the compound TC.

A tetrazolinone compound in which $X^1$, $X^2$, and $R^L$ are L9 shown in Table 44, and the substituent Y is any one of substituent numbers 1 to 558 in the compound TC.

A tetrazolinone compound in which $X^1$, $X^2$, and $R^L$ are L10 shown in Table 44, and the substituent Y is any one of substituent numbers 1 to 558 in the compound TC.

A tetrazolinone compound in which $X^1$, $X^2$, and $R^L$ are L11 shown in Table 44, and the substituent Y is any one of substituent numbers 1 to 558 in the compound TC.

A tetrazolinone compound in which $X^1$, $X^2$, and $R^L$ are L12 shown in Table 44, and the substituent Y is any one of substituent numbers 1 to 558 in the compound TC.

A tetrazolinone compound in which $X^1$, $X^2$, and $R^L$ are L13 shown in Table 44, and the substituent Y is any one of substituent numbers 1 to 558 in the compound TC.

A tetrazolinone compound in which $X^1$, $X^2$, and $R^L$ are L14 shown in Table 44, and the substituent Y is any one of substituent numbers 1 to 558 in the compound TC.

A tetrazolinone compound in which $X^1$, $X^2$, and $R^L$ are L15 shown in Table 44, and the substituent Y is any one of substituent numbers 1 to 558 in the compound TC.

A tetrazolinone compound in which $X^1$, $X^2$, and $R^L$ are L16 shown in Table 44, and the substituent Y is any one of substituent numbers 1 to 558 in the compound TC.

A tetrazolinone compound in which $X^1$, $X^2$, and $R^L$ are L17 shown in Table 44, and the substituent Y is any one of substituent numbers 1 to 558 in the compound TC.

A tetrazolinone compound in which $X^1$, $X^2$, and $R^L$ are L18 shown in Table 44, and the substituent Y is any one of substituent numbers 1 to 558 in the compound TC.

A tetrazolinone compound in which $X^1$, $X^2$, and $R^L$ are L19 shown in Table 44, and the substituent Y is any one of substituent numbers 1 to 558 in the compound TC.

A tetrazolinone compound in which $X^1$, $X^2$, and $R^L$ are L20 shown in Table 44, and the substituent Y is any one of substituent numbers 1 to 558 in the compound TC.

A tetrazolinone compound in which $X^1$, $X^2$, and $R^L$ are L21 shown in Table 44, and the substituent Y is any one of substituent numbers 1 to 558 in the compound TC.

A tetrazolinone compound in which $X^1$, $X^2$, and $R^L$ are L22 shown in Table 44, and the substituent Y is any one of substituent numbers 1 to 558 in the compound TC.

A tetrazolinone compound in which $X^1$, $X^2$, and $R^L$ are L23 shown in Table 44, and the substituent Y is any one of substituent numbers 1 to 558 in the compound TC.

A tetrazolinone compound in which $X^1$, $X^2$, and $R^L$ are L24 shown in Table 44, and the substituent Y is any one of substituent numbers 1 to 558 in the compound TC.

A tetrazolinone compound in which $X^1$, $X^2$, and $R^L$ are L25 shown in Table 44, and the substituent Y is any one of substituent numbers 1 to 558 in the compound TC.

A tetrazolinone compound in which $X^1$, $X^2$, and $R^L$ are L26 shown in Table 44, and the substituent Y is any one of substituent numbers 1 to 558 in the compound TC.

A tetrazolinone compound in which $X^1$, $X^2$, and $R^L$ are L27 shown in Table 44, and the substituent Y is any one of substituent numbers 1 to 558 in the compound TC.

A tetrazolinone compound in which $X^1$, $X^2$, and $R^L$ are L28 shown in Table 44, and the substituent Y is any one of substituent numbers 1 to 558 in the compound TC.

A tetrazolinone compound in which $X^1$, $X^2$, and $R^L$ are L29 shown in Table 44, and the substituent Y is any one of substituent numbers 1 to 558 in the compound TC.

A tetrazolinone compound in which $X^1$, $X^2$, and $R^L$ are L30 shown in Table 45, and the substituent Y is any one of substituent numbers 1 to 558 in the compound TC.

A tetrazolinone compound in which $X^1$, $X^2$, and $R^L$ are L31 shown in Table 45, and the substituent Y is any one of substituent numbers 1 to 558 in the compound TC.

A tetrazolinone compound in which $X^1$, $X^2$, and $R^L$ are L32 shown in Table 45, and the substituent Y is any one of substituent numbers 1 to 558 in the compound TC.

A tetrazolinone compound in which $X^1$, $X^2$, and $R^L$ are L33 shown in Table 45, and the substituent Y is any one of substituent numbers 1 to 558 in the compound TC.

A tetrazolinone compound in which $X^1$, $X^2$, and $R^L$ are L34 shown in Table 45, and the substituent Y is any one of substituent numbers 1 to 558 in the compound TC.

A tetrazolinone compound in which $X^1$, $X^2$, and $R^L$ are L35 shown in Table 45, and the substituent Y is any one of substituent numbers 1 to 558 in the compound TC.

A tetrazolinone compound in which $X^1$, $X^2$, and $R^L$ are L36 shown in Table 45, and the substituent Y is any one of substituent numbers 1 to 558 in the compound TC.

A tetrazolinone compound in which $X^1$, $X^2$, and $R^L$ are L37 shown in Table 45, and the substituent Y is any one of substituent numbers 1 to 558 in the compound TC.

A tetrazolinone compound in which $X^1$, $X^2$, and $R^L$ are L38 shown in Table 45, and the substituent Y is any one of substituent numbers 1 to 558 in the compound TC.

A tetrazolinone compound in which $X^1$, $X^2$, and $R^L$ are L39 shown in Table 45, and the substituent Y is any one of substituent numbers 1 to 558 in the compound TC.

A tetrazolinone compound in which $X^1$, $X^2$, and $R^L$ are L40 shown in Table 45, and the substituent Y is any one of substituent numbers 1 to 558 in the compound TC.

A tetrazolinone compound in which $X^1$, $X^2$, and $R^L$ are L41 shown in Table 45, and the substituent Y is any one of substituent numbers 1 to 558 in the compound TC.

A tetrazolinone compound in which $X^1$, $X^2$, and $R^L$ are L42 shown in Table 45, and the substituent Y is any one of substituent numbers 1 to 558 in the compound TC.

A tetrazolinone compound in which $X^1$, $X^2$, and $R^L$ are L43 shown in Table 45, and the substituent Y is any one of substituent numbers 1 to 558 in the compound TC.

A tetrazolinone compound in which $X^1$, $X^2$, and $R^L$ are L44 shown in Table 45, and the substituent Y is any one of substituent numbers 1 to 558 in the compound TC.

A tetrazolinone compound in which $X^1$, $X^2$, and $R^L$ are L45 shown in Table 45, and the substituent Y is any one of substituent numbers 1 to 558 in the compound TC.

A tetrazolinone compound in which $X^1$, $X^2$, and $R^L$ are L46 shown in Table 45, and the substituent Y is any one of substituent numbers 1 to 558 in the compound TC.

A tetrazolinone compound in which $X^1$, $X^2$, and $R^L$ are L47 shown in Table 45, and the substituent Y is any one of substituent numbers 1 to 558 in the compound TC.

A tetrazolinone compound in which $X^1$, $X^2$, and $R^L$ are L48 shown in Table 45, and the substituent Y is any one of substituent numbers 1 to 558 in the compound TC.

A tetrazolinone compound in which $X^1$, $X^2$, and $R^L$ are L49 shown in Table 45, and the substituent Y is any one of substituent numbers 1 to 558 in the compound TC.

A tetrazolinone compound in which $X^1$, $X^2$, and $R^L$ are L50 shown in Table 45, and the substituent Y is any one of substituent numbers 1 to 558 in the compound TC.

A tetrazolinone compound in which $X^1$, $X^2$, and $R^L$ are L51 shown in Table 45, and the substituent Y is any one of substituent numbers 1 to 558 in the compound TC.

A tetrazolinone compound in which $X^1$, $X^2$, and $R^L$ are L52 shown in Table 45, and the substituent Y is any one of substituent numbers 1 to 558 in the compound TC.

A tetrazolinone compound in which $X^1$, $X^2$, and $R^L$ are L53 shown in Table 45, and the substituent Y is any one of substituent numbers 1 to 558 in the compound TC.

A tetrazolinone compound in which $X^1$, $X^2$, and $R^L$ are L54 shown in Table 45, and the substituent Y is any one of substituent numbers 1 to 558 in the compound TC.

A tetrazolinone compound in which $X^1$, $X^2$, and $R^L$ are L55 shown in Table 45, and the substituent Y is any one of substituent numbers 1 to 558 in the compound TC.

A tetrazolinone compound in which $X^1$, $X^2$, and $R^L$ are L56 shown in Table 45, and the substituent Y is any one of substituent numbers 1 to 558 in the compound TC.

A tetrazolinone compound in which $X^1$, $X^2$, and $R^L$ are L57 shown in Table 45, and the substituent Y is any one of substituent numbers 1 to 558 in the compound TC.

A tetrazolinone compound in which $X^1$, $X^2$, and $R^L$ are L1 shown in Table 44, and the substituent Y is any one of substituent numbers 1 to 558 in a compound represented by formula (TB) (referred to as the compound TB).

A tetrazolinone compound in which $X^1$, $X^2$, and $R^L$ are L2 shown in Table 44, and the substituent Y is any one of substituent numbers 1 to 558 in the compound TB.

A tetrazolinone compound in which $X^1$, $X^2$, and $R^L$ are L3 shown in Table 44, and the substituent Y is any one of substituent numbers 1 to 558 in the compound TB.

A tetrazolinone compound in which $X^1$, $X^2$, and $R^L$ are L4 shown in Table 44, and the substituent Y is any one of substituent numbers 1 to 558 in the compound TB.

A tetrazolinone compound in which $X^1$, $X^2$, and $R^L$ are L5 shown in Table 44, and the substituent Y is any one of substituent numbers 1 to 558 in the compound TB.

A tetrazolinone compound in which $X^1$, $X^2$, and $R^L$ are L6 shown in Table 44, and the substituent Y is any one of substituent numbers 1 to 558 in the compound TB.

A tetrazolinone compound in which $X^1$, $X^2$, and $R^L$ are L7 shown in Table 44, and the substituent Y is any one of substituent numbers 1 to 558 in the compound TB.

A tetrazolinone compound in which $X^1$, $X^2$, and $R^L$ are L8 shown in Table 44, and the substituent Y is any one of substituent numbers 1 to 558 in the compound TB.

A tetrazolinone compound in which $X^1$, $X^2$, and $R^L$ are L9 shown in Table 44, and the substituent Y is any one of substituent numbers 1 to 558 in the compound TB.

A tetrazolinone compound in which $X^1$, $X^2$, and $R^L$ are L10 shown in Table 44, and the substituent Y is any one of substituent numbers 1 to 558 in the compound TB.

A tetrazolinone compound in which $X^1$, $X^2$, and $R^L$ are L11 shown in Table 44, and the substituent Y is any one of substituent numbers 1 to 558 in the compound TB.

A tetrazolinone compound in which $X^1$, $X^2$, and $R^L$ are L12 shown in Table 44, and the substituent Y is any one of substituent numbers 1 to 558 in the compound TB.

A tetrazolinone compound in which $X^1$, $X^2$, and $R^L$ are L13 shown in Table 44, and the substituent Y is any one of substituent numbers 1 to 558 in the compound TB.

A tetrazolinone compound in which $X^1$, $X^2$, and $R^L$ are L14 shown in Table 44, and the substituent Y is any one of substituent numbers 1 to 558 in the compound TB.

A tetrazolinone compound in which $X^1$, $X^2$, and $R^L$ are L15 shown in Table 44, and the substituent Y is any one of substituent numbers 1 to 558 in the compound TB.

A tetrazolinone compound in which $X^1$, $X^2$, and $R^L$ are L16 shown in Table 44, and the substituent Y is any one of substituent numbers 1 to 558 in the compound TB.

A tetrazolinone compound in which $X^1$, $X^2$, and $R^L$ are L17 shown in Table 44, and the substituent Y is any one of substituent numbers 1 to 558 in the compound TB.

A tetrazolinone compound in which $X^1$, $X^2$, and $R^L$ are L18 shown in Table 44, and the substituent Y is any one of substituent numbers 1 to 558 in the compound TB.

A tetrazolinone compound in which $X^1$, $X^2$, and $R^L$ are L19 shown in Table 44, and the substituent Y is any one of substituent numbers 1 to 558 in the compound TB.

A tetrazolinone compound in which $X^1$, $X^2$, and $R^L$ are L20 shown in Table 44, and the substituent Y is any one of substituent numbers 1 to 558 in the compound TB.

A tetrazolinone compound in which $X^1$, $X^2$, and $R^L$ are L21 shown in Table 44, and the substituent Y is any one of substituent numbers 1 to 558 in the compound TB.

A tetrazolinone compound in which $X^1$, $X^2$, and $R^L$ are L22 shown in Table 44, and the substituent Y is any one of substituent numbers 1 to 558 in the compound TB.

A tetrazolinone compound in which $X^1$, $X^2$, and $R^L$ are L23 shown in Table 44, and the substituent Y is any one of substituent numbers 1 to 558 in the compound TB.

A tetrazolinone compound in which $X^1$, $X^2$, and $R^L$ are L24 shown in Table 44, and the substituent Y is any one of substituent numbers 1 to 558 in the compound TB.

A tetrazolinone compound in which $X^1$, $X^2$, and $R^L$ are L25 shown in Table 44, and the substituent Y is any one of substituent numbers 1 to 558 in the compound TB.

A tetrazolinone compound in which $X^1$, $X^2$, and $R^L$ are L26 shown in Table 44, and the substituent Y is any one of substituent numbers 1 to 558 in the compound TB.

A tetrazolinone compound in which $X^1$, $X^2$, and $R^L$ are L27 shown in Table 44, and the substituent Y is any one of substituent numbers 1 to 558 in the compound TB.

A tetrazolinone compound in which $X^1$, $X^2$, and $R^L$ are L28 shown in Table 44, and the substituent Y is any one of substituent numbers 1 to 558 in the compound TB.

A tetrazolinone compound in which $X^1$, $X^2$, and $R^L$ are L29 shown in Table 44, and the substituent Y is any one of substituent numbers 1 to 558 in the compound TB.

A tetrazolinone compound in which $X^1$, $X^2$, and $R^L$ are L30 shown in Table 45, and the substituent Y is any one of substituent numbers 1 to 558 in the compound TB.

A tetrazolinone compound in which $X^1$, $X^2$, and $R^L$ are L31 shown in Table 45, and the substituent Y is any one of substituent numbers 1 to 558 in the compound TB.

A tetrazolinone compound in which $X^1$, $X^2$, and $R^L$ are L32 shown in Table 45, and the substituent Y is any one of substituent numbers 1 to 558 in the compound TB.

A tetrazolinone compound in which $X^1$, $X^2$, and $R^L$ are L33 shown in Table 45, and the substituent Y is any one of substituent numbers 1 to 558 in the compound TB.

A tetrazolinone compound in which $X^1$, $X^2$, and $R^L$ are L34 shown in Table 45, and the substituent Y is any one of substituent numbers 1 to 558 in the compound TB.

A tetrazolinone compound in which $X^1$, $X^2$, and $R^L$ are L35 shown in Table 45, and the substituent Y is any one of substituent numbers 1 to 558 in the compound TB.

A tetrazolinone compound in which $X^1$, $X^2$, and $R^L$ are L36 shown in Table 45, and the substituent Y is any one of substituent numbers 1 to 558 in the compound TB.

A tetrazolinone compound in which $X^1$, $X^2$, and $R^L$ are L37 shown in Table 45, and the substituent Y is any one of substituent numbers 1 to 558 in the compound TB.

A tetrazolinone compound in which $X^1$, $X^2$, and $R^L$ are L38 shown in Table 45, and the substituent Y is any one of substituent numbers 1 to 558 in the compound TB.

A tetrazolinone compound in which $X^1$, $X^2$, and $R^L$ are L39 shown in Table 45, and the substituent Y is any one of substituent numbers 1 to 558 in the compound TB.

A tetrazolinone compound in which $X^1$, $X^2$, and $R^L$ are L40 shown in Table 45, and the substituent Y is any one of substituent numbers 1 to 558 in the compound TB.

A tetrazolinone compound in which $X^1$, $X^2$, and $R^L$ are L41 shown in Table 45, and the substituent Y is any one of substituent numbers 1 to 558 in the compound TB.

A tetrazolinone compound in which $X^1$, $X^2$, and $R^L$ are L42 shown in Table 45, and the substituent Y is any one of substituent numbers 1 to 558 in the compound TB.

A tetrazolinone compound in which $X^1$, $X^2$, and $R^L$ are L43 shown in Table 45, and the substituent Y is any one of substituent numbers 1 to 558 in the compound TB.

A tetrazolinone compound in which $X^1$, $X^2$, and $R^L$ are L44 shown in Table 45, and the substituent Y is any one of substituent numbers 1 to 558 in the compound TB.

A tetrazolinone compound in which $X^1$, $X^2$, and $R^L$ are L45 shown in Table 45, and the substituent Y is any one of substituent numbers 1 to 558 in the compound TB.

A tetrazolinone compound in which $X^1$, $X^2$, and $R^L$ are L46 shown in Table 45, and the substituent Y is any one of substituent numbers 1 to 558 in the compound TB.

A tetrazolinone compound in which $X^1$, $X^2$, and $R^L$ are L47 shown in Table 45, and the substituent Y is any one of substituent numbers 1 to 558 in the compound TB.

A tetrazolinone compound in which $X^1$, $X^2$, and $R^L$ are L48 shown in Table 45, and the substituent Y is any one of substituent numbers 1 to 558 in the compound TB.

A tetrazolinone compound in which $X^1$, $X^2$, and $R^L$ are L49 shown in Table 45, and the substituent Y is any one of substituent numbers 1 to 558 in the compound TB.

A tetrazolinone compound in which $X^1$, $X^2$, and $R^L$ are L50 shown in Table 45, and the substituent Y is any one of substituent numbers 1 to 558 in the compound TB.

A tetrazolinone compound in which $X^1$, $X^2$, and $R^L$ are L51 shown in Table 45, and the substituent Y is any one of substituent numbers 1 to 558 in the compound TB.

A tetrazolinone compound in which $X^1$, $X^2$, and $R^L$ are L52 shown in Table 45, and the substituent Y is any one of substituent numbers 1 to 558 in the compound TB.

A tetrazolinone compound in which $X^1$, $X^2$, and $R^L$ are L53 shown in Table 45, and the substituent Y is any one of substituent numbers 1 to 558 in the compound TB.

A tetrazolinone compound in which $X^1$, $X^2$, and $R^L$ are L54 shown in Table 45, and the substituent Y is any one of substituent numbers 1 to 558 in the compound TB.

A tetrazolinone compound in which $X^1$, $X^2$, and $R^L$ are L55 shown in Table 45, and the substituent Y is any one of substituent numbers 1 to 558 in the compound TB.

A tetrazolinone compound in which $X^1$, $X^2$, and $R^L$ are L56 shown in Table 45, and the substituent Y is any one of substituent numbers 1 to 558 in the compound TB.

A tetrazolinone compound in which $X^1$, $X^2$, and $R^L$ are L57 shown in Table 45, and the substituent Y is any one of substituent numbers 1 to 558 in the compound TB.

A tetrazolinone compound in which $X^1$, $X^2$, and $R^L$ are L1 shown in Table 44, and the substituent Y is any one of substituent numbers 1 to 558 in a compound represented by formula (TI) (referred to as the compound TI).

A tetrazolinone compound in which $X^1$, $X^2$, and $R^L$ are L2 shown in Table 44, and the substituent Y is any one of substituent numbers 1 to 558 in the compound TI.

A tetrazolinone compound in which $X^1$, $X^2$, and $R^L$ are L3 shown in Table 44, and the substituent Y is any one of substituent numbers 1 to 558 in the compound TI.

A tetrazolinone compound in which $X^1$, $X^2$, and $R^L$ are L4 shown in Table 44, and the substituent Y is any one of substituent numbers 1 to 558 in the compound TI.

A tetrazolinone compound in which $X^1$, $X^2$, and $R^L$ are L5 shown in Table 44, and the substituent Y is any one of substituent numbers 1 to 558 in the compound TI.

A tetrazolinone compound in which $X^1$, $X^2$, and $R^L$ are L6 shown in Table 44, and the substituent Y is any one of substituent numbers 1 to 558 in the compound TI.

A tetrazolinone compound in which $X^1$, $X^2$, and $R^L$ are L7 shown in Table 44, and the substituent Y is any one of substituent numbers 1 to 558 in the compound TI.

A tetrazolinone compound in which $X^1$, $X^2$, and $R^L$ are L8 shown in Table 44, and the substituent Y is any one of substituent numbers 1 to 558 in the compound TI.

A tetrazolinone compound in which $X^1$, $X^2$, and $R^L$ are L9 shown in Table 44, and the substituent Y is any one of substituent numbers 1 to 558 in the compound TI.

A tetrazolinone compound in which $X^1$, $X^2$, and $R^L$ are L10 shown in Table 44, and the substituent Y is any one of substituent numbers 1 to 558 in the compound TI.

A tetrazolinone compound in which $X^1$, $X^2$, and $R^L$ are L11 shown in Table 44, and the substituent Y is any one of substituent numbers 1 to 558 in the compound TI.

A tetrazolinone compound in which $X^1$, $X^2$, and $R^L$ are L12 shown in Table 44, and the substituent Y is any one of substituent numbers 1 to 558 in the compound TI.

A tetrazolinone compound in which $X^1$, $X^2$, and $R^L$ are L13 shown in Table 44, and the substituent Y is any one of substituent numbers 1 to 558 in the compound TI.

A tetrazolinone compound in which $X^1$, $X^2$, and $R^L$ are L14 shown in Table 44, and the substituent Y is any one of substituent numbers 1 to 558 in the compound TI.

A tetrazolinone compound in which $X^1$, $X^2$, and $R^L$ are L15 shown in Table 44, and the substituent Y is any one of substituent numbers 1 to 558 in the compound TI.

A tetrazolinone compound in which $X^1$, $X^2$, and $R^L$ are L16 shown in Table 44, and the substituent Y is any one of substituent numbers 1 to 558 in the compound TI.

A tetrazolinone compound in which $X^1$, $X^2$, and $R^L$ are L17 shown in Table 44, and the substituent Y is any one of substituent numbers 1 to 558 in the compound TI.

A tetrazolinone compound in which $X^1$, $X^2$, and $R^L$ are L18 shown in Table 44, and the substituent Y is any one of substituent numbers 1 to 558 in the compound TI.

A tetrazolinone compound in which $X^1$, $X^2$, and $R^L$ are L19 shown in Table 44, and the substituent Y is any one of substituent numbers 1 to 558 in the compound TI.

A tetrazolinone compound in which $X^1$, $X^2$, and $R^L$ are L20 shown in Table 44, and the substituent Y is any one of substituent numbers 1 to 558 in the compound TI.

A tetrazolinone compound in which $X^1$, $X^2$, and $R^L$ are L21 shown in Table 44, and the substituent Y is any one of substituent numbers 1 to 558 in the compound TI.

A tetrazolinone compound in which $X^1$, $X^2$, and $R^L$ are L22 shown in Table 44, and the substituent Y is any one of substituent numbers 1 to 558 in the compound TI.

A tetrazolinone compound in which $X^1$, $X^2$, and $R^L$ are L23 shown in Table 44, and the substituent Y is any one of substituent numbers 1 to 558 in the compound TI.

A tetrazolinone compound in which $X^1$, $X^2$, and $R^L$ are L24 shown in Table 44, and the substituent Y is any one of substituent numbers 1 to 558 in the compound TI.

A tetrazolinone compound in which $X^1$, $X^2$, and $R^L$ are L25 shown in Table 44, and the substituent Y is any one of substituent numbers 1 to 558 in the compound TI.

A tetrazolinone compound in which $X^1$, $X^2$, and $R^L$ are L26 shown in Table 44, and the substituent Y is any one of substituent numbers 1 to 558 in the compound TI.

A tetrazolinone compound in which $X^1$, $X^2$, and $R^L$ are L27 shown in Table 44, and the substituent Y is any one of substituent numbers 1 to 558 in the compound TI.

A tetrazolinone compound in which $X^1$, $X^2$, and $R^L$ are L28 shown in Table 44, and the substituent Y is any one of substituent numbers 1 to 558 in the compound TI.

A tetrazolinone compound in which $X^1$, $X^2$, and $R^L$ are L29 shown in Table 44, and the substituent Y is any one of substituent numbers 1 to 558 in the compound TI.

A tetrazolinone compound in which $X^1$, $X^2$, and $R^L$ are L30 shown in Table 45, and the substituent Y is any one of substituent numbers 1 to 558 in the compound TI.

A tetrazolinone compound in which $X^1$, $X^2$, and $R^L$ are L31 shown in Table 45, and the substituent Y is any one of substituent numbers 1 to 558 in the compound TI.

A tetrazolinone compound in which $X^1$, $X^2$, and $R^L$ are L32 shown in Table 45, and the substituent Y is any one of substituent numbers 1 to 558 in the compound TI.

A tetrazolinone compound in which $X^1$, $X^2$, and $R^L$ are L33 shown in Table 45, and the substituent Y is any one of substituent numbers 1 to 558 in the compound TI.

A tetrazolinone compound in which $X^1$, $X^2$, and $R^L$ are L34 shown in Table 45, and the substituent Y is any one of substituent numbers 1 to 558 in the compound TI.

A tetrazolinone compound in which $X^1$, $X^2$, and $R^L$ are L35 shown in Table 45, and the substituent Y is any one of substituent numbers 1 to 558 in the compound TI.

A tetrazolinone compound in which $X^1$, $X^2$, and $R^L$ are L36 shown in Table 45, and the substituent Y is any one of substituent numbers 1 to 558 in the compound TI.

A tetrazolinone compound in which $X^1$, $X^2$, and $R^L$ are L37 shown in Table 45, and the substituent Y is any one of substituent numbers 1 to 558 in the compound TI.

A tetrazolinone compound in which $X^1$, $X^2$, and $R^L$ are L38 shown in Table 45, and the substituent Y is any one of substituent numbers 1 to 558 in the compound TI.

A tetrazolinone compound in which $X^1$, $X^2$, and $R^L$ are L39 shown in Table 45, and the substituent Y is any one of substituent numbers 1 to 558 in the compound TI.

A tetrazolinone compound in which $X^1$, $X^2$, and $R^L$ are L40 shown in Table 45, and the substituent Y is any one of substituent numbers 1 to 558 in the compound TI.

A tetrazolinone compound in which $X^1$, $X^2$, and $R^L$ are L41 shown in Table 45, and the substituent Y is any one of substituent numbers 1 to 558 in the compound TI.

A tetrazolinone compound in which $X^1$, $X^2$, and $R^L$ are L42 shown in Table 45, and the substituent Y is any one of substituent numbers 1 to 558 in the compound TI.

A tetrazolinone compound in which $X^1$, $X^2$, and $R^L$ are L43 shown in Table 45, and the substituent Y is any one of substituent numbers 1 to 558 in the compound TI.

A tetrazolinone compound in which $X^1$, $X^2$, and $R^L$ are L44 shown in Table 45, and the substituent Y is any one of substituent numbers 1 to 558 in the compound TI.

A tetrazolinone compound in which $X^1$, $X^2$, and $R^L$ are L45 shown in Table 45, and the substituent Y is any one of substituent numbers 1 to 558 in the compound TI.

A tetrazolinone compound in which $X^1$, $X^2$, and $R^L$ are L46 shown in Table 45, and the substituent Y is any one of substituent numbers 1 to 558 in the compound TI.

A tetrazolinone compound in which $X^1$, $X^2$, and $R^L$ are L47 shown in Table 45, and the substituent Y is any one of substituent numbers 1 to 558 in the compound TI.

A tetrazolinone compound in which $X^1$, $X^2$, and $R^L$ are L48 shown in Table 45, and the substituent Y is any one of substituent numbers 1 to 558 in the compound TI.

A tetrazolinone compound in which $X^1$, $X^2$, and $R^L$ are L49 shown in Table 45, and the substituent Y is any one of substituent numbers 1 to 558 in the compound TI.

A tetrazolinone compound in which $X^1$, $X^2$, and $R^L$ are L50 shown in Table 45, and the substituent Y is any one of substituent numbers 1 to 558 in the compound TI.

A tetrazolinone compound in which $X^1$, $X^2$, and $R^L$ are L51 shown in Table 45, and the substituent Y is any one of substituent numbers 1 to 558 in the compound TI.

A tetrazolinone compound in which $X^1$, $X^2$, and $R^L$ are L52 shown in Table 45, and the substituent Y is any one of substituent numbers 1 to 558 in the compound TI.

A tetrazolinone compound in which $X^1$, $X^2$, and $R^L$ are L53 shown in Table 45, and the substituent Y is any one of substituent numbers 1 to 558 in the compound TI.

A tetrazolinone compound in which $X^1$, $X^2$, and $R^L$ are L54 shown in Table 45, and the substituent Y is any one of substituent numbers 1 to 558 in the compound TI.

A tetrazolinone compound in which $X^1$, $X^2$, and $R^L$ are L55 shown in Table 45, and the substituent Y is any one of substituent numbers 1 to 558 in the compound TI.

A tetrazolinone compound in which $X^1$, $X^2$, and $R^L$ are L56 shown in Table 45, and the substituent Y is any one of substituent numbers 1 to 558 in the compound TI.

A tetrazolinone compound in which $X^1$, $X^2$, and $R^L$ are L57 shown in Table 45, and the substituent Y is any one of substituent numbers 1 to 558 in the compound TI.

A tetrazolinone compound in which $X^1$, $X^2$, and $R^L$ are L1 shown in Table 44, and the substituent Y is any one of substituent numbers 1 to 558 in a compound represented by formula (TM) (referred to as the compound TM).

A tetrazolinone compound in which $X^1$, $X^2$, and $R^L$ are L2 shown in Table 44, and the substituent Y is any one of substituent numbers 1 to 558 in the compound TM.

A tetrazolinone compound in which $X^1$, $X^2$, and $R^L$ are L3 shown in Table 44, and the substituent Y is any one of substituent numbers 1 to 558 in the compound TM.

A tetrazolinone compound in which $X^1$, $X^2$, and $R^L$ are L4 shown in Table 44, and the substituent Y is any one of substituent numbers 1 to 558 in the compound TM.

A tetrazolinone compound in which $X^1$, $X^2$, and $R^L$ are L5 shown in Table 44, and the substituent Y is any one of substituent numbers 1 to 558 in the compound TM.

A tetrazolinone compound in which $X^1$, $X^2$, and $R^L$ are L6 shown in Table 44, and the substituent Y is any one of substituent numbers 1 to 558 in the compound TM.

A tetrazolinone compound in which $X^1$, $X^2$, and $R^L$ are L7 shown in Table 44, and the substituent Y is any one of substituent numbers 1 to 558 in the compound TM.

A tetrazolinone compound in which $X^1$, $X^2$, and $R^L$ are L8 shown in Table 44, and the substituent Y is any one of substituent numbers 1 to 558 in the compound TM.

A tetrazolinone compound in which $X^1$, $X^2$, and $R^L$ are L9 shown in Table 44, and the substituent Y is any one of substituent numbers 1 to 558 in the compound TM.

A tetrazolinone compound in which $X^1$, $X^2$, and $R^L$ are L10 shown in Table 44, and the substituent Y is any one of substituent numbers 1 to 558 in the compound TM.

A tetrazolinone compound in which $X^1$, $X^2$, and $R^L$ are L11 shown in Table 44, and the substituent Y is any one of substituent numbers 1 to 558 in the compound TM.

A tetrazolinone compound in which $X^1$, $X^2$, and $R^L$ are L12 shown in Table 44, and the substituent Y is any one of substituent numbers 1 to 558 in the compound TM.

A tetrazolinone compound in which $X^1$, $X^2$, and $R^L$ are L13 shown in Table 44, and the substituent Y is any one of substituent numbers 1 to 558 in the compound TM.

A tetrazolinone compound in which $X^1$, $X^2$, and $R^L$ are L14 shown in Table 44, and the substituent Y is any one of substituent numbers 1 to 558 in the compound TM.

A tetrazolinone compound in which $X^1$, $X^2$, and $R^L$ are L15 shown in Table 44, and the substituent Y is any one of substituent numbers 1 to 558 in the compound TM.

A tetrazolinone compound in which $X^1$, $X^2$, and $R^L$ are L16 shown in Table 44, and the substituent Y is any one of substituent numbers 1 to 558 in the compound TM.

A tetrazolinone compound in which $X^1$, $X^2$, and $R^L$ are L17 shown in Table 44, and the substituent Y is any one of substituent numbers 1 to 558 in the compound TM.

A tetrazolinone compound in which $X^1$, $X^2$, and $R^L$ are L18 shown in Table 44, and the substituent Y is any one of substituent numbers 1 to 558 in the compound TM.

A tetrazolinone compound in which $X^1$, $X^2$, and $R^L$ are L19 shown in Table 44, and the substituent Y is any one of substituent numbers 1 to 558 in the compound TM.

A tetrazolinone compound in which $X^1$, $X^2$, and $R^L$ are L20 shown in Table 44, and the substituent Y is any one of substituent numbers 1 to 558 in the compound TM.

A tetrazolinone compound in which $X^1$, $X^2$, and $R^L$ are L21 shown in Table 44, and the substituent Y is any one of substituent numbers 1 to 558 in the compound TM.

A tetrazolinone compound in which $X^1$, $X^2$, and $R^L$ are L22 shown in Table 44, and the substituent Y is any one of substituent numbers 1 to 558 in the compound TM.

A tetrazolinone compound in which $X^1$, $X^2$, and $R^L$ are L23 shown in Table 44, and the substituent Y is any one of substituent numbers 1 to 558 in the compound TM.

A tetrazolinone compound in which $X^1$, $X^2$, and $R^L$ are L24 shown in Table 44, and the substituent Y is any one of substituent numbers 1 to 558 in the compound TM.

A tetrazolinone compound in which $X^1$, $X^2$, and $R^L$ are L25 shown in Table 44, and the substituent Y is any one of substituent numbers 1 to 558 in the compound TM.

A tetrazolinone compound in which $X^1$, $X^2$, and $R^L$ are L26 shown in Table 44, and the substituent Y is any one of substituent numbers 1 to 558 in the compound TM.

A tetrazolinone compound in which $X^1$, $X^2$, and $R^L$ are L27 shown in Table 44, and the substituent Y is any one of substituent numbers 1 to 558 in the compound TM.

A tetrazolinone compound in which $X^1$, $X^2$, and $R^L$ are L28 shown in Table 44, and the substituent Y is any one of substituent numbers 1 to 558 in the compound TM.

A tetrazolinone compound in which $X^1$, $X^2$, and $R^L$ are L29 shown in Table 44, and the substituent Y is any one of substituent numbers 1 to 558 in the compound TM.

A tetrazolinone compound in which $X^1$, $X^2$, and $R^L$ are L30 shown in Table 45, and the substituent Y is any one of substituent numbers 1 to 558 in the compound TM.

A tetrazolinone compound in which $X^1$, $X^2$, and $R^L$ are L31 shown in Table 45, and the substituent Y is any one of substituent numbers 1 to 558 in the compound TM.

A tetrazolinone compound in which $X^1$, $X^2$, and $R^L$ are L32 shown in Table 45, and the substituent Y is any one of substituent numbers 1 to 558 in the compound TM.

A tetrazolinone compound in which $X^1$, $X^2$, and $R^L$ are L33 shown in Table 45, and the substituent Y is any one of substituent numbers 1 to 558 in the compound TM.

A tetrazolinone compound in which $X^1$, $X^2$, and $R^L$ are L34 shown in Table 45, and the substituent Y is any one of substituent numbers 1 to 558 in the compound TM.

A tetrazolinone compound in which $X^1$, $X^2$, and $R^L$ are L35 shown in Table 45, and the substituent Y is any one of substituent numbers 1 to 558 in the compound TM.

A tetrazolinone compound in which $X^1$, $X^2$, and $R^L$ are L36 shown in Table 45, and the substituent Y is any one of substituent numbers 1 to 558 in the compound TM.

A tetrazolinone compound in which $X^1$, $X^2$, and $R^L$ are L37 shown in Table 45, and the substituent Y is any one of substituent numbers 1 to 558 in the compound TM.

A tetrazolinone compound in which $X^1$, $X^2$, and $R^L$ are L38 shown in Table 45, and the substituent Y is any one of substituent numbers 1 to 558 in the compound TM.

A tetrazolinone compound in which $X^1$, $X^2$, and $R^L$ are L39 shown in Table 45, and the substituent Y is any one of substituent numbers 1 to 558 in the compound TM.

A tetrazolinone compound in which $X^1$, $X^2$, and $R^L$ are L40 shown in Table 45, and the substituent Y is any one of substituent numbers 1 to 558 in the compound TM.

A tetrazolinone compound in which $X^1$, $X^2$, and $R^L$ are L41 shown in Table 45, and the substituent Y is any one of substituent numbers 1 to 558 in the compound TM.

A tetrazolinone compound in which $X^1$, $X^2$, and $R^L$ are L42 shown in Table 45, and the substituent Y is any one of substituent numbers 1 to 558 in the compound TM.

A tetrazolinone compound in which $X^1$, $X^2$, and $R^L$ are L43 shown in Table 45, and the substituent Y is any one of substituent numbers 1 to 558 in the compound TM.

A tetrazolinone compound in which $X^1$, $X^2$, and $R^L$ are L44 shown in Table 45, and the substituent Y is any one of substituent numbers 1 to 558 in the compound TM.

A tetrazolinone compound in which $X^1$, $X^2$, and $R^L$ are L45 shown in Table 45, and the substituent Y is any one of substituent numbers 1 to 558 in the compound TM.

A tetrazolinone compound in which $X^1$, $X^2$, and $R^L$ are L46 shown in Table 45, and the substituent Y is any one of substituent numbers 1 to 558 in the compound TM.

A tetrazolinone compound in which $X^1$, $X^2$, and $R^L$ are L47 shown in Table 45, and the substituent Y is any one of substituent numbers 1 to 558 in the compound TM.

A tetrazolinone compound in which $X^1$, $X^2$, and $R^L$ are L48 shown in Table 45, and the substituent Y is any one of substituent numbers 1 to 558 in the compound TM.

A tetrazolinone compound in which $X^1$, $X^2$, and $R^L$ are L49 shown in Table 45, and the substituent Y is any one of substituent numbers 1 to 558 in the compound TM.

A tetrazolinone compound in which $X^1$, $X^2$, and $R^L$ are L50 shown in Table 45, and the substituent Y is any one of substituent numbers 1 to 558 in the compound TM.

A tetrazolinone compound in which $X^1$, $X^2$, and $R^L$ are L51 shown in Table 45, and the substituent Y is any one of substituent numbers 1 to 558 in the compound TM.

A tetrazolinone compound in which $X^1$, $X^2$, and $R^L$ are L52 shown in Table 45, and the substituent Y is any one of substituent numbers 1 to 558 in the compound TM.

A tetrazolinone compound in which $X^1$, $X^2$, and $R^L$ are L53 shown in Table 45, and the substituent Y is any one of substituent numbers 1 to 558 in the compound TM.

A tetrazolinone compound in which $X^1$, $X^2$, and $R^L$ are L54 shown in Table 45, and the substituent Y is any one of substituent numbers 1 to 558 in the compound TM.

A tetrazolinone compound in which $X^1$, $X^2$, and $R^L$ are L55 shown in Table 45, and the substituent Y is any one of substituent numbers 1 to 558 in the compound TM.

A tetrazolinone compound in which $X^1$, $X^2$, and $R^L$ are L56 shown in Table 45, and the substituent Y is any one of substituent numbers 1 to 558 in the compound TM.

A tetrazolinone compound in which $X^1$, $X^2$, and $R^L$ are L57 shown in Table 45, and the substituent Y is any one of substituent numbers 1 to 558 in the compound TM.

A tetrazolinone compound in which $X^1$, $X^2$, and $R^L$ are L1 shown in Table 44, and the substituent Y is any one of substituent numbers 1 to 558 in a compound represented by formula (TE) (referred to as the compound TE).

A tetrazolinone compound in which $X^1$, $X^2$, and $R^L$ are L2 shown in Table 44, and the substituent Y is any one of substituent numbers 1 to 558 in the compound TE.

A tetrazolinone compound in which $X^1$, $X^2$, and $R^L$ are L3 shown in Table 44, and the substituent Y is any one of substituent numbers 1 to 558 in the compound TE.

A tetrazolinone compound in which $X^1$, $X^2$, and $R^L$ are L4 shown in Table 44, and the substituent Y is any one of substituent numbers 1 to 558 in the compound TE.

A tetrazolinone compound in which $X^1$, $X^2$, and $R^L$ are L5 shown in Table 44, and the substituent Y is any one of substituent numbers 1 to 558 in the compound TE.

A tetrazolinone compound in which $X^1$, $X^2$, and $R^L$ are L6 shown in Table 44, and the substituent Y is any one of substituent numbers 1 to 558 in the compound TE.

A tetrazolinone compound in which $X^1$, $X^2$, and $R^L$ are L7 shown in Table 44, and the substituent Y is any one of substituent numbers 1 to 558 in the compound TE.

A tetrazolinone compound in which $X^1$, $X^2$, and $R^L$ are L8 shown in Table 44, and the substituent Y is any one of substituent numbers 1 to 558 in the compound TE.

A tetrazolinone compound in which $X^1$, $X^2$, and $R^L$ are L9 shown in Table 44, and the substituent Y is any one of substituent numbers 1 to 558 in the compound TE.

A tetrazolinone compound in which $X^1$, $X^2$, and $R^L$ are L10 shown in Table 44, and the substituent Y is any one of substituent numbers 1 to 558 in the compound TE.

A tetrazolinone compound in which $X^1$, $X^2$, and $R^L$ are L11 shown in Table 44, and the substituent Y is any one of substituent numbers 1 to 558 in the compound TE.

A tetrazolinone compound in which $X^1$, $X^2$, and $R^L$ are L12 shown in Table 44, and the substituent Y is any one of substituent numbers 1 to 558 in the compound TE.

A tetrazolinone compound in which $X^1$, $X^2$, and $R^L$ are L13 shown in Table 44, and the substituent Y is any one of substituent numbers 1 to 558 in the compound TE.

A tetrazolinone compound in which $X^1$, $X^2$, and $R^L$ are L14 shown in Table 44, and the substituent Y is any one of substituent numbers 1 to 558 in the compound TE.

A tetrazolinone compound in which $X^1$, $X^2$, and $R^L$ are L15 shown in Table 44, and the substituent Y is any one of substituent numbers 1 to 558 in the compound TE.

A tetrazolinone compound in which $X^1$, $X^2$, and $R^L$ are L16 shown in Table 44, and the substituent Y is any one of substituent numbers 1 to 558 in the compound TE.

A tetrazolinone compound in which $X^1$, $X^2$, and $R^L$ are L17 shown in Table 44, and the substituent Y is any one of substituent numbers 1 to 558 in the compound TE.

A tetrazolinone compound in which $X^1$, $X^2$, and $R^L$ are L18 shown in Table 44, and the substituent Y is any one of substituent numbers 1 to 558 in the compound TE.

A tetrazolinone compound in which $X^1$, $X^2$, and $R^L$ are L19 shown in Table 44, and the substituent Y is any one of substituent numbers 1 to 558 in the compound TE.

A tetrazolinone compound in which $X^1$, $X^2$, and $R^L$ are L20 shown in Table 44, and the substituent Y is any one of substituent numbers 1 to 558 in the compound TE.

A tetrazolinone compound in which $X^1$, $X^2$, and $R^L$ are L21 shown in Table 44, and the substituent Y is any one of substituent numbers 1 to 558 in the compound TE.

A tetrazolinone compound in which $X^1$, $X^2$, and $R^L$ are L22 shown in Table 44, and the substituent Y is any one of substituent numbers 1 to 558 in the compound TE.

A tetrazolinone compound in which $X^1$, $X^2$, and $R^L$ are L23 shown in Table 44, and the substituent Y is any one of substituent numbers 1 to 558 in the compound TE.

A tetrazolinone compound in which $X^1$, $X^2$, and $R^L$ are L24 shown in Table 44, and the substituent Y is any one of substituent numbers 1 to 558 in the compound TE.

A tetrazolinone compound in which $X^1$, $X^2$, and $R^L$ are L25 shown in Table 44, and the substituent Y is any one of substituent numbers 1 to 558 in the compound TE.

A tetrazolinone compound in which $X^1$, $X^2$, and $R^L$ are L26 shown in Table 44, and the substituent Y is any one of substituent numbers 1 to 558 in the compound TE.

A tetrazolinone compound in which $X^1$, $X^2$, and $R^L$ are L27 shown in Table 44, and the substituent Y is any one of substituent numbers 1 to 558 in the compound TE.

A tetrazolinone compound in which $X^1$, $X^2$, and $R^L$ are L28 shown in Table 44, and the substituent Y is any one of substituent numbers 1 to 558 in the compound TE.

A tetrazolinone compound in which $X^1$, $X^2$, and $R^L$ are L29 shown in Table 44, and the substituent Y is any one of substituent numbers 1 to 558 in the compound TE.

A tetrazolinone compound in which $X^1$, $X^2$, and $R^L$ are L30 shown in Table 45, and the substituent Y is any one of substituent numbers 1 to 558 in the compound TE.

A tetrazolinone compound in which $X^1$, $X^2$, and $R^L$ are L31 shown in Table 45, and the substituent Y is any one of substituent numbers 1 to 558 in the compound TE.

A tetrazolinone compound in which $X^1$, $X^2$, and $R^L$ are L32 shown in Table 45, and the substituent Y is any one of substituent numbers 1 to 558 in the compound TE.

A tetrazolinone compound in which $X^1$, $X^2$, and $R^L$ are L33 shown in Table 45, and the substituent Y is any one of substituent numbers 1 to 558 in the compound TE.

A tetrazolinone compound in which $X^1$, $X^2$, and $R^L$ are L34 shown in Table 45, and the substituent Y is any one of substituent numbers 1 to 558 in the compound TE.

A tetrazolinone compound in which $X^1$, $X^2$, and $R^L$ are L35 shown in Table 45, and the substituent Y is any one of substituent numbers 1 to 558 in the compound TE.

A tetrazolinone compound in which $X^1$, $X^2$, and $R^L$ are L36 shown in Table 45, and the substituent Y is any one of substituent numbers 1 to 558 in the compound TE.

A tetrazolinone compound in which $X^1$, $X^2$, and $R^L$ are L37 shown in Table 45, and the substituent Y is any one of substituent numbers 1 to 558 in the compound TE.

A tetrazolinone compound in which $X^1$, $X^2$, and $R^L$ are L38 shown in Table 45, and the substituent Y is any one of substituent numbers 1 to 558 in the compound TE.

A tetrazolinone compound in which $X^1$, $X^2$, and $R^L$ are L39 shown in Table 45, and the substituent Y is any one of substituent numbers 1 to 558 in the compound TE.

A tetrazolinone compound in which $X^1$, $X^2$, and $R^L$ are L40 shown in Table 45, and the substituent Y is any one of substituent numbers 1 to 558 in the compound TE.

A tetrazolinone compound in which $X^1$, $X^2$, and $R^L$ are L41 shown in Table 45, and the substituent Y is any one of substituent numbers 1 to 558 in the compound TE.

A tetrazolinone compound in which $X^1$, $X^2$, and $R^L$ are L42 shown in Table 45, and the substituent Y is any one of substituent numbers 1 to 558 in the compound TE.

A tetrazolinone compound in which $X^1$, $X^2$, and $R^L$ are L43 shown in Table 45, and the substituent Y is any one of substituent numbers 1 to 558 in the compound TE.

A tetrazolinone compound in which $X^1$, $X^2$, and $R^L$ are L44 shown in Table 45, and the substituent Y is any one of substituent numbers 1 to 558 in the compound TE.

A tetrazolinone compound in which $X^1$, $X^2$, and $R^L$ are L45 shown in Table 45, and the substituent Y is any one of substituent numbers 1 to 558 in the compound TE.

A tetrazolinone compound in which $X^1$, $X^2$, and $R^L$ are L46 shown in Table 45, and the substituent Y is any one of substituent numbers 1 to 558 in the compound TE.

A tetrazolinone compound in which $X^1$, $X^2$, and $R^L$ are L47 shown in Table 45, and the substituent Y is any one of substituent numbers 1 to 558 in the compound TE.

A tetrazolinone compound in which $X^1$, $X^2$, and $R^L$ are L48 shown in Table 45, and the substituent Y is any one of substituent numbers 1 to 558 in the compound TE.

A tetrazolinone compound in which $X^1$, $X^2$, and $R^L$ are L49 shown in Table 45, and the substituent Y is any one of substituent numbers 1 to 558 in the compound TE.

A tetrazolinone compound in which $X^1$, $X^2$, and $R^L$ are L50 shown in Table 45, and the substituent Y is any one of substituent numbers 1 to 558 in the compound TE.

A tetrazolinone compound in which $X^1$, $X^2$, and $R^L$ are L51 shown in Table 45, and the substituent Y is any one of substituent numbers 1 to 558 in the compound TE.

A tetrazolinone compound in which $X^1$, $X^2$, and $R^L$ are L52 shown in Table 45, and the substituent Y is any one of substituent numbers 1 to 558 in the compound TE.

A tetrazolinone compound in which $X^1$, $X^2$, and $R^L$ are L53 shown in Table 45, and the substituent Y is any one of substituent numbers 1 to 558 in the compound TE.

A tetrazolinone compound in which $X^1$, $X^2$, and $R^L$ are L54 shown in Table 45, and the substituent Y is any one of substituent numbers 1 to 558 in the compound TE.

A tetrazolinone compound in which $X^1$, $X^2$, and $R^L$ are L55 shown in Table 45, and the substituent Y is any one of substituent numbers 1 to 558 in the compound TE.

A tetrazolinone compound in which $X^1$, $X^2$, and $R^L$ are L56 shown in Table 45, and the substituent Y is any one of substituent numbers 1 to 558 in the compound TE.

A tetrazolinone compound in which $X^1$, $X^2$, and $R^L$ are L57 shown in Table 45, and the substituent Y is any one of substituent numbers 1 to 558 in the compound TE.

A tetrazolinone compound in which $X^1$, $X^2$, and $R^L$ are L1 shown in Table 44, and the substituent Y is any one of substituent numbers 1 to 558 in a compound represented by formula (TV) (referred to as the compound TV).

A tetrazolinone compound in which $X^1$, $X^2$, and $R^L$ are L2 shown in Table 44, and the substituent Y is any one of substituent numbers 1 to 558 in the compound TV.

A tetrazolinone compound in which $X^1$, $X^2$, and $R^L$ are L3 shown in Table 44, and the substituent Y is any one of substituent numbers 1 to 558 in the compound TV.

A tetrazolinone compound in which $X^1$, $X^2$, and $R^L$ are L4 shown in Table 44, and the substituent Y is any one of substituent numbers 1 to 558 in the compound TV.

A tetrazolinone compound in which $X^1$, $X^2$, and $R^L$ are L5 shown in Table 44, and the substituent Y is any one of substituent numbers 1 to 558 in the compound TV.

A tetrazolinone compound in which $X^1$, $X^2$, and $R^L$ are L6 shown in Table 44, and the substituent Y is any one of substituent numbers 1 to 558 in the compound TV.

A tetrazolinone compound in which $X^1$, $X^2$, and $R^L$ are L7 shown in Table 44, and the substituent Y is any one of substituent numbers 1 to 558 in the compound TV.

A tetrazolinone compound in which $X^1$, $X^2$, and $R^L$ are L8 shown in Table 44, and the substituent Y is any one of substituent numbers 1 to 558 in the compound TV.

A tetrazolinone compound in which $X^1$, $X^2$, and $R^L$ are L9 shown in Table 44, and the substituent Y is any one of substituent numbers 1 to 558 in the compound TV.

A tetrazolinone compound in which $X^1$, $X^2$, and $R^L$ are L10 shown in Table 44, and the substituent Y is any one of substituent numbers 1 to 558 in the compound TV.

A tetrazolinone compound in which $X^1$, $X^2$, and $R^L$ are L11 shown in Table 44, and the substituent Y is any one of substituent numbers 1 to 558 in the compound TV.

A tetrazolinone compound in which $X^1$, $X^2$, and $R^L$ are L12 shown in Table 44, and the substituent Y is any one of substituent numbers 1 to 558 in the compound TV.

A tetrazolinone compound in which $X^1$, $X^2$, and $R^L$ are L13 shown in Table 44, and the substituent Y is any one of substituent numbers 1 to 558 in the compound TV.

A tetrazolinone compound in which $X^1$, $X^2$, and $R^L$ are L14 shown in Table 44, and the substituent Y is any one of substituent numbers 1 to 558 in the compound TV.

A tetrazolinone compound in which $X^1$, $X^2$, and $R^L$ are L15 shown in Table 44, and the substituent Y is any one of substituent numbers 1 to 558 in the compound TV.

A tetrazolinone compound in which $X^1$, $X^2$, and $R^L$ are L16 shown in Table 44, and the substituent Y is any one of substituent numbers 1 to 558 in the compound TV.

A tetrazolinone compound in which $X^1$, $X^2$, and $R^L$ are L17 shown in Table 44, and the substituent Y is any one of substituent numbers 1 to 558 in the compound TV.

A tetrazolinone compound in which $X^1$, $X^2$, and $R^L$ are L18 shown in Table 44, and the substituent Y is any one of substituent numbers 1 to 558 in the compound TV.

A tetrazolinone compound in which $X^1$, $X^2$, and $R^L$ are L19 shown in Table 44, and the substituent Y is any one of substituent numbers 1 to 558 in the compound TV.

A tetrazolinone compound in which $X^1$, $X^2$, and $R^L$ are L20 shown in Table 44, and the substituent Y is any one of substituent numbers 1 to 558 in the compound TV.

A tetrazolinone compound in which $X^1$, $X^2$, and $R^L$ are L21 shown in Table 44, and the substituent Y is any one of substituent numbers 1 to 558 in the compound TV.

A tetrazolinone compound in which $X^1$, $X^2$, and $R^L$ are L22 shown in Table 44, and the substituent Y is any one of substituent numbers 1 to 558 in the compound TV.

A tetrazolinone compound in which $X^1$, $X^2$, and $R^L$ are L23 shown in Table 44, and the substituent Y is any one of substituent numbers 1 to 558 in the compound TV.

A tetrazolinone compound in which $X^1$, $X^2$, and $R^L$ are L24 shown in Table 44, and the substituent Y is any one of substituent numbers 1 to 558 in the compound TV.

A tetrazolinone compound in which $X^1$, $X^2$, and $R^L$ are L25 shown in Table 44, and the substituent Y is any one of substituent numbers 1 to 558 in the compound TV.

A tetrazolinone compound in which $X^1$, $X^2$, and $R^L$ are L26 shown in Table 44, and the substituent Y is any one of substituent numbers 1 to 558 in the compound TV.

A tetrazolinone compound in which $X^1$, $X^2$, and $R^L$ are L27 shown in Table 44, and the substituent Y is any one of substituent numbers 1 to 558 in the compound TV.

A tetrazolinone compound in which $X^1$, $X^2$, and $R^L$ are L28 shown in Table 44, and the substituent Y is any one of substituent numbers 1 to 558 in the compound TV.

A tetrazolinone compound in which $X^1$, $X^2$, and $R^L$ are L29 shown in Table 44, and the substituent Y is any one of substituent numbers 1 to 558 in the compound TV.

A tetrazolinone compound in which $X^1$, $X^2$, and $R^L$ are L30 shown in Table 45, and the substituent Y is any one of substituent numbers 1 to 558 in the compound TV.

A tetrazolinone compound in which $X^1$, $X^2$, and $R^L$ are L31 shown in Table 45, and the substituent Y is any one of substituent numbers 1 to 558 in the compound TV.

A tetrazolinone compound in which $X^1$, $X^2$, and $R^L$ are L32 shown in Table 45, and the substituent Y is any one of substituent numbers 1 to 558 in the compound TV.

A tetrazolinone compound in which $X^1$, $X^2$, and $R^L$ are L33 shown in Table 45, and the substituent Y is any one of substituent numbers 1 to 558 in the compound TV.

A tetrazolinone compound in which $X^1$, $X^2$, and $R^L$ are L34 shown in Table 45, and the substituent Y is any one of substituent numbers 1 to 558 in the compound TV.

A tetrazolinone compound in which $X^1$, $X^2$, and $R^L$ are L35 shown in Table 45, and the substituent Y is any one of substituent numbers 1 to 558 in the compound TV.

A tetrazolinone compound in which $X^1$, $X^2$, and $R^L$ are L36 shown in Table 45, and the substituent Y is any one of substituent numbers 1 to 558 in the compound TV.

A tetrazolinone compound in which $X^1$, $X^2$, and $R^L$ are L37 shown in Table 45, and the substituent Y is any one of substituent numbers 1 to 558 in the compound TV.

A tetrazolinone compound in which $X^1$, $X^2$, and $R^L$ are L38 shown in Table 45, and the substituent Y is any one of substituent numbers 1 to 558 in the compound TV.

A tetrazolinone compound in which $X^1$, $X^2$, and $R^L$ are L39 shown in Table 45, and the substituent Y is any one of substituent numbers 1 to 558 in the compound TV.

A tetrazolinone compound in which $X^1$, $X^2$, and $R^L$ are L40 shown in Table 45, and the substituent Y is any one of substituent numbers 1 to 558 in the compound TV.

A tetrazolinone compound in which $X^1$, $X^2$, and $R^L$ are L41 shown in Table 45, and the substituent Y is any one of substituent numbers 1 to 558 in the compound TV.

A tetrazolinone compound in which $X^1$, $X^2$, and $R^L$ are L42 shown in Table 45, and the substituent Y is any one of substituent numbers 1 to 558 in the compound TV.

A tetrazolinone compound in which $X^1$, $X^2$, and $R^L$ are L43 shown in Table 45, and the substituent Y is any one of substituent numbers 1 to 558 in the compound TV.

A tetrazolinone compound in which $X^1$, $X^2$, and $R^L$ are L44 shown in Table 37, and the substituent Y is any one of substituent numbers 1 to 558 in the compound TV.

A tetrazolinone compound in which $X^1$, $X^2$, and $R^L$ are L45 shown in Table 45, and the substituent Y is any one of substituent numbers 1 to 558 in the compound TV.

A tetrazolinone compound in which $X^1$, $X^2$, and $R^L$ are L46 shown in Table 45, and the substituent Y is any one of substituent numbers 1 to 558 in the compound TV.

A tetrazolinone compound in which $X^1$, $X^2$, and $R^L$ are L47 shown in Table 45, and the substituent Y is any one of substituent numbers 1 to 558 in the compound TV.

A tetrazolinone compound in which $X^1$, $X^2$, and $R^L$ are L48 shown in Table 45, and the substituent Y is any one of substituent numbers 1 to 558 in the compound TV.

A tetrazolinone compound in which $X^1$, $X^2$, and $R^L$ are L49 shown in Table 45, and the substituent Y is any one of substituent numbers 1 to 558 in the compound TV.

A tetrazolinone compound in which $X^1$, $X^2$, and $R^L$ are L50 shown in Table 45, and the substituent Y is any one of substituent numbers 1 to 558 in the compound TV.

A tetrazolinone compound in which $X^1$, $X^2$, and $R^L$ are L51 shown in Table 45, and the substituent Y is any one of substituent numbers 1 to 558 in the compound TV.

A tetrazolinone compound in which $X^1$, $X^2$, and $R^L$ are L52 shown in Table 45, and the substituent Y is any one of substituent numbers 1 to 558 in the compound TV.

A tetrazolinone compound in which $X^1$, $X^2$, and $R^L$ are L53 shown in Table 45, and the substituent Y is any one of substituent numbers 1 to 558 in the compound TV.

A tetrazolinone compound in which $X^1$, $X^2$, and $R^L$ are L54 shown in Table 45, and the substituent Y is any one of substituent numbers 1 to 558 in the compound TV.

A tetrazolinone compound in which $X^1$, $X^2$, and $R^L$ are L55 shown in Table 45, and the substituent Y is any one of substituent numbers 1 to 558 in the compound TV.

A tetrazolinone compound in which $X^1$, $X^2$, and $R^L$ are L56 shown in Table 45, and the substituent Y is any one of substituent numbers 1 to 558 in the compound TV.

A tetrazolinone compound in which $X^1$, $X^2$, and $R^L$ are L57 shown in Table 45, and the substituent Y is any one of substituent numbers 1 to 558 in the compound TV.

A tetrazolinone compound in which $X^1$, $X^2$, and $R^L$ are L1 shown in Table 44, and the substituent Y is any one of substituent numbers 1 to 558 in a compound represented by formula (TCY) (referred to as the compound TCY).

A tetrazolinone compound in which $X^1$, $X^2$, and $R^L$ are L2 shown in Table 44, and the substituent Y is any one of substituent numbers 1 to 558 in the compound TCY.

A tetrazolinone compound in which $X^1$, $X^2$, and $R^L$ are L3 shown in Table 44, and the substituent Y is any one of substituent numbers 1 to 558 in the compound TCY.

A tetrazolinone compound in which $X^1$, $X^2$, and $R^L$ are L4 shown in Table 44, and the substituent Y is any one of substituent numbers 1 to 558 in the compound TCY.

A tetrazolinone compound in which $X^1$, $X^2$, and $R^L$ are L5 shown in Table 44, and the substituent Y is any one of substituent numbers 1 to 558 in the compound TCY.

A tetrazolinone compound in which $X^1$, $X^2$, and $R^L$ are L6 shown in Table 44, and the substituent Y is any one of substituent numbers 1 to 558 in the compound TCY.

A tetrazolinone compound in which $X^1$, $X^2$, and $R^L$ are L7 shown in Table 44, and the substituent Y is any one of substituent numbers 1 to 558 in the compound TCY.

A tetrazolinone compound in which $X^1$, $X^2$, and $R^L$ are L8 shown in Table 44, and the substituent Y is any one of substituent numbers 1 to 558 in the compound TCY.

A tetrazolinone compound in which $X^1$, $X^2$, and $R^L$ are L9 shown in Table 44, and the substituent Y is any one of substituent numbers 1 to 558 in the compound TCY.

A tetrazolinone compound in which $X^1$, $X^2$, and $R^L$ are L10 shown in Table 44, and the substituent Y is any one of substituent numbers 1 to 558 in the compound TCY.

A tetrazolinone compound in which $X^1$, $X^2$, and $R^L$ are L11 shown in Table 36, and the substituent Y is any one of substituent numbers 1 to 558 in the compound TCY.

A tetrazolinone compound in which $X^1$, $X^2$, and $R^L$ are L12 shown in Table 44, and the substituent Y is any one of substituent numbers 1 to 558 in the compound TCY.

A tetrazolinone compound in which $X^1$, $X^2$, and $R^L$ are L13 shown in Table 44, and the substituent Y is any one of substituent numbers 1 to 558 in the compound TCY.

A tetrazolinone compound in which $X^1$, $X^2$, and $R^L$ are L14 shown in Table 44, and the substituent Y is any one of substituent numbers 1 to 558 in the compound TCY.

A tetrazolinone compound in which $X^1$, $X^2$, and $R^L$ are L15 shown in Table 44, and the substituent Y is any one of substituent numbers 1 to 558 in the compound TCY.

A tetrazolinone compound in which $X^1$, $X^2$, and $R^L$ are L16 shown in Table 44, and the substituent Y is any one of substituent numbers 1 to 558 in the compound TCY.

A tetrazolinone compound in which $X^1$, $X^2$, and $R^L$ are L17 shown in Table 44, and the substituent Y is any one of substituent numbers 1 to 558 in the compound TCY.

A tetrazolinone compound in which $X^1$, $X^2$, and $R^L$ are L18 shown in Table 44, and the substituent Y is any one of substituent numbers 1 to 558 in the compound TCY.

A tetrazolinone compound in which $X^1$, $X^2$, and $R^L$ are L19 shown in Table 44, and the substituent Y is any one of substituent numbers 1 to 558 in the compound TCY.

A tetrazolinone compound in which $X^1$, $X^2$, and $R^L$ are L20 shown in Table 44, and the substituent Y is any one of substituent numbers 1 to 558 in the compound TCY.

A tetrazolinone compound in which $X^1$, $X^2$, and $R^L$ are L21 shown in Table 44, and the substituent Y is any one of substituent numbers 1 to 558 in the compound TCY.

A tetrazolinone compound in which $X^1$, $X^2$, and $R^L$ are L22 shown in Table 44, and the substituent Y is any one of substituent numbers 1 to 558 in the compound TCY.

A tetrazolinone compound in which $X^1$, $X^2$, and $R^L$ are L23 shown in Table 44, and the substituent Y is any one of substituent numbers 1 to 558 in the compound TCY.

A tetrazolinone compound in which $X^1$, $X^2$, and $R^L$ are L24 shown in Table 44, and the substituent Y is any one of substituent numbers 1 to 558 in the compound TCY.

A tetrazolinone compound in which $X^1$, $X^2$, and $R^L$ are L25 shown in Table 44, and the substituent Y is any one of substituent numbers 1 to 558 in the compound TCY.

A tetrazolinone compound in which $X^1$, $X^2$, and $R^L$ are L26 shown in Table 44, and the substituent Y is any one of substituent numbers 1 to 558 in the compound TCY.

A tetrazolinone compound in which $X^1$, $X^2$, and $R^L$ are L27 shown in Table 44, and the substituent Y is any one of substituent numbers 1 to 558 in the compound TCY.

A tetrazolinone compound in which $X^1$, $X^2$, and $R^L$ are L28 shown in Table 44, and the substituent Y is any one of substituent numbers 1 to 558 in the compound TCY.

A tetrazolinone compound in which $X^1$, $X^2$, and $R^L$ are L29 shown in Table 44, and the substituent Y is any one of substituent numbers 1 to 558 in the compound TCY.

A tetrazolinone compound in which $X^1$, $X^2$, and $R^L$ are L30 shown in Table 45, and the substituent Y is any one of substituent numbers 1 to 558 in the compound TCY.

A tetrazolinone compound in which $X^1$, $X^2$, and $R^L$ are L31 shown in Table 45, and the substituent Y is any one of substituent numbers 1 to 558 in the compound TCY.

A tetrazolinone compound in which $X^1$, $X^2$, and $R^L$ are L32 shown in Table 45, and the substituent Y is any one of substituent numbers 1 to 558 in the compound TCY.

A tetrazolinone compound in which $X^1$, $X^2$, and $R^L$ are L33 shown in Table 45, and the substituent Y is any one of substituent numbers 1 to 558 in the compound TCY.

A tetrazolinone compound in which $X^1$, $X^2$, and $R^L$ are L34 shown in Table 45, and the substituent Y is any one of substituent numbers 1 to 558 in the compound TCY.

A tetrazolinone compound in which $X^1$, $X^2$, and $R^L$ are L35 shown in Table 45, and the substituent Y is any one of substituent numbers 1 to 558 in the compound TCY.

A tetrazolinone compound in which $X^1$, $X^2$, and $R^L$ are L36 shown in Table 45, and the substituent Y is any one of substituent numbers 1 to 558 in the compound TCY.

A tetrazolinone compound in which $X^1$, $X^2$, and $R^L$ are L37 shown in Table 45, and the substituent Y is any one of substituent numbers 1 to 558 in the compound TCY.

A tetrazolinone compound in which $X^1$, $X^2$, and $R^L$ are L38 shown in Table 45, and the substituent Y is any one of substituent numbers 1 to 558 in the compound TCY.

A tetrazolinone compound in which $X^1$, $X^2$, and $R^L$ are L39 shown in Table 45, and the substituent Y is any one of substituent numbers 1 to 558 in the compound TCY.

A tetrazolinone compound in which $X^1$, $X^2$, and $R^L$ are L40 shown in Table 45, and the substituent Y is any one of substituent numbers 1 to 558 in the compound TCY.

A tetrazolinone compound in which $X^1$, $X^2$, and $R^L$ are L41 shown in Table 45, and the substituent Y is any one of substituent numbers 1 to 558 in the compound TCY.

A tetrazolinone compound in which $X^1$, $X^2$, and $R^L$ are L42 shown in Table 45, and the substituent Y is any one of substituent numbers 1 to 558 in the compound TCY.

A tetrazolinone compound in which $X^1$, $X^2$, and $R^L$ are L43 shown in Table 45, and the substituent Y is any one of substituent numbers 1 to 558 in the compound TCY.

A tetrazolinone compound in which $X^1$, $X^2$, and $R^L$ are L44 shown in Table 45, and the substituent Y is any one of substituent numbers 1 to 558 in the compound TCY.

A tetrazolinone compound in which $X^1$, $X^2$, and $R^L$ are L45 shown in Table 45, and the substituent Y is any one of substituent numbers 1 to 558 in the compound TCY.

A tetrazolinone compound in which $X^1$, $X^2$, and $R^L$ are L46 shown in Table 45, and the substituent Y is any one of substituent numbers 1 to 558 in the compound TCY.

A tetrazolinone compound in which $X^1$, $X^2$, and $R^L$ are L47 shown in Table 45, and the substituent Y is any one of substituent numbers 1 to 558 in the compound TCY.

A tetrazolinone compound in which $X^1$, $X^2$, and $R^L$ are L48 shown in Table 45, and the substituent Y is any one of substituent numbers 1 to 558 in the compound TCY.

A tetrazolinone compound in which $X^1$, $X^2$, and $R^L$ are L49 shown in Table 45, and the substituent Y is any one of substituent numbers 1 to 558 in the compound TCY.

A tetrazolinone compound in which $X^1$, $X^2$, and $R^L$ are L50 shown in Table 45, and the substituent Y is any one of substituent numbers 1 to 558 in the compound TCY.

A tetrazolinone compound in which $X^1$, $X^2$, and $R^L$ are L51 shown in Table 45, and the substituent Y is any one of substituent numbers 1 to 558 in the compound TCY.

A tetrazolinone compound in which $X^1$, $X^2$, and $R^L$ are L52 shown in Table 45, and the substituent Y is any one of substituent numbers 1 to 558 in the compound TCY.

A tetrazolinone compound in which $X^1$, $X^2$, and $R^L$ are L53 shown in Table 45, and the substituent Y is any one of substituent numbers 1 to 558 in the compound TCY.

A tetrazolinone compound in which $X^1$, $X^2$, and $R^L$ are L54 shown in Table 45, and the substituent Y is any one of substituent numbers 1 to 558 in the compound TCY.

A tetrazolinone compound in which $X^1$, $X^2$, and $R^L$ are L55 shown in Table 45, and the substituent Y is any one of substituent numbers 1 to 558 in the compound TCY.

A tetrazolinone compound in which $X^1$, $X^2$, and $R^L$ are L56 shown in Table 45, and the substituent Y is any one of substituent numbers 1 to 558 in the compound TCY.

A tetrazolinone compound in which $X^1$, $X^2$, and $R^L$ are L57 shown in Table 45, and the substituent Y is any one of substituent numbers 1 to 558 in the compound TCY.

A tetrazolinone compound in which $X^1$, $X^2$, and $R^L$ are L1 shown in Table 44, and the substituent Y is any one of substituent numbers 1 to 558 in a compound represented by formula (TMO) (referred to as the compound TMO).

A tetrazolinone compound in which $X^1$, $X^2$, and $R^L$ are L2 shown in Table 44, and the substituent Y is any one of substituent numbers 1 to 558 in the compound TMO.

A tetrazolinone compound in which $X^1$, $X^2$, and $R^L$ are L3 shown in Table 44, and the substituent Y is any one of substituent numbers 1 to 558 in the compound TMO.

A tetrazolinone compound in which $X^1$, $X^2$, and $R^L$ are L4 shown in Table 44, and the substituent Y is any one of substituent numbers 1 to 558 in the compound TMO.

A tetrazolinone compound in which $X^1$, $X^2$, and $R^L$ are L5 shown in Table 44, and the substituent Y is any one of substituent numbers 1 to 558 in the compound TMO.

A tetrazolinone compound in which $X^1$, $X^2$, and $R^L$ are L6 shown in Table 44, and the substituent Y is any one of substituent numbers 1 to 558 in the compound TMO.

A tetrazolinone compound in which $X^1$, $X^2$, and $R^L$ are L7 shown in Table 44, and the substituent Y is any one of substituent numbers 1 to 558 in the compound TMO.

A tetrazolinone compound in which $X^1$, $X^2$, and $R^L$ are L8 shown in Table 44, and the substituent Y is any one of substituent numbers 1 to 558 in the compound TMO.

A tetrazolinone compound in which $X^1$, $X^2$, and $R^L$ are L9 shown in Table 44, and the substituent Y is any one of substituent numbers 1 to 558 in the compound TMO.

A tetrazolinone compound in which $X^1$, $X^2$, and $R^L$ are L10 shown in Table 44, and the substituent Y is any one of substituent numbers 1 to 558 in the compound TMO.

A tetrazolinone compound in which $X^1$, $X^2$, and $R^L$ are L11 shown in Table 44, and the substituent Y is any one of substituent numbers 1 to 558 in the compound TMO.

A tetrazolinone compound in which $X^1$, $X^2$, and $R^L$ are L12 shown in Table 44, and the substituent Y is any one of substituent numbers 1 to 558 in the compound TMO.

A tetrazolinone compound in which $X^1$, $X^2$, and $R^L$ are L13 shown in Table 44, and the substituent Y is any one of substituent numbers 1 to 558 in the compound TMO.

A tetrazolinone compound in which $X^1$, $X^2$, and $R^L$ are L14 shown in Table 44, and the substituent Y is any one of substituent numbers 1 to 558 in the compound TMO.

A tetrazolinone compound in which $X^1$, $X^2$, and $R^L$ are L15 shown in Table 44, and the substituent Y is any one of substituent numbers 1 to 558 in the compound TMO.

A tetrazolinone compound in which $X^1$, $X^2$, and $R^L$ are L16 shown in Table 44, and the substituent Y is any one of substituent numbers 1 to 558 in the compound TMO.

A tetrazolinone compound in which $X^1$, $X^2$, and $R^L$ are L17 shown in Table 44, and the substituent Y is any one of substituent numbers 1 to 558 in the compound TMO.

A tetrazolinone compound in which $X^1$, $X^2$, and $R^L$ are L18 shown in Table 44, and the substituent Y is any one of substituent numbers 1 to 558 in the compound TMO.

A tetrazolinone compound in which $X^1$, $X^2$, and $R^L$ are L19 shown in Table 44, and the substituent Y is any one of substituent numbers 1 to 558 in the compound TMO.

A tetrazolinone compound in which $X^1$, $X^2$, and $R^L$ are L20 shown in Table 44, and the substituent Y is any one of substituent numbers 1 to 558 in the compound TMO.

A tetrazolinone compound in which $X^1$, $X^2$, and $R^L$ are L21 shown in Table 44, and the substituent Y is any one of substituent numbers 1 to 558 in the compound TMO.

A tetrazolinone compound in which $X^1$, $X^2$, and $R^L$ are L22 shown in Table 44, and the substituent Y is any one of substituent numbers 1 to 558 in the compound TMO.

A tetrazolinone compound in which $X^1$, $X^2$, and $R^L$ are L23 shown in Table 44, and the substituent Y is any one of substituent numbers 1 to 558 in the compound TMO.

A tetrazolinone compound in which $X^1$, $X^2$, and $R^L$ are L24 shown in Table 44, and the substituent Y is any one of substituent numbers 1 to 558 in the compound TMO.

A tetrazolinone compound in which $X^1$, $X^2$, and $R^L$ are L25 shown in Table 44, and the substituent Y is any one of substituent numbers 1 to 558 in the compound TMO.

A tetrazolinone compound in which $X^1$, $X^2$, and $R^L$ are L26 shown in Table 44, and the substituent Y is any one of substituent numbers 1 to 558 in the compound TMO.

A tetrazolinone compound in which $X^1$, $X^2$, and $R^L$ are L27 shown in Table 44, and the substituent Y is any one of substituent numbers 1 to 558 in the compound TMO.

A tetrazolinone compound in which $X^1$, $X^2$, and $R^L$ are L28 shown in Table 44, and the substituent Y is any one of substituent numbers 1 to 558 in the compound TMO.

A tetrazolinone compound in which $X^1$, $X^2$, and $R^L$ are L29 shown in Table 44, and the substituent Y is any one of substituent numbers 1 to 558 in the compound TMO.

A tetrazolinone compound in which $X^1$, $X^2$, and $R^L$ are L30 shown in Table 45, and the substituent Y is any one of substituent numbers 1 to 558 in the compound TMO.

A tetrazolinone compound in which $X^1$, $X^2$, and $R^L$ are L31 shown in Table 45, and the substituent Y is any one of substituent numbers 1 to 558 in the compound TMO.

A tetrazolinone compound in which $X^1$, $X^2$, and $R^L$ are L32 shown in Table 45, and the substituent Y is any one of substituent numbers 1 to 558 in the compound TMO.

A tetrazolinone compound in which $X^1$, $X^2$, and $R^L$ are L33 shown in Table 45, and the substituent Y is any one of substituent numbers 1 to 558 in the compound TMO.

A tetrazolinone compound in which $X^1$, $X^2$, and $R^L$ are L34 shown in Table 45, and the substituent Y is any one of substituent numbers 1 to 558 in the compound TMO.

A tetrazolinone compound in which $X^1$, $X^2$, and $R^L$ are L35 shown in Table 45, and the substituent Y is any one of substituent numbers 1 to 558 in the compound TMO.

A tetrazolinone compound in which $X^1$, $X^2$, and $R^L$ are L36 shown in Table 45, and the substituent Y is any one of substituent numbers 1 to 558 in the compound TMO.

A tetrazolinone compound in which $X^1$, $X^2$, and $R^L$ are L37 shown in Table 45, and the substituent Y is any one of substituent numbers 1 to 558 in the compound TMO.

A tetrazolinone compound in which $X^1$, $X^2$, and $R^L$ are L38 shown in Table 45, and the substituent Y is any one of substituent numbers 1 to 558 in the compound TMO.

A tetrazolinone compound in which $X^1$, $X^2$, and $R^L$ are L39 shown in Table 45, and the substituent Y is any one of substituent numbers 1 to 558 in the compound TMO.

A tetrazolinone compound in which $X^1$, $X^2$, and $R^L$ are L40 shown in Table 45, and the substituent Y is any one of substituent numbers 1 to 558 in the compound TMO.

A tetrazolinone compound in which $X^1$, $X^2$, and $R^L$ are L41 shown in Table 45, and the substituent Y is any one of substituent numbers 1 to 558 in the compound TMO.

A tetrazolinone compound in which $X^1$, $X^2$, and $R^L$ are L42 shown in Table 45, and the substituent Y is any one of substituent numbers 1 to 558 in the compound TMO.

A tetrazolinone compound in which $X^1$, $X^2$, and $R^L$ are L43 shown in Table 45, and the substituent Y is any one of substituent numbers 1 to 558 in the compound TMO.

A tetrazolinone compound in which $X^1$, $X^2$, and $R^L$ are L44 shown in Table 45, and the substituent Y is any one of substituent numbers 1 to 558 in the compound TMO.

A tetrazolinone compound in which $X^1$, $X^2$, and $R^L$ are L45 shown in Table 45, and the substituent Y is any one of substituent numbers 1 to 558 in the compound TMO.

A tetrazolinone compound in which $X^1$, $X^2$, and $R^L$ are L46 shown in Table 45, and the substituent Y is any one of substituent numbers 1 to 558 in the compound TMO.

A tetrazolinone compound in which $X^1$, $X^2$, and $R^L$ are L47 shown in Table 45, and the substituent Y is any one of substituent numbers 1 to 558 in the compound TMO.

A tetrazolinone compound in which $X^1$, $X^2$, and $R^L$ are L48 shown in Table 45, and the substituent Y is any one of substituent numbers 1 to 558 in the compound TMO.

A tetrazolinone compound in which $X^1$, $X^2$, and $R^L$ are L49 shown in Table 45, and the substituent Y is any one of substituent numbers 1 to 558 in the compound TMO.

A tetrazolinone compound in which $X^1$, $X^2$, and $R^L$ are L50 shown in Table 45, and the substituent Y is any one of substituent numbers 1 to 558 in the compound TMO.

A tetrazolinone compound in which $X^1$, $X^2$, and $R^L$ are L51 shown in Table 45, and the substituent Y is any one of substituent numbers 1 to 558 in the compound TMO.

A tetrazolinone compound in which $X^1$, $X^2$, and $R^L$ are L52 shown in Table 45, and the substituent Y is any one of substituent numbers 1 to 558 in the compound TMO.

A tetrazolinone compound in which $X^1$, $X^2$, and $R^L$ are L53 shown in Table 45, and the substituent Y is any one of substituent numbers 1 to 558 in the compound TMO.

A tetrazolinone compound in which $X^1$, $X^2$, and $R^L$ are L54 shown in Table 45, and the substituent Y is any one of substituent numbers 1 to 558 in the compound TMO.

A tetrazolinone compound in which $X^1$, $X^2$, and $R^L$ are L55 shown in Table 45, and the substituent Y is any one of substituent numbers 1 to 558 in the compound TMO.

A tetrazolinone compound in which $X^1$, $X^2$, and $R^L$ are L56 shown in Table 45, and the substituent Y is any one of substituent numbers 1 to 558 in the compound TMO.

A tetrazolinone compound in which $X^1$, $X^2$, and $R^L$ are L57 shown in Table 45, and the substituent Y is any one of substituent numbers 1 to 558 in the compound TMO.

A tetrazolinone compound in which $X^1$, $X^2$, and $R^L$ are L1 shown in Table 44, and the substituent Y is any one of substituent numbers 1 to 558 in a compound represented by formula (TMT) (referred to as the compound TMT).

A tetrazolinone compound in which $X^1$, $X^2$, and $R^L$ are L2 shown in Table 44, and the substituent Y is any one of substituent numbers 1 to 558 in the compound TMT.

A tetrazolinone compound in which $X^1$, $X^2$, and $R^L$ are L3 shown in Table 44, and the substituent Y is any one of substituent numbers 1 to 558 in the compound TMT.

A tetrazolinone compound in which $X^1$, $X^2$, and $R^L$ are L4 shown in Table 44, and the substituent Y is any one of substituent numbers 1 to 558 in the compound TMT.

A tetrazolinone compound in which $X^1$, $X^2$, and $R^L$ are L5 shown in Table 44, and the substituent Y is any one of substituent numbers 1 to 558 in the compound TMT.

A tetrazolinone compound in which $X^1$, $X^2$, and $R^L$ are L6 shown in Table 44, and the substituent Y is any one of substituent numbers 1 to 558 in the compound TMT.

A tetrazolinone compound in which $X^1$, $X^2$, and $R^L$ are L7 shown in Table 44, and the substituent Y is any one of substituent numbers 1 to 558 in the compound TMT.

A tetrazolinone compound in which $X^1$, $X^2$, and $R^L$ are L8 shown in Table 44, and the substituent Y is any one of substituent numbers 1 to 558 in the compound TMT.

A tetrazolinone compound in which $X^1$, $X^2$, and $R^L$ are L9 shown in Table 44, and the substituent Y is any one of substituent numbers 1 to 558 in the compound TMT.

A tetrazolinone compound in which $X^1$, $X^2$, and $R^L$ are L10 shown in Table 44, and the substituent Y is any one of substituent numbers 1 to 558 in the compound TMT.

A tetrazolinone compound in which $X^1$, $X^2$, and $R^L$ are L11 shown in Table 44, and the substituent Y is any one of substituent numbers 1 to 558 in the compound TMT.

A tetrazolinone compound in which $X^1$, $X^2$, and $R^L$ are L12 shown in Table 44, and the substituent Y is any one of substituent numbers 1 to 558 in the compound TMT.

A tetrazolinone compound in which $X^1$, $X^2$, and $R^L$ are L13 shown in Table 44, and the substituent Y is any one of substituent numbers 1 to 558 in the compound TMT.

A tetrazolinone compound in which $X^1$, $X^2$, and $R^L$ are L14 shown in Table 44, and the substituent Y is any one of substituent numbers 1 to 558 in the compound TMT.

A tetrazolinone compound in which $X^1$, $X^2$, and $R^L$ are L15 shown in Table 44, and the substituent Y is any one of substituent numbers 1 to 558 in the compound TMT.

A tetrazolinone compound in which $X^1$, $X^2$, and $R^L$ are L16 shown in Table 44, and the substituent Y is any one of substituent numbers 1 to 558 in the compound TMT.

A tetrazolinone compound in which $X^1$, $X^2$, and $R^L$ are L17 shown in Table 44, and the substituent Y is any one of substituent numbers 1 to 558 in the compound TMT.

A tetrazolinone compound in which $X^1$, $X^2$, and $R^L$ are L18 shown in Table 44, and the substituent Y is any one of substituent numbers 1 to 558 in the compound TMT.

A tetrazolinone compound in which $X^1$, $X^2$, and $R^L$ are L19 shown in Table 44, and the substituent Y is any one of substituent numbers 1 to 558 in the compound TMT.

A tetrazolinone compound in which $X^1$, $X^2$, and $R^L$ are L20 shown in Table 44, and the substituent Y is any one of substituent numbers 1 to 558 in the compound TMT.

A tetrazolinone compound in which $X^1$, $X^2$, and $R^L$ are L21 shown in Table 44, and the substituent Y is any one of substituent numbers 1 to 558 in the compound TMT.

A tetrazolinone compound in which $X^1$, $X^2$, and $R^L$ are L22 shown in Table 44, and the substituent Y is any one of substituent numbers 1 to 558 in the compound TMT.

A tetrazolinone compound in which $X^1$, $X^2$, and $R^L$ are L23 shown in Table 44, and the substituent Y is any one of substituent numbers 1 to 558 in the compound TMT.

A tetrazolinone compound in which $X^1$, $X^2$, and $R^L$ are L24 shown in Table 44, and the substituent Y is any one of substituent numbers 1 to 558 in the compound TMT.

A tetrazolinone compound in which $X^1$, $X^2$, and $R^L$ are L25 shown in Table 44, and the substituent Y is any one of substituent numbers 1 to 558 in the compound TMT.

A tetrazolinone compound in which $X^1$, $X^2$, and $R^L$ are L26 shown in Table 44, and the substituent Y is any one of substituent numbers 1 to 558 in the compound TMT.

A tetrazolinone compound in which $X^1$, $X^2$, and $R^L$ are L27 shown in Table 44, and the substituent Y is any one of substituent numbers 1 to 558 in the compound TMT.

A tetrazolinone compound in which $X^1$, $X^2$, and $R^L$ are L28 shown in Table 44, and the substituent Y is any one of substituent numbers 1 to 558 in the compound TMT.

A tetrazolinone compound in which $X^1$, $X^2$, and $R^L$ are L29 shown in Table 44, and the substituent Y is any one of substituent numbers 1 to 558 in the compound TMT.

A tetrazolinone compound in which $X^1$, $X^2$, and $R^L$ are L30 shown in Table 45, and the substituent Y is any one of substituent numbers 1 to 558 in the compound TMT.

A tetrazolinone compound in which $X^1$, $X^2$, and $R^L$ are L31 shown in Table 45, and the substituent Y is any one of substituent numbers 1 to 558 in the compound TMT.

A tetrazolinone compound in which $X^1$, $X^2$, and $R^L$ are L32 shown in Table 45, and the substituent Y is any one of substituent numbers 1 to 558 in the compound TMT.

A tetrazolinone compound in which $X^1$, $X^2$, and $R^L$ are L33 shown in Table 45, and the substituent Y is any one of substituent numbers 1 to 558 in the compound TMT.

A tetrazolinone compound in which $X^1$, $X^2$, and $R^L$ are L34 shown in Table 45, and the substituent Y is any one of substituent numbers 1 to 558 in the compound TMT.

A tetrazolinone compound in which $X^1$, $X^2$, and $R^L$ are L35 shown in Table 45, and the substituent Y is any one of substituent numbers 1 to 558 in the compound TMT.

A tetrazolinone compound in which $X^1$, $X^2$, and $R^L$ are L36 shown in Table 45, and the substituent Y is any one of substituent numbers 1 to 558 in the compound TMT.

A tetrazolinone compound in which $X^1$, $X^2$, and $R^L$ are L37 shown in Table 45, and the substituent Y is any one of substituent numbers 1 to 558 in the compound TMT.

A tetrazolinone compound in which $X^1$, $X^2$, and $R^L$ are L38 shown in Table 45, and the substituent Y is any one of substituent numbers 1 to 558 in the compound TMT.

A tetrazolinone compound in which $X^1$, $X^2$, and $R^L$ are L39 shown in Table 37, and the substituent Y is any one of substituent numbers 1 to 558 in the compound TMT.

A tetrazolinone compound in which $X^1$, $X^2$, and $R^L$ are L40 shown in Table 45, and the substituent Y is any one of substituent numbers 1 to 558 in the compound TMT.

A tetrazolinone compound in which $X^1$, $X^2$, and $R^L$ are L41 shown in Table 45, and the substituent Y is any one of substituent numbers 1 to 558 in the compound TMT.

A tetrazolinone compound in which $X^1$, $X^2$, and $R^L$ are L42 shown in Table 45, and the substituent Y is any one of substituent numbers 1 to 558 in the compound TMT.

A tetrazolinone compound in which $X^1$, $X^2$, and $R^L$ are L43 shown in Table 45, and the substituent Y is any one of substituent numbers 1 to 558 in the compound TMT.

A tetrazolinone compound in which $X^1$, $X^2$, and $R^L$ are L44 shown in Table 45, and the substituent Y is any one of substituent numbers 1 to 558 in the compound TMT.

A tetrazolinone compound in which $X^1$, $X^2$, and $R^L$ are L45 shown in Table 45, and the substituent Y is any one of substituent numbers 1 to 558 in the compound TMT.

A tetrazolinone compound in which $X^1$, $X^2$, and $R^L$ are L46 shown in Table 45, and the substituent Y is any one of substituent numbers 1 to 558 in the compound TMT.

A tetrazolinone compound in which $X^1$, $X^2$, and $R^L$ are L47 shown in Table 45, and the substituent Y is any one of substituent numbers 1 to 558 in the compound TMT.

A tetrazolinone compound in which $X^1$, $X^2$, and $R^L$ are L48 shown in Table 45, and the substituent Y is any one of substituent numbers 1 to 558 in the compound TMT.

A tetrazolinone compound in which $X^1$, $X^2$, and $R^L$ are L49 shown in Table 45, and the substituent Y is any one of substituent numbers 1 to 558 in the compound TMT.

A tetrazolinone compound in which $X^1$, $X^2$, and $R^L$ are L50 shown in Table 45, and the substituent Y is any one of substituent numbers 1 to 558 in the compound TMT.

A tetrazolinone compound in which $X^1$, $X^2$, and $R^L$ are L51 shown in Table 45, and the substituent Y is any one of substituent numbers 1 to 558 in the compound TMT.

A tetrazolinone compound in which $X^1$, $X^2$, and $R^L$ are L52 shown in Table 45, and the substituent Y is any one of substituent numbers 1 to 558 in the compound TMT.

A tetrazolinone compound in which $X^1$, $X^2$, and $R^L$ are L53 shown in Table 45, and the substituent Y is any one of substituent numbers 1 to 558 in the compound TMT.

A tetrazolinone compound in which $X^1$, $X^2$, and $R^L$ are L54 shown in Table 45, and the substituent Y is any one of substituent numbers 1 to 558 in the compound TMT.

A tetrazolinone compound in which $X^1$, $X^2$, and $R^L$ are L55 shown in Table 45, and the substituent Y is any one of substituent numbers 1 to 558 in the compound TMT.

A tetrazolinone compound in which $X^1$, $X^2$, and $R^L$ are L56 shown in Table 45, and the substituent Y is any one of substituent numbers 1 to 558 in the compound TMT.

A tetrazolinone compound in which $X^1$, $X^2$, and $R^L$ are L57 shown in Table 45, and the substituent Y is any one of substituent numbers 1 to 558 in the compound TMT.

A tetrazolinone compound in which $X^1$, $X^2$, and $R^L$ are L1 shown in Table 44, and the substituent Y is any one of substituent numbers 1 to 558 in a compound represented by formula (TCF) (referred to as the compound TCF).

A tetrazolinone compound in which $X^1$, $X^2$, and $R^L$ are L2 shown in Table 44, and the substituent Y is any one of substituent numbers 1 to 558 in the compound TCF.

A tetrazolinone compound in which $X^1$, $X^2$, and $R^L$ are L3 shown in Table 44, and the substituent Y is any one of substituent numbers 1 to 558 in the compound TCF.

A tetrazolinone compound in which $X^1$, $X^2$, and $R^L$ are L4 shown in Table 44, and the substituent Y is any one of substituent numbers 1 to 558 in the compound TCF.

A tetrazolinone compound in which $X^1$, $X^2$, and $R^L$ are L5 shown in Table 44, and the substituent Y is any one of substituent numbers 1 to 558 in the compound TCF.

A tetrazolinone compound in which $X^1$, $X^2$, and $R^L$ are L6 shown in Table 44, and the substituent Y is any one of substituent numbers 1 to 558 in the compound TCF.

A tetrazolinone compound in which $X^1$, $X^2$, and $R^L$ are L7 shown in Table 44, and the substituent Y is any one of substituent numbers 1 to 558 in the compound TCF.

A tetrazolinone compound in which $X^1$, $X^2$, and $R^L$ are L8 shown in Table 44, and the substituent Y is any one of substituent numbers 1 to 558 in the compound TCF.

A tetrazolinone compound in which $X^1$, $X^2$, and $R^L$ are L9 shown in Table 44, and the substituent Y is any one of substituent numbers 1 to 558 in the compound TCF.

A tetrazolinone compound in which $X^1$, $X^2$, and $R^L$ are L10 shown in Table 44, and the substituent Y is any one of substituent numbers 1 to 558 in the compound TCF.

A tetrazolinone compound in which $X^1$, $X^2$, and $R^L$ are L11 shown in Table 44, and the substituent Y is any one of substituent numbers 1 to 558 in the compound TCF.

A tetrazolinone compound in which $X^1$, $X^2$, and $R^L$ are L12 shown in Table 44, and the substituent Y is any one of substituent numbers 1 to 558 in the compound TCF.

A tetrazolinone compound in which $X^1$, $X^2$, and $R^L$ are L13 shown in Table 44, and the substituent Y is any one of substituent numbers 1 to 558 in the compound TCF.

A tetrazolinone compound in which $X^1$, $X^2$, and $R^L$ are L14 shown in Table 44, and the substituent Y is any one of substituent numbers 1 to 558 in the compound TCF.

A tetrazolinone compound in which $X^1$, $X^2$, and $R^L$ are L15 shown in Table 44, and the substituent Y is any one of substituent numbers 1 to 558 in the compound TCF.

A tetrazolinone compound in which $X^1$, $X^2$, and $R^L$ are L16 shown in Table 44, and the substituent Y is any one of substituent numbers 1 to 558 in the compound TCF.

A tetrazolinone compound in which $X^1$, $X^2$, and $R^L$ are L17 shown in Table 44, and the substituent Y is any one of substituent numbers 1 to 558 in the compound TCF.

A tetrazolinone compound in which $X^1$, $X^2$, and $R^L$ are L18 shown in Table 44, and the substituent Y is any one of substituent numbers 1 to 558 in the compound TCF.

A tetrazolinone compound in which $X^1$, $X^2$, and $R^L$ are L19 shown in Table 44, and the substituent Y is any one of substituent numbers 1 to 558 in the compound TCF.

A tetrazolinone compound in which $X^1$, $X^2$, and $R^L$ are L20 shown in Table 44, and the substituent Y is any one of substituent numbers 1 to 558 in the compound TCF.

A tetrazolinone compound in which $X^1$, $X^2$, and $R^L$ are L21 shown in Table 44, and the substituent Y is any one of substituent numbers 1 to 558 in the compound TCF.

A tetrazolinone compound in which $X^1$, $X^2$, and $R^L$ are L22 shown in Table 44, and the substituent Y is any one of substituent numbers 1 to 558 in the compound TCF.

A tetrazolinone compound in which $X^1$, $X^2$, and $R^L$ are L23 shown in Table 44, and the substituent Y is any one of substituent numbers 1 to 558 in the compound TCF.

A tetrazolinone compound in which $X^1$, $X^2$, and $R^L$ are L24 shown in Table 44, and the substituent Y is any one of substituent numbers 1 to 558 in the compound TCF.

A tetrazolinone compound in which $X^1$, $X^2$, and $R^L$ are L25 shown in Table 44, and the substituent Y is any one of substituent numbers 1 to 558 in the compound TCF.

A tetrazolinone compound in which $X^1$, $X^2$, and $R^L$ are L26 shown in Table 44, and the substituent Y is any one of substituent numbers 1 to 558 in the compound TCF.

A tetrazolinone compound in which $X^1$, $X^2$, and $R^L$ are L27 shown in Table 44, and the substituent Y is any one of substituent numbers 1 to 558 in the compound TCF.

A tetrazolinone compound in which $X^1$, $X^2$, and $R^L$ are L28 shown in Table 44, and the substituent Y is any one of substituent numbers 1 to 558 in the compound TCF.

A tetrazolinone compound in which $X^1$, $X^2$, and $R^L$ are L29 shown in Table 44, and the substituent Y is any one of substituent numbers 1 to 558 in the compound TCF.

A tetrazolinone compound in which $X^1$, $X^2$, and $R^L$ are L30 shown in Table 45, and the substituent Y is any one of substituent numbers 1 to 558 in the compound TCF.

A tetrazolinone compound in which $X^1$, $X^2$, and $R^L$ are L31 shown in Table 45, and the substituent Y is any one of substituent numbers 1 to 558 in the compound TCF.

A tetrazolinone compound in which $X^1$, $X^2$, and $R^L$ are L32 shown in Table 45, and the substituent Y is any one of substituent numbers 1 to 558 in the compound TCF.

A tetrazolinone compound in which $X^1$, $X^2$, and $R^L$ are L33 shown in Table 45, and the substituent Y is any one of substituent numbers 1 to 558 in the compound TCF.

A tetrazolinone compound in which $X^1$, $X^2$, and $R^L$ are L34 shown in Table 45, and the substituent Y is any one of substituent numbers 1 to 558 in the compound TCF.

A tetrazolinone compound in which $X^1$, $X^2$, and $R^L$ are L35 shown in Table 45, and the substituent Y is any one of substituent numbers 1 to 558 in the compound TCF.

A tetrazolinone compound in which $X^1$, $X^2$, and $R^L$ are L36 shown in Table 45, and the substituent Y is any one of substituent numbers 1 to 558 in the compound TCF.

A tetrazolinone compound in which $X^1$, $X^2$, and $R^L$ are L37 shown in Table 45, and the substituent Y is any one of substituent numbers 1 to 558 in the compound TCF.

A tetrazolinone compound in which $X^1$, $X^2$, and $R^L$ are L38 shown in Table 45, and the substituent Y is any one of substituent numbers 1 to 558 in the compound TCF.

A tetrazolinone compound in which $X^1$, $X^2$, and $R^L$ are L39 shown in Table 45, and the substituent Y is any one of substituent numbers 1 to 558 in the compound TCF.

A tetrazolinone compound in which $X^1$, $X^2$, and $R^L$ are L40 shown in Table 45, and the substituent Y is any one of substituent numbers 1 to 558 in the compound TCF.

A tetrazolinone compound in which $X^1$, $X^2$, and $R^L$ are L41 shown in Table 45, and the substituent Y is any one of substituent numbers 1 to 558 in the compound TCF.

A tetrazolinone compound in which $X^1$, $X^2$, and $R^L$ are L42 shown in Table 45, and the substituent Y is any one of substituent numbers 1 to 558 in the compound TCF.

A tetrazolinone compound in which $X^1$, $X^2$, and $R^L$ are L43 shown in Table 45, and the substituent Y is any one of substituent numbers 1 to 558 in the compound TCF.

A tetrazolinone compound in which $X^1$, $X^2$, and $R^L$ are L44 shown in Table 45, and the substituent Y is any one of substituent numbers 1 to 558 in the compound TCF.

A tetrazolinone compound in which $X^1$, $X^2$, and $R^L$ are L45 shown in Table 45, and the substituent Y is any one of substituent numbers 1 to 558 in the compound TCF.

A tetrazolinone compound in which $X^1$, $X^2$, and $R^L$ are L46 shown in Table 45, and the substituent Y is any one of substituent numbers 1 to 558 in the compound TCF.

A tetrazolinone compound in which $X^1$, $X^2$, and $R^L$ are L47 shown in Table 45, and the substituent Y is any one of substituent numbers 1 to 558 in the compound TCF.

A tetrazolinone compound in which $X^1$, $X^2$, and $R^L$ are L48 shown in Table 45, and the substituent Y is any one of substituent numbers 1 to 558 in the compound TCF.

A tetrazolinone compound in which $X^1$, $X^2$, and $R^L$ are L49 shown in Table 45, and the substituent Y is any one of substituent numbers 1 to 558 in the compound TCF.

A tetrazolinone compound in which $X^1$, $X^2$, and $R^L$ are L50 shown in Table 45, and the substituent Y is any one of substituent numbers 1 to 558 in the compound TCF.

A tetrazolinone compound in which $X^1$, $X^2$, and $R^L$ are L51 shown in Table 45, and the substituent Y is any one of substituent numbers 1 to 558 in the compound TCF.

A tetrazolinone compound in which $X^1$, $X^2$, and $R^L$ are L52 shown in Table 45, and the substituent Y is any one of substituent numbers 1 to 558 in the compound TCF.

A tetrazolinone compound in which $X^1$, $X^2$, and $R^L$ are L53 shown in Table 45, and the substituent Y is any one of substituent numbers 1 to 558 in the compound TCF.

A tetrazolinone compound in which $X^1$, $X^2$, and $R^L$ are L54 shown in Table 45, and the substituent Y is any one of substituent numbers 1 to 558 in the compound TCF.

A tetrazolinone compound in which $X^1$, $X^2$, and $R^L$ are L55 shown in Table 45, and the substituent Y is any one of substituent numbers 1 to 558 in the compound TCF.

A tetrazolinone compound in which $X^1$, $X^2$, and $R^L$ are L56 shown in Table 45, and the substituent Y is any one of substituent numbers 1 to 558 in the compound TCF.

A tetrazolinone compound in which $X^1$, $X^2$, and $R^L$ are L57 shown in Table 45, and the substituent Y is any one of substituent numbers 1 to 558 in the compound TCF.

A tetrazolinone compound in which $X^1$, $X^2$, and $R^L$ are L1 shown in Table 44, and the substituent Y is any one of substituent numbers 1 to 558 in a compound represented by formula (TCFF) (referred to as the compound TCFF).

A tetrazolinone compound in which $X^1$, $X^2$, and $R^L$ are L2 shown in Table 44, and the substituent Y is any one of substituent numbers 1 to 558 in the compound TCFF.

A tetrazolinone compound in which $X^1$, $X^2$, and $R^L$ are L3 shown in Table 44, and the substituent Y is any one of substituent numbers 1 to 558 in the compound TCFF.

A tetrazolinone compound in which $X^1$, $X^2$, and $R^L$ are L4 shown in Table 44, and the substituent Y is any one of substituent numbers 1 to 558 in the compound TCFF.

A tetrazolinone compound in which $X^1$, $X^2$, and $R^L$ are L5 shown in Table 44, and the substituent Y is any one of substituent numbers 1 to 558 in the compound TCFF.

A tetrazolinone compound in which $X^1$, $X^2$, and $R^L$ are L6 shown in Table 44, and the substituent Y is any one of substituent numbers 1 to 558 in the compound TCFF.

A tetrazolinone compound in which $X^1$, $X^2$, and $R^L$ are L7 shown in Table 44, and the substituent Y is any one of substituent numbers 1 to 558 in the compound TCFF.

A tetrazolinone compound in which $X^1$, $X^2$, and $R^L$ are L8 shown in Table 44, and the substituent Y is any one of substituent numbers 1 to 558 in the compound TCFF.

A tetrazolinone compound in which $X^1$, $X^2$, and $R^L$ are L9 shown in Table 44, and the substituent Y is any one of substituent numbers 1 to 558 in the compound TCFF.

A tetrazolinone compound in which $X^1$, $X^2$, and $R^L$ are L10 shown in Table 44, and the substituent Y is any one of substituent numbers 1 to 558 in the compound TCFF.

A tetrazolinone compound in which $X^1$, $X^2$, and $R^L$ are L11 shown in Table 44, and the substituent Y is any one of substituent numbers 1 to 558 in the compound TCFF.

A tetrazolinone compound in which $X^1$, $X^2$, and $R^L$ are L12 shown in Table 44, and the substituent Y is any one of substituent numbers 1 to 558 in the compound TCFF.

A tetrazolinone compound in which $X^1$, $X^2$, and $R^L$ are L13 shown in Table 44, and the substituent Y is any one of substituent numbers 1 to 558 in the compound TCFF.

A tetrazolinone compound in which $X^1$, $X^2$, and $R^L$ are L14 shown in Table 44, and the substituent Y is any one of substituent numbers 1 to 558 in the compound TCFF.

A tetrazolinone compound in which $X^1$, $X^2$, and $R^L$ are L15 shown in Table 44, and the substituent Y is any one of substituent numbers 1 to 558 in the compound TCFF.

A tetrazolinone compound in which $X^1$, $X^2$, and $R^L$ are L16 shown in Table 44, and the substituent Y is any one of substituent numbers 1 to 558 in the compound TCFF.

A tetrazolinone compound in which $X^1$, $X^2$, and $R^L$ are L17 shown in Table 44, and the substituent Y is any one of substituent numbers 1 to 558 in the compound TCFF.

A tetrazolinone compound in which $X^1$, $X^2$, and $R^L$ are L18 shown in Table 44, and the substituent Y is any one of substituent numbers 1 to 558 in the compound TCFF.

A tetrazolinone compound in which $X^1$, $X^2$, and $R^L$ are L19 shown in Table 44, and the substituent Y is any one of substituent numbers 1 to 558 in the compound TCFF.

A tetrazolinone compound in which $X^1$, $X^2$, and $R^L$ are L20 shown in Table 44, and the substituent Y is any one of substituent numbers 1 to 558 in the compound TCFF.

A tetrazolinone compound in which $X^1$, $X^2$, and $R^L$ are L21 shown in Table 44, and the substituent Y is any one of substituent numbers 1 to 558 in the compound TCFF.

A tetrazolinone compound in which $X^1$, $X^2$, and $R^L$ are L22 shown in Table 44, and the substituent Y is any one of substituent numbers 1 to 558 in the compound TCFF.

A tetrazolinone compound in which $X^1$, $X^2$, and $R^L$ are L23 shown in Table 44, and the substituent Y is any one of substituent numbers 1 to 558 in the compound TCFF.

A tetrazolinone compound in which $X^1$, $X^2$, and $R^L$ are L24 shown in Table 44, and the substituent Y is any one of substituent numbers 1 to 558 in the compound TCFF.

A tetrazolinone compound in which $X^1$, $X^2$, and $R^L$ are L25 shown in Table 44, and the substituent Y is any one of substituent numbers 1 to 558 in the compound TCFF.

A tetrazolinone compound in which $X^1$, $X^2$, and $R^L$ are L26 shown in Table 44, and the substituent Y is any one of substituent numbers 1 to 558 in the compound TCFF.

A tetrazolinone compound in which $X^1$, $X^2$, and $R^L$ are L27 shown in Table 44, and the substituent Y is any one of substituent numbers 1 to 558 in the compound TCFF.

A tetrazolinone compound in which $X^1$, $X^2$, and $R^L$ are L28 shown in Table 44, and the substituent Y is any one of substituent numbers 1 to 558 in the compound TCFF.

A tetrazolinone compound in which $X^1$, $X^2$, and $R^L$ are L29 shown in Table 44, and the substituent Y is any one of substituent numbers 1 to 558 in the compound TCFF.

A tetrazolinone compound in which $X^1$, $X^2$, and $R^L$ are L30 shown in Table 45, and the substituent Y is any one of substituent numbers 1 to 558 in the compound TCFF.

A tetrazolinone compound in which $X^1$, $X^2$, and $R^L$ are L31 shown in Table 45, and the substituent Y is any one of substituent numbers 1 to 558 in the compound TCFF.

A tetrazolinone compound in which $X^1$, $X^2$, and $R^L$ are L32 shown in Table 45, and the substituent Y is any one of substituent numbers 1 to 558 in the compound TCFF.

A tetrazolinone compound in which $X^1$, $X^2$, and $R^L$ are L33 shown in Table 45, and the substituent Y is any one of substituent numbers 1 to 558 in the compound TCFF.

A tetrazolinone compound in which $X^1$, $X^2$, and $R^L$ are L34 shown in Table 45, and the substituent Y is any one of substituent numbers 1 to 558 in the compound TCFF.

A tetrazolinone compound in which $X^1$, $X^2$, and $R^L$ are L35 shown in Table 45, and the substituent Y is any one of substituent numbers 1 to 558 in the compound TCFF.

A tetrazolinone compound in which $X^1$, $X^2$, and $R^L$ are L36 shown in Table 45, and the substituent Y is any one of substituent numbers 1 to 558 in the compound TCFF.

A tetrazolinone compound in which $X^1$, $X^2$, and $R^L$ are L37 shown in Table 45, and the substituent Y is any one of substituent numbers 1 to 558 in the compound TCFF.

A tetrazolinone compound in which $X^1$, $X^2$, and $R^L$ are L38 shown in Table 45, and the substituent Y is any one of substituent numbers 1 to 558 in the compound TCFF.

A tetrazolinone compound in which $X^1$, $X^2$, and $R^L$ are L39 shown in Table 45, and the substituent Y is any one of substituent numbers 1 to 558 in the compound TCFF.

A tetrazolinone compound in which $X^1$, $X^2$, and $R^L$ are L40 shown in Table 45, and the substituent Y is any one of substituent numbers 1 to 558 in the compound TCFF.

A tetrazolinone compound in which $X^1$, $X^2$, and $R^L$ are L41 shown in Table 45, and the substituent Y is any one of substituent numbers 1 to 558 in the compound TCFF.

A tetrazolinone compound in which $X^1$, $X^2$, and $R^L$ are L42 shown in Table 45, and the substituent Y is any one of substituent numbers 1 to 558 in the compound TCFF.

A tetrazolinone compound in which $X^1$, $X^2$, and $R^L$ are L43 shown in Table 45, and the substituent Y is any one of substituent numbers 1 to 558 in the compound TCFF.

A tetrazolinone compound in which $X^1$, $X^2$, and $R^L$ are L44 shown in Table 45, and the substituent Y is any one of substituent numbers 1 to 558 in the compound TCFF.

A tetrazolinone compound in which $X^1$, $X^2$, and $R^L$ are L45 shown in Table 45, and the substituent Y is any one of substituent numbers 1 to 558 in the compound TCFF.

A tetrazolinone compound in which $X^1$, $X^2$, and $R^L$ are L46 shown in Table 45, and the substituent Y is any one of substituent numbers 1 to 558 in the compound TCFF.

A tetrazolinone compound in which $X^1$, $X^2$, and $R^L$ are L47 shown in Table 45, and the substituent Y is any one of substituent numbers 1 to 558 in the compound TCFF.

A tetrazolinone compound in which $X^1$, $X^2$, and $R^L$ are L48 shown in Table 45, and the substituent Y is any one of substituent numbers 1 to 558 in the compound TCFF.

A tetrazolinone compound in which $X^1$, $X^2$, and $R^L$ are L49 shown in Table 45, and the substituent Y is any one of substituent numbers 1 to 558 in the compound TCFF.

A tetrazolinone compound in which $X^1$, $X^2$, and $R^L$ are L50 shown in Table 45, and the substituent Y is any one of substituent numbers 1 to 558 in the compound TCFF.

A tetrazolinone compound in which $X^1$, $X^2$, and $R^L$ are L51 shown in Table 45, and the substituent Y is any one of substituent numbers 1 to 558 in the compound TCFF.

A tetrazolinone compound in which $X^1$, $X^2$, and $R^L$ are L52 shown in Table 45, and the substituent Y is any one of substituent numbers 1 to 558 in the compound TCFF.

A tetrazolinone compound in which $X^1$, $X^2$, and $R^L$ are L53 shown in Table 45, and the substituent Y is any one of substituent numbers 1 to 558 in the compound TCFF.

A tetrazolinone compound in which $X^1$, $X^2$, and $R^L$ are L54 shown in Table 45, and the substituent Y is any one of substituent numbers 1 to 558 in the compound TCFF.

A tetrazolinone compound in which $X^1$, $X^2$, and $R^L$ are L55 shown in Table 45, and the substituent Y is any one of substituent numbers 1 to 558 in the compound TCFF.

A tetrazolinone compound in which $X^1$, $X^2$, and $R^L$ are L56 shown in Table 45, and the substituent Y is any one of substituent numbers 1 to 558 in the compound TCFF.

A tetrazolinone compound in which $X^1$, $X^2$, and $R^L$ are L57 shown in Table 45, and the substituent Y is any one of substituent numbers 1 to 558 in the compound TCFF.

For example, a compound in which $X^1$, $X^2$, and $R^L$ are L1 shown in Table 44, and Y is a substituent number 1 in the formula (TF) represents the following compound.

(TF-L1-1)

Examples of the present control agent include:
a pest control composition comprising any one of the present compound 1 to the present compound 221, and prothioconazole at a ratio of 0.1:1;

a pest control composition comprising any one of the present compound 1 to the present compound 221, and prothioconazole at a ratio of 1:1;
a pest control composition comprising any one of the present compound 1 to the present compound 221, and prothioconazole at a ratio of 10:1;
a pest control composition comprising any one of the present compound 1 to the present compound 221, and bromuconazole at a ratio of 0.1:1;
a pest control composition comprising any one of the present compound 1 to the present compound 221, and bromuconazole at a ratio of 1:1;
a pest control composition comprising any one of the present compound 1 to the present compound 221, and bromuconazole at a ratio of 10:1;
a pest control composition comprising any one of the present compound 1 to the present compound 221, and metconazole at a ratio of 0.1:1;
a pest control composition comprising any one of the present compound 1 to the present compound 221, and metconazole at a ratio of 1:1;
a pest control composition comprising any one of the present compound 1 to the present compound 221, and metconazole at a ratio of 10:1;
a pest control composition comprising any one of the present compound 1 to the present compound 221, and tebuconazole at a ratio of 0.1:1;
a pest control composition comprising any one of the present compound 1 to the present compound 221, and tebuconazole at a ratio of 1:1;
a pest control composition comprising any one of the present compound 1 to the present compound 221, and tebuconazole at a ratio of 10:1;
a pest control composition comprising any one of the present compound 1 to the present compound 221, and tetraconazole at a ratio of 0.1:1;
a pest control composition comprising any one of the present compound 1 to the present compound 221, and tetraconazole at a ratio of 1:1;
a pest control composition comprising any one of the present compound 1 to the present compound 221, and tetraconazole at a ratio of 10:1;
a pest control composition comprising any one of the present compound 1 to the present compound 221, and cyproconazole at a ratio of 0.1:1;
a pest control composition comprising any one of the present compound 1 to the present compound 221, and cyproconazole at a ratio of 1:1;
a pest control composition comprising any one of the present compound 1 to the present compound 221, and cyproconazole at a ratio of 10:1;
a pest control composition comprising any one of the present compound 1 to the present compound 221, and flusilazole at a ratio of 0.1:1;
a pest control composition comprising any one of the present compound 1 to the present compound 221, and flusilazole at a ratio of 1:1;
a pest control composition comprising any one of the present compound 1 to the present compound 221, and flusilazole at a ratio of 10:1;
a pest control composition comprising any one of the present compound 1 to the present compound 221, and prochloraz at a ratio of 0.1:1;
a pest control composition comprising any one of the present compound 1 to the present compound 221, and prochloraz at a ratio of 1:1;
a pest control composition comprising any one of the present compound 1 to the present compound 221, and prochloraz at a ratio of 10:1;
a pest control composition comprising any one of the present compound 1 to the present compound 221, and azoxystrobin at a ratio of 0.1:1;
a pest control composition comprising any one of the present compound 1 to the present compound 221, and azoxystrobin at a ratio of 1:1;
a pest control composition comprising any one of the present compound 1 to the present compound 221, and azoxystrobin at a ratio of 10:1;
a pest control composition comprising any one of the present compound 1 to the present compound 221, and pyraclostrobin at a ratio of 0.1:1;
a pest control composition comprising any one of the present compound 1 to the present compound 221, and pyraclostrobin at a ratio of 1:1;
a pest control composition comprising any one of the present compound 1 to the present compound 221, and pyraclostrobin at a ratio of 10:1;
a pest control composition comprising any one of the present compound 1 to the present compound 221, and picoxystrobin at a ratio of 0.1:1;
a pest control composition comprising any one of the present compound 1 to the present compound 221, and picoxystrobin at a ratio of 1:1;
a pest control composition comprising any one of the present compound 1 to the present compound 221, and picoxystrobin at a ratio of 10:1;
a pest control composition comprising any one of the present compound 1 to the present compound 221, and fluoxastrobin at a ratio of 0.1:1;
a pest control composition comprising any one of the present compound 1 to the present compound 221, and fluoxastrobin at a ratio of 1:1;
a pest control composition comprising any one of the present compound 1 to the present compound 221, and fluoxastrobin at a ratio of 10:1;
a pest control composition comprising any one of the present compound 1 to the present compound 221, and trifloxystrobin at a ratio of 0.1:1;
a pest control composition comprising any one of the present compound 1 to the present compound 221, and trifloxystrobin at a ratio of 1:1;
a pest control composition comprising any one of the present compound 1 to the present compound 221, and trifloxystrobin at a ratio of 10:1;
a pest control composition comprising any one of the present compound 1 to the present compound 221, and mandestrobin at a ratio of 0.1:1;
a pest control composition comprising any one of the present compound 1 to the present compound 221, and mandestrobin at a ratio of 1:1;
a pest control composition comprising any one of the present compound 1 to the present compound 221, and mandestrobin at a ratio of 10:1;
a pest control composition comprising any one of the present compound 1 to the present compound 221, and fluoxastrobin at a ratio of 0.1:1;
a pest control composition comprising any one of the present compound 1 to the present compound 221, and fluoxastrobin at a ratio of 1:1;
a pest control composition comprising any one of the present compound 1 to the present compound 221, and fluoxastrobin at a ratio of 10:1;

a pest control composition comprising any one of the present compound 1 to the present compound 221, and bixafen at a ratio of 0.1:1;
a pest control composition comprising any one of the present compound 1 to the present compound 221, and bixafen at a ratio of 1:1;
a pest control composition comprising any one of the present compound 1 to the present compound 221, and bixafen at a ratio of 10:1;
a pest control composition comprising any one of the present compound 1 to the present compound 221, and isopyrazam at a ratio of 0.1:1;
a pest control composition comprising any one of the present compound 1 to the present compound 221, and isopyrazam at a ratio of 1:1;
a pest control composition comprising any one of the present compound 1 to the present compound 221, and isopyrazam at a ratio of 10:1;
a pest control composition comprising any one of the present compound 1 to the present compound 221, and fluopyram at a ratio of 0.1:1;
a pest control composition comprising any one of the present compound 1 to the present compound 221, and fluopyram at a ratio of 1:1;
a pest control composition comprising any one of the present compound 1 to the present compound 221, and fluopyram at a ratio of 10:1;
a pest control composition comprising any one of the present compound 1 to the present compound 221, and penthiopyrad at a ratio of 0.1:1;
a pest control composition comprising any one of the present compound 1 to the present compound 221, and penthiopyrad at a ratio of 1:1;
a pest control composition comprising any one of the present compound 1 to the present compound 221, and penthiopyrad at a ratio of 10:1;
a pest control composition comprising any one of the present compound 1 to the present compound 221, and benzovindiflupyr at a ratio of 0.1:1;
a pest control composition comprising any one of the present compound 1 to the present compound 221, and benzovindiflupyr at a ratio of 1:1;
a pest control composition comprising any one of the present compound 1 to the present compound 221, and benzovindiflupyr at a ratio of 10:1;
a pest control composition comprising any one of the present compound 1 to the present compound 221, and fluxapyroxad at a ratio of 0.1:1;
a pest control composition comprising any one of the present compound 1 to the present compound 221, and fluxapyroxad at a ratio of 1:1;
a pest control composition comprising any one of the present compound 1 to the present compound 221, and fluxapyroxad at a ratio of 10:1;
a pest control composition comprising any one of the present compound 1 to the present compound 221, and boscalid at a ratio of 0.1:1;
a pest control composition comprising any one of the present compound 1 to the present compound 221, and boscalid at a ratio of 1:1;
a pest control composition comprising any one of the present compound 1 to the present compound 221, and boscalid at a ratio of 10:1;
a pest control composition comprising any one of the present compound 1 to the present compound 221, and N-[2-(3,4-difluorophenyl)phenyl]-3-trifluoromethylpyrazine-2-carboxylic acid amide at a ratio of 0.1:1;
a pest control composition comprising any one of the present compound 1 to the present compound 221, and N-[2-(3,4-difluorophenyl)phenyl]-3-trifluoromethylpyrazine-2-carboxylic acid amide at a ratio of 1:1;
a pest control composition comprising any one of the present compound 1 to the present compound 221, and N-[2-(3,4-difluorophenyl)phenyl]-3-trifluoromethylpyrazine-2-carboxylic acid amide at a ratio of 10:1;
a pest control composition comprising any one of the present compound 1 to the present compound 221, and (R)-(−)-N-(1,1,3-trimethylindan-4-yl)-1-methyl-3-difluoromethyl-pyrazole-4-carboxylic acid amide at a ratio of 0.1:1;
a pest control composition comprising any one of the present compound 1 to the present compound 221, and (R)-(−)-N-(1,1,3-trimethylindan-4-yl)-1-methyl-3-difluoromethyl-pyrazole-4-carboxylic acid amide at a ratio of 1:1;
a pest control composition comprising any one of the present compound 1 to the present compound 221, and (R)-(−)-N-(1,1,3-trimethylindan-4-yl)-1-methyl-3-difluoromethyl-pyrazole-4-carboxylic acid amide at a ratio of 10:1;
a pest control composition comprising any one of the present compound 1 to the present compound 221, and 3-chloro-4-(2,6-difluorophenyl)-6-methyl-5-phenylpyridazine at a ratio of 0.1:1;
a pest control composition comprising any one of the present compound 1 to the present compound 221, and 3-chloro-4-(2,6-difluorophenyl)-6-methyl-5-phenylpyridazine at a ratio of 1:1;
a pest control composition comprising any one of the present compound 1 to the present compound 221, and 3-chloro-4-(2,6-difluorophenyl)-6-methyl-5-phenylpyridazine at a ratio of 10:1;
a pest control composition comprising any one of the present compound 1 to the present compound 221, and 3-cyano-4-(2,6-difluorophenyl)-6-methyl-5-phenylpyridazine at a ratio of 0.1:1;
a pest control composition comprising any one of the present compound 1 to the present compound 221, and 3-cyano-4-(2,6-difluorophenyl)-6-methyl-5-phenylpyridazine at a ratio of 1:1;
a pest control composition comprising any one of the present compound 1 to the present compound 221, and 3-cyano-4-(2,6-difluorophenyl)-6-methyl-5-phenylpyridazine at a ratio of 10:1;
a pest control composition comprising any one of the present compound 1 to the present compound 221, and fenpropimorph at a ratio of 0.1:1;
a pest control composition comprising any one of the present compound 1 to the present compound 221, and fenpropimorph at a ratio of 1:1;
a pest control composition comprising any one of the present compound 1 to the present compound 221, and fenpropimorph at a ratio of 10:1;
a pest control composition comprising any one of the present compound 1 to the present compound 221, and fenpropidin at a ratio of 0.1:1;
a pest control composition comprising any one of the present compound 1 to the present compound 221, and fenpropidin at a ratio of 1:1;
a pest control composition comprising any one of the present compound 1 to the present compound 221, and fenpropidin at a ratio of 10:1;
a pest control composition comprising any one of the present compound 1 to the present compound 221, and spiroxamine at a ratio of 0.1:1;

a pest control composition comprising any one of the present compound 1 to the present compound 221, and spiroxamine at a ratio of 1:1;
a pest control composition comprising any one of the present compound 1 to the present compound 221, and spiroxamine at a ratio of 10:1;
a pest control composition comprising any one of the present compound 1 to the present compound 221, and cyprodinil at a ratio of 0.1:1;
a pest control composition comprising any one of the present compound 1 to the present compound 221, and cyprodinil at a ratio of 1:1;
a pest control composition comprising any one of the present compound 1 to the present compound 221, and cyprodinil at a ratio of 10:1;
a pest control composition comprising any one of the present compound 1 to the present compound 221, and pyrimethanil at a ratio of 0.1:1;
a pest control composition comprising any one of the present compound 1 to the present compound 221, and pyrimethanil at a ratio of 1:1;
a pest control composition comprising any one of the present compound 1 to the present compound 221, and pyrimethanil at a ratio of 10:1;
a pest control composition comprising any one of the present compound 1 to the present compound 221, and fludioxonil at a ratio of 0.1:1;
a pest control composition comprising any one of the present compound 1 to the present compound 221, and fludioxonil at a ratio of 1:1;
a pest control composition comprising any one of the present compound 1 to the present compound 221, and fludioxonil at a ratio of 10:1;
a pest control composition comprising any one of the present compound 1 to the present compound 221, and procymidone at a ratio of 0.1:1;
a pest control composition comprising any one of the present compound 1 to the present compound 221, and procymidone at a ratio of 1:1;
a pest control composition comprising any one of the present compound 1 to the present compound 221, and procymidone at a ratio of 10:1;
a pest control composition comprising any one of the present compound 1 to the present compound 221, and iprodione at a ratio of 0.1:1;
a pest control composition comprising any one of the present compound 1 to the present compound 221, and iprodione at a ratio of 1:1;
a pest control composition comprising any one of the present compound 1 to the present compound 221, and iprodione at a ratio of 10:1;
a pest control composition comprising any one of the present compound 1 to the present compound 221, and thiophanate-methyl at a ratio of 0.1:1;
a pest control composition comprising any one of the present compound 1 to the present compound 221, and thiophanate-methyl at a ratio of 1:1;
a pest control composition comprising any one of the present compound 1 to the present compound 221, and thiophanate-methyl at a ratio of 10:1;
a pest control composition comprising any one of the present compound 1 to the present compound 221, and carbendazim at a ratio of 0.1:1;
a pest control composition comprising any one of the present compound 1 to the present compound 221, and carbendazim at a ratio of 1:1;
a pest control composition comprising any one of the present compound 1 to the present compound 221, and carbendazim at a ratio of 10:1;
a pest control composition comprising any one of the present compound 1 to the present compound 221, and diethofencarb at a ratio of 0.1:1;
a pest control composition comprising any one of the present compound 1 to the present compound 221, and diethofencarb at a ratio of 1:1;
a pest control composition comprising any one of the present compound 1 to the present compound 221, and diethofencarb at a ratio of 10:1;
a pest control composition comprising any one of the present compound 1 to the present compound 221, and fenpyrazamine at a ratio of 0.1:1;
a pest control composition comprising any one of the present compound 1 to the present compound 221, and fenpyrazamine at a ratio of 1:1;
a pest control composition comprising any one of the present compound 1 to the present compound 221, and fenpyrazamine at a ratio of 10:1;
a pest control composition comprising any one of the present compound 1 to the present compound 221, and chlorothalonil at a ratio of 0.1:1;
a pest control composition comprising any one of the present compound 1 to the present compound 221, and chlorothalonil at a ratio of 1:1;
a pest control composition comprising any one of the present compound 1 to the present compound 221, and chlorothalonil at a ratio of 10:1;
a pest control composition comprising any one of the present compound 1 to the present compound 221, and manzeb at a ratio of 0.1:1;
a pest control composition comprising any one of the present compound 1 to the present compound 221, and manzeb at a ratio of 1:1;
a pest control composition comprising any one of the present compound 1 to the present compound 221, and manzeb at a ratio of 10:1;
a pest control composition comprising any one of the present compound 1 to the present compound 221, and folpet at a ratio of 0.1:1;
a pest control composition comprising any one of the present compound 1 to the present compound 221, and folpet at a ratio of 1:1;
a pest control composition comprising any one of the present compound 1 to the present compound 221, and folpet at a ratio of 10:1;
a pest control composition comprising any one of the present compound 1 to the present compound 221, and metiram at a ratio of 0.1:1;
a pest control composition comprising any one of the present compound 1 to the present compound 221, and metiram at a ratio of 1:1;
a pest control composition comprising any one of the present compound 1 to the present compound 221, and metiram at a ratio of 10:1;
a pest control composition comprising any one of the present compound 1 to the present compound 221, and clothianidin at a ratio of 1:1;
a pest control composition comprising any one of the present compound 1 to the present compound 221, and clothianidin at a ratio of 1:10;
a pest control composition comprising any one of the present compound 1 to the present compound 221, and clothianidin at a ratio of 1:50;

a pest control composition comprising any one of the present compound 1 to the present compound 221, and imidacloprid at a ratio of 1:1;
a pest control composition comprising any one of the present compound 1 to the present compound 221, and imidacloprid at a ratio of 1:10;
a pest control composition comprising any one of the present compound 1 to the present compound 221, and imidacloprid at a ratio of 1:50;
a pest control composition comprising any one of the present compound 1 to the present compound 221, and thiametoxam at a ratio of 1:1;
a pest control composition comprising any one of the present compound 1 to the present compound 221, and thiametoxam at a ratio of 1:10;
a pest control composition comprising any one of the present compound 1 to the present compound 221, and thiametoxam at a ratio of 1:50;
a pest control composition comprising any one of the present compound 1 to the present compound 221, and dinotefuran at a ratio of 1:1;
a pest control composition comprising any one of the present compound 1 to the present compound 221, and dinotefuran at a ratio of 1:10;
a pest control composition comprising any one of the present compound 1 to the present compound 221, and dinotefuran at a ratio of 1:50;
a pest control composition comprising any one of the present compound 1 to the present compound 221, and sulfoxaflor at a ratio of 1:1;
a pest control composition comprising any one of the present compound 1 to the present compound 221, and sulfoxaflor at a ratio of 1:10;
a pest control composition comprising any one of the present compound 1 to the present compound 221, and sulfoxaflor at a ratio of 1:50;
a pest control composition comprising any one of the present compound 1 to the present compound 221, and chlorantraniliprole at a ratio of 1:1;
a pest control composition comprising any one of the present compound 1 to the present compound 221, and chlorantraniliprole at a ratio of 1:10;
a pest control composition comprising any one of the present compound 1 to the present compound 221, and chlorantraniliprole at a ratio of 1:50;
a pest control composition comprising any one of the present compound 1 to the present compound 221, and cyantraniliprole at a ratio of 1:1;
a pest control composition comprising any one of the present compound 1 to the present compound 221, and cyantraniliprole at a ratio of 1:10;
a pest control composition comprising any one of the present compound 1 to the present compound 221, and cyantraniliprole at a ratio of 1:50;
a pest control composition comprising any one of the present compound 1 to the present compound 221, and cyclaniliprole at a ratio of 1:1;
a pest control composition comprising any one of the present compound 1 to the present compound 221, and cyclaniliprole at a ratio of 1:10;
a pest control composition comprising any one of the present compound 1 to the present compound 221, and cyclaniliprole at a ratio of 1:50;
a pest control composition comprising any one of the present compound 1 to the present compound 221, and abamectin at a ratio of 1:1;
a pest control composition comprising any one of the present compound 1 to the present compound 221, and abamectin at a ratio of 1:10;
a pest control composition comprising any one of the present compound 1 to the present compound 221, and abamectin at a ratio of 1:50;
a pest control composition comprising any one of the present compound 1 to the present compound 221, and 4-oxo-4-(2-phenylethyl)aminobutyric acid at a ratio of 5:1;
a pest control composition comprising any one of the present compound 1 to the present compound 221, and 4-oxo-4-(2-phenylethyl)aminobutyric acid at a ratio of 1:10;
a pest control composition comprising any one of the present compound 1 to the present compound 221, and 4-oxo-4-(2-phenylethyl)aminobutyric acid at a ratio of 1:50;
a pest control composition comprising any one of the present compound 1 to the present compound 221, and methyl 5-(trifluoromethyl)benzo[b]thiophene-2-carbonate at a ratio of 5:1;
a pest control composition comprising any one of the present compound 1 to the present compound 221, and methyl 5-(trifluoromethyl)benzo[b]thiophene-2-carbonate at a ratio of 1:10;
a pest control composition comprising any one of the present compound 1 to the present compound 221, and methyl 5-(trifluoromethyl)benzo[b]thiophene-2-carbonate at a ratio of 1:50;
a pest control composition comprising any one of the present compound 1 to the present compound 221, and 5-(trifluoromethyl)benzo[b]thiophene-2-carboxylic acid at a ratio of 5:1;
a pest control composition comprising any one of the present compound 1 to the present compound 221, and 5-(trifluoromethyl)benzo[b]thiophene-2-carboxylic acid at a ratio of 1:10; and
a pest control composition comprising any one of the present compound 1 to the present compound 221, and 5-(trifluoromethyl)benzo[b]thiophene-2-carboxylic acid at a ratio of 1:50.

Formulation Examples will be shown below. Parts are by weight.

Formulation Example 1

Fifty parts (50 parts) of any one of the present compounds 1 to 221, 3 parts of calcium ligninsulfoate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 221 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 221, 88 parts of kaolin clay, and 10 parts of talc are thoroughly ground and mixed to obtain each formulation.

Formulation Example 4

Five parts (5 parts) of any one of the present compounds 1 to 221, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 221, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 221, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present control compound with that on an untreated plant. The untreated plant is a plant tested under the same conditions as in Test Examples, except that foliar or foliage application of a solution of a formulation containing the present compound with water is not performed.

Test Example 1

Each of plastic pots was filled with sandy loam and barley (cultivar: MIKAMO GOLDEN) was sowed and grown in a greenhouse for 7 days. The present compound 1 was diluted with water to adjust to a predetermined concentration of 3.1 ppm. The obtained diluted solution was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with the present compound 1 was 30% or less of that on an untreated plant.

Test Example 2

Each of plastic pots was filled with sandy loam and cucumber (cultivar: SAGAMI HANJIRO) was sowed and grown in a greenhouse for 12 days. Each of the present compounds 35, 40, 61, 64, 92, 100, 101, 107, 110, 143, 148, 167 to 169, 172 to 174, 176 to 180, 206, 209, 210, and 215 to 217 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with each of the present compounds 35, 40, 61, 64, 92, 100, 101, 107, 110, 143, 148, 167 to 169, 172 to 174, 176 to 180, 206, 209, 210, and 215 to 217 was 30% or less of that on an untreated plant.

Test Example 3

Each of plastic pots was filled with sandy loam and rice (cultivar: NIHONBARE) was sowed and grown in a greenhouse for 20 days. Each of the present compounds 2, 4, 6, 14, 18, 39, 40, 62, 65, 98, 109, 117, 119, 120, 122, 125, 131, 136, 137, 139 to 141, 153, and 157 was diluted with water to adjust to a predetermined concentration of 500 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compounds 2, 4, 6, 14, 18, 39, 40, 62, 65, 98, 109, 117, 119, 120, 122, 125, 131, 136, 137, 139 to 141, 153, and 157 were 30% or less with respect to the lesion area on the non-treated plant.

Test Example 4

Each of plastic pots was filled with sandy loam and rice (cultivar: NIHONBARE) was sowed and grown in a greenhouse for 20 days. Each of the present compounds 1, 5, 7, 8, 11, 13, 15, 19, 21, 37, 46, 48, 49, 55 to 58, 60, 66, 67, 69, 70, 72 to 74, 84, 86, 87, 91, 92, 94, 97, 101, 103, 106, 110, 112, 116, 118, 124, 126, 128, 132, 134, 138, 144, 149, 150, 151, 152, 167, 169 to 174, 176, 178 to 180, 209, 210, and 215 to 217 was diluted with water to adjust to a predetermined concentration of 200 ppm. The obtained diluted solutions were sprayed over stems and leaves so that they sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) were left to stand for 6 days at 24° C. in the daytime and 20° C. at night under high humidity condition, while being in contact with each other, and then the area of lesion spots was investigated. As a result, the lesion areas on the plant treated with the present compounds 1, 5, 7, 8, 11, 13, 15, 19, 21, 37, 46, 48, 49, 55 to 58, 60, 66, 67, 69, 70, 72 to 74, 84, 86, 87, 91, 92, 94, 97, 101, 103, 106, 110, 112, 116, 118, 124, 126, 128, 132, 134, 138, 144, 149, 150, 151, 152, 167, 169 to 174, 176, 178 to 180, 209, 210, and 215 to 217 were 30% or less with respect to the lesion area on the non-treated plant.

Test Example 5

Each of plastic pots was filled with sandy loam and wheat (cultivar: SHIROGANE) was sowed and grown in a greenhouse for 9 days. Each of the present compounds 4, 5, 11, 13, 14, 23, 39, 48, 65, 66, 98, 101, 116, 117, 119, 120, 122, 125, 126, 131, 137, 139 to 141, and 157 was diluted with water to adjust to a predetermined concentration of 500 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with each of the present compounds 4, 5, 11, 13, 14, 23, 39, 48, 65, 66, 98, 101, 116, 117, 119, 120, 122, 125, 126, 131, 137, 139 to 141, and 157 was 30% or less of that on an untreated plant.

Test Example 6

Each of plastic pots was filled with sandy loam and wheat (cultivar: SHIROGANE) was sowed and grown in a greenhouse for 9 days. Each of the present compounds 2, 6 to 8, 19, 20, 26, 37, 40 to 44, 46, 49, 50, 53, 55 to 58, 60, 67 to 70, 72 to 74, 92, 93, 100, 102, 106, 107, 112, 118, 121, 128, 134, 136, 138, 143, 148, 153, 158, 163, 164, 166, 169 to 172, 174, 177 to 181, 209, 210, 215, and 217 was diluted with water to adjust to a predetermined concentration of 200 ppm. The obtained diluted solution was sprayed over stems and leaves of the wheat so that they sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with each of the present compounds 2, 6 to 8, 19, 20, 26, 37, 40 to 44, 46, 49, 50, 53, 55 to 58, 60, 67 to 70, 72 to 74, 92, 93, 100, 102, 106, 107, 112, 118, 121, 128, 134, 136, 138, 143, 148, 153, 158, 163, 164, 166, 169 to 172, 174, 177 to 181, 209, 210, 215, and 217 was 30% or less of that on an untreated plant.

Test Example 7

Each of plastic pots was filled with sandy loam and barley (cultivar: MIKAMO GOLDEN) was sowed and grown in a greenhouse for 7 days. Each of the present compounds 1 to 8, 10, 11, 13 to 16, 18 to 27, 29, 31, 35, 37 to 50, 52 to 57, 59 to 75, 77, 80, 81, 83 to 88, 90 to 94, 96 to 104, 107, 109, 110, 112 to 114, 116 to 122, 124 to 129, 131 to 144, 147 to 164, and 165 was diluted with water to adjust to a predetermined concentration of 500 ppm. The obtained diluted solution was sprayed over stems and leaves of the barley so that they sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with each of the present compounds 1 to 8, 10, 11, 13 to 16, 18 to 27, 29, 31, 35, 37 to 50, 52 to 57, 59 to 75, 77, 80, 81, 83 to 88, 90 to 94, 96 to 104, 107, 109, 110, 112 to 114, 116 to 122, 124 to 129, 131 to 144, 147 to 164, and 165 was 30% or less of that on an untreated plant.

Test Example 8

Each of plastic pots was filled with sandy loam and barley (cultivar: MIKAMO GOLDEN) was sowed and grown in a greenhouse for 7 days. Each of the present compounds 12, 17, 36, 51, 58, 79, 106, 166 to 181, 206, 208 to 210, and 215 to 217 was diluted with water to adjust to a predetermined concentration of 200 ppm. The obtained diluted solution was sprayed over stems and leaves of the barley so that they sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with each of the present compounds 12, 17, 36, 51, 58, 79, 106, 166 to 181, 206, 208 to 210, and 215 to 217 was 30% or less of that on an untreated plant.

Test Example 9

Each of plastic pots was filled with sandy loam and kidney bean (cultivar: NAGAUZURA NATANE) was sowed and grown in a greenhouse for 8 days. Each of the present compounds 4, 5, 8, 15, 18 to 21, 27, 39, 45, 46, 50, 54, 55, 59, 60, 65, 70, 74, 75, 77, 79 to 84, 90 to 94, 97 to 99, 101 to 103, 116 to 122, 125, 126, 144, 160 to 162, and 164 was diluted with water to adjust to a predetermined concentration of 500 ppm. The obtained diluted solution was sprayed over stems and leaves of the kidney bean so that they sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with any one of the present compounds 4, 5, 8, 15, 18 to 21, 27, 39, 45, 46, 50, 54, 55, 59, 60, 65, 70, 74, 75, 77, 79 to 84, 90 to 94, 97 to 99, 101 to 103, 116 to 122, 125, 126, 144, 160 to 162, and 164 was 30% or less of that on an untreated plant.

Test Example 10

Each of plastic pots was filled with sandy loam and kidney bean (cultivar: NAGAUZURA NATANE) was sowed and grown in a greenhouse for 8 days. Each of the present compounds 6, 14, 40, 48, 58, 69, 138, 139, 168, 169, 171, 174, 178, 206, and 210 was diluted with water to adjust to a predetermined concentration of 200 ppm. The obtained diluted solution was sprayed over stems and leaves of the kidney bean so that they sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with any one of the present compounds 6, 14, 40, 48, 58, 69, 138, 139, 168, 169, 171, 174, 178, 206, and 210 was 30% or less of that on an untreated plant.

Test Example 11

Each of plastic pots was filled with sandy loam and wheat (cultivar: APOGEE) was sowed and grown in a greenhouse for 10 days. Each of the present compounds 1 to 8, 10, 11, 13 to 15, 18 to 23, 25, 26, 37, 39 to 50, 52 to 62, 64 to 70, 72 to 75, 78, 82, 84 to 87, 90 to 94, 96 to 98, 100 to 103, 109 to 113, 116 to 122, 124 to 127, 131, 134 to 137, 139 to 141, 149, 150, 152, 153, 157, 161, 162, 164, and 165 was diluted with water to adjust to a predetermined concentration of 500 ppm. The obtained diluted solution was sprayed over stems and leaves of the wheat so that they sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with each of the present compounds 1 to 8, 10, 11, 13 to 15, 18 to 23, 25, 26, 37, 39 to 50, 52 to 62, 64 to 70, 72 to 75, 78, 82, 84 to 87, 90 to 94, 96 to 98, 100 to 103, 109 to 113, 116 to 122, 124 to 127, 131, 134 to 137, 139 to 141, 149, 150, 152, 153, 157, 161, 162, 164, and 165 was 30% or less of that on an untreated plant.

Test Example 12

Each of plastic pots was filled with sandy loam and wheat (cultivar: APOGEE) was sowed and grown in a greenhouse for 10 days. Each of the present compounds 16, 27, 31, 32, 35, 38, 51, 77, 80, 95, 99, 104, 114, 128, 138, 142, 143, 145, 146, 148, 151, 154 to 156, 158, 159, 163, 166, 168 to 181, 206, 208 to 210, and 215 to 217 was diluted with water to adjust to a predetermined concentration of 200 ppm. The obtained diluted solution was sprayed over stems and leaves of the wheat so that they sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with each of the present compounds 16, 27, 31, 32, 35, 38, 51, 77, 80, 95, 99, 104, 114, 128, 138, 142, 143, 145, 146, 148, 151, 154 to 156, 158, 159, 163, 166, 168 to 181, 206, 208 to 210, and 215 to 217 was 30% or less of that on an untreated plant.

Test Example 13

Each of plastic pots was filled with sandy loam and wheat (cultivar: APOGEE) was sowed and grown in a greenhouse for 10 days. Thereafter, an aqueous suspension containing spores of wheat leaf blotch fungus (*Septoria tritici*) was sprayed over the wheat to inoculate the spores. The plant was left to stand at 18° C. under high humidity condition for 3 days and air-dried. Each of the present compounds 2, 4 to 6, 8, 11, 13 to 15, 19, 23, 37, 39 to 44, 46, 48, 49, 55 to 58, 60, 65, 66, 68 to 70, 72, 73, 92, 93, 98, 101, 102, 112, 116, 117, 119, 120, 122, 124 to 126, 128, 131, 134, 136, 137, 139 to 141, 153, 154, 157, 169 to 172, 174, 175, 177 to 181, 206, 209, 210, and 215 to 217 was diluted with water to adjust to a predetermined concentration of 200 ppm. The obtained diluted solution was sprayed over stems and leaves of the wheat so that they sufficiently adhered to the surface of the leaves of the wheat. After spraying, the plant was air-dried and also left to stand under illumination for 14 to 18 days, and then the area of lesion spots was investigated. As a result, the area of lesion spots on the plant treated with each of the present compounds 2, 4 to 6, 8, 11, 13 to 15, 19, 23, 37, 39 to 44, 46, 48, 49, 55 to 58, 60, 65, 66, 68 to 70, 72, 73, 92, 93, 98, 101, 102, 112, 116, 117, 119, 120, 122, 124 to 126, 128, 131, 134, 136, 137, 139 to 141, 153, 154, 157, 169 to 172, 174, 175, 177 to 181, 206, 209, 210, and 215 to 217 was 30% or less of that on an untreated plant.

Test Example 14

Each of plastic pots was filled with sandy loam and cucumber (cultivar: SAGAMI HANJIRO) was sowed and grown in a greenhouse for 12 days. Each of the present compounds 1 to 8, 11, 13 to 15, 18 to 23, 27, 37 to 50, 52, 53, 55 to 60, 65, 66, 68 to 70, 72, 74, 77, 91, 93, 94, 97 to 99, 102, 103, 109, 111, 116 to 122, 124 to 128, 131, 132, 136 to 141, 144, 149 to 154, 157, 159, 163, 164, and 165 was diluted with water to adjust to a predetermined concentration of 500 ppm. The obtained diluted solution was sprayed over stems and leaves of the cucumber so that they sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with each of the present compounds 1 to 8, 11, 13 to 15, 18 to 23, 27, 37 to 50, 52, 53, 55 to 60, 65, 66, 68 to 70, 72, 74, 77, 91, 93, 94, 97 to 99, 102, 103, 109, 111, 116 to 122, 124 to 128, 131, 132, 136 to 141, 144, 149 to 154, 157, 159, 163, 164, and 165 was 30% or less of that on an untreated plant.

Test Example 15

Each of plastic pots was filled with sandy loam and soybean (cultivar: KUROSENGOKU) was sowed and grown in a greenhouse for 13 days. Each of the present compounds 11, 12, 19, 39, 57, 58, 65, 69, 70, 74, 98, 104, 119, 122, 137, 140, 141, 143, 144, 157, 161, 169, 170, 172, 178, and 179 was diluted with water to adjust to a predetermined concentration of 200 ppm. The obtained diluted solution was sprayed over stems and leaves of the soybean so that they sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with each of the present compounds 11, 12, 19, 39, 57, 58, 65, 69, 70, 74, 98, 104, 119, 122, 137, 140, 141, 143, 144, 157, 161, 169, 170, 172, 178, and 179 was 30% or less of that on an untreated plant.

Test Example 16

Each of plastic pots was filled with sandy loam and barley (cultivar: MIKAMO GOLDEN) was sowed and grown in a greenhouse for 7 days. Each of the present compounds 1 to 8, 11, 13 to 23, 27, 32, 35, 37, 39 to 42, 44 to 46, 48 to 50, 53 to 60, 62, 64 to 66, 68 to 70, 72 to 74, 83 to 85, 88, 90 to 95, 97 to 104, 107, 110 to 112, 114 to 122, 124 to 126, 128, 131, 134, 136 to 141, 143, 144, 146, 148 to 150, 152 to 155, 157, 159, 161 to 163, 164, 166 to 181, 206, 208 to 210, and 215 to 217 was diluted with water to adjust to a predetermined concentration of 200 ppm. The obtained diluted solution was sprayed over stems and leaves of the barley so that they sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with each of the present compounds 1 to 8, 11, 13 to 23, 27, 32, 35, 37, 39 to 42, 44 to 46, 48 to 50, 53 to 60, 62, 64 to 66, 68 to 70, 72 to 74, 83 to 85, 88, 90 to 95, 97 to 104, 107, 110 to 112, 114 to 122, 124 to 126, 128, 131, 134, 136 to 141, 143, 144, 146, 148 to 150, 152 to 155, 157, 159, 161 to 163, 164, 166 to 181, 206, 208 to 210, and 215 to 217 was 30% or less of that on an untreated plant.

Test Example 17

Each of plastic pots was filled with sandy loam and tomato (cultivar: PATIO) was sowed and grown in a greenhouse for 20 days. The present compound 57 was diluted with water to adjust to a predetermined concentration of 500 ppm. The obtained diluted solution was sprayed over stems and leaves of the tomato seedling so that it sufficiently adhered to the surface of the leaves of the tomato seedling. After spraying, the plant was air-dried. After 2 days, an aqueous suspension containing spores of tomato late blight fungus (*Phytophthora infestans*) was sprayed to inoculate the spores. After completion of the inoculation, the seedling was at first left to stand at 23° C. under high humidity condition for one day and then cultivated in an air-conditioned room at 20° C. for 4 days. Thereafter, the area of lesion spots was investigated. As a result, it has been found that the area of lesion spots on the plant treated with the present compound 57 was 30% or less of that on an untreated plant.

Test Example 18

Each of plastic pots was filled with sandy loam and cucumber (cultivar: SAGAMI HANJIRO) was sowed and grown in a greenhouse for 19 days. Each of the present compounds 4 to 6, 11, 13, 14, 19 to 23, 25 to 32, 35, 37 to 41, 46, 48, 50, 52, 55 to 62, 64 to 66, 68 to 70, 72 to 74, 76, 78 to 80, 86, 87, 92, 98 to 103, 149, 152, 157, 158, 166 to 174, 176 to 181, 206, 208 to 210, 215, and 217 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried. After one day, the plant was inoculated by sprinkling with spores of cucumber *corynespora* leaf spot fungus (*Corynespora cassicola*). After the inoculation, the plant was cultivated in a greenhouse at 24° C. in the daytime and 20° C. at night for 7 days, and then the area of lesion spots was investigated. As a result, the area of lesion spots on the plant treated with each of the present compounds 4 to 6, 11, 13, 14, 19 to 23, 25 to 32, 35, 37 to 41, 46, 48, 50, 52, 55 to 62, 64 to 66, 68 to 70, 72 to 74, 76, 78 to 80, 86, 87, 92, 98 to 103, 149, 152, 157, 158, 166 to 174, 176 to 181, 206, 208 to 210, 215, and 217 was 30% or less of that on an untreated plant.

Test Example 19

Each of plastic pots was filled with sandy loam and cucumber (cultivar: SAGAMI HANJIRO) was sowed and grown in a greenhouse for 19 days. Each of the present compounds 4, 5, 8, 11, 13 to 16, 18, 19, 21, 23, 26, 31, 35, 37, 39, 40, 44 to 46, 48, 50, 55 to 60, 62, 65, 67 to 70, 72 to 74, 92, 93, 96, 98, 100, 102, 103, 112, 116 to 120, 122, 124 to 127, 129, 131, 132, 134, 136 to 143, 145, 147, 148, 152, 157, 166 to 170, 172, 174, 176, 178 to 180, 208 to 210, and 217 was diluted with water to adjust to a predetermined concentration of 200 ppm. The obtained diluted solution was sprayed over stems and leaves of the cucumber so that they sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with each of the present compounds 4, 5, 8, 11, 13 to 16, 18, 19, 21, 23, 26, 31, 35, 37, 39, 40, 44 to 46, 48, 50, 55 to 60, 62, 65, 67 to 70, 72 to 74, 92, 93, 96, 98, 100, 102, 103, 112, 116 to 120, 122, 124 to 127, 129, 131, 132, 134, 136 to 143, 145, 147, 148, 152, 157, 166 to 170, 172, 174, 176, 178 to 180, 208 to 210, and 217 was 30% or less of that on an untreated plant.

Test Example 20

Each of the present compounds 44, 111, 119, 122, 128, 134, 135, 139, 142, 143, 159, and 165 was diluted with deionized water to adjust to a predetermined concentration of 500 ppm, thus obtaining a test chemical solution.

Thirty (30) heads of cotton aphid (*Aphis gossypii*) (including adults and larvae) were released on the leaves of cucumber (cultivar: SAGAMI HANJIRO FUSHINARI) grown in a polyethylene cup until the first true leaf was developed. Next day, 20 mL of the above test chemical solution was sprayed. After 6 days, the number of the surviving insects was counted and the control value was calculated by the following equation.

Control value (%)={1−($Cb \times Tai$)/($Cai \times Tb$)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.

As a result, the present compound 44, 111, 119, 122, 128, 134, 135, 139, 142, 143, 159, or 165 showed 90% or more of the control value.

Test Example 21

Each of the present compounds 23, 60, 66, and 73 was diluted with deionized water to adjust to a predetermined concentration of 500 ppm, thus obtaining a test chemical solution.

The above test chemical solution (0.7 mL) was added to 100 mL of deionized water to adjust an active ingredient concentration to 3.5 ppm. Twenty (20) heads of last instar larvae of common house mosquito (*Culex pipiens pallens*) were released in the solution and the number of dead insects was counted after 8 days.

Mortality was determined by the following equation.

Mortality (%)=(number of dead insects/number of test insects)×100

As a result, the present compound 23, 60, 66, or 73 exhibited mortality of 100%.

Test Example 22

Each of the present compounds 25, 52, and 120 was diluted with deionized water to adjust to a predetermined concentration of 500 ppm, thus obtaining a test chemical solution.

Cabbage (cultivar: GREEN BALL) was planted in each of polyethylene cups and grown until the third true leaf or the fourth true leaf was developed. The above test chemical solution was sprayed over the cabbage at a rate of 20 mL/cup. After drying the chemical solution, the polyethylene cup having a diameter of 5.5 cm covered with a filter paper laid on the bottom, the cabbage cut out from the root was placed and 5 heads of third instar larvae of cabbage moth (*Plutella xylostella*) were released in the cup and the cup was covered with the lid. The cup was held at 25° C. and, after 5 days, the number of the surviving insects was counted and the mortality of insects was calculated by the following equation.

Mortality (%)=(number of dead insects/number of test insects)×100

As a result, the present compound 25, 52, or 120 exhibited mortality of 80% or more.

Test Example 23

The present compound 67 was diluted with deionized water to adjust to a predetermined concentration of 500 ppm, thus obtaining a test chemical solution.

On each of polyethylene cups having a diameter of 5.5 cm, a filter paper having the same size was laid. The above test chemical solution (0.7 ml) was dropped on the filter paper and 30 mg of sucrose was placed as bait. Two (2) heads of male adult German cockroach (*Blattella germanica*) were released in the polyethylene cup and the cup was covered with the lid. After 6 days, the life or death of German cockroach was investigated and mortality was determined by the following equation.

Mortality (%)=(number of dead insects/number of test insects)×100

As a result, the present compound 67 exhibited mortality of 100%.

Test Example 24

Each of the present compounds 19, 20, 28, 29, and 52 was diluted with deionized water to adjust to a predetermined concentration of 500 ppm, thus obtaining a test chemical solution.

The above test chemical solution (0.7 mL) was added to 100 mL of deionized water to adjust an active ingredient concentration to 3.5 ppm. Twenty (20) heads of last instar larvae of common house mosquito (*Culex pipiens pallens*) were released in the solution and, after one day, the number of dead insects was counted.

Mortality was determined by the following equation.

Mortality (%)=(number of dead insects/number of test insects)×100

As a result, the present compounds 19, 20, 28, 29, and 52 exhibited mortality of 100%.

Test Example 25

The present compound 52 was diluted with deionized water to adjust to a predetermined concentration of 500 ppm, thus obtaining a test chemical solution.

On each of polyethylene cups having a diameter of 5.5 cm, a filter paper having the same size was laid. Insecta LF (manufactured by NOSAN CORPORATION) was sliced to 6 mm in thickness, cut into half, and then placed on the filter paper. Then, 2 mL of the test chemical solution was poured into the polyethylene cup. After air-drying, 5 heads of third instar larvae of common cutworm (*Spodoptela litura*) were released in the polyethylene cup and the cup was sealed with a lid. After 6 days, the number of dead insects was counted. Mortality was calculated according to the following equation.

Mortality (%)=(number of dead insects/number of test insects)×100

As a result, the present compound 52 exhibited mortality of 100%.

Test Example 26

The present compound 52 was diluted with deionized water to adjust to a predetermined concentration of 500 ppm, thus obtaining a test chemical solution.

On each of polyethylene cups having a diameter of 5.5 cm, a filter paper having the same size was laid. Silkmate 2S (manufactured by NOSAN CORPORATION) was sliced to 2 mm in thickness, and then placed on the filter paper. Then, 1 mL of the test chemical solution was poured into the polyethylene cup. After air-drying, 30 heads of first instar larvae of apple root-knot nematode (*Adoxophyes orana*) were released in the polyethylene cup and the cup was sealed with a lid. After 7 days, the number of dead insects was counted. Mortality was calculated according to the following equation.

Mortality (%)=(number of dead insects/number of test insects)×100

As a result, the present compound 52 exhibited mortality of 100%.

Comparative Example 1

Each of plastic pots was filled with sandy loam and barley (cultivar: MIKAMO GOLDEN) was sowed and grown in a greenhouse for 7 days. A control compound 1-methyl-4-[2-

(6-phenylpyridin-2-yloxymethyl)-phenyl]-1,4-dihydrotetrazol-5-one was diluted with water to adjust to a predetermined concentration of 3.1 ppm. The obtained diluted solution was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at -continued Q2 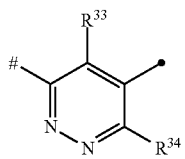

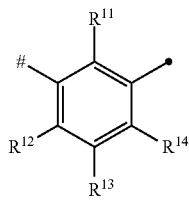  Q3

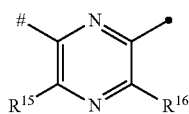  Q4

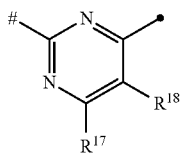  Q5

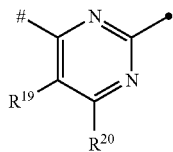  Q6

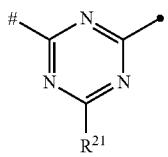  Q7

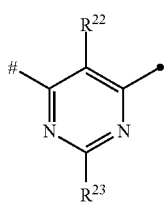  Q8

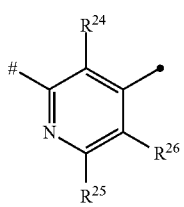  Q9

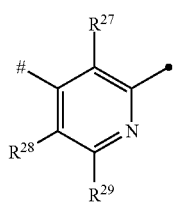  Q10

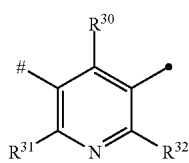

-continued

Q11

Q12

$R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ each independently representing a hydrogen atom, a halogen atom, a C1-C6 alkyl group optionally substituted with one or more atoms or groups selected from Group $P^1$, a C3-C6 cycloalkyl group optionally substituted with one or more atoms or groups selected from Group $P^1$, a C1-C6 alkoxy group, a C1-C6 haloalkoxy group, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, an amino group optionally substituted with a C1-C6 alkyl group, an amino group optionally substituted with a C1-C6 haloalkyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C9 trialkylsilyl group, a C2-C6 alkylcarbonyl group, a C2-C6 alkoxycarbonyl group, or an aminocarbonyl group optionally substituted with a C1-C6 alkyl group; and X represents an oxygen atom or a sulfur atom:

Group P: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an amino group optionally substituted with a C1-C6 alkyl group, an aminosulfonyl group optionally substituted with a C1-C6 alkyl group and/or a C6-C12 aryl group, and an aminocarbonyl group optionally substituted with a C1-C6 alkyl group; and Group $P^1$: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group.

2. The tetrazolinone compound according to claim 1, wherein Q is Q1.

3. The tetrazolinone compound according to claim 1, wherein Q is Q2.

4. The tetrazolinone compound according to claim 1, wherein Q is Q3.

5. The tetrazolinone compound according to claim 1, wherein Q is Q4.

6. The tetrazolinone compound according to claim 1, wherein Q is Q5.

7. The tetrazolinone compound according to claim 1, wherein Q is Q6.

8. The tetrazolinone compound according to claim 1, wherein Q is Q7.

9. The tetrazolinone compound according to claim 1, wherein Q is Q8.

10. The tetrazolinone compound according to claim 1, wherein Q is Q9.

11. The tetrazolinone compound according to claim 1, wherein Q is Q10.

12. The tetrazolinone compound according to claim 1, wherein Q is Q11.

13. The tetrazolinone compound according to claim 1, wherein Q is Q12.

14. The tetrazolinone compound according to claim 1, wherein $R^1$, $R^2$, $R^4$, $R^5$, and $R^6$ are hydrogen atoms;
$R^7$ is a methyl group; and
X is an oxygen atom.

15. The tetrazolinone compound according to claim 1, wherein A is a C6-C16 aryl group optionally substituted with one or more atoms or groups selected from Group P (provided that when the C6-C16 aryl group has two or more atoms or groups selected from Group P, each atom or group may be the same as or different from at least one other atom or group).

16. The tetrazolinone compound according to claim 1, wherein A is formula (2):

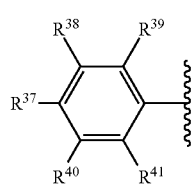

(2)

wherein
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an aminosulfonyl group optionally substituted with a C1-C6 alkyl group and/or a C6-C12 aryl group, or an aminocarbonyl group optionally substituted with a C1-C6 alkyl group.

17. The tetrazolinone compound according to claim 16, wherein $R^3$ is a methyl group, a cyclopropyl group, a chlorine atom, a bromine atom, an ethyl group, or a methoxy group;
$R^{37}$ is a methoxy group, a trifluoromethoxy group, a fluorine atom, a chlorine atom, or a bromine atom; and
$R^{38}$, $R^{39}$, $R^{40}$, and $R^{41}$ each independently represents a hydrogen atom or a fluorine atom.

18. The tetrazolinone compound according to claim 16, wherein Q is Q2;
$R^3$ is a C1-C3 alkyl group, a C3-C4 cycloalkyl group, a halogen atom, a C1-C3 haloalkyl group, a C2-C3 alkenyl group, a C1-C3 alkoxy group, a C1-C2 alkylthio group, a C2-C3 alkynyl group, a C1-C3 haloalkoxy group, or a C1-C2 haloalkylthio group;
$R^{11}$, $R^{12}$, $R^{13}$ and $R^{14}$ each independently represents a hydrogen atom, a halogen atom, a C1-C6 alkyl group optionally having a group selected from Group $P^1$, a C3-C6 cycloalkyl group optionally having a group selected from Group $P^1$, a C1-C6 alkoxy group, or a C1-C6 haloalkoxy group;
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C1-C6 alkoxy group, a C1-C6 haloalkoxy group, a C1-C6 alkylthio group, a C3-C6 cycloalkyloxy group, a C2-C6 alkylcarbonyloxy group, a formyl group, a C2-C6 alkoxycarbonyl group, a C2-C6 alkylcarbonyl group, a nitro group, a cyano group, a hydroxyl group, a C6-C16 aryloxy group, a C1-C6 alkylsulfonyl group, a C1-C6 alkylsulfinyl group, an aminosulfonyl group optionally having a C1-C6 alkyl group and/or a C6-C12 aryl group, or an aminocarbonyl group optionally having a C1-C6 alkyl group.

19. The tetrazolinone compound according to claim 16, wherein $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; and
$R^{37}$, $R^{38}$, $R^{39}$, $R^{40}$, and $R^{41}$ each independently represents a halogen atom, a hydrogen atom, a C1-C3 alkyl group, a C1-C3 haloalkyl group, a C1-C3 alkoxy group, or a C1-C3 haloalkoxy group.

20. The tetrazolinone compound according to claim 16, wherein $R^3$ is a methyl group, a cyclopropyl group, a chlorine atom, a bromine atom, an ethyl group, or a methoxy group;
$R^{37}$ is a methoxy group, a trifluoromethoxy group, a fluorine atom, a chlorine atom, or a bromine atom; and
$R^{38}$, $R^{39}$, $R^{40}$, and $R^{41}$ each independently represents a hydrogen atom or a fluorine atom.

21. The tetrazolinone compound according to claim 16, wherein $R^3$ is a methyl group, a cyclopropyl group, a chlorine atom, a bromine atom, an ethyl group, or a methoxy group;
$R^{37}$ is a methoxy group, a trifluoromethoxy group, a fluorine atom, a chlorine atom, or a bromine atom;
$R^{38}$, $R^{39}$, and $R^{40}$ each independently represents a hydrogen atom or a fluorine atom; and
$R^{41}$ is a hydrogen atom, a methoxy group, or an ethoxy group.

22. The tetrazolinone compound according to claim 1, wherein Q is Q1;
$R^3$ is a C1-C3 alkyl group, a C3-C4 cycloalkyl group, a halogen atom, a C1-C3 haloalkyl group, a C2-C3 alkenyl group, a C1-C3 alkoxy group, a C1-C2 alkylthio group, a C2-C3 alkynyl group, a C1-C3 haloalkoxy group, or a C1-C2 haloalkylthio group;
$R^8$, $R^9$, and $R^{10}$ each independently represents a hydrogen atom, a halogen atom, a C1-C6 alkyl group optionally substituted with a group selected from Group $P^1$, a C3-C6 cycloalkyl group optionally substituted with a group selected from Group $P^1$, a C1-C6 alkoxy group, or a C1-C6 haloalkoxy group;
$R^{37}$, $R^{38}$, $R^{39}$, $R^{40}$, and $R^{41}$ each independently represents a halogen atom, a hydrogen atom, a C1-C6 alkyl group, a C1-C6 haloalkyl group, a C1-C6 alkoxy group, a C1-C6 haloalkoxy group, a C1-C6 alkylthio group, a C3-C6 cycloalkyloxy group, a C2-C6 alkylcarbonyloxy group, a formyl group, a C2-C6 alkoxycarbonyl group, a C2-C6 alkylcarbonyl group, a nitro group, a cyano group, a hydroxyl group, a C6-C16 aryloxy group, a C1-C6 alkylsulfonyl group, a C1-C6 alkylsulfinyl group, an aminosulfonyl group optionally substituted with a C1-C6 alkyl group and/or a C6-C12 aryl group, or an aminocarbonyl group optionally substituted with a C1-C6 alkyl group.

23. The tetrazolinone compound according to claim 1, wherein $R^3$ is a C1-C3 alkyl group, a C3-C4 cycloalkyl group, a halogen atom, a C1-C3 haloalkyl group, a C2-C3 alkenyl group, a C1-C3 alkoxy group, a C2-C3 alkynyl group, or a C1-C3 haloalkoxy group; and
$R^{37}$, $R^{38}$, $R^{39}$, $R^{40}$, and $R^{41}$ each independently represents a halogen atom, a hydrogen atom, a C1-C3 alkyl group, a C1-C3 haloalkyl group, a C1-C3 alkoxy group, or a C1-C3 haloalkoxy group.

24. The tetrazolinone compound according to claim 1, wherein A is a C3-C12 cycloalkyl group optionally substituted with one or more atoms or groups selected from Group P, a C2-C9 heterocyclyl group optionally substituted with one or more atoms or groups selected from Group P provided that the C2-C9 heterocyclyl group has, as a ring-constituent atom, one or more atoms selected from the group consisting of a nitrogen atom, an oxygen atom, and a sulfur atom, and when the C2-C9 heterocyclyl group has two or more atoms selected from the group consisting of a nitrogen atom, an oxygen atom, and a sulfur atom, each atom may be the same as or different from at least one other atom, and the carbon or nitrogen atom constituting the ring of the C2-C9 heterocyclyl group is bound to Q, or a C3-C12 cycloalkenyl group optionally substituted with one or more atoms or groups selected from Group P,
provided that, when the C3-C12 cycloalkyl group, the C2-C9 heterocyclyl group, and the C3-C12 cycloalkenyl group have two or more atoms or groups selected from Group P, each atom or group may be the same as or different from at least one other atom or group.

25. The tetrazolinone compound according to claim 1, wherein A is a C2-C9 heteroaryl group optionally substituted with one or more atoms or groups selected from Group P.

26. A tetrazolinone compound represented by formula (1):

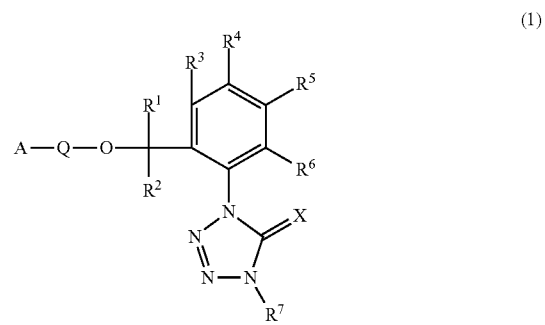

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally substituted with a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxyl group, a thiol group, an amino group optionally substituted with a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;
$R^4$, $R^5$, and $R^6$ each independently represents a hydrogen atom, a halogen atom, a C1-C4 alkyl group, a C1-C4 haloalkyl group, a C3-C5 cycloalkyl group, a C3-C5 halocycloalkyl group, a C1-C4 alkoxy group, or a C1-C4 haloalkoxy group;

R⁷ represents a C1-C6 alkyl group, a hydrogen atom, a C1-C6 haloalkyl group, a C2-C6 alkenyl group, a C2-C6 haloalkenyl group, a C2-C6 alkoxyalkyl group, a C3-C6 cycloalkyl group, or a C3-C6 halocycloalkyl group;

A represents a C6-C16 aryl group optionally substituted with one or more atoms or groups selected from Group P, a C3-C12 cycloalkyl group optionally substituted with one or more atoms or groups selected from Group P, a C2-C9 heterocyclyl group optionally substituted with one or more atoms or groups selected from Group P (provided that the C2-C9 heterocyclyl group has, as a ring-constituent atom, one or more atoms selected from the group consisting of a nitrogen atom, an oxygen atom, and a sulfur atom and, when the C2-C9 heterocyclyl group has two or more atoms selected from the group consisting of a nitrogen atom, an oxygen atom, and a sulfur atom, each atom may be the same as or different from at least one other group, and also the carbon or nitrogen atom constituting the ring of the C2-C9 heterocyclyl group is bound to Q), or a C3-C12 cycloalkenyl group optionally substituted with one or more atoms or groups selected from Group P (provided that the C6-C16 aryl group, the C3-C12 cycloalkyl group, the C2-C9 heterocyclyl group, and the C3-C12 cycloalkenyl group optionally have one or more atoms or groups selected from Group P and, when these groups have two or more atoms or groups selected from Group P, each atom or group may be the same as or different from at least one other atom or group);

Q represents the following group Q1 {the symbol # represents a binding site for A, and the symbol • represents a binding site for an oxygen atom};

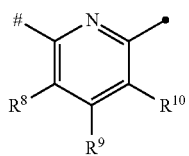

Q1

R⁸, R⁹ and R¹⁰ each independently representing a hydrogen atom, a halogen atom, a C1-C6 alkyl group optionally substituted with one or more atoms or groups selected from Group P¹, a C3-C6 cycloalkyl group optionally substituted with one or more atoms or groups selected from Group P¹, a C1-C6 alkoxy group, a C1-C6 haloalkoxy group, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, an amino group optionally substituted with a C1-C6 alkyl group, an amino group optionally substituted with a C1-C6 haloalkyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C9 trialkylsilyl group, a C2-C6 alkylcarbonyl group, a C2-C6 alkoxycarbonyl group, or an aminocarbonyl group optionally substituted with a C1-C6 alkyl group; and X represents an oxygen atom or a sulfur atom:

Group P: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an amino group optionally substituted with a C1-C6 alkyl group, an aminosulfonyl group optionally substituted with a C1-C6 alkyl group and/or a C6-C12 aryl group, and an aminocarbonyl group optionally substituted with a C1-C6 alkyl group; and Group P¹: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and A is formula (4):

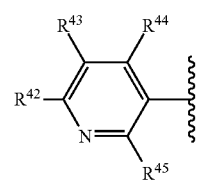

(4)

wherein

R⁴², R⁴³, R⁴⁴, and R⁴⁵ each independently represents a halogen atom, a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxyl group, a C6-C16 aryl group, a C6-C16 haloaryl group, a C6-C16 aryloxy group, a C6-C16 haloaryloxy group, a C6-C16 arylthio group, a C6-C16 haloarylthio group, a C7-C18 aralkyl group, a C7-C18 haloaralkyl group, a C7-C18 arylalkoxy group, a C7-C18 haloarylalkoxy group, a thiol group, a pentafluorosulfanyl group, a C3-C12 trialkylsilyl group, a C5-C14 trialkylsilylethynyl group, a C1-C6 alkylsulfonyl group, a C1-C6 haloalkylsulfonyl group, a C6-C16 arylsulfonyl group, a C6-C16 haloarylsulfonyl group, a C1-C6 alkylsulfinyl group, a C1-C6 haloalkylsulfinyl group, a C6-C16 arylsulfinyl group, a C6-C16 haloarylsulfinyl group, an aminosulfonyl group optionally substituted with a C1-C6 alkyl group and/or a C6-C12 aryl group, or an aminocarbonyl group optionally substituted with a C1-C6 alkyl group.

27. The tetrazolinone compound according to claim 26, wherein $R^3$ is a methyl group, a cyclopropyl group, a chlorine atom, bromine atom, an ethyl group, or a methoxy group;
$R^{42}$ is a hydrogen atom, a methoxy group, an ethoxy group, a fluorine atom, a chlorine atom, a bromine atom, a methyl group, an ethyl group, or a trifluoromethyl group;
$R^{43}$ and $R^{44}$ each independently represents a hydrogen atom or a fluorine atom; and
$R^{45}$ is a hydrogen atom, a methoxy group, or an ethoxy group.

28. A pest control agent comprising the tetrazolinone compound according to claim 1.

29. A method for controlling pests, which comprises treating plants or soil with an effective amount of the tetrazolinone compound according to claim 1.

30. A tetrazolinone compound represented by formula (3):

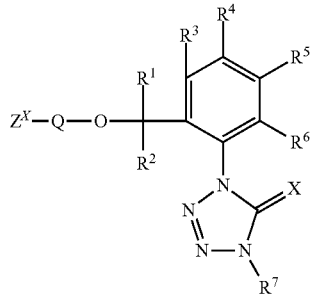

(3)

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally substituted with a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxyl group, a thiol group, an amino group optionally substituted with a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;
$R^4$, $R^5$, and $R^6$ each independently represents a hydrogen atom, a halogen atom, a C1-C4 alkyl group, a C1-C4 haloalkyl group, a C3-C5 cycloalkyl group, a C3-C5 halocycloalkyl group, a C1-C4 alkoxy group, or a C1-C4 haloalkoxy group;
$R^7$ represents a C1-C6 alkyl group, a hydrogen atom, a C1-C6 haloalkyl group, a C2-C6 alkenyl group, a C2-C6 haloalkenyl group, a C2-C6 alkoxyalkyl group, a C3-C6 cycloalkyl group, or a C3-C6 halocycloalkyl group;
$Z^X$ represents a halogen atom;
Q represents the following group Q1, Q2, Q3, Q4, Q5, Q6, Q7, Q8, Q9, Q10, Q11, or Q12 {the symbol # represents a binding site for $Z^x$, and the symbol • represents a binding site for an oxygen atom};

Q:

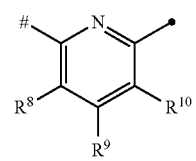

Q1

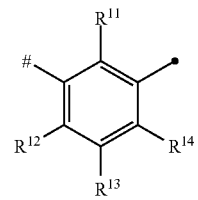

Q2

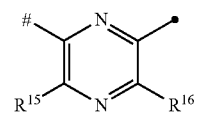

Q3

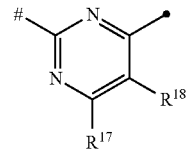

Q4

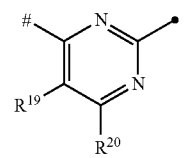

Q5

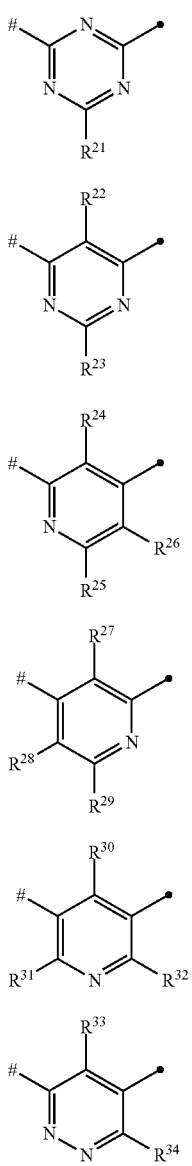

Q6

Q7

Q8

Q9

Q10

Q11

Q12

$R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, and $R^{36}$ each independently representing a hydrogen atom, a halogen atom, a C1-C6 alkyl group optionally substituted with one or more atoms or groups selected from Group $P^1$, a C3-C6 cycloalkyl group optionally substituted with one or more atoms or groups selected from Group $P^1$, a C1-C6 alkoxy group, a C1-C6 haloalkoxy group, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, an amino group optionally substituted with a C1-C6 alkyl group, an amino group optionally substituted with a C1-C6 haloalkyl group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C9 trialkylsilyl group, a C2-C6 alkylcarbonyl group, a C2-C6 alkoxycarbonyl group, or an aminocarbonyl group optionally substituted with a C1-C6 alkyl group; and X represents an oxygen atom or a sulfur atom:

Group $P^1$: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group.

31. The tetrazolinone compound according to claim 30, wherein Q is Q1, Q2, or Q4;

$R^3$ is a methyl group, a cyclopropyl group, a chlorine atom, a bromine atom, an ethyl group, or a methoxy group;

$R^1$, $R^2$, $R^4$, $R^5$, and $R^6$ are hydrogen atoms;

$R^7$ is a methyl group; and

X is an oxygen atom.

* * * * *